(12) United States Patent
Wacker et al.

(10) Patent No.: US 9,764,018 B2
(45) Date of Patent: Sep. 19, 2017

(54) BIOSYNTHETIC SYSTEM THAT PRODUCES IMMUNOGENIC POLYSACCHARIDES IN PROKARYOTIC CELLS

(71) Applicant: GlycoVaxyn AG, Schlieren (CH)

(72) Inventors: Michael Wacker, Unterengstringen (CH); Charles Waechter, Lexington, KY (US)

(73) Assignee: GLYCOVAXYN AG (CH)

( * ) Notice: Subject to any disclaimer, the term of this patent is extended or adjusted under 35 U.S.C. 154(b) by 0 days.

(21) Appl. No.: 14/462,261

(22) Filed: Aug. 18, 2014

(65) Prior Publication Data

US 2015/0190492 A1 Jul. 9, 2015

Related U.S. Application Data

(63) Continuation of application No. 13/510,859, filed as application No. PCT/US2010/002980 on Nov. 16, 2010, now Pat. No. 8,846,342.

(60) Provisional application No. 61/272,931, filed on Nov. 19, 2009.

(51) Int. Cl.
| | | |
|---|---|---|
| *A61K 39/00* | (2006.01) | |
| *A61K 39/02* | (2006.01) | |
| *A61K 39/385* | (2006.01) | |
| *A61K 39/108* | (2006.01) | |
| *A61K 39/112* | (2006.01) | |
| *A61K 47/48* | (2006.01) | |

(52) U.S. Cl.
CPC ...... *A61K 39/0258* (2013.01); *A61K 39/0283* (2013.01); *A61K 39/385* (2013.01); *A61K 47/4833* (2013.01); *A61K 2039/6068* (2013.01)

(58) Field of Classification Search
CPC .................................................. A61K 39/0258
USPC ...................................................... 424/178.1
See application file for complete search history.

(56) References Cited

U.S. PATENT DOCUMENTS

| | | | |
|---|---|---|---|
| 5,242,809 A | 9/1993 | Adams et al. | |
| 5,643,758 A | 7/1997 | Guan et al. | |
| 6,365,723 B1 | 4/2002 | Blattner et al. | |
| 7,265,085 B2 | 9/2007 | DeFrees et al. | |
| 7,541,043 B2 | 6/2009 | Kopecko et al. | |
| 8,703,471 B2 * | 4/2014 | Aebi ............... | A61K 47/48092 435/193 |
| 8,753,864 B2 * | 6/2014 | Aebi ............... | C07K 14/205 424/94.61 |
| 8,846,342 B2 * | 9/2014 | Wacker ............ | A61K 39/0283 424/190.1 |
| 8,871,491 B2 * | 10/2014 | Wacker ............ | A61K 39/085 435/200 |
| 8,895,014 B2 * | 11/2014 | Fernandez ........ | A61K 39/0258 424/178.1 |
| 9,221,898 B2 * | 12/2015 | Szymanski ........ | A61K 39/105 |
| 9,309,493 B2 * | 4/2016 | Ilg ................... | A61K 39/0275 |
| 2002/0019342 A1 | 2/2002 | Bayer | |
| 2002/0132320 A1 | 9/2002 | Wang et al. | |
| 2002/0150968 A1 | 10/2002 | Wang et al. | |
| 2004/0067557 A1 | 4/2004 | Endo et al. | |
| 2004/0265954 A1 * | 12/2004 | Aebi ............... | A61K 47/48092 435/69.1 |
| 2005/0287628 A1 * | 12/2005 | Aebi ............... | A61K 47/48092 435/69.1 |
| 2011/0097357 A1 | 4/2011 | Fernandez et al. | |
| 2011/0223646 A1 | 9/2011 | Schwartz et al. | |
| 2011/0236934 A1 | 9/2011 | Samain et al. | |
| 2011/0274720 A1 | 11/2011 | Wacker et al. | |
| 2012/0100177 A1 | 4/2012 | Ilg et al. | |
| 2012/0156723 A1 * | 6/2012 | Wren ............... | C12N 9/1051 435/69.3 |
| 2013/0029413 A1 | 1/2013 | Geisler et al. | |
| 2013/0266604 A1 | 10/2013 | Szymanski et al. | |
| 2014/0323700 A1 * | 10/2014 | Aebi ............... | C07K 14/205 530/395 |
| 2014/0335127 A1 * | 11/2014 | Aebi ............... | A61K 47/48092 424/234.1 |
| 2014/0336366 A1 * | 11/2014 | Faridmoayer ..... | C07K 14/22 530/395 |
| 2015/0044254 A1 * | 2/2015 | Fernandez ........ | A61K 39/0258 424/197.11 |
| 2015/0273043 A1 * | 10/2015 | Wacker ............ | A61K 39/092 530/395 |

(Continued)

FOREIGN PATENT DOCUMENTS

| | | |
|---|---|---|
| CA | 1340184 | 12/1998 |
| CA | 2360205 | 8/2000 |

(Continued)

OTHER PUBLICATIONS

Feldman, Mario F et al, PNAS, pp. 3016-3021, Feb. 22, 2005, vol. 102(8), Engineering N-linked protein glycosylation with diverse ) antigen lipopolysaccharide structures in *Escherichia coli*.*
Glover, Kerney J. et al, Chemistry and Biology, vol. 12, pp. 1311-1316, Dec. 2005.*
Szymanski et al, Mol. Microbiology, vol. 32(5), pp. 1022-1030, 1999.*
Abdian et al., 2000, "Identification of essential amino acids in the bacterial α-mannosyltransferase aceA", J Biol Chem; 275(51):40568-40575.

(Continued)

*Primary Examiner* — Albert Navarro
(74) *Attorney, Agent, or Firm* — Eric Kron

(57) ABSTRACT

The invention is directed to bioconjugate vaccines comprising N-glycosylated proteins. Further, the present invention is directed to a recombinant prokaryotic biosynthetic system comprising nucleic acids encoding an epimerase that synthesizes an oligo- or polysaccharide having N-acetylgalactosamine at the reducing terminus. The invention is further directed to N-glycosylated proteins containing an oligo- or polysaccharide having N-acetylgalactosamine at the reducing terminus and an expression system and methods for producing such N-glycosylated proteins.

20 Claims, 14 Drawing Sheets

(56) References Cited

U.S. PATENT DOCUMENTS

2015/0328301 A1* 11/2015 Wren .............. A61K 39/0208
424/190.1

FOREIGN PATENT DOCUMENTS

| CA | 2477794 | | 3/2003 | |
|---|---|---|---|---|
| EP | 1481057 | | 2/2006 | |
| WO | WO 94/26906 | | 11/1994 | |
| WO | WO 00/52135 | | 9/2000 | |
| WO | WO 01/88117 | | 11/2001 | |
| WO | WO 02/00856 | | 1/2002 | |
| WO | WO 03/074687 | | 9/2003 | |
| WO | WO 2004/013151 | A2 | 2/2004 | |
| WO | WO 2005/116063 | A1 | 12/2005 | |
| WO | 2006/119987 | * | 11/2006 | |
| WO | WO 2006/119987 | A2 | 11/2006 | |
| WO | WO 2009/089396 | A2 | 7/2009 | |
| WO | 2009/104074 | * | 8/2009 | ............. A61F 39/02 |
| WO | WO 2009/104074 | A2 | 8/2009 | |

OTHER PUBLICATIONS

Aebi et al., 1996, "Cloning and characterization of the ALG3 gene of *Saccharomyces cerevisiae*", Glycobiology; 6:439-444.
Ahmed et al., 2006, "Safety and immunogenicity of *Escherichia coli* O157 O-specific polysaccharide conjugate vaccine in 2-5 year old children", J Infect Dis; 193(4):515-521.
Alaimo et al., 2006, "Two distinct but interchangeable mechanisms for flipping of lipid-linked oligosaccharides", EMBO J; 25:967-976.
Alexander et al., 1994, "Role of the rfe gene in the biosynthesis of the *Escherichia coli* O7-specific lipopolysaccharide and other O-specific polysaccharides containing N-acetylglucosamine", J Bacteriol; 176:7079-7084.
Allard et al., 2001, "Epimerases:structure, function and mechanism", Cell Mol Life Sci; 58:1650-1665.
Altmann et al., 1999, "Insect cells as hosts for the expression of recombinant glycoproteins", Glycoconjugate Journal; 16:109-123.
Amor et al., 1997, "Molecular and functional analysis of genes required for expression of group IB K antigens in *Escherichia coli*: characterization of the his-region containing gene clusters for multiple cell-surface polysaccharides", Mol Microbiol; 26:145-161.
Anderson, 1983, "Antibody responses to Haemophilus influenzae type b and diphtheria toxin induced by conjugates of oligosaccharides of the type b capsule with the nontoxic protein $CRM_{197}$", Infection and Immunity; 39(1):233-238.
Arbeit et al., 1984, "Predominance of two newly described capsular polysaccharide types among clinical isolates of *Staphylococcus aureus*", Diagn Microbiol Infect Dis; 2:85-91.
Avery et al., 1929, "Chemo-immunological studies on conjugated carbohydrate-proteins. II Immunological specificity of synthetic sugar-protein antigens", J Exp Med; 50(4):533-550.
Baggett et al., 2004, "Community-onset methicillin-resistant *Staphylococcus aureus* associated with antibiotic use and the cytotoxin Panton-Valentine leukocidin during a furunculosis outbreak in rural Alaska", J Infect Dis; 189:1565-1573.
Baneyx et al., 1999, "Recombinant protein expression in *Escherichia coli*", Curr Opin Biotechnol; 10:411-421.
Baqar et al., 1995, "Safety and immunogenicity of a prototype oral whole-cell killed Campylobacter vaccine administered with a mucosal adjuvant in non-human primates",Vaccine; 13(1):22-28.
Bematchez et al., 2005, "A single bifunctional UDP-ClcNAc/Glc 4-epimerase supports the synthesis of three cell surface glycoconjugates in Campylobacter jejuni", J Biol Chem; 280:4792-4802.
Berg et al., 1997, "2-oxo acid dehydrogenase multienzyme complexes: the central role of the lipoyl domain", Biological Chemistry; 378:617-634.
Berg et al. 2001, "Sequence properties of the 1,2-diacylglycerol 3-glucosyltransferase from acholeplasma laidlawii membranes", J Biol Chem; 276(25):22056-22063.

Bhasin et al., 1998, "Identification of a gene essential for o-acetylation of the *Staphylococcus aureus* type 5 capsular polysaccharide", Mol Microbiol; 27:9-21.
Bigge et al., 1995, "Nonselective and efficient fluorescent labeling of glycans using 2-amino benzamide and anthranilic acid", Anal Biochem; 230(2):229-238.
Bill et al., 1995, "Expression and mutagenesis of recombinant human and murine erythropoietins in *Escherichia coli*", Biochimica et Biophysica Acta; 1261:35-43.
Billman-Jacobe, 1996, "Expression in bacteria other than *Escherichia coli*", Curr Opin Biotechnol; 7:500-504.
Bligh et al., 1959, "A rapid method of total lipid extraction and purification", Can J Biochem Physiol; 37(8):911-917.
Bourne et al., 2001, "Glycoside hydrolases and glycosyltransferases: families and functional modules", Current Opinion in Structural Biology; 11:593-600.
Branden et al., 1991, "Introduction to protein structure", Garland Publishing Inc., New York; pp. 247-268.
Breton et al., 1999, "Structure/function studies of glycosyltransferases", Current Opinion in Structural Biology; 9:563-571.
Bubeck Wardenburg et al., 2008, "Panton-Valentine leukocidin is not a virulence determinant in murine models of community-associated methicillin-resistant *Staphylococcus aureus* disease", J Infect Dis; 198:1166-1170.
Bugg et al., 1994, "From peptidoglycan to glycoproteins: common features of lipid-linked oligosaccharide biosynthesis", FEMS Microbiol Lett; 119:255-262.
Burda et al., 1999, "The dolichol pathway of N-linked glycosylation", Biochimica et Biophysica Acta; 1426:239-257.
Burr et al., 2005, "Prevention of disease in ferrets fed an inactivated whole cell Campylobacter jejuni vaccine", Vaccine; 23:4315-4321.
Butzler, 2004, "Campylobacter, from obscurity to celebrity", Clinical Microbiology and Infection; pp. 868-876.
Campbell et al., 1997, "A classification of nucleotide-diphospho-sugar glycosyltransferases based on amino acid sequence similarities", Biochem J; 326:929-939.
Canals et al., 2006, "The UDP N-acetylgalactosamine 4-epimerase gene is essential for mesophilic Aeromaonas hydrophila serotype O34 virulence", Infect & Immun; 74(1):537-548.
Cardini et al., 1957, "Enzymatic formation of acetylgalactosamine", J Biol Chem; 225:317-327.
Casburn-Jones et al., 2004, "Traveler's diarrhea", Journal of Gastroenterology and Hepatology, 19:610-618.
CAZy (Carbohydrate-Active enZYmes) Database—GlycosylTransferase family classification (AFMB—CNRS—Universites Aix-Marseille I & II) last update: Oct. 25, 2010 at www.cazy.org/GlycosylTransferases.html.
CAZy (Carbohydrate-Active enZYmes) Database—Home (AFMB—CNRS—Universites Aix-Marseille I & II) last update: Oct. 25, 2010 at http://www.cazy.org.
Chang et al., 2003, "Infection with vancomycin-resistant *Staphylococcus aureus* containing the vanA resistance gene", New Engl J Med; 348:1342-1347.
Chart et al., 1991, "Serological identification of *Escherichia coli* O157:H7 infection in haemolytic uraemic syndrome", The Lancet; 337:138-140.
Choi et al., 2004, "Secretory and extracellular production of recombinant proteins using *Escherichia coli*", Appl Microbiol Biotcchnol; 64:625-635.
Consortium for Functional Glycomics (CFG) Nature, Functional glycomics gateway—Nomenclature, last update: Apr. 28, 2010 at ww.functionalglycomics.org/static/consortium/Nomenclature.shtml.
Coutinho et al., 1999, "Life with no sugars?", J Mol Microbiol Biotech; 1(2):307-308.
Crooks et al., 2004, "WebLogo: A sequence logo generator", Genome Research; 14(6):1188-1190.
Cruezenet et al., 2000, "Expression, purification, and biochemical characterization of WbpP, a new UDP-GlcNAc C4 epimerase from Pseudomonas aeruginosa sertype O6", J Biol Chem; 275(25):19060-19067.

(56) References Cited

OTHER PUBLICATIONS

Crushell et al., 2004, "Enteric Campylobacter: purging its secrets?" Pediatric Research; 55(1):3-12.
Cunnion et al., 2001, "Capsule production and growth phase influence binding of complement to *Staphylococcus aureus*", Infect Immun; 69:6796-6803.
Datsenko et al., 2000, "One-step inactivation of chromosomal genes in *Escherichia coli* K-12 using PCR products", Proc Natl Acad Sci USA; 97:6640-6645.
Dean et al., 1999, "Characterization of the serogroup O11 O-antigen locus of Pseudomonas aeruginosa PA103", J Bacteriol; 181:4275-4284.
Dejonge et al., 2007, "Clinical trial of safety and efficacy of INH-A21 for the prevention of nosocomial staphylococcal bloodstream infection in premature infants", J Pediatr; 151:260-265.
Dmitriev et al., 1979, "Somatic antigens of Shigella", Eur J Biochem, 98:309-316.
Doig et al., 1996, "Characterization of a post-translational modification of Campylobacter flagellin: identification of a sero-specific glycosyl moiety", Molecular Microbiology; 19(2):379-387.
Dunphy et al., 1967, "The plurality of long chain isoprenoid alcohols (polyprenols) from natural sources", Biochim Biophys Acta; 136: 136-147.
Expression Library Screening (Procaryotic) Using AP-fusion proteins (last visited Nov. 1, 2010) at www.protocol-online.org/cgi-bin/prt/view_cache.cgi?ID=2752.
Fairweather et al, 1986, "Cloning, nucleotide sequencing, and expression of tetanus toxin fragment C in *Escherichia coli*", Journal of Bacteriology; 165(1):21-27.
Falt et al., 1996, "Construction of recombinant aroA salmonellae stably producing the Shigella Sysenteriae sertype 1 O-antigen and structural characterization of the *Salmonella*/Shigella hybrid LPS", Microb Pathog; 20(1):11-30.
Faridmoayer et al., 2007, "Functional characterization of bacterial oligosaccharyltransferases involved in O-linked protein glycosylation", J Bacteriol; 189(22):8088-8098.
Fass et al., 1991, "Use of high densitycultures of *Escherichia coli* for high level production of recombinant Pseudomonas aeruginosa exotoxin A", Applied Microbiology and Biotechnolgy, 36(1):65-69.
Fattom et al., 1990, "Synthesis and immunologic properties in mice of vaccines composed of *Staphylococcus aureus* type 5 and type 8 capsular polusaccharidcs conjugated to Pseudomonas aeruginosa exotoxin A", Infect Immun; 58:2367-2374.
Fattom et al., 1993, "Laboratory and clinical evaluation of conjugate vaccines composed of *Staphylococcus aureus* type 5 and type 8 capsular polysaccharides bound to Pseudomonas aeruginosa recombinant exoprotein A", Infection and Immunity; 61(3):1023-1032.
Fattom et al., 1996, "A *Staphylococcus aureus* capsular polysaccharide (CP) vaccine and CP-specific antibodies protect mice against bacterial challenge", Infect Immun; 64:1659-1665.
Fattom et al., 1998, "Antigenic determinants of *S. aureus* type 5 and type 8 capsular polysaccharide vaccines", Infect Immun; 66:4588-4592.
Feldman et al., 2005, "Engineering N-liked protein glycosylation with diverse O antigen lipopolysaccharide structures in *Escherichia coli*", Proc Natl Acad Sci USA; 102:3016-3021.
Feng et al., 2005, "Structural and genetic characterization of the Shigella boydii type 18 O antigen", Gene; 355:79-86.
Field et al., 2003, "Structural and mechanistic basis of bacterial sugar nucleotide-modifying enzymes", Biochemistry; 42:7637-7647.
Foster et al., 1998, "Surface protein adhesins of *Staphylococcus aureus*", Trends Microbiol; 6:484-488.
Foster, 2005, "Immune evasion by staphylococci", Nature Reviews Microbiology; 3:948-958.
Francisco et al., 1992, "Transport and anchoring of β-lactamase to the external surface of *Escherichia coli*", Proc Natl Acad Sci USA: 89:2713-2717.
Fridkin et al., 2005, "Methicillin-resistant *Staphylococcus aureus* disease in three communities", N Engl J Med; 352:1436-1411.
Fry et al., 1998, "The lipopolysaccharide biosynthesis locus of Campylobacter jejuni 81116", Microbiology; 144:2049-2061.
Fujita et al., 2000, "Synthesis of neoglycoenzymes with homogenous N-linked oligosaccharides using immobilized endo-S-N-acetylglucosaminidase A", Biochmeical and Biophysical Research Communications, 267:134-138.
Gavel et al., 1990, "Sequence differences between glycosylated and non-glycosylated Asn-X-Thr/Ser acceptor sites: implications for protein engineering", Protein Eng; 3:433-442.
Gilbert et al., 2006, "Outbreak in Alberta of community-acquired (USA300) methicillin-resistant *Staphylococcus aureus* in people with a history of drug use, homelessness or incarceration", Canad Med Assoc J; 175:149-154.
Global Alliance for Vaccines and Immunization—Press releases (Mar. 11, 2006) at www.gavialliance.org/media_centre/press_releases/2006_03_09_en_pr_queenrania_delhi.php.
Glover et al., 2005, "Chemoenzymatic synthesis of glycopeptides with PglB, a bacterial oligosaccharyl transferase from Campylobacter jejuni", Chemistry & Biology; 12:1311-1316.
Glover et al., 2005, "In vitro assembly of the undecaprenylpyrophosphate-linked heptasaccharide for prokaryotic N-linked glycosylation", Proc Natl Acad Sci USA; 102(40):14255-14259.
"GlycoVaxyn AG appoints renowned vaccinologist Dr. Stanley Plotkin to supervisory board", Press Release (Oct. 6, 2009) available at www.glycovaxyn.com/content/news/releases/09%2010%2006.pdf.
"GlycoVaxyn AG completes CHF 11.5 million series A financing to advance novel conjugated vaccine pipeline towards clinic", Press Release (Jul. 16, 2007) available at www.glycovaxyn.com/content/news/releases/06%2010%2019.pdf.
"GlycoVaxyn AG raises CHF 25 million in financing led by Edmond de Rothschild Investment Partners", Press Release (Mar. 5, 2009) available at www.glycovaxyn.com/downloads/GlycoVaxyn%20Financing%20Release%2005-03-09.pdf.
"GlycoVaxyn appoints Philippe Dro as CEO", Press Release (May 20, 2008) available at www.sofinnova.fr/glycovaxyn-appoints-philippe-dro-as-cco-actu-736.php.
"GlycoVaxyn opens to partnerships; series C financing round planned for 2011, CEO says mergermarket", pp. 1-2 (Nov. 25, 2009) at www.mergermarket.com/home/.
"GlycoVaxyn phase I clinical study shows positive data with Shigella dysenteriae vaccine candidate", (Oct. 8, 2010) available at www.glycovaxyn.com/content/news/releases/10%2010%2008.pdf.
"GlycoVaxyn winner of the life sciences prize 2006", Press Release (Oct. 19, 2006) available at www.glycovaxyn.com/content/news/releases/06%2010%2019.pdf.
"GlycoVaxyn's first clinical study with bioconjugate vaccine initiated", Press Release (Feb. 23, 2010) available at www.glycovaxyn.com/content/news/releases/10%2002%2023.pdf.
Goebel et al., 1929, "Chemo-immunological studies on conjugated carbohydrate-proteins" Journal of Experimental Medicine; 50(4):521-531.
Goldberg et al., 1992, "Cloning and surface expression of Pseudomonas aeruginosa O antigen in *Escherichia coli*", Proc Natl Acad Sci USA; 89(22):10716-10720.
Gordon et al., 1956, "Rapid paper chromatography of carbohydrates and related compounds", Anal Chem; 28:849-855.
Grabenhorst et al., 1999, "Genetic engineering of recombinant glycoproteins and the glycosylation pathway in mammalian host cells", Glycoconjugate Journal; 16:81-97.
Gray, 1979, "ELISA methodology for polysaccharide antigens: protein coupling of polysaccharides for adsorption to plastic tubes", J Immunol; 28:187-192.
Guan et al., 2005, "Extraction and identification by mass spectrometry of undecaprenyl diphosphate-MurNAc-pentapeptide-GlcNAc from *Escherichia coli*", Anal Biochem; 345:336-339.
Guerry et al., 1996, "Identification and characterization of genes required for post-translational modification of Campylobacter coli VC167 flagellin", Molecular Microbiology; 19(2):369-378.
Guo et al., 2007, "Three UDP-hexose 4-epimerases with overlapping substrate specificity coexist in *E. coli* O86:B7", Biochem Biophys Res Commun; 356:604-609.

(56) References Cited

OTHER PUBLICATIONS

Haberberger et al., 1994, "Prospects and problems for development of a vaccine against diarrhea caused by Campylobacter", Vaccine Research; 3:15-22.
Helenius et al., 2004, "Roles of N-linked glycans in the endopasmic reticulum", Annu Rev Biochem; 73:1019-1049.
Higgins et al., 2004, "Structure of the periplasmic component of a bacterial drug efflux pump", Proc Natl Acad Sci USA; 101:9994-9999.
Ho et al., 2006, "Preclinical laboratory evaluation of a bivalent Staphylococcus aureus saccharide-exotoxin A protein conjugate vaccine", Hum Vaccin; 2:89-98.
Hoffmeister et al., 2001, "Two sequence elements of glycosyltransferases involved in urdamycin biosynthesis are responsible for substrate specificity and enzymatic activity", Chem & Bio; 8:557-567.
Hofmann et al., 1993, "A database of membrane spanning protein segments", Biol Chem; 374:166 (abstract).
Hoiseth et al., 1981, "Aromatic-dependent Salmonella typhimurium are non-virulent and effective as live vaccines", Nature; 291:238-239.
Ihssen et al., 2010, "Production of glycoprotein vaccines in Escherichia coli", Microbial Cell Factories; 9(1):61.
Imperiali et al., 1991, "Differences between Asn-Xaa-Thr-containing peptides; a comparison of solution conformation and substrate behavior with oligosaccharyl-transferase", Biochemistry; 30:4374-4380.
International Search Report of International application No. PCT/CH03/00153, dated May 19, 2003.
International Search Report of International application No. PCT/EP2006/004397, dated Dec. 13, 2006.
International Search Report of International application No. PCT/EP2011/057111, dated Jul. 28, 2011.
Jeong et al., 2001, "Secretory production of human granulocyte colony-stimulating factor in Escherichia coli", Protein Expression and Purification; 23:211-318.
Johnson et al., 1999, "Alignment and structure prediction of divergent protein families: periplasmic and outer membrane proteins of bacterial efflux pumps", J Mol Biol; 287:695-715.
Johnson et al., 1999, "Synthesis of oligosaccharides by bacterial enzymes", Glycoconjugate Journal; 16:141-146.
Jones et al., 2005, "Revised structures for the capsular polysaccharides from Staphylococcus aureus types 5 and 8, components of novel glycoconjugate vaccines", Carbohydr Res; 340:1097-1106.
Josefsson et al., 2001, "Protection against experimental Staphylococcus aureus arthritis by vaccination with clumping factor A, a novel virulence determinant", Journal of Infectious Diseases; 184:1572-1580.
Jursch et al., 1994, "Histidine residues near the N terminus of staphylococcal alpha-toxin as reporters of regions that are critical for oligomerization and pore formation", Infect Immum; 62(6):2249-2256.
Kaniuk et al., 2004, "Investigation of the structural requirements in the lipopolysaccharide core acceptor for ligation of O antigens in the genus Salmonella: WaaL 'ligase' is not the sole determinant of acceptor specificity", J Biol Chem; 279:36470-36480.
Kapitonov et al., 1999, "Conserved domains of glycosyltransferases", Glycobiol; 9(10):961-978.
Karlyshev et al., 2004, "The Campylobacter jejuni general glycosylation system is important for attachment to human epithelial cells and in the colonization of chicks", Microbiology; 150; 1957-1964.
Kazakova et al., 2005, "A clone of methicillin-resistant Staphylococcus aureus among professional football players", N Engl J Med; 352:468-475.
Kean, 1966, "Separation of gluco- and galactocerebrosides by means of borate thin-layer chromatography", J Lipid Res; 7:449-452.
King et al., 2006, "Emergence of community-acquired methicillin-resistant Staphylococcus aureus USA 300 clone as the predominant cause of skin and soft-tissue infections", Ann Intern Med; 144:309-317.
Kiser et al., 1999, "Staphylococcus aureus cap5P encodes a UDP-N-acetylglucosamine 2-epimerase with functional redundancy", J Bacteriol; 181(16):4818-4824.
Klevens et al., 2007, "Invasive methicillin-resistant Staphylococcus aureus infections in the United States," Jama 298: 1763-71.
Knirel et al., 1988, "Somatic antigens of Shigella: structure of the O-specific polysaccharide chain of the Shigella dysenteriae type 7 lipoplysacharide."
Kollef eta l., 2005, "Epidemiology and outcomes of health-care associated pneumonia: results from a large US database of culture-positive pneumonia." Chest 128:3854-3862.
Konadu et al. 1998, "Investigational vaccine for Escherichia coli O157: phase 1 study of O157 O-specific polysaccharide-pseudomonas aeruginosa recombinant exoprotein A conjugates in adults", Journal of Infectious Diseases; 177(2):383-387.
Konadu et al., 1994, "Preparation, characterization, and immunological properties in mice of Escherichia coli O157 O-specific polysaccharide-protien conjugate vaccines", Infection and Immunity; 62(11):5048-5054.
Konadu et al., 1999, "Syntheses and immunologic properties of Escherichia coli O157 O-specific polysaccharide and shiga Toxin 1 B subunit conjugates in mice," Infection and Immunity; 67(11):6191-6193.
Kowarik et aI., 2006, "N-Linked glycosylation of folded proteins by the bacterial oIigosaccharvltransferase", Science; 314:1148-1150.
Kowarik et al., 2006, "Definition of the bacterial N-glycosylation site consensus sequence", EMBO J; 25(9):1957-1966.
Kuwajima et al., 1986, "Nucleotide sequence of the hag gene encoding flagellin of Escherichia coli", J Bacteriol; 168(3):1479-1483.
Laemmill, 1970, "Cleavage of Structural Proteins during the Assembly of the Head of bacteriophage T4." Nature 227:680-685.
Law, 2000, "Virulence factors of Escherichia coli O157 and other Shiga Toxin-producing E-coli." J. App. Microbiol. 88:729-745.
Lee et al., 1997, "Protective efficacy of antibodies to the Staphylococcus aureus type 5 capsular polysaccharide in a modified model of endocarditis in rats." Infect Immun. 65:4146-51.
Lee et al., 1999, "Evaluation of a truncated recombinant flagellin subunit vaccine against Campy/obaeter jejuni", Infection and Immunity; 67(11):5799-5805.
Lefebre, 2002, "Construction and Evaluation of Plasmind vectors Optimized for Consitutive and Regulated Gene Expression in Burkholderia cepacia Complex Isolates," Appl. Environ Microbiol. 68:5956-5964.
Linton et al., 2002, "Identification of N-acetylgalactosamine-containing glycoproteins PEB3 and CgpA in Campylobacter jejuni", Molecular Microbiology; 43(2):497-508.
Linton et al., 2005, "Functional analysis of the Campylobacter jejuni N-linked protein glycoylation pathway", Molecular Microbiology; 55(6):1695-1703.
Liu et al., 2008, "Structure and genetics of Shigella O antigens." FEMS Microbiol. 32:627-653.
Lodish et al., 2000 "DNA Cloning with Plasmid vectors." Molec. Cell. Biology; 7.1 at www/ncbi.nlm.nih.gov/bookshelf/br.fcgi?book=mcb&part=A1582.
Lodish et al., 2000 "Protein Glycosylation in the ER and Golgi Complex"; 17.7 at www/ncbi.nlm.nih.gov/bookshelf/br.fcgi?book=mcb&part=A4816.
Lowy, 1998, "Staphylococcus aureus infections." New Eng. J Med. 339:520-32.
Lukac et al., 1988, "Toxoid of pseudomonas aeruginosa exotoxin A generated by deletion of an active-site residue", Infection and Immunity; 56(12):3095-3098.
Malissard et al., 1999, "The yeast expression system for recombinant glycosyltransferases", Glycoconjugate Journal; 16:125-139.
Maras et al., 1999, "Filamentous fungi as production organisms for glycoproteins of bio-medical interest", Glycoconjugate Journal; 16:99-107.

(56) References Cited

OTHER PUBLICATIONS

Marolda et al., 2006, "Interplay of the wzx translocase and the corresponding polymerase and chain length regulator proteins in the translocation and periplasmic assembly of lipopolysaccharide O antigen", Journal of Bacteriology; 188(14):5124-5135.
Marth et al., 1999, "Essentials of Glycobiology" Chapter 7 (Varki et al. eds.) available at www/ncbi.nlm.nih.gov/bookshelf/br.fcgi?book=glyco&part=A465.
McDevitt eta l., 1995, "Indentification of the ligand-binding domain of the surface-located fibrinogen receptor (clumping factor) of *Staphylococcus aureus*." Molecular Microbiology 16:895-907.
McDougal et al., 2003, "Pulsed-field gel electrophoresis typing of oxacillin-resistant *Staphylococcus aureus* isolates from the United States; establishing a national database." J. Clin. Microbiol. 41:5113-20.
Meier-Dieter, 1990, "Biosyntehsis of enterobacterial common antigen in *Escherichia coli*." J. Biol. Chem.; 265:13490-13497.
Menzies et al., 1996, "Passive immunization with antiserum to a nontoxic alpha-toxin mutant from *Staphylococcus aureus* is protective in a murine model." Infect Immun. 64:1839-41.
Merry et al., 2002, "Recovery of intact 2-aminobenzamide-labeled O-glycans released from glycoproteins by Hhydrazinolysis." Anal Biochem; 304(1):91-99.
Messner, 1997, "Bacterial glycoproteins," Glycoconjugate Journal 14:3-11.
Middlebrook et al., 1984, "Bacterial toxins: cellular mechanisms of action", Microbiological Reviews; 48(3): 199-221.
Mikusova et al., 2005, "Decaprenylphosphoryl Arabinofuranose, the Donor of the D-Arabinofuranosyl Residues of Mycobacterial Arabinan, is formed via a Two-Step Epimerization of Decaprenylphosphoryl Ribose." J. Bacteriol. 187:8020-8025.
Moreillon et al., 1995, "Role of *Staphylococcus aureus* coagulase and clumping factor in pathogenesis of experimental endocarditis." Infection & Immunity; 63:4738-43.
Muller et al., 2005, "An ATP-binding cassette-type cysteine transporter in Campylobacter jejuni inferred from the structure of an extracytoplasmic solute receptor protein", Mol Microbial; 57:143-155.
Nairn et al., 1990, "Solutions, emulsions, suspensions and extracts", Remington's Pharmaceutical Sciences, 18th ed., Mack Publishing Co., Chapter 83, pp. 1519-1544.
Nanra et al, 2009, "Heterogenous in vivo expression of clumping factor A and capsular polysacchardie *Staphylococcus aureus*: Implications for vaccine design." Vaccine; 27:3276-80.
Nilsson et al.m, 1997, "The role of Staphylococcal polysaccharide microcapsule expression in septicemia and septic arthritis." Infect Immun 65:4216-4221.
Nita-Lazar et al., 2005, "The N-X-S/T consensus sequence is required but not sufficient for bacterial N-linked protein glycosylation", Glycobiology; 15(4):361-367.
O'Riordan et al., 2004, "*Staphylococcus aureus* capsular polysaccharides." Clin Microbiol Rev. 17(1):218-34.
Paetzel et al., 2002, "Signal peptidases", Chem Rev; 102:4549-4580.
Panina-Bordignon et al., 1989, "Universally immunogenic T cell epitopes: promiscuous binding to human MHC class II and promiscuous recognition by T cells" European Journal of Immunolgy; 19:2237-2242.
Parkhill et al., 2000, "The genome sequence of the food-borne pathogen Campylobacter jejuni reveals hypervariable sequences", Nature; 403:665-668.
Passwell et al., 2001, "Safety and immunogenicity of improved Shegella O-specific polysaccharide-protein conjugate vaccines in adults in Israel", Infection and Immunity, 69(3):1351-1357.
Paton & Paton, 1999, "Molecular Characterization of the Locus Encoding Biosynthesis of the Lipopolysaccharide O Antigen of *Escherichia coli* Serotype O113," Infect & Immun. 67(11): 5930-5937.
Pawlowski, 2000, "Preparation of pneumococcal capsular polysaccharide-protein conjugate vaccines utilizing new fragmentation and conjugation technologies." Vaccine 18:1873-1885.
Pearson et al., 2003, "Comparative genome analysis of Campylobacter jejuni using whole genome DNA microarrays", FEBS Letter; 554: 224-230, FEBS 27782.
Perry, 1986, "Structure of the O-chain polysaccharide of the phenol-phase soluble lipopolysaccharide of *Escherichia coli* 0:157:h7." Biochem. Cell Biol.; 64:21-28.
Petrescu et al., 2004, "Statistical analysis of the protein environment of N-glycosylation sites: implications for occupancy, structure, and folding", Glycobiology; 14(2):103-114.
Pozscay et al., 1999, "Protein conjugates of synthetic saccharides elicit higher levels of serum IgG lipopolysaccharide antibodies in mice than do those of the O-specific polysaccharide from Shigella dysenteriae type 1", Proc Natl Acad Sci USA; 96:5194-5197.
Pozsgay, 1998, "Synthesis of glycoconjugate vaccines again Shigella dysenteriae type 1", Journal of Organic Chemistry; 63:5983-5999.
Qian et al., 2007, "Conjugating recombinant proteins to Psudomonas aeruglnosa Exoprotein A: A strategy for enhancing immunogenicity to malaria vaccine candidates." Vaccine 25:3923-3933.
Raetz et al., 2002, "Lipopolysaccharide endotoxins", NIH-PA author manuscript, pp. 1-57, 19-25 (published in final edited form as: Annual Rev Biochem; 71:635-700, 2002.
Reeves et al., 1996, "Bacterial polysaccharide synthesis and gene nomenclature", Reviews, Elseview Science Ltd., pp. 495-503.
Robbins et al, 2009, "Synthesis, characterization, and immunogenicity in mice on Shigella sonnei O-specific oligosacchardie-core-protein conjugates." Proc. Natl. Acad Sci USA 106:7974-7978.
Royle et al., 2002, "An analytical and structural database provides a strategy for sequencing O-glycans from microgram quantities of glycoproteins." Anal Biochem; 304(1): 70-90.
Rubires, 1997, "A gene (wbbL) from Serratia marcesens N28b (O4) complements the rfb-50 mutation of *Escherichia coli* K-12 derivatives" J Bacteriol 179(23):7581-7586.
Rudd et al., 1997, "Glycosylation: heterogeneity and the 3D structure of proteins", Crit Rev Biochem Mol Biol; 32:1-100.
Rush, 1997, "Polyisoprenyl phosphate specificity of UDP-GlcNAc: undecaprenyl phosphate N-acetylgluosaminyl 1-P transferase from *E. coli*" Glycobiology; 7:315-322.
Rush et al., 2010, "A novel epimerase that converts GlcNAc-P-P-undecaprenol to GalNAc-P-P-undecaprenol in *Escherichia coli* O157", Journal of Biological Chemistry, 285(3):1671-1680.
Sambrook & Russell, "2006, Screening Bacterial Colonies by Hybridization: Small Numbers." Cold Spring Harb. Protoc; doi:10.1101/pdb.prot3925 at http://cshprotocols.cshlp.org/cgi/content/full/2006/2/pdb.prot3925.
Samuel, 2003, "Biosynthesis of O-antigens: genes and pathways involved in nucleotide sugar precursor synthesis and O-antigen assembly." Carbohydrate Res. 338: 2503-2519.
Sau et al., 1997, "The *Staphylococcus aureus* allelic genetic loci for serotype 5 and 8 capsule expression contain the type-specific genes flanked by common genes." Microbiology 143: 2395-405.
Schaad et al., 1991, "Safety and immunogenicity of Pseudomonas aeruginosa conjugate A vaccine in cystic fibrosis", The Lancet; 338:1236-1237.
Schaffer et al, 2008, "Vaccination and passive immunisation against *Staphylococcus aureus*" Ing J Antimicrob Agents 32 Suppl. 1:S71-78.
Schneerson et al., 1991, "Preparation, characterization, and immunogenicity of Haemophilus influenzae type B polysaccharide-proteins conjugates", Journal of Experimental Medicine; 152:361-376.
Schultz et al., 1998, "Prototype of a heme chaperone essential for cytochrome c maturation", Science; 281:1197-1200.
Schwimmer et al., 1956, "Reagent for Differentiation on 1,4- and 1,6-Linked Glucosaccharides." Science; 123:543-544.
Scott, 1997, "Vaccines against Campylobacter jejuni", Journal of Infectious Diseases; 176(Suppl. 2):S183-S188.

(56) References Cited

OTHER PUBLICATIONS

Seffernick et al., 2001, "Melamine deaminase and atrazine chlorohydrolase: 98 percent identical but functionally different", J Bacteriol; 183(8):2405-2410.
Shorr, 2007, "Epidemiology and economic impact of meticillin-resistant Staphylococcus aureus: review and analysis of the literature." Phamacoeconomis 25: 751-68.
Simons et al., 1984, "High-level expression of human interferon gamma in Escherichia coli under control of the $p_L$ promoter of bacteriophage lambda", Gene; 28:55-64.
Spears et al., 2006, "A comparison of enterphathogenic Escherichia coli pathogenesis," FEMS Microbiol. Lett 255:187-202.
Spirig et al., 1997, "The STT3 protein is a component of the yast oligosaccharyltransferase complex." Mol. Gen Genet 356:628-637.
Stenutz, 2006, "The structures of Escherichia coli O-polysaccharide antigens." FEMS Microbiol. Rev. 30:382-403.
Stephan et al., 2004, "First isolation and further characterization of enteropathogenic Escherichia coli (EPC) O 157:H45 strains from cattle" BMC Microbiol. 4:10.
Stevenson, 1994, "Structure of the O Antigen of Escherichia coli K-12 and the Sequence of rib Gene Cluster." J Bacteriol.; 176:4144-4156.
Sullam, 1996, "Diminished platelet binding in vitro by Staphylococcus areus is associated reduced virulence in a rabbit model of infective endocarditis." Infection & Immun. 66:5183-5189.
Szu et al., 1994, "Laboratory and preliminary clinical characterization of Vi capsular polysaccharide-protein conjugate vaccines", Infection and Immunity; 62(10):4440-4444.
Szymanski et al., 1999, "Evidence for a system of general protein glycosylation in Campylobacter jejuni", Molecular Microbiology; 32(5):1022-1030.
Szymanski et al., 2002, "Campylobacter protein glycosyation affects host cell interactions", Infection and Immunity; 70(4):2242-2244.
Szymanski et al., 2005, "Protein glycosylation in bacterial mucosal pathogens", Nature Reviews, Microbiology; 3:225-237.
Taylor et al., 1993, "Synthesis, characterization and clinical evaluation of conjugate vaccines composed of the O-specific polysaccharides of Shigella dysenteriae type 1, Shigella flexneri type 2a, and Shigella sonnei (Plesiomonas shigelloides) bound to bacterial toxoids", Infection and Immunity; 61(9):3678-3687.
Thakker et al., 1998, "Staphylococcus aureus serotype 5 capsular polysaccharide is antiphagocytic and enhances bacterial virulence in a murine bactermia model." Infect Immun. 66:5183-5189.
Thibault et al., 2001, "Identification of the carbohydrate moieties and glycosylation motifs in Campylobactor jejuni flagellin", J Biol Chem; 276(37):34862-34870.
Tsai et al., 1982, "A sensitive silver stain for detecting lipopolysaccharides in polyacrylamide gels." Anal Biochem. 119:115-119.
Tuchscherr, 2008, "Antibodies to capsular polysaccharide and clumping factor A prevent mastitis and the emergence of uncapsulated and small-colony variants of Staphylococcus aureus in mice." Infect Immun 76:5738-44.
Unligil et al., 2000, "Glycosyltransferase structre and mechanism." Curr. Op. Struck Bio. 10:510-517.
Valvano, 2003, "Export of O-specific lipopolysaccharide", Front Biosci; 8:s452-471.
Vanbleu et al., 2004, "Genetic and physical map of the pLAFR1 vector DNA seq." 15(3): 225-227.
Vandaux et al, 1995, "Use of adhesion-defective mutants of Staphylococcus aureus to define the role of specific plasma proteins in promoting bacterial adhesion to canine arteriovenous shuts." Infect & Immunity 63:585-90.

Varki et al., 1999, "Essentials of Glycobiology", Cold Spring Harbor Laboratory Press; Cold Spring Harbor, New York pp. 85-100.
Vernachio et al., 2003, "Anti-clumping factor A immunoglobulin reduces the duration of methicillin-resistant Staphylococcus aureus bacteremia in an experimental model of infective endocarditis," Antimicrobial Agents & Chemotherapy, 47:3400-3406.
Wacheter et al., 1976, "Lipid Intermediates involved in the Assembly of Membrane-Associated Glycoproteins in Calf Brain White Matter." Arch Biochem Biophys.; 174:726-737.
Wacker et al., 2001, "PgIB, an oligosaccharyltransferase in the eubacterium Campylobacter jejuni?", Glycobiology; 11:871.
Wacker et al., 2002, "N-linked glycosylation in Campylobacter jejuni and its functional transfer into E. coli", Science; 298:1790-1793.
Wacker et al., 2006, "Substrate specificity of bacterial oligosaccharyltransferase suggests a common transfer mechanism for the bacterial and eukaryotic systems", Proc Natl Acad Sci; 103:7088-7093.
Waechter et al., 1977, "Evidence for the Enzymatic Transfer of N-Acetylglucosamine form UDP-N-Acetylglucosamine into Dolichol Derivates and glycoproteins by Calf Brain Membrane." Arch. Biochem. Biophys. 181:185-198.
Wang et al., 2002, "The O-Antigen gene Cluster of Escherichia coli O55:H7 and Identification of a New UDP-GlcNAc C4 Epimerase Gene." J Bacteriol 184:2620-2625.
Wang et al.,1998, "Organization of Escherichia coli 0157 O Antigen Gene cluster and Identification of its specific genes." Infect. Immune 66:3545-3551.
Watts et al. 2005, "Staphylococcus aureus strains that express serotype 5 of srotype 8 capsular polysaccharides differ in virulence," Infect Immun. 73:3502-11.
Wernerus et al., 2004, "Biotechnological applications for surface-engineered bacteria", Biotechnol Appl Biochem; 40:209-228.
Whisstock et al., 2003, "Prediction of protein function from protein sequence and structure", Q Rev Biophys; 36(3):307-340.
Whitfield et al., 1999, "Structure, assembly and regulation of express of capsules in Escherichia coli", Molecular Microbiology; 31(5):1307-1319.
Whitfield et al., 2006, "Biosynthesis and Assembly of Capsular Polysaccharides in Escherichia coli." Annu Rev. Biochem. 75:39-68.
Witkowski et al., 1999, "Conversion of a beta-ketoacyl synthase to a malonyl decarboxylase by replacement of the active-site cysteine with glutamine", Biochemistry; 38(36):11643-11650.
Wolfe et al., 1993, "Reactions adding Sugar Units to Proteins in the ER and Golgi Complex, Molecular and Cellular Biology." Wadsworth Publishing Co., CA 873-75.
Wyszynska et al., 2004, "Oral immunization of chickens with avirlent Salmonella vaccine strain carrying C. jejuni 72Dz/92 cjaA gene elicits specific humoral immune response associated with protection against challenge with wild-type Campylobacter", Vaccine; 22:1379-1389.
Yao et al., 1994, "Isolation of motile and non-motile insertional mutants of Campylobacter jejuni: the role of motility in adherance and invasion of eukaryotic cells", Molecular Microbiology; 14(5):883-893.
Young et al., 2002,"Structure of the N-linked glycan present on multiple glycoproteins in the gramnegative bacterium, Campylobacter jejuni", J Biol Chem; 277(45):42530-42539.
Zhang et al., 1997, "Molecular and chemical characterization of the lipopolysaccharide O-antigen and its role in the virulence of Yersinia enterocolitica serotype O:8." Mol. Microbiol. 23:63-76.
Zufferey et al., 1995, "STT3, a highly conserved protein required for yeast oligosaccharyl transferase activity in vivo." The EMBO Journal 14(20):4949-4960.

* cited by examiner

BIOSYNTHETIC SYSTEM THAT PRODUCES IMMUNOGENIC POLYSACCHARIDES IN PROKARYOTIC CELLS

CROSS-REFERENCE TO RELATED APPLICATION

This application claims the benefit under 35 U.S.C. §119 (e) of U.S. Provisional Patent Application No. 61/272,931, filed Nov. 19, 2009, herein incorporated by reference in its entirety.

FIELD OF THE INVENTION

The present invention relates to the use of a biosynthetic system and proteins for preparing a vaccine. In addition, the invention relates to a recombinant prokaryotic biosynthetic system having an epimerase that initiates the synthesis of an oligo- or polysaccharide with a specified monosaccharide at the reducing terminus. The invention further relates to N-glycosylated proteins produced with glycans in an expression system and bioconjugate vaccines made from said N-glycosylated proteins comprising immunogenic glycans, and provides methods for producing N-glycosylated proteins.

BACKGROUND OF THE INVENTION

Glycoproteins are proteins that have one or more covalently attached sugar polymers. N-linked protein glycosylation is an essential and conserved process occurring in the endoplasmic reticulum of eukaryotic organisms. It is important for protein folding, oligomerization, stability, quality control, sorting and transport of secretory and membrane proteins (Helenius. A., and Aebi, M. (2004). Roles of N-linked glycans in the endoplasmic reticulum. Annu. Rev. Biochem. 73, 1019-1049).

Protein glycosylation has a profound influence on the immunogenicity, the stability and the half-life of a protein. In addition, glycosylation can assist the purification of proteins by chromatography, e.g. affinity chromatography with lectin ligands bound to a solid phase interacting with glycosylated moieties of the protein. It is therefore established practice to produce many glycosylated proteins recombinantly in eukaryotic cells to provide biologically and pharmaceutically useful glycosylation patterns.

WO 200307467 (Aebi et al.) demonstrated that the food-borne pathogen *Campylobacter jejuni*, which is a bacterium, could N-glycosylate its proteins, which was a unique feature among known prokaryotic organisms except for certain species of archaea. The machinery required for glycosylation is encoded by 12 genes that are clustered in the so-called pgl locus. Disruption of N-glycosylation affects invasion and pathogenesis of *C. jejuni* but is not lethal as in most eukaryotic organisms (Burda P. and M. Aebi, (1999). The dolichol pathway of N-linked glycosylation. Biochem Biophys Acta 1426(2):239-57). It is possible to reconstitute the N-glycosylation of *C. jejuni* proteins by recombinantly expressing the pgl locus and acceptor glycoprotein in *E. coli* the same time (Wacker et al. (2002). N-linked glycosylation in *Campylobacter jejuni* and its functional transfer into *E. coli*. Science 298, 1790-1793).

N-glycans have a glycan attached to a consensus sequence in a protein. The known N-glycosylation consensus sequence in a protein allows for the N-glycosylation of recombinant target proteins in prokaryotic organisms. Such organisms comprise an oligosaccharyl transferase ("OT"; "OTase"), such as, for example, an oligosaccharyl transferase of *C. jejuni*, which is an enzyme that transfers the glycan to the consensus sequence of the protein.

WO 200307467 (Aebi et al.) teaches a prokaryotic organism into which is introduced a nucleic acid encoding for (i) specific glycosyltransferases for the assembly of an oligosaccharide on a lipid carrier, (ii) a recombinant target protein comprising a consensus sequence "N-X-S/T", wherein X can be any amino acid except proline, and (iii) an oligosaccharyl transferase, such as, for example, an oligosaccharyl transferase of *C. jejuni* that covalently links said oligosaccharide to the consensus sequence of the target protein. Said prokaryotic Organism produces N-glycans with a specific structure which is defined by the type of the specific glycosyltransferases.

WO 2006/119987 (Aebi et al.) describes proteins, as well as means and methods for producing proteins, with efficiency for N-glycosylation in prokaryotic organisms in vivo. It further describes an efficient introduction of N-glycans into recombinant proteins for modifying immunogenicity, stability, biological, prophylactic and/or therapeutic activity of said proteins, and the provision of a host cell that efficiently displays recombinant N-glycosylated proteins of the present invention on its surface. In addition, it describes a recombinant N-glycosylated protein comprising one or more of the following N-glycosylated optimized amino acid sequence(s):

D/E-X-N-Z-S/T (optimized consensus sequence),
wherein X and Z may be any natural amino acid except Pro, and wherein at least one of said N-glycosylated partial amino acid sequence(s) is introduced. The introduction of specific partial amino acid sequence(s) (optimized consensus sequence(s)) into proteins leads to proteins that are efficiently N-glycosylated by an oligosaccharyl transferase in these introduced positions.

The biosynthesis of different polysaccharides is conserved in bacterial cells. The polysaccharides are assembled on carrier lipids from common precursors (activated sugar nucleotides) at the cytoplasmic membrane by different glycosyltransferases with defined specificity. Lipopolysaccharides ("LPS") are provided in gram-negative bacteria only, e.g. *Shigella* spp., *Pseudomonas* spp. and *E. coli* (ExPEC, EHEC).

The synthesis of LPS starts with the addition of a monosaccharide to the carrier lipid undecaprenyl phosphate ("Und-P-P") at the cytoplasmic side of the membrane. The antigen is built up by sequential addition of monosaccharides from activated sugar nucleotides by different glycosyltransferases, and the lipid-linked polysaccharide is flipped through the membrane by a flippase. The antigen-repeating unit is polymerized by an enzymatic reaction. The polysaccharide is then transferred to the Lipid A by the Ligase WaaL forming the LPS that is exported to the surface, whereas the capsular polysaccharide is released from the carrier lipid after polymerization and exported to the surface. The biosynthetic pathway of these polysaccharides enables the production of LPS bioconjugates in vivo, capturing the polysaccharides in the periplasm to a protein carrier.

Such synthesized complexes of oligo- or polysaccharides (i.e., sugar residues) and proteins (i.e., protein carriers) can be used as conjugate vaccines to protect against a number of bacterial infections. Conjugate vaccines have been successfully used to protect against bacterial infections. The conjugation of an antigenic polysaccharide to a protein carrier is required for protective memory response, as polysaccharides are T-cell independent immunogens. Polysaccharides have been conjugated to protein carriers by different chemical methods, using activation reactive groups in the polysaccharide as well as the protein carrier.

Conjugate vaccines can be administered to children to protect against bacterial infections and also can provide a long lasting immune response to adults. Constructs of WO 2009/04074 (Fernandez, et al.) have been found to generate an IgG response in animals. It has been found that an IgG response to a *Shigella* O-specific polysaccharide-protein conjugate vaccine in humans correlates with immune protection in humans. (Passwell, J. H. et al., "Safety and Immunogenicity of Improved *Shigella* O-Specific Polysaccharide-Protein Conjugate Vaccines in Adults in Israel" Infection and Immunity, 69(3):1351-1357 (March 2001).) It is believed that the polysaccharide (i.e. sugar residues) triggers a short-term immune response that is sugar-specific. Indeed, the human immune system generates a strong response to specific polysaccharide surface structures of bacteria, such as O-antigens and capsular polysaccharides. However, since the immune response to polysaccharides is IgM dependent, the immune system develops no memory. The protein carrier that carries the polysaccharide triggers an IgG response that is T-cell dependent and that provides long lasting protection since the immune system develops memory.

*E. coli* O157 is an enterohemorrhagic strain responsible for approximately two-thirds of all recent cases of hemolytic-uremic syndrome and poses serious human health concerns (Law, D. (2000) *J. App. Microbiol.*, 88, 729-745; Wang, L., and Reeves, P. R. (1998) *Infect. Immun.* 66, 3545-3551).

*Escherichia coli* strain O157 produces an O-antigen containing the repeating tetrasaccharide unit (4-N-acetyl perosamine→fucose→glucose→GalNAc) (α-D-PerNAc-α-L-Fuc-β-D-Glc-α-D-GalNAc) (Perry, M. B., MacLean, L. and Griffith, D. W. (1986) *Biochem. Cell. Biol.*, 64, 21-28). The tetrasaccharide is preassembled on undecaprenyl pyrophosphate. The *E. coli* cell envelope contains an inner plasma membrane, a stress-hearing peptidoglycan layer and an asymmetric outer membrane consisting of a phospholipid inner monolayer and an outer monolayer composed of bacterial LPS. LPS contains three components, the lipid A anchor, the 3-deoxy-D-manno-oct-2-ulosonic acid-containing core, and the O-antigen region (see: Raetz, C. R. H. and Whitfield, C. (2002) *Annu. Rev. Biochem.*, 71, 635-700; Whitfield, C. (2006) *Ann. Rev. Biochem.* 75, 39-68; Samuel, G. and Reeves, P. R. (2003) *Carbohydrate Research*, 338, 2503-2519; and refs, therein for reviews on the assembly of O-antigens of bacterial LPS).

The O-antigen components of bacterial LPS are large, extremely diverse polysaccharides that can be either homopolymeric, composed of a single repeating monosaccharide, or heteropolymeric, containing 10-30 repeats of 3-6 sugar units (Reeves, P. R., Hobbs, M., Valvano, M. A., Skurnik, M., Whitfield, C., Coplin, D., Kido, N., Klena, J., Maskell, D., Raetz, C. R. H., and Rick, P. D. (1996) *Trends Microbial.*, 4, 495-503). O-Antigens are, Thus, the Dominant Feature of the bacterial cell surface and constitute important determinants of virulence and pathogenicity (Law, D. (2000) *J. App. Microbiol.*, 88, 729-745; Spears, K. J., Roe, A. J. and Golly, D. L. (2006) *FEMS Microbiol. Lett.*, 255, 187-202; Liu, B., Knirel, Y. A., Feng, L., Perepelov, A. V., Senchenkova, S. N., Wang, Q., Reeves, P. R. and Wang, L (2008) *FEMS Microbiol. Rev.* 32, 627-653; Stenutz, R., Weintraub, A. and Widmalm, G. (2006) *FEMS Microbiol. Rev.* 30, 382-403). *E. coli* strains with more than 180 individual O-serotypes, attributed to unique O-antigen structures, have been identified (Stenutz, R., Weintraub, A. and Widmalm, G. (2006) *FEMS Microbiol. Rev.* 30, 382-403).

O-antigen repeat units are pre-assembled on the cytosolic face of the inner membrane attached to undecaprenyl pyrophosphate. The lipid-linked repeat units diffuse transversely (flip-flop) to the periplasmic surface of the inner membrane and are polymerized before transport to the outer membrane and ligation to LPS. Most heteropolymeric O-antigen repeat units have either N-acetylglucosamine ("GlcNAc") or N-acetylgalactosamine ("GalNAc") at the reducing terminus.

It had been assumed that the biosynthesis of the lipid intermediates is initiated by the transfer of GlcNAc-9 or GalNAc-P from their respective sugar nucleotide derivatives to undecaprenyl monophosphate ("Und-P") catalyzed by WecA (Samuel, G. and Reeves, P. R. (2003) *Carbohydrate Research*, 338, 2503-2519; Alexander, D. C. and Valvano, M. A. (1994) *J. Bacteriol.*, 176, 7079-7084; Zhang, L., Radziejewska-Lebrecht, J., Krajewska-Pietrasik, D., Tolvanen, P. and Skurkik. M. (1997) *Mol. Microbiol.* 23, 63-76; Amor, P. A. and Whitfield, C. (1997) *Mol. Microbiol.* 26 (145-161); Wang, L. and Reeves, P. R. (1998) *Infect. Immun.* 66, 3545-3551). Although the properties and specificity of the GlcNAc-phosphotransferase activity of WecA have been characterized (Rush, J. S., Rick, P. D. and Waechter, C. J. (1997) Glycobiology, 7, 315-322), the conclusion that WecA catalyzes the synthesis of GalNAc-P-P-Und was based on genetic studies (Wang, L. and Reeves, P. R. (1998) *Infect. Immun.* 66, 3545-3551). Such earlier genetic studies indicated that the biosynthesis of the lipid-linked tetrasaccharide intermediate was initiated by the enzymatic transfer of GalNAc-P from UDP-GalNAc to Und-P catalyzed by WecA (Wang, L. and Reeves, P. R. (1998) *Infect. Immun.* 66, 3545-3551). However, there was no direct enzymological evidence demonstrating that WecA utilizes UDP-GalNAc as a GalNAc-P donor.

Furthermore, the *E. coli* O55 gne and gne1 genes were previously proposed to encode a UDP-GlcNAc 4-epimerase (Wang, L., Huskic, S., Cisterne, A., Rothemund, D. and Reeves, P. R. (2002) *J. Bacteriol.* 184, 2620-2625; Guo, H., Yi, W., Li, L. and Wang, P. G. (2007) *Biochem. Biophys. Res. Commun.*, 356, 604-609). Previous reports identified two genes from *E. coli* O55 (Wang, L., Huskic, S., Cisterne, A., Rothemund, D. and Reeves, P. R. (2002) *J. Bacteriol.* 184, 2620-2625) and *E. coli* O86 (Guo, H., Yi, W., Li, L. and Wang, P. G. (2007) *Biochem. Biophys. Res. Commun.*, 356, 604-609), *E. coli* O55 gne and *E. coli* O86 gne1, respectively, that are 100% identical to a Z3206 gene within the same gene family.

Accordingly, one of skill would have been led to believe that the Z3206 gene also encodes a UDP-GlcNAc/UDP-GalNAc epimerase.

BRIEF SUMMARY OF THE INVENTION

It has now been surprisingly discovered that an epimerase encoded by the 3206 gene in *E. coli* O157 catalyzes a reaction that synthesizes N-acetylgalactosamine ("GalNAc") undecaprenyl pyrophosphate, which initiates the formation of an oligo- or polysaccharide.

In one aspect, the present invention relates to a recombinant prokaryotic biosynthetic system that produces all or a portion of a polysaccharide comprising an epimerase that synthesizes GalNAc on undecaprenyl pyrophosphate. The invention further includes glycosyltransferases that synthesize all or a portion of a polysaccharide having GalNAc at the reducing terminus, and still further includes glycosyltransferases that synthesize all or a portion of an antigenic polysaccharide having GalNAc at the reducing terminus.

In another aspect, the invention is directed to an epimerase to produce GalNAc on undecaprenyl pyrophosphate, and, in a further aspect, the epimerase is encoded by the Z3206 gene.

In an additional aspect, the present invention is directed to an expression system for producing an N-glycosylated protein comprising: a nucleotide sequence encoding an oligosaccharyl transferase; a nucleotide sequence encoding a protein carrier; at least one oligo- or polysaccharide gene cluster from at least one bacterium, wherein the polysaccharide contains GalNAc at the reducing terminus; and a nucleic acid sequence encoding an epimerase.

In a still further aspect, the instant invention is directed to a recombinant prokaryotic biosynthetic system comprising Z3206 gene which encodes an epimerase that converts GlcNAc-P-P-Und to GalNAc-P-P-Und.

In yet an additional aspect, the present invention is directed to a recombinant prokaryotic biosynthetic system comprising E. coli O55 gne gene or E. coli O86 gne1 gene which encodes an epimerase that converts GlcNAc-P-P-Und to GalNAc-P-P-Und.

In yet another aspect, the present invention relates to an N-glycosylated protein comprising at least one introduced consensus sequence, D/E-X-N-Z-S/T, wherein X and Z can be any natural amino acid except proline, and a glycan having N-acetylgalactosamine at the reducing terminus.

In still another aspect, the present invention is directed to a bioconjugate vaccine comprising an N-glycosylated protein having at least one introduced consensus sequence, D/E-X-N-Z-S/T, wherein X and Z can be any natural amino acid except proline: an immunogenic glycan having N-acetylgalactosamine at the reducing terminus; and an adjuvant.

In an addition aspect, the invention relates to method for producing an N-linked glycosylated protein in a host cell comprising nucleic acids encoding: glycosyltransferases that assemble at least one oligo- or polysaccharide from at least one bacterium containing GalNAc at the reducing terminus; a protein carrier; an oligosaccharyl transferase; and an epimerase.

In a further aspect, the present invention relates to the use of a biosynthetic system and proteins for preparing a bioconjugate vaccine.

In an additional aspect, the present invention is directed to methods for producing mono-, oligo- and polysaccharides, and in a still further aspect the invention directed to methods for producing antigenic glycans and N-glycosylated proteins.

BRIEF DESCRIPTION OF THE DRAWINGS

FIG. 3A, preparative thin layer chromatogram of [$^3$H]HexNAc lipids on borate-impregnated silica gel G (Quantum 1) after purification on DEAE-cellulose is shown. FIG. 3B, thin layer chromatography of purified [$^3$H]GalNAc-P-P-Und on borate-impregnated silica gel G (Baker, Si250) after recovery from the preparative plate in panel A is shown. FIG. 3C. descending paper chromatogram (borate-impregnated Whatman No. 1 paper) of the [$^3$H]-amino sugar recovered after mild acid hydrolysis of [$^3$H]GalNAc-P-P-Und purified in FIG. 3B is shown. FIG. 3D, descending paper chromatogram (Whatman No. 3MM) of the [$^3$H]HexNAc-alditol produced by reduction of the [$^3$H] amino sugar from FIG. 3C with NaBH$_4$.

DETAILED DESCRIPTION OF THE INVENTION

Figure 1:
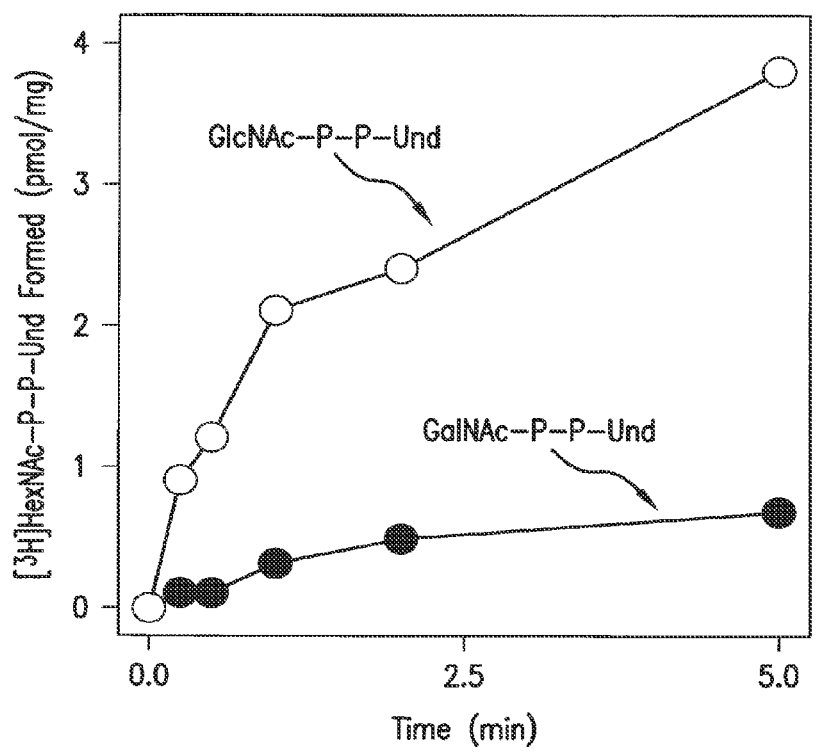
FIG. 1 shows the time course of [$^3$H]GlcNAc/GalNAc-P-P-Und synthesis by membrane fractions from E. coli O157. The membrane fraction from E. coli strain O157 was incubated with UDP-[$^3$H]GlcNAc for the indicated times at 37° C. The [$^3$H]lipid products were extracted and the incorporation of [$^3$H]GlcNAc into [$^3$H]GlcNAc-P-P-Und (O) and [$^3$H]GalNAc-P-P-Und (•) was assayed as described in Example 2.

The present invention encompasses a recombinant prokaryotic biosynthetic system comprising nucleic acids encoding an epimerase that synthesizes an oligo- or polysaccharide having N-acetylgalactosamine at the reducing terminus, and N-glycosylated proteins having N-acetylgalactosamine at the reducing terminus of the glycan.

The term "partial amino acid sequence(s)" is also referred to as "optimized consensus sequence(s)" or "consensus sequence(s)." The optimized consensus sequence is N-glycosylated by an oligosaccharyl transferase ("OST," "OTase"), much more efficiently than the regular consensus sequence "N-X-ST."

In general, the term "recombinant N-glycosylated protein" refers to any poly- or oligopeptide produced in a host cell that does not naturally comprise the nucleic acid encoding said protein. In the context of the present invention, this term refers to a protein produced recombinantly in a prokaryotic host cell, for example, *Escherichia* spp., *Campylobacter* spp., *Salmonella* spp., *Shigella* spp., *Helicobacter* spp., *Pseudomonas* spp., *Bacillus* spp., and in further embodiments *Escherichia* cell, *Campylobacter jejuni*, *Salmonella typhimurium* etc., wherein the nucleic acid encoding said protein has been introduced into said host cell and wherein the encoded protein is N-glycosylated by the OTase, said transferase enzyme naturally occurring in or being introduced recombinantly into said host cell.

In accordance with the internationally accepted one letter code for amino acids the abbreviations D, E, N, S and T denote aspartic acid, glutamic acid, asparagine, serine, and threonine, respectively.

Proteins according to the invention comprise one or more of an optimized consensus sequence(s) D/E-X-N-Z-S/T that is/are introduced into the protein and N-glycosylated. Hence, the proteins of the present invention differ from the naturally occurring *C. jejuni* N-glycoproteins which also contain the optimized consensus sequence but do not comprise any additional (introduced) optimized consensus sequences.

The introduction of the optimized consensus sequence can be accomplished by the addition, deletion and/or substitution of one or more amino acids. The addition, deletion and/or substitution of one or more amino acids for the purpose of introducing the optimized consensus sequence can be accomplished by chemical synthetic Strategies, which, in view of the instant invention, would be well known to those skilled in the art such as solid phase-assisted chemical peptide synthesis. Alternatively, and preferred for larger polypeptides, the proteins of the present invention can be prepared by recombinant techniques that would be art-standard techniques in light of the invention.

The proteins of the present invention have the advantage that they may be produced with high efficiency and in any host. In one embodiment of the invention, the host comprises a functional pgl operon from *Campylobacter* spp., for example, from *C. jejuni*. In further embodiments, oligosaccharyl transferases from *Campylobacter* spp. for practicing the invention are from *Campylobacter coli* or *Campylobacter lari*. In view of the invention, oligosaccharyl transferases would be apparent to one of skill in the art. For example, oligosaccharyl transferases are disclosed in references such as Szymanski, C. M. and Wren, B. W. (2005) Protein glycosylation in bacterial mucosal pathogens, Nat. Rev. Microbiol. 3:225-237. The functional pgl operon may be present naturally when said prokaryotic host is *Campylobacter* spp., or, for example, *C. jejuni*. However, as demonstrated before in the art and mentioned above, the pgl operon can be transferred into cells and remain functional in said new cellular environment.

The term "functional pgl operon from *Campylobacter* spp., preferably *C. jejuni*" is meant to refer to the cluster of nucleic acids encoding the functional oligosaccharyl transferase (OTase) of *Campylobacter* spp., for example, *C. jejuni*, and one or more specific glycosyltransferases capable of assembling an oligosaccharide on a lipid carrier, and wherein said oligosaccharide can be transferred from the lipid carrier to the target protein having one or more optimized amino acid sequence(s): D/E-X-N-Z-S/T by the OTase. It to be understood that the term "functional pgl operon from *Campylobacter* spp., preferably *C. jejuni*" in the context of this invention does not necessarily refer to an operon as a singular transcriptional unit. The term merely requires the presence of the functional components for N-glycosylation of the recombinant protein in one host cell. These components may be transcribed as one or more separate mRNAs and may be regulated together or separately. For example, the term also encompasses functional components positioned in genomic DNA and plasmid(s) in one host cell. For the purpose of efficiency, in one embodiment all components of the functional pgl operon are regulated and expressed simultaneously.

The oligosaccharyl transferase can originate, in some embodiments, from *Campylobacter* spp., and in other embodiments, from *C. jejuni*. In additional embodiments, the oligosaccharyl transferase can originate from other organisms which are known to those of skill in the art as having an oligosaccharyl transferase, such as, for example, *Wolinella* spp. and eukaryotic organisms.

The one or more specific glycosyltransferases capable of assembling an oligosaccharide on a lipid carrier may originate from the host cell or be introduced recombinantly into said host cell, the only functional limitation being that the oligosaccharide assembled by said glycosyltransferases can be transferred from the lipid carrier to the target protein having one or more optimized consensus sequences by the OTase. Hence, the selection of the host cell comprising specific glycosyltransferases naturally and/or replacing specific glycosyltransferases naturally present in said host as well as the introduction of heterologous specific glycosyltransferases will enable those skilled in the art to vary the N-glycans bound to the optimized N-glycosylation consensus site in the proteins of the present invention.

As a result of the above, the present invention provides for the individual design of N-glycan-patterns on the proteins of the present invention. The proteins can therefore be individualized in their N-glycan pattern to suit biological, pharmaceutical and purification needs.

In embodiments of the present invention, the proteins may comprise one but also more than one, such as at least two, at least 3 or at least 5 of said N-glycosylated optimized amino acid sequences.

The presence of one or more N-glycosylated optimized amino acid sequence(s) in the proteins of the present invention can be of advantage for increasing their immunogenicity, increasing their stability, affecting their biological activity, prolonging their biological half-life and/or simplifying their purification.

The optimized consensus sequence may include any amino acid except proline in position(s) X and Z. The term "any amino acids" is meant to encompass common and rare natural amino acids as well as synthetic amino acid derivatives and analogs that will still allow the optimized consensus sequence to be N-glycosylated by the OTase. Naturally occurring common and rare amino acids are preferred for X and Z. X and Z may be the same or different.

It is noted that X and Z may differ for each optimized consensus sequence in a protein according to the present invention.

The N-glycan bound to the optimized consensus sequence will be determined by the specific glycosyltransferases and their interaction when assembling the oligosaccharide on a lipid carrier for transfer by the OTase. In view of the instant invention, those skilled in the art would be able to design the N-glycan by varying the type(s) and amount of the specific glycosyltransferases present in the desired host cell.

"Monosaccharide" as used herein refers to one sugar residue. "Oligo- and polysaccharide" refer to two or more sugar residues. The term "glycans" as used herein refers to mono-, oligo- or polysaccharides. "N-glycans" are defined herein as mono-, oligo- or polysaccharides of variable compositions that are linked to an ε-amide nitrogen of an asparagine residue in a protein via an N-glycosidic linkage. In an embodiment, the N-glycans transferred by the OTase are assembled on an undecaprenol pyrophosphate ("Und-P-P") lipid-anchor that is present in the cytoplasmic membrane of gram-negative or positive bacteria. They are involved in the synthesis of O antigen, O polysaccharide and peptidoglycan (Bugg, T. D., and Brandish, P. E. (1994). From peptidoglycan to glycoproteins: common features of lipid-linked oligosaccharide biosynthesis. FEMS Microbiol Lett 119, 255-262; Valvano, M. A. (2003). Export of O-specific lipopolysaccharide. Front Biosci 8, s452-471).

Studies were conducted to determine whether the biosynthesis of a lipid-linked repeating tetrasaccharide (4-N-acetyl perosamine→fucose→glucose→GalNAc) was initiated by the formation of GalNAc-P-P-Und by WecA. When membrane fractions from E. coli strains K12, O157, and PR4019, a WecA-overexpressing strain, were incubated with UDP-[$^3$H]GalNAc, neither the enzymatic synthesis of [$^3$H]GlcNAc-P-P-Und nor [$^3$H]GalNAc-P-P-Und was detected. However, when membrane fractions from strain O157 were incubated with UDP-[$^3$H]GlcNAc, two enzymatically labeled products were observed with the chemical and chromatographic properties of [$^3$H]GlcNAc-P-P-Und and [$^3$H]GalNAc-P-P-Und, confirming that strain O157 contained an epimerase capable of interconverting GlcNAc-P-P-Und and GalNAc-P-P-Und. The presence of an epimerase was also confirmed by showing that exogenous [$^3$H]GlcNAc-P-P-Und was converted to [$^3$H]GalNAc-P-P-Und when incubated with membranes from strain O157. When strain O157 was metabolically labeled with [$^3$H]GlcNAc, both [$^3$H]GlcNAc-P-P-Und and [$^3$H]GalNAc-P-P-Und were detected. Transformation of E. coli strain 21546 with the Z3206 gene enabled these cells to synthesize GalNAc-P-P-Und in vivo and in vitro. The reversibility of the epimerase reaction was demonstrated by showing that [$^3$H]GlcNAc-P-P-Und was reformed when membranes from strain O157 were incubated with exogenous [$^3$H]GalNAc-P-P-Und. The inability of Z3206 to complement the loss of the gne gene in the expression of the Campylobacter jejuni N-glycosylation system in E. coli indicated that it does not function as a UDP-GlcNAc/UDP-GalNAc epimerase. Based on these results, it was confirmed that GalNAc-P-P-Und is synthesized reversibly by a GlcNAc-P-P-Und epimerase following the formation of GlcNAc-P-P-Und by WecA in E. coli O157.

The initiating reaction of E. coli O157 O-antigen subunit assembly was investigated to confirm that GalNAc-P-P-Und synthesis is catalyzed by some previously unknown mechanism rather than by WecA. The evidence presented herein shows that GalNAc-P-P-Und is not synthesized by GalNAc-P transfer from UDP-GalNAc catalyzed by WecA but rather by the reversible epimerization of the 4-OH of GlcNAc-P-P-Und catalyzed by an epimerase encoded by the Z3206 gene in E. coli O157.

Accordingly, the invention encompasses a novel biosynthetic pathway for the assembly of an important bacterial cell surface component as well as a new biosynthetic route for the synthesis of GalNAc-P-P-Und. A further embodiment of the invention includes the bacterial epimerase as a new target for antimicrobial agents.

E. coli O157 synthesizes an O-antigen with the repeating tetrasaccharide structure (4-N-acetyl perosamine→fucose-→glucose→GalNAc). It is shown herein that the biosynthesis of the lipid-linked tetrasaccharide intermediate was not initiated by the enzymatic transfer of GalNAc-P from UDP-GalNAc to Und-P catalyzed by WecA, contrary to earlier genetic studies (Wang. L. and Reeves, P. R. (1998) Infect. Immun. 66, 3545-3551). The invention described herein, obtained by homology searches and then confirmed by results from genetic, enzymology, and metabolic labeling experiments, demonstrates that WecA does not utilize UDP-GalNAc as a substrate, but that WecA is required to synthesize GlcNAc-P-P-Und which is then reversibly converted to GalNAc-P-P-Und by an epimerase encoded by the Z3206 gene in strain O157.

The Z3206 gene of the present invention belongs to a family of genes present in several strains that produce surface O-antigen repeat units containing GalNAc residues at their reducing termini (Table 1). The Z3206 gene sequence is shown in SEQ ID NO: 1. Previous reports identified two genes from E. coli O55 (Wang, L., Huskic, S., Cisterne, A., Rothemund, D. and Reeves, P. R. (2002) J. Bacteriol. 184, 2620-2625) and E. coli O86 (Gun, H., Yi, W., Li, L. and Wang, P. G. (2007) Biochem. Biophys. Res. Comm., 356, 604-609), E. coli O55 gne and E. coli O86 gne1, respectively, that are 100% identical to a Z3206 gene (Table 1). The E. coli O55 gne gene sequence is shown as SEQ ID NO: 3, and E. coli O86 gne1 gene sequence is shown as SEQ ID NO: 5.

TABLE 1

Correlation of Z3206 gene in bacterial strains expressing O-antigen chains with GalNAc at the reducing termini.

| | % Identity with Z3206 | GalNAc at the reducing terminus of O-antigen repeat unit |
|---|---|---|
| E. coli O55 gne (SEQ ID NO: 3) | 100 | Yes |
| E. coli O86 gne1 (SEQ ID NO: 5) | 100 | Yes |
| Shigella boydii O18 gne (SEQ ID NO: 7) | 88 | Yes |
| Salmonella enterica O30 gne (SEQ ID NO: 9) | 94 | Yes |
| C. jejuni gne (SEQ ID NO: 11) | 21 | No |
| E. coli K12 galE (SEQ ID NO: 13) | 27 | No |
| E. coli O86 gne2 (SEQ ID NO: 15) | 18 | Yes |

Accordingly, we conclude that E. coli O55 gne and E. coli O86 gne1 also encode epimerases capable of converting GlcNAc-P-P-Und to GalNAc-P-P-Und in strains O55 and O86, respectively, which also produce O-antigen repeat units with GalNAc at the reducing termini (Table 1).

Figure 8:
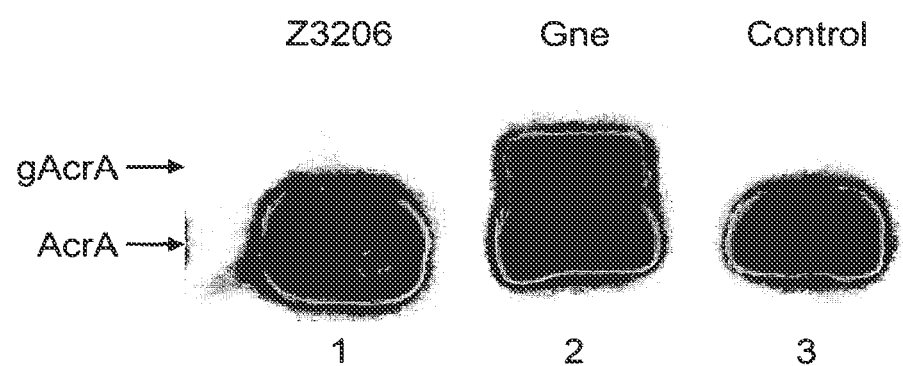
FIG. 8 shows SDS-PAGE analysis of unglycosylated and glycosylated AcrA protein. Periplasmic extracts prepared from *E. coli* DH5α cells carrying the AcrA expression plasmid and the pgl operon Agile complemented with pMLBAD:Z3206 (lane 1), pMLBAD:gne (lane 2) or the vector control pMLBAD (lane 3) were separated by 10% SDS-PAGE and transferred to nitrocellulose membranes. AcrA and its glycosylated forms were detected with anti AcrA antisera. The position of bands corresponding to unglycosylated (AcrA) and glycosylated AcrA (gAcrA) is indicated.

Two experimental approaches in this study indicate that the Z3206 protein does not catalyze the epimerization of UDP-GlcNAc to UDP-GalNAc in strain O157. First, when membranes from strain O157 were incubated with [$^3$H] UDP-GalNAc, neither [$^3$H]GlcNAc-P-P-Und nor [$^3$H]Gal-NAc-P-P-Und was detected (Table 3). If Z3206 catalyzed the conversion of [$^3$H]UDP-GalNAc to [$^3$H]UDP-GlcNAc, it would be expected that [$^3$H]GlcNAc-P-P-Und should be observed. Second, we have shown that hemagglutinin-tagged Z3206 was incapable of complementing the UDP-GalNAc-dependent C. jejuni N-glycosylation reporter system (FIG. 8).

E. coli O55 gne gene from strain O55 (Wang, L., Huskic, S., Cisterne, A., Rothemund, D. and Reeves, P. R. (2002) J. Bacteriol. 184, 2620-2625) was also assayed for epimerase activity by incubating crude extracts with UDP-GalNAc and indirectly assaying the conversion to UDP-GlcNAc by measuring an increase in reactivity with p-dimethylaminobenzaldehyde after acid hydrolysis. In both studies, the formation of the product was based on changes in reactivity with p-dimethylaminobenzaldehyde, and not a definitive characterization of the sugar nucleotide end product. A 90% pure polyhistidine-tagged E. coli O86 gne1 was also shown to have a low level of UDP-glucose epimerase activity relative to Gne2 in a coupled assay.

Accordingly, an embodiment of the invention is directed to a recombinant prokaryotic biosynthetic system containing Z3206 gene, E. coli O55 gne gene or E. coli O86 gne1 gene that converts GlcNAc-P-P-Und to GalNAc-P-P-Und.

It is significant that E. coli O86, which synthesizes an O-antigen containing two GalNAc residues, which would presumably require UDP-GalNAc as the glycosyl donor for the additional, non-reducing terminal GalNAc, also possesses an additional GlcNAc 4-epimerase gene, termed gne2, within the O-antigen gene cluster (Guo. B, Yi, W., Li, L. and Wang, P. G. (2007) Biochem. Biophys. Res. Commun., 356, 604-609). This additional epimerase gene has high homology with the galE gene of the colanic acid gene cluster and appears to be a UDP-GlcNAc 4-epimerase capable of synthesizing UDP-GalNAc.

The Z3206 gene appears to be highly conserved in E. coli O-serotypes initiated with GalNAc. In a recent study, 62 E. coli strains, with established O-antigen repeat unit structures, were screened for expression of Z3206 by a polymerase chain reaction based method using nucleotide primers designed to specifically detect the E. coli O157 Z3206 gene (Wang, L., Huskic, Cisterne, A., Rothemund, D. and Reeves, P. R. (2002) J. Bacteriol. 184, 2620-2625). In this study Z3206 was detected in 16 of the 22 E. coli strains that were known to contain GalNAc, and in only 4 of the 40 strains lacking GalNAc. Moreover, a similar screen of the 22 GalNAc-containing strains with primers designed to detect an alternative epimerase with UDP-GlcNAc 4-epimerase activity (the GalE gene of E. coli O113) detected no strains carrying this gene, indicating that Z3206 is the GlcNAc 4-epimerase gene most commonly associated with the presence of a reducing-terminal GalNAc in O-antigen repeat units of E. coli.

Analysis of the Z3206 protein sequence by a variety of web-based topological prediction algorithms indicates that the Z3206 protein is not highly hydrophobic. The majority of the topological prediction algorithms indicate that Z3206 is a soluble 37 kDa protein, although TMPred (Hofmann, K., and Stoffel, W. (1993) Biol. Chem. Hoppe-Seyler 374, 166 (abstr.)) predicted a single weak N-terminal transmembrane helix. However, Western blotting after SDS-PAGE of cellular fractions from E. coli cells expressing hemagglutinin-tagged Z3206 clearly shows that the tagged protein is associated with the particulate fraction following hypotonic lysis of the cells. Preliminary experiments show that the protein remains associated with the particulate fraction following incubation of the membrane fraction with 1 M KCl, but is solubilized in an active form by incubation with 0.1% Triton X-100.

E. coli O157 Z3206 has significant sequence homology with the short-chain dehydrogenase/reductase family of oxido-reductases including the GXXGXXG motif (Rossman fold), consistent with the NAD(P) binding pocket (Allard, S. T. M., Giraud, M. F., and Naismith, J. H. (2001) Cell. Mol. Life Sci. 58, 1650-1655) and the conserved $SX_{24}YX_3K$ sequence, involved in proton abstraction and donation (Field, R. A. and Naismith, J. H. (2003) Biochemistry 42, 7637-7647). Molecular modeling based on crystal structures of UDP-Glc 4-epimerase, another member of the short-chain dehydrogenase/reductase family, suggests that, after hydride abstraction, the 4-keto intermediate rotates around the β phosphate of UDP to present the opposite face of the keto intermediate and allow re-insertion of hydride from the opposite side, thus inverting the configuration of the hydroxyl at carbon 4. The presence of these conserved sequences suggests that Z3206 likely functions via a similar mechanism. Although the equilibrium distribution of the epimerase products, seen in FIG. 7, seems to favor the formation of GlcNAc-P-P-Und, the utilization of GalNAc-P-P-Und for O-antigen repeat unit assembly would drive the epimerization reaction in the direction of GalNAc-P-P-Und by mass action.

Epimerization of the glycosyl moieties of polyisoprenoid lipid intermediates has not been widely reported in nature. In one previous study the 2-epimerization of ribosyl-P-decaprenol to form arabinosyl-P-decaprenol, an arabinosyl donor in arabinogalactan biosynthesis in mycobacteria, was reported (Mikusová, K., Huang, H., Yagi, T., Holsters, M., Vereecke, D., D'Haeze, W., Scherman, M. S., Brennan, P. J., McNeil, M. R., and Crick, D. C. (2005) J. Bacterial. 187, 8020-8025). Arabinosyl-P-decaprenol is formed via a two-step oxidation/reduction reaction requiring two mycobacterial proteins, Rv3790 and Rv3791. Although epimerization was modestly stimulated by the addition of NAD and NADP, neither Rv3790 nor Rv3791 contain either the Rossman fold or the $SX_{24}YXXXK$ motif, characteristic of the short-chain dehydrogenase/reductase family (Allard, S. T. M., Giraud, M.-F. and Naismith, J. H. (2001) *Cell. Mol. Life Sci.* 58, 1650-1655; Field, R. A. and Naismith, J. H. (2003) *Biochemistry* 42, 7637-7647).

In summary, a novel biosynthetic pathway for the formation of GalNAc-P-P-Und by the epimerization of GlcNAc-P-P-Und, is described.

Several antibiotics have been shown to inhibit the synthesis of GlcNAc-P-P-Und, but are limited in their utility because they also block the synthesis of GlcNAc-P-P-dolichol, the initiating dolichol-linked intermediate of the protein N-glycosylation pathway. Although GlcNAc-P-P-dolichol is a structurally related mammalian counterpart of the bacterial glycolipid intermediate, GlcNAc-P-P-Und, there is no evidence for a similar epimerization reaction converting GlcNAc-P-P-dolichol to GalNAc-P-P-dolichol in eukaryotic cells. Thus, this raises the possibility that in strains where the surface O-antigen containing GalNAc at the reducing termini are involved in a pathological process, O-antigen synthesis could potentially be blocked by inhibiting the bacterial epimerases.

An embodiment of the present invention involves an epimerase that converts GlcNAc-P-P-Und (N-acetylglucosaminylpyrophosphorylundecaprenol) to GalNAc-P-P-Und (N-acetylgalactosaminylpyrophosphorylundecaprenol) in *E. coli* O157. A still further exemplary aspect of the invention involves the initiation of synthesis of lipid-bound repeating tetrasaccharide having GalNAc at the reducing terminus.

The basis of another aspect of the invention includes the discovery that *Campylobacter jejuni* contains a general N-linked protein glycosylation system. Various proteins of *C. jejuni* have been shown to be modified by a heptasaccharide. This heptasaccharide is assembled on undecaprenyl pyrophosphate, the carrier lipid, at the cytoplasmic side of the inner membrane by the stepwise addition of nucleotide activated monosaccharides catalyzed by specific glycosyltransferases. The lipid-linked oligosaccharide then flip-flops (diffuses transversely) into the periplasmic space by a flippase, e.g., PglK. In the final step of N-linked protein glycosylation, the oligosaccharyltransferase (e.g., PglB) catalyzes the transfer of the oligosaccharide from the carrier lipid to asparagine (Asn) residues within the consensus sequence D/E-X-N-Z-S/T, where the X and Z can be any amino acid except Pro. The glycosylation cluster for the heptasaccharide had been successfully transferred into *E. coli* and N-linked glycoproteins of *Campylobacter* had been produced.

It had been demonstrated that PglB does not have a strict specificity for the lipid-linked sugar substrate. The antigenic polysaccharides assembled on undecaprenyl pyrophosphate are captured by PglB in the periplasm and transferred to a protein carrier (Feldman, 2005; Wacker, M., et al., Substrate specificity of bacterial oligosaccharyltransferase suggests a common transfer mechanism for the bacterial and eukaryotic systems. Proc Natl. Acad Sci USA. 2006. 103(18): p. 7088-93.) The enzyme will also transfer a diverse array of undecaprenyl pyrophosphate (UPP) linked oligosaccharides if they contain an N-acetylated hexosamine at the reducing terminus. The nucleotide sequence for pglB and the amino acid sequence for pglB are published at WO2009/04074.

Accordingly, one embodiment of the invention involves a recombinant N-glycosylated protein comprising: one or more of an introduced consensus sequence. D/E-X-N-Z-S/T, wherein X and Z can be any natural amino acid except proline; and an oligo- or polysaccharide having N-acetylgalactosamine at the reducing terminus and N-linked to each of said one or more introduced consensus sequences by an N-glycosidic linkage.

In a further embodiment, the present invention is directed to a recombinant prokaryotic biosynthetic system for producing all or a portion of a polysaccharide comprising an epimerase that synthesizes N-acetylgalactosamine ("GalNAc") on undecaprenyl pyrophosphate. In a further embodiment, all or a portion of the polysaccharide is antigenic.

In another embodiment, the present invention is directed to a recombinant prokaryotic biosynthetic system comprising: an epimerase that synthesizes GalNAc on undecaprenyl pyrophosphate; and glycosyltransferases that synthesize a polysaccharide having GalNAc at the reducing terminus.

An embodiment of the invention further comprises a recombinant prokaryotic biosynthetic system comprising an epimerase that synthesizes GalNAc on undecaprenyl pyrophosphate and glycosyltransferases that synthesize a polysaccharide, wherein said polysaccharide has the following structure: α-D-PerNAc-α-L-Fuc-β-D-Glc-α-D-GalNAc; and wherein GalNAc is at the reducing terminus of said polysaccharide.

The recombinant prokaryotic biosynthetic system can produce mono-, oligo- or polysaccharides of various origins. Embodiments of the invention are directed to oligo- and polysaccharides of various origins. Such oligo- and polysaccharides can be of prokaryotic or eukaryotic origin. Oligo- or polysaccharides of prokaryotic origin may be from gram-negative or gram-positive bacteria. In one embodiment of the invention, the oligo- or polysaccharide is from *E. coli*. In a further aspect of the invention, said oligo- or polysaccharide is from *E. coli* O157. In another embodiment, said oligo- or polysaccharide comprises the following structure: α-D-PerNAc-α-L-Fuc-P-D-Glc-α-D-GalNAc. In a further embodiment of the invention, the oligo- or polysaccharide is from *Shigella flexneri*. In a still further embodiment, the oligo- or polysaccharide is from *Shigella flexneri* 6. In a still further aspect, said oligo- or polysaccharide comprises the following structure:

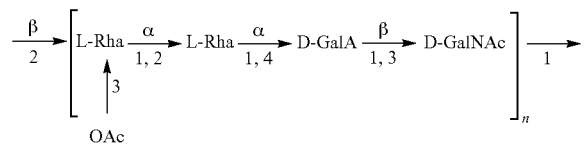

Embodiments of the invention further include proteins of various origins. Such proteins include proteins native to prokaryotic and eukaryotic organisms. The protein carrier can be, for example, AcrA or a protein carrier that has been modified to contain the consensus sequence for protein glycosylation, i.e., D/E-X-N-Z-S/T, wherein X and Z can be any amino acid except proline (e.g., a modified Exotoxin *Pseudomonas aeruginosa* ("EPA")). In one embodiment of the invention, the protein is *Pseudomonas aeruginosa* EPA.

A further aspect of the invention involves novel bioconjugate vaccines having GalNAc at the reducing terminus of the N-glycan. An additional embodiment of the invention involves a novel approach for producing such bioconjugate vaccines that uses recombinant bacterial cells that contain an epimerase which produces GalNAc on undecaprenyl pyrophosphate. In one embodiment, bioconjugate vaccines can be used to treat or prevent bacterial diseases. In further embodiments, bioconjugate vaccines may have therapeutic and/or prophylactic potential for cancer or other diseases.

A typical vaccination dosage for humans is about 1 to 25 µg, preferably about 1 µg to about 10 µg, most preferably about 10 µg. Optionally, a vaccine, such as a bioconjugate vaccine of the present invention, includes an adjuvant.

In an additional embodiment, the present invention is directed to an expression system for producing a bioconjugate vaccine against at least one bacterium comprising: a nucleotide sequence encoding an oligosaccharyl transferase; a nucleotide sequence encoding a protein carrier; at least one polysaccharide gene cluster from the at least one bacterium, wherein the polysaccharide contains GalNAc at the reducing terminus; and a nucleic acid sequence encoding an epimerase. In a further embodiment, the polysaccharide gene cluster encodes an antigenic polysaccharide.

In still a further embodiment, the present invention is directed to an expression system for producing a bioconjugate vaccine against at least one bacterium comprising: a nucleotide sequence encoding an oligosaccharyl transferase; a nucleotide sequence encoding a protein carrier comprising at least one inserted consensus sequence, D/E-X-N-Z-S/T, wherein X and Z may be any natural amino acid except proline; at least one polysaccharide gene cluster from the at least one bacterium, wherein the polysaccharide contains GalNAc at the reducing terminus; and the Z3206 gene. In a further embodiment, the polysaccharide gene cluster encodes an antigenic polysaccharide.

In yet another embodiment, the present invention is directed to a bioconjugate vaccine comprising: a protein carrier; at least one immunogenic polysaccharide chain linked to the protein carrier, wherein said polysaccharide has GalNAc at the reducing terminus, and further wherein said GalNAc is directly linked to the protein carrier; and an adjuvant.

In yet an additional embodiment, the present invention is directed to a bioconjugate vaccine comprising: a protein carrier comprising at least one inserted consensus sequence, D/E-X-N-Z-S/T, wherein X and Z may be any natural amino acid except proline; least one immunogenic polysaccharide from at least one bacterium, linked to the protein carrier, wherein the at least one immunogenic polysaccharide contains GalNAc at the reducing terminus directly linked to the protein carrier; and, optionally, an adjuvant.

Another embodiment of the invention is directed to a method of producing a bioconjugate vaccine, said method comprising: assembling a polysaccharide having GalNAc at the reducing terminus in a recombinant organism through the use of glycosyltransferases; linking said GalNAc to an asparagine residue of one or more target proteins in said recombinant organism, wherein said one or more target proteins contain one or more T-cell epitopes.

In a further embodiment, the present invention is directed to a method of producing a bioconjugate vaccine, said method comprising: introducing genetic information encoding for a metabolic apparatus that carries out N-glycosylation of a target protein into a prokaryotic organism to produce a modified prokaryotic organism; wherein the genetic information required for the expression of one or more recombinant target proteins is introduced into said prokaryotic organism; wherein the genetic information required for the expression of E. coli strain O157 epimerase is introduced into said prokaryotic organism; and wherein the metabolic apparatus comprises glycosyltransferases of a type that assembles a polysaccharide having GalNAc at the reducing terminus on a lipid carrier, and an oligosaccharyltransferase, the oligosaccharyltransferase covalently linking GalNAc of the polysaccharide to an asparagine residue of the target protein, and the target protein containing at least one T-cell epitope; producing a culture of the modified prokaryotic organism; and obtaining glycosylated proteins from the culture medium.

A further aspect of the present invention relates to a pharmaceutical composition. An additional aspect of the invention involves a pharmaceutical composition comprising at least one N-glycosylated protein according to the invention. In light of the disclosure herein, the preparation of medicaments comprising proteins would be well known in the art. A still further aspect of the invention relates to a pharmaceutical composition comprising an antibiotic that inhibits an epimerase that converts GlcNAc-P-P-Und to GalNAc-P-P-Und. In a preferred embodiment, the pharmaceutical composition of the invention comprises a pharmaceutically acceptable excipient, diluent and/or adjuvant.

Suitable excipients, diluents and/or adjuvants are well-known in the art. An excipient or diluent may be a solid, semi-solid or liquid material which may serve as a vehicle or medium for the active ingredient. One of ordinary skill in the art in the field of preparing compositions can readily select the proper form and mode of administration depending upon the particular characteristics of the product selected, the disease or condition to be treated, the stage of the disease or condition, and other relevant circumstances (Remington's Pharmaceutical Sciences, Mack Publishing Co. (1990)). The proportion and nature of the pharmaceutically acceptable diluent or excipient are determined by the solubility and chemical properties of the pharmaceutically active compound selected, the chosen route of administration, and standard pharmaceutical practice. The pharmaceutical preparation may be adapted for oral, parenteral or topical use and may be administered to the patient in the form of tablets, capsules, suppositories, solution, suspensions, or the like. The pharmaceutically active compounds of the present invention, while effective themselves, can be formulated and administered in the form of their pharmaceutically acceptable salts, such as acid addition salts or base addition salts, for purposes of stability, convenience of crystallization, increased solubility, and the like.

In instances where specific nucleotide or amino acid sequences are noted, it will be understood that the present invention encompasses homologous sequences that still embody the same functionality as the noted sequences. In an embodiment of the invention, such sequences are at least 85% homologous. In another embodiment, such sequences are at least 90% homologous. In still further embodiments, such sequences are at least 95% homologous.

The determination of percent identity between two nucleotide or amino acid sequences is known to one of skill in the art.

Nucleic acid sequences described herein, such as those described in the sequence listing below, are examples only, and it will be apparent to one of skill in the art that the sequences can be combined in different ways. Additional embodiments of the invention include variants of nucleic acids. A variant of a nucleic acid (e.g., a codon-optimized nucleic acid) can be substantially identical, that is, at least 80% identical, for example, 80%, 85%, 90%, 91%, 92%, 93%, 94%, 95%, 96%, 97%, 98%, 99% or 99.5% identical, to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 or SEQ ID NO: 29. Nucleic acid variants of a sequence that contains SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 or SEQ ID NO: 29 include nucleic acids with a substitution, variation, modification, replacement, deletion, and/or addition of one or more nucleotides (for example, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175 or 200 nucleotides) from a sequence that contains SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 or SEQ ID NO: 29, or parts thereof.

For example, in an embodiment of the instant invention, such variants include nucleic acids that encode an epimerase which converts GlcNAc-P-P-Und to GalNAc-P-P-Und and that i) are expressed in a host cell, such as, for example, *E. coli* and ii) are substantially identical to SEQ ID NO: 1, SEQ ID NO: 3, SEQ ID NO: 5, SEQ ID NO: 7 or SEQ ID NO: 9, or parts thereof.

Nucleic acids described herein include recombinant DNA and synthetic (e.g., chemically synthesized) DNA. Nucleic acids can be double-stranded or single-stranded. In the case of single-stranded nucleic acids, the nucleic acid can be a sense strand or antisense strand. Nucleic acids can be synthesized using oligonucleotide analogs or derivatives.

Plasmids that include a nucleic acid described herein can be transfected or transformed into host cells for expression. Techniques for transfection and transformation are known to those of skill in the art.

All publications mentioned herein are incorporated by reference in their entirety. It is to be understood that the term "or," as used herein, denotes alternatives that may, where appropriate, be combined; that is, the term "or" includes each listed alternative separately as well as their combination. As used herein, unless the context clearly dictates otherwise, references to the singular, such as the singular forms "a," an," and "the," include the plural, and references to the plural include the singular.

The invention is further defined by reference to the following examples that further describe the compositions and methods of the present invention, as well as its utility. It will be apparent to those skilled in the art that modifications, both to compositions and methods, may be practiced which are within the scope of the invention.

EXAMPLES

Bacterial Strains and Plasmids—

*E. coli* strains PR4019 (Rush, J. S., Rick, P. D. and Waechter, C. J. (1997) *Glycobiology*, 7, 315-322) and PR21546 (Meier-Dieter, U., Starman, R., Barr, K., Mayer, H. and Rick, P. I). (1990) *J. Biol. Chem.*, 265, 13490-13497) were generous gifts from Dr. Paul Rick, Bethesda, Md., and *E. coli* O157:H45 (Stephan, R., Borel, N., Zweifel, C., Blanco, M, and Blanco, J. E. (2004) *BMC Microbiol* 4:10) was a gift from Dr. Claudio Zweifel, Veterinary Institute, University of Zurich, *E. coli* DH5α (Invitrogen) was used as the host for cloning experiments and for protein glycosylation analysis. Plasmids used are listed in Table 2.

TABLE 2

Plasmids used in Examples

| Plasmid | Description | Ref |
|---|---|---|
| pMLBAD | Cloning vector, Tmp$^R$ | Lefebre & Valvano (2002) |
| pMLBAD:Z3206 (SEQ ID NO: 23) | Z3206 in pMLBAD, Tmp$^R$, expression controlled by arabinose-inducible promoter | Examples herein |
| pMLBAD:gne (SEQ ID NO: 24) | gne in pMLBAD, Tmp$^R$, expression controlled by arabinose-inducible promoter | Examples herein |
| pACYCpgl | *C. jejuni* pgl cluster Cm$^R$ | Wacker, et al. (2002) |
| pACYCgne::kan | *C. jejuni* pgl cluster containing a kan cassette in gne, Cm$^R$, Kan$^R$ | Linton, et al. (2005) |
| pWA2 | Soluble periplasmic hexa-His-tagged AcrA under control of Tet promoter in pBR322, Amp$^R$ | Feldman, et al. (2005) |

Materials—

[1,6-$^3$H]GlcNAc (30 Ci/mmol), UDP-[1-$^3$H]GlcNAc (20 Ci/mmol) and UDP-[6-$^3$H]GalNAc (20 Ci/mmol) were obtained from American Radiolabeled Chemicals (St. Louis, Mo.). Quantum 1 silica gel G thin layer plates are a product of Quantum Industries (Fairfield, N.J.), and Baker Si250 Silica Gel G plates are manufactured by Mallinekrodt Chemical Works. Yeast extract and Bacto-peptone were products of BD Biosciences. All other chemicals were obtained from standard commercial sources. Trimethoprim (50 μg/ml), chloramphenicol (20 μg/ml), ampicillin (100 μg/ml), and kanamycin (50 μg/ml) were added to the media as needed.

Construction of Recombinant Plasmids—

*E. coli* strain DH5α was used for DNA cloning experiments and constructed plasmids were verified by DNA sequencing. The Z3206 gene was amplified from *E. coli* O157:H45 by PCR with oligonucleotides Z3206-Fw and Z3206-RvHA (AAA<u>CCCGGG</u>ATGAACGATAACG TTTTGCTC (SEQ ID NO: 17) and AAA<u>TCTAGA</u>TTAAGCGTAATCTGGAACATCGTATGGGTA CTCAGAAACAA ACGTTATGTC (SEQ ID NO: 18): restriction sites are underlined). The PCR fragment was digested with SmaI and XbaI and ligated into SmaI-XbaI cleaved pMLBAD vector (Lefebre, M. D. and Valvano M. A. (2002) *Appl Environ Microbiol* 68: 5956-5964). This resulted in plasmid pMLBAD:Z3206 (SEQ ID NO: 23) encoding Z3206 with a C-terminal hemagglutinin tag.

The gne gene was amplified from pACYCpgl (Wacker, M., Linton, D., Hitchen, P. G., Nita-Lazar, M., Haslam, S. M., North, S. J., Panico, M., Morris, H. R., Dell, A., Wrenn, B. W., Aebi, M. (2002) *Science* 298, 1790-1793), encoding *Campylobacter jejuni* pgl cluster, with oligonucleotides gne-Fw and gne-RV (AAA<u>CCATGG</u>AT GAAAATTCTTATTAGCGG (SEQ ID NO: 19) and AAA<u>TCTAGA</u>TTAAGCGTAATCTGGAACATCGTATGGGTA GCACTGTTTTTC CCAATC (SEQ ID NO: 20); restriction sites are underlined). The PCR product was digested with NcoI and XbaI and ligated into the same sites of pMLBAD to generate plasmid pMLBAD:gne (SEQ ID NO: 24) which encodes One with a C-terminal hemagglutinin tag (Table 2).

Growth Conditions, Protein Expression and Immunodetection—

*E. coli* strains were cultured in Luria-Bertani medium (1% yeast extract, 2% Bacto-peptone, 0.6% NaCl) at 37° C. with vigorous shaking. Arabinose inducible expression was achieved by adding arabinose at a final concentration of 0.02-0.2% (w/v) to E. coli cells grown up to an $A_{600}$ of 0.05-0.4. The same amount of arabinose was added again 5 h post-induction, and incubation continued for 4-15 h.

Analytical Procedures—

Protein concentrations were determined using the BCA protein assay (Pierce) after precipitation of membrane proteins with deoxycholate and trichloroacetic acid according to the Pierce Biotechnology bulletin "Eliminate Interfering Substances from Samples for BCA Protein Assay." Samples were analyzed for radioactivity by scintillation spectrometry in a Packard Tri-Carb 2100TR liquid scintillation spectrometer after the addition of 0.5 ml of 1% SDS and 4 ml of Econosafe Economical Biodegradable Counting Mixture (Research Products International, Corp., Mount Prospect, Ill.).

Example 1: Identification of an E. coli O157 Gene Encoding GlcNAc-P-P-Und 4-Epimerase We describe herein the surprising discovery of a new biosynthetic pathway in which GalNAc-P-P-Und is formed by the epimerization of the 4-OH of GlcNAc-P-P-Und catalyzed by the previously unknown action of a 4-epimerase. In this pathway, GlcNAc-P-P-Und is formed by the transfer of GlcNAc-P from UDP-GlcNAc, catalyzed by WecA, and then GlcNAc-P-P-Und is epimerized to GalNAc-P-P-Und by GlcNAc-P-P-Und-4-epimerase, which was a previously unknown pathway (FIG. 2.

The gene encoding a candidate for the GlcNAc-P-P-Und 4-epimerase was identified by DNA homology searches. Homology searches were performed using the U.S. National Library of Medicine databases found at http:blast.ncbi.nlm-.nih.govBlast.cgi. Genomic sequences of different bacteria encoding O antigen repeating units having a GalNAc at the reducing terminus were screened. One group with a repeating unit containing a GalNAc at the reducing terminus, and a second group lacking a terminal GalNAc in the repeating unit were compared to identify potential epimerases. Using these criteria, Z3206 was identified as a candidate GlcNAc-P-P-Und 4-epimerase (Table 1).

The GlcNAc 4-epimerase genes present in E. coli strains with O-antigen repeat units containing GalNAc can be separated into two homology groups as shown in Table 1. It was surprisingly discovered that one homology group (containing grid) clearly was correlated with the presence of GalNAc as the initiating sugar on the O-antigen repeat unit. It was further surprisingly discovered that the second group (containing gne2) exhibits a high degree of similarity to the UDP-Glc epimerase, GalE, and is found in E. coli strains that do not initiate O-antigen repeat unit synthesis with GalNAc. Z3206 in E. coli O157, a gene with a high degree of homology to gne1, was identified as a candidate GlcNAc-P-P-Und 4-epimerase. The genomic location of the Z3206 gene is consistent with a role in this pathway, as it resides between galF of the O-antigen cluster and wcaM which belongs to the colanic acid cluster.

The research described in Examples 2-11 further confirms the above discoveries, including identifying the GlcNAc 4-epimerase (E. coli O157 Z3206) as catalyzing the formation of GalNAc-P-P-Und.

Example 2: UDP-GalNAc is not a Substrate for E. coli WecA (GlcNAc-phosphotransferase)

To determine if E. coli WecA will utilize UDP-GalNAc as a GalNAc-P donor to form GalNAc-P-P-Und, membrane fractions from E. coli strains K12, PR4019, a WecA-overexpressing strain, and O157, which synthesize a tetrasaccharide O-antigen repeat unit with GalNAc at the reducing terminus presumably initiated by the synthesis of GalNAc-P-P-Und, were incubated with UDP-[$^3$H]GalNAc.

Preparation of E. coli Membranes—

Bacterial cells were collected by centrifugation at 1,000×g for 10 min, washed once in ice-cold phosphate-buffered saline, once with cold water, and once with 10 mM Tris-HCl, pH 7.4, 0.25 M sucrose. The cells were resuspended to a density of ~200 $A_{600}$ units/ml in 10 mM Tris-HCl, pH 7.4, 0.25 M sucrose, 10 mM EDTA containing 0.2 mg/ml lysozyme, and incubated at 30° C. for 30 min. Bacterial cells were recovered by centrifugation at 1,000×g for 10 min, quickly resuspended in 40 volumes of ice-cold 10 mM Tris-HCl, pH 7.4, and placed on ice. After 10 min the cells were homogenized with 15 strokes with a tight-fitting Dounce homogenizer and supplemented with 0.1 mM phenylmethylsulfonyl fluoride and sucrose to a final concentration of 0.25 M. Unbroken cells were removed by centrifugation at 1,000×g for 10 min, and cell envelopes were recovered by centrifugation at 40,000×g for 20 min. The membrane fraction was resuspended in 10 mM Tris-HCl, pH 7.4, 0.25 M sucrose, 1 mM EDTA and again sedimented at 40,000×g and resuspended in the same buffer to a protein concentration of ~20 mg/ml. Membrane fractions were stored at −20° C. until needed.

Assay for the Biosynthesis of [$^3$H]GlcNAc-P-P-Und and [$^3$H]GalNAc-P-P-Und in E. coli Membranes In Vitro—

Reaction mixtures for the synthesis of GlcNAc-P-P-Und and GalNAc-P-P-Und contained 50 mM Tris-HCl, pH 8, 40 mM $MgCl_2$, 5 mM dithiothreitol, 5 mM 5' AMP. E. coli membrane fraction (50-200 μg membrane protein, and either 5 μm UDP-[$^3$H]GlcNAc/GalNAc (500-2500 dpm/pmol) in a total volume of 0.05 ml. After incubation at 37° C., reactions were terminated by the addition of 40 volumes of $CHCl_3$/$CH_3OH$ (2:1), and the total lipid extract containing [$^3$H] HexNAc-P-P-undecaprenols was prepared as described previously (Waechter. C. J., Kennedy, J. L. and Harford, J. B. (1976) Arch. Biochem, Biophys. 174, 726-737). After partitioning, the organic phase was dried under a stream of nitrogen and redissolved in 1 ml $CHCl_3$/$CH_3OH$ (2:1), and an aliquot (0.2 ml) was removed, dried in a scintillation vial, and analyzed for radioactivity by liquid scintillation spectrometry in a Packard Tri-Carb 2100 TR liquid scintillation spectrometer. To determine the rate of synthesis of [$^3$H] GlcNAc-P-P-Und or [$^3$H]GalNAc-P-P-Und, the lipid extract was dried under a stream of nitrogen, redissolved in a small volume of $CHCl_3$/$CH_3OH$ (2:1), and spotted on a 10×20-cm borate-impregnated Baker Si250 silica gel plate, and the plate was developed with $CHCl_3$, $CH_3OH$, $H_2O$, 0.2 M sodium borate (65:25:2:2). Individual glycolipids were detected with a Bioscan AR2000 Imaging Scanner (Bioscan, Washington, D.C.). The biosynthetic rates for each glycolipid were calculated by multiplying the total amount of radioactivity in [$^3$H]GlcNAc/GalNAc-P-P-Und by the percentage of the individual [$^3$H] glycolipids.

Membrane fractions from different E. coli strains (K12, PR4019 and O157) were incubated with either UDP-[$^3$H]GlcNAc or UDP-[$^3$H]GalNAc and the incorporation into [$^3$H]GlcNAc/GalNAc-P-P-Und was determined as described above. As seen in Table 3, no labeled glycolipids were detected after the incubation with UDP-[$^3$H]GalNAc, only GlcNAc-P-P-Und was detectable when membrane fractions were incubated with UDP-[$^3$H]GlcNAc

TABLE 3

Synthesis of [³H]GlcNAc/GalNAc-P-P-undecaprenol in E. coli membrane fractions using either UDP-[³H]GlcNAc or UDP-[³H]GalNAc as substrate

| | | [³H]Glycolipid formed | |
|---|---|---|---|
| Source of membranes | Sugar nucleotide added | GlcNAc-P-P-Und (pmol/mg) | GalNAc-P-P-Und (pmol/mg) |
| K12 | UDP-[³H]GlcNAc | 6.4 | <0.01 |
| K12 | UDP-[³H]GalNAc | <0.01 | <0.01 |
| PR4019 | UDP-[³H]GlcNAc | 44 | <0.01 |
| PR4019 | UDP-[³H]GalNAc | <0.01 | <0.01 |
| O157 | UDP-[³H]GlcNAc | 1.5 | 0.5 |
| O157 | UDP-[³H]GalNAc | <0.01 | <0.01 |

Moreover, neither the addition of exogenous Und-P to incubations with membranes from PR4019, the WecA-overexpressing strain, or the addition of cytosolic fractions from O157 cells resulted in the formation of GalNAc-P-P-Und from UDP-GalNAc. These results demonstrate that UDP-GalNAc is not a substrate for WecA and suggest that GalNAc-P-P-Und is formed by an alternative mechanism.

When membranes from strain K12 were incubated with UDP-[³H]GlcNAc, [³H]GlcNAc-P-P-Und was synthesized as expected (Rush, J. S., Rick, P. D. and Waechter, C. J. (1997) Glycobiology, 7, 315-322). However, when membranes from strain O157 were incubated with UDP-[³H] GlcNAc, in addition to [³H]GlcNAc-P-P-Und, a second labeled lipid shown to be [³H]GalNAc-P-P-Und (see below) was observed. When the time course for the formation of the two glycolipids was examined, the incorporation of radioactivity into [³H]GlcNAc-P-P-Und (FIG. 1, ○) occurred more quickly and to a higher extent than into [³H]GalNAc-P-P-Und (FIG. 1, ●), compatible with a precursor-product relationship (FIG. 2).

Figure 2:
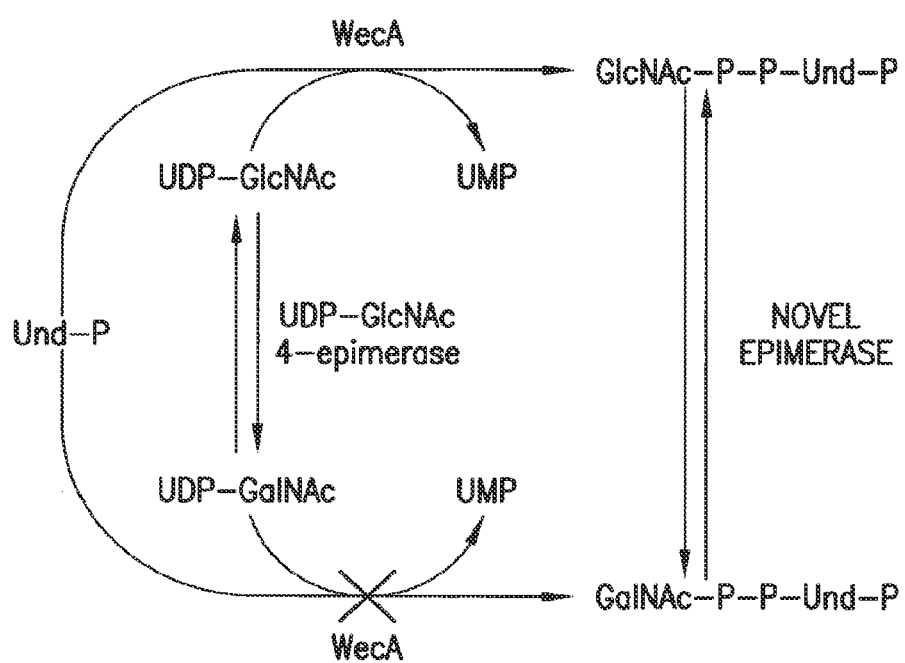
FIG. 2 shows the proposed biosynthetic pathway for the formation of GalNAc-P-P-Und from GlcNAc-P-P-Und.

The observation that E. coli O157 membranes do not utilize UDP-GalNAc as a GalNAc-P donor for the synthesis of GalNAc-P-P-Und is one example which confirms the biosynthetic pathway for the formation of GalNAc-P-P-Und illustrated in FIG. 2. In this scheme, GlcNAc-P-P-Und is formed by the transfer of GlcNAc-P from UDP-GlcNAc, catalyzed by WecA, and then GlcNAc-P-P-Und is epimerized by the action of a previously unknown 4-epimerase to produce GalNAc-P-P-Und.

Example 3: Characterization of [³H]GalNAc-P-P-Und Formed In Vitro with Membrane Fractions from E. coli Strain O157

Consistent with the additional O157-specific glycolipid product detected in FIG. 1, as GalNAc-P-P-Und, it was stable to mild alkaline methanolysis (toluene/methanol 1:3, containing 0.1 N KOH, 0° C., 60 min), retained by DEAE-cellulose equilibrated in $CHCl_3/CH_3OH/H_2O$ (10:10:3), and eluted with $CHCl_3/CH_3OH/H_2O$ (10:10:3) containing 20 mM ammonium acetate as reported previously for [³H] $GlcNAc_{1-2}$-P-P-Dol (Waechter, J. and Harford, B. (1977) Arch. Biochem. Biophys. 181, 185-198).

Figure 3A:
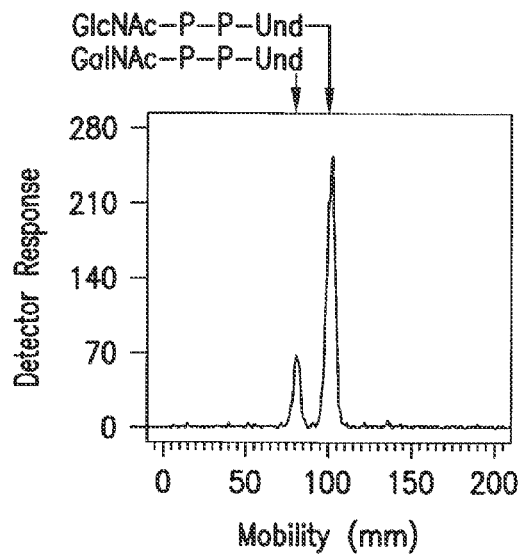
FIGS. 3A, 3B, 3C, and 3D shows purification and characterization of [$^3$H]GalNAc-P-P-Und synthesized by membrane fractions from E. coli strain O157. Membrane fractions from E. coli O157 were incubated with UDP-[$^3$H] GlcNAc, and the [$^3$H]GalNAc lipids were purified as described in Example 3.
Figure 3B:
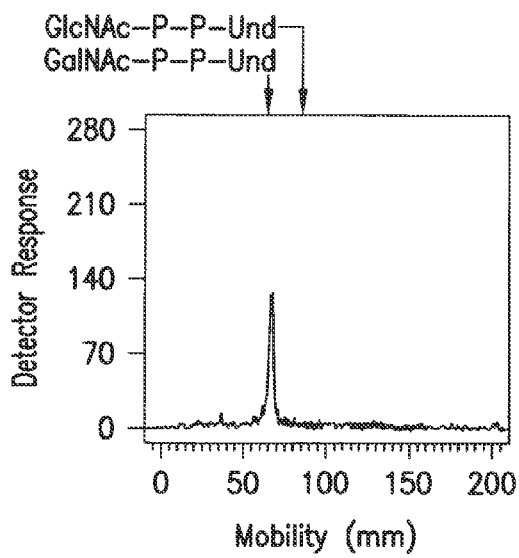

[³H]GalNAc-P-P-Und was clearly resolved from [³H]GalNAc-P-P-Und by thin layer chromatography on borate-impregnated silica gel G (Kean, E. L. (1966) J. Lipid Res. 7, 149-452) and purified by preparative TLC as shown in FIG. 3A and FIG. 3B.

Preparation of Borate-Impregnated Thin Layer Plates and Whatman No. 1 Paper—

Silica gel thin layer plates were impregnated with sodium borate by briefly immersing the plates in 2.5% $Na_2B_4O_7.10$ $H_2O$ in 95% methanol as described by Kean (Kean, E. L. (1966) J. Lipid Res. 7.449-452). The borate-impregnated TLC plates were dried overnight at room temperature and stored in a vacuum dessicator over Drierite until use. Immediately before chromatography, the plates were activated by heating briefly (~10-15 min) to 100° C. Whatman No. 1 paper was impregnated with sodium borate by dipping 20×30-cm sheets of Whatman 1 paper in 0.2 M $Na_2B_4O_7.10H_2O$. The Whatman No. 1 paper sheets were pressed firmly between two sheets of Whatman No. 3MM paper and allowed to dry at room temperature for several days, as described by Cardini and Leloir (Cardini, C. E. and Leloir, L. F. (1957) J. Biol. Chem. 225, 317-324).

Characterization of Glycan Products Formed in In Vitro Reactions—

The glycans of the individual glycolipids ([³H]GalNAc-P-P-Und and [³H]GlcNAc-P-P-Und) were characterized by descending paper chromatography after release by mild acid hydrolysis. The GlcNAc/GalNAc lipids were dried under a stream of nitrogen in a conical screw-cap tube and heated to 100° C., 15 min in 0.2 ml 0.01 M HCl. After hydrolysis the samples were applied to a 0.8-ml mixed-bed ion-exchange column containing 0.4 ml of AG50WX8 (H⁺) and 0.4 ml AG1X8 (acetate form) and eluted with 1.5 ml water. The eluate was dried under a stream of nitrogen, redissolved in a small volume of $H_2O$ (0.02 ml), spotted on a 30-cm strip of borate-impregnated Whatman No. 1 paper, and developed in descending mode with butanol/pyridine/water (6:4:3) for 40-50 h. After drying, the paper strips were cut into 1-cm zones and analyzed for radioactivity by scintillation spectrometry. GlcNAc and GalNAc standards were detected using an aniline-diphenylamine dip reagent (Schwimmer, S. and Benvenue, A. (1956) Science 123, 543-544).

Glycan products were converted to their corresponding alditols by reduction with 0.1 M $NaBH_4$ in 0.1 M NaOH (final volume ml) following mild acid hydrolysis as described above. After incubation at room temperature overnight, the reactions were quenched with several drops of glacial acetic acid and dried under a stream of nitrogen out of methanol containing 1 drop of acetic acid, several times. The alditols were dissolved in water, desalted by passage over 0.5 ml columns of AG50WX8 (H+) and AG1X8 (acetate), dried under nitrogen, and spotted on 30-cm strips of Whatman No. 3MM paper. The Whatman No. 3 MM strips were developed overnight in descending mode with ethyl acetate, pyridine, 0.1 M boric acid (65:25:20), dried, cut into 1-cm zones, and analyzed for radioactivity by scintillation spectrometry. GlcNAcitol and GalNAcitol standards were visualized using a modification of the periodate-benzidine dip procedure (Gordon, H. T., Thornburg, W. and Werum, L. N. (1956) Anal. Chem. 28, 849-855). The paper strips were dipped in acetone, 0.1 M $NaIO_4$ (95:5), allowed to air dry for 3 min, and then dipped in acetone/acetic acid/$H_2O$/o-tolidine (96:0.6:4.4:0.2 gm). Alditols containing cis-diols stain as yellow spots on a blue background.

Mass Spectrometry ("MS") of Glycolipids—

Purified glycolipids were analyzed using an ABI/MDS Sciex 4000 Q-Trap hybrid triple quadrupole linear ion trap mass spectrometer with an ABI Turbo V electrospray ion-source (ABIMDS-Sciex, Toronto, Canada). In brief, samples were infused at 10 μl/min with ion source settings determined empirically, and MS/MS (mass spectroscopy in a second dimension) information was obtained by fragmentation of the molecular ion in linear ion trap mode.

Figure 3C:
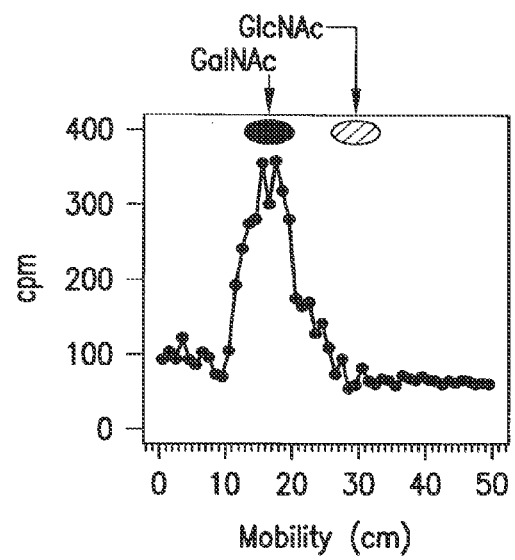
Figure 3D:
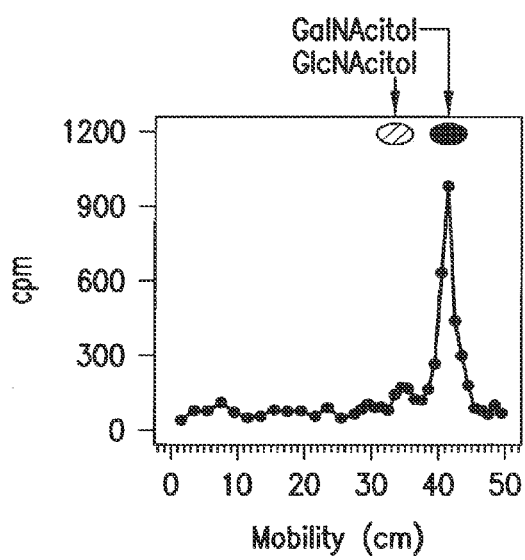

When the glycolipid was treated with mild acid (0.01 N HCl, 100° C., 15 min), the water-soluble product co-chromatographed with [³H]GalNAc on descending paper chromatography with borate-impregnated Whatman No. 1 paper (FIG. 3C). In addition, when the labeled sugar was reduced, it was converted to [$^3$H]alditol, GalNAc-OH (FIG. 3D). Moreover, negative-ion MS analysis yielded the [M-H]-ion of m/z=1128, expected for GalNAc-P-P-Und, and the MS/MS daughter ion spectrum showed a prominent ion at m/z=907, expected for a glycolipid containing P-P-Und (Guan, Z., Breazeale, S. D. and Raetz, C. R. (2005) *Anal. Biochem.* 345, 336-339). The identification of the glycolipid product formed by strain O157 as GalNAc-P-P-Und is also supported by its formation from exogenous GlcNAc-P-P-Und (see Example 7).

Example 4: Metabolic Labeling of [$^3$H]GalNAc-P-P-Und (In Vivo) with [$^3$H]GlcNAc in *E. coli* Cells Expressing the Z3206 Gene To investigate whether expression of the *E. coli* O157 Z3206 gene enabled cells to synthesize GalNAc-P-P-Und, *E. coli* strain 21546 (Meier-Dieter, U., Starman, R., Barr, K., Mayer, H. and Rick, P. D. (1990) *J. Biol. Chem.*, 265, 13490-13497) expressing the Z3206 gene was labeled metabolically with [$^3$H]GlcNAc and analyzed for [$^3$H]GlcNAc/GalNAc-P-P-Und formation.

Metabolic Labeling of Bacterial Cells—

*E. coli* cells were cultured with vigorous shaking in Luria-Bertani medium at 37° C. to an $A_{600}$ of 0.5-1. [$^3$H]GlcNAc was added to a final concentration of 1 μCi/ml and the incubation was continued for 5 min at 37° C. The incorporation of radiolabel into glycolipids was terminated by the addition of 0.5 gm/ml crushed ice, and the cultures were thoroughly mixed. The bacterial cells were recovered by centrifugation at 4000×g for 10 min, and the supernatant was discarded. The cells were washed with ice-cold phosphate-buffered saline two times, resuspended by vigorous vortex mixing in 10 volumes (cell pellet) of methanol, and sonicated briefly with a probe sonicator at 40% full power. After sonication, 20 volumes of chloroform were added, and the extracts were mixed vigorously and allowed to stand at room temperature for 15 min. The insoluble material was sedimented by centrifugation, and the pellet was re-extracted with a small volume of CHCl$_3$/CH$_3$OH (2:1) twice. The combined organic extracts were then processed as described below.

Purification of GlcNAc-P-P-Und and GalNAc-P-P-Und—

GlcNAc/GalNAc-P-P-Und was extracted with CHCl$_3$/CH$_3$OH (2:1) and freed of water-soluble material by partitioning as described elsewhere (Waechter, C. J., Kennedy, J. L. and Harford, J. B. (1976) *Arch. Biochem. Biophys.* 174, 726-737). The organic extract was then dried under a stream of nitrogen, and the bulk glycerophospholipids were destroyed by deacylation in toluene/methanol (1:3) containing 0.1 N KOH at 0° C. for 60 min. The deacylation reaction was neutralized with acetic acid, diluted with 4 volumes of CHCl$_3$/CH$_3$OH (2:1), and washed with 15 volume of 0.9% NaCl. The organic (lower) phase was washed with 13 volume of CHCl$_3$, CH$_3$OH, 0.9% NaCl (3:48:47), and the aqueous phase was discarded. The organic phase was diluted with sufficient methanol to accommodate the residual aqueous phase in the organic phase and applied to a DEAE-cellulose column (5 ml) equilibrated with CHCl$_3$/CH$_3$OH (2:1). The column was washed with 20 column volumes of CHCl$_3$/CH$_3$OH/H$_2$O (10:10:3) and then eluted with CHCl$_3$/CH$_3$OH/H$_2$O (10:10:3) containing 20 mM ammonium acetate. Fractions (2 ml) were collected and monitored for either radioactivity, or GlcNAc/GalNAc-P-P-Und using an anisaldehyde spray reagent (Dunphy, P. J., Kerr, J. D., Pennock, J. F., Whittle, K. J., and Feeney, J. (1967) *Biochim. Biophys. Acta* 136, 136-147) after resolution by thin layer chromatography on borate-impregnated silica plates (as described earlier).

Figure 4A:
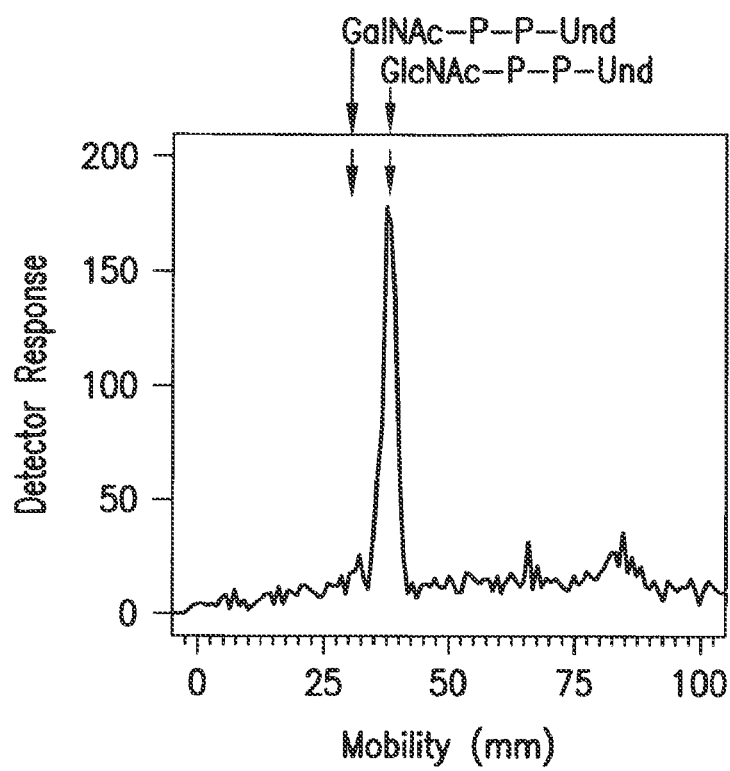
FIGS. 4A and 4B shows metabolic labeling of E. coli 21546 cells and E. coli 21546 cells after transformation with pMLBAD:Z3206. E. coli 21546 (FIG. 4A) and E. coli 21546:pMLBAD/Z3206 (FIG. 4B) were labeled metabolically with [$^3$H]GlcNAc for 5 min at 37° C. [$^3$H]GlcNAc/GalNAc-P-P-Und were extracted, freed of water soluble contaminants and separated by thin layer chromatography on borate-impregnated silica gel plates (Baker Si250) as described in Example 3. Radioactive lipids were detected using a Bioscan chromatoscanner. The chromatographic positions of GalNAc-P-P-Und and GlcNAc-P-P-Und are indicated by arrows.
Figure 4B:
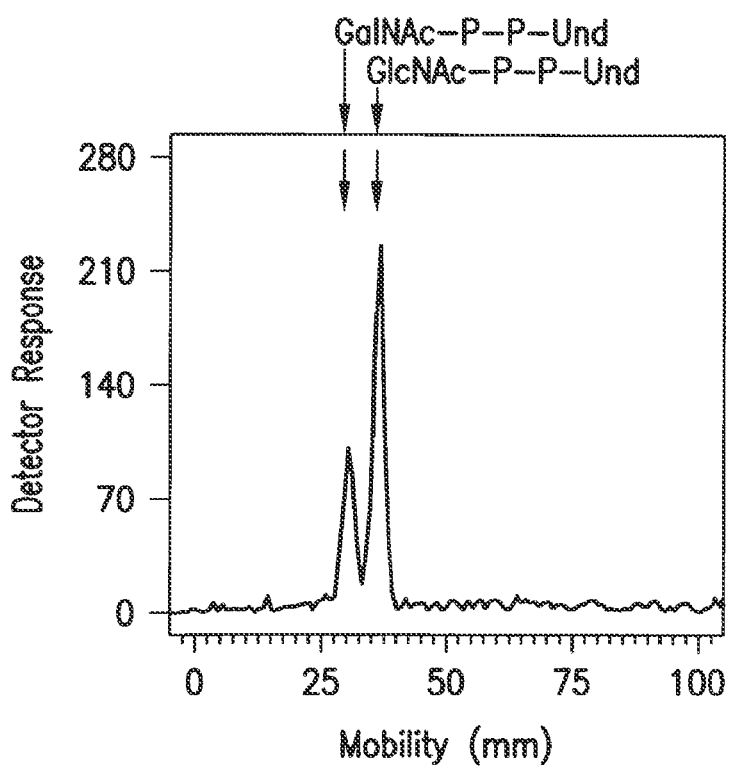

*E. coli* strain 21546 was selected as the host for the Z3206 expression studies because a mutation in UDP-ManNAcA synthesis results in a block in the utilization of GlcNAc-P-P-Und for the synthesis of the enterobacterial common antigen. Because *E. coli* 21546 is derived from *E. coli* K12 it does not synthesize an O-antigen repeat as well (Stevenson, G., Neal, B., Liu, D., Hobbs, M., Packer, N. H., Batley, M., Redmond, J. W., Lindquist, L. and Reeves, P. (1994) *J. Bacterial.*, 176, 4144-4156), and thus, larger amounts of GlcNAc-P-P-Und accumulate for the conversion to GalNAc-P-P-Und. When strain 21546 and the transformant expressing the Z3206 gene were labeled with [$^3$H]GlcNAc and the radiolabeled lipids were analyzed by thin layer chromatography on borate-impregnated silica gel plates, the parental strain (FIG. 4A) synthesized only one labeled lipid, GlcNAc-P-P-Und. However, 21546 cells expressing the Z3206 gene (FIG. 4B) also synthesized an additional labeled lipid shown to be GalNAc-P-P-Und.

Figure 5A:
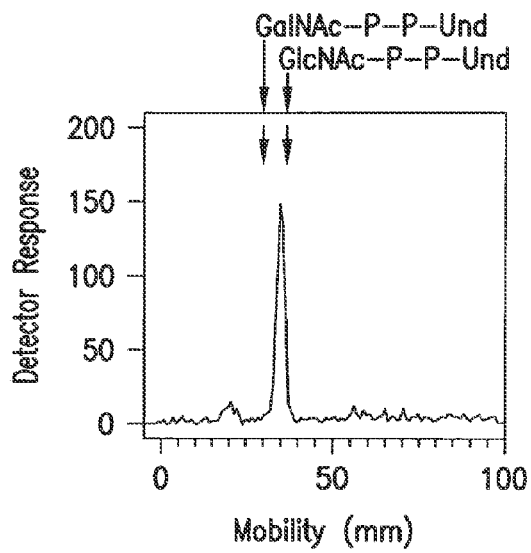
FIGS. 5A, 5B, 5C, and 5D shows thin layer chromatography of [$^3$H]GlcNAc/GalNAc-P-P-Und formed by incubation of membrane fractions from E. coli strains with UDP-[$^3$H]GlcNAc. Membrane fractions from E. coli strains K12 (FIG. 5A), O157 (FIG. 5B), 21546 (FIG. 5C), and 21546: pMLBAD/Z3206 (FIG. 5D) were incubated with UDP-[$^3$H] GlcNAc for 10 min at 37° C., and the [$^3$H]lipid products were extracted, freed of water-soluble contaminants by partitioning, and separated by thin layer chromatography on borate-impregnated silica gel plates (Baker Si250) as described in Example 3. The chromatographic positions of GalNAc-P-P-Und and GlcNAc-P-P-Und are indicated by arrows.
Figure 5C:
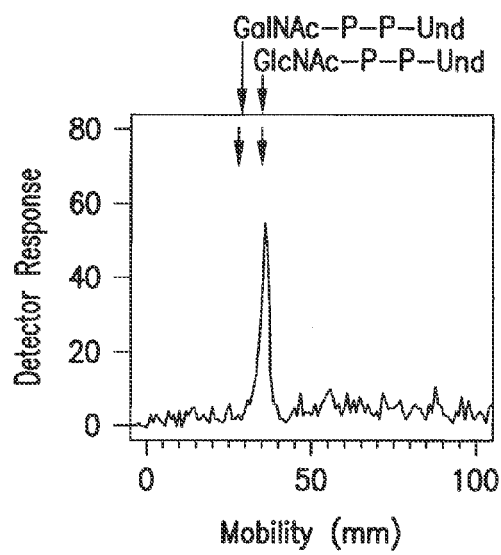
Figure 5B:
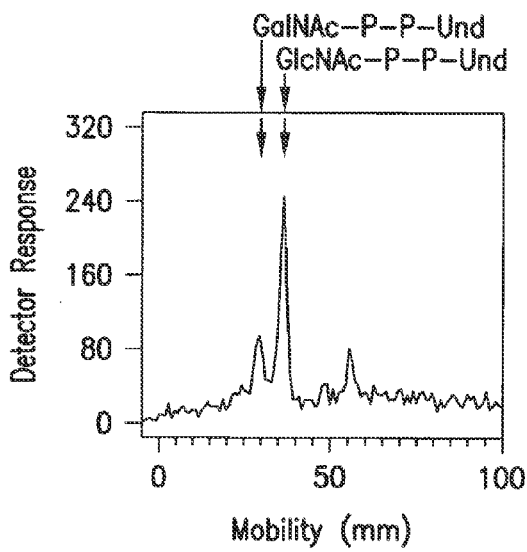
Figure 5D:
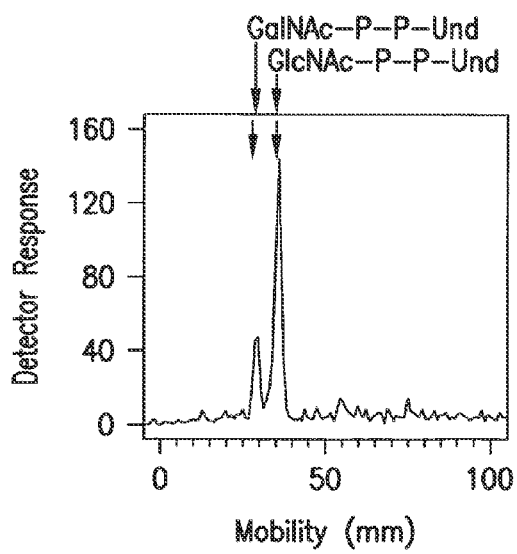

Example 5: Membrane Fractions from *E. coli* Cells Expressing the Z3206 Gene Synthesize GalNAc-P-P-Und In Vitro To corroborate that the protein encoded by the *E. coli* O157 Z3206 gene catalyzed the synthesis of GalNAc-P-P-Und, membrane fractions from *E. coli* cells expressing the Z3206 gene were incubated with [$^3$H]UDP-GlcNAc and the [$^3$H]glycolipid products were analyzed by thin layer chromatography (chromatographic preparation and characterization methods are described in Example 3) on borate-impregnated silica gel plates as shown in FIG. 5. When membrane fractions from *E. coli* K12 or the host strain *E. coli* 21546 cells were incubated with UDP-[$^3$H]GlcNAc, only [$^3$H]GlcNAc-P-P-Und was observed (FIG. 5A and FIG. 5C). However, membrane fractions from *E. Coli* O157 and *E. coli* 21546 expressing Z3206 formed GalNAc-P-P-Und as well (FIG. 5B and FIG. 5D).

Example 6: Formation of GlcNAc-P-P-Und, but not GalNAc-P-P-Und, is Reversed in the Presence of UMP To provide additional evidence that GalNAc-P-P-Und is synthesized from GlcNAc-P-P-Und, and not by the action of WecA using UDP-GalNAc as a glycosyl donor, the effect of discharging endogenous, pre-labeled [$^3$H]GlcNAc-P-P-Und and [$^3$H]GalNAc-P-P-Und with UMP was examined. The GlcNAc-phosphotransferase reaction catalyzed by WecA is freely reversible by the addition of excess UMP re-synthesizing UDP-GlcNAc and releasing Und-P.

Figure 6A:
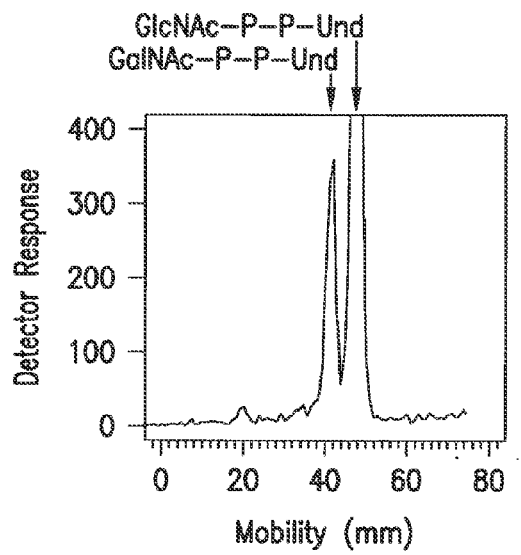
FIGS. 6A, 6B, and 6C shows discharge of GlcNAc-P by incubation with UMP. Membrane fractions from E. coli 21546:Z3206 were preincubated with UDP-[$^3$H]GlcNAc to enzymatically label GlcNAc-P-P-Und for 10 min (FIG. 6A) at 37° C. followed by a second incubation period with 1 mM UMP included for either 1 min (FIG. 6B) or 2 min (FIG. 6C). After the indicated incubation periods [$^3$H]GlcNAc/GalNAc-P-P-Und were extracted and resolved by thin layer chromatography on borate-impregnated silica gel plates (Baker Si250) as described in Example 3. The chromatographic positions of GalNAc-P-P-Und and GlcNAc-P-P-Und are indicated by arrows.
Figure 6B:
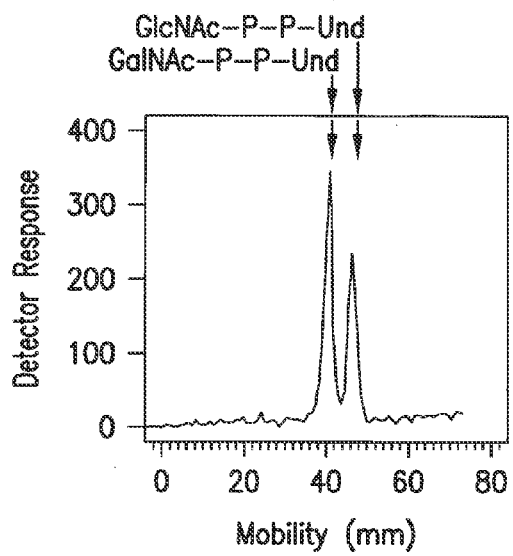
Figure 6C:
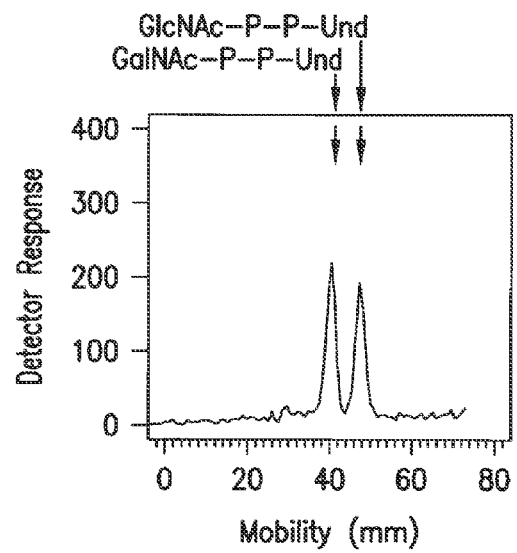

In this experiment membrane fractions from *E. coli* strain 21546 expressing Z3206 were pre-labeled for 10 min with UDP-[$^3$H]GlcNAc followed by the addition of 1 mM UMP, and the amount of each labeled glycolipid remaining was determined. The results illustrated in FIG. 6A show the relative amounts of [$^3$H]GlcNAc-P-P-Und and [$^3$H]GalNAc-P-P-Und at the end of the 10 min labeling period. After incubation with 1 mM UMP for 1 min it can be seen that there is a substantial loss of [$^3$H]GalNAc-P-P-Und, whereas the [$^3$H]GalNAc-P-P-Und peak is relatively unchanged (FIG. 6B) (chromatographic preparation and characterization methods are described in Example 5), This observation is consistent with the results in Table 3 indicating that WecA does not catalyze the transfer of GalNAc-P into GalNAc-P-P-Und from UDP-GalNAc. It is noteworthy that during the second minute of incubation with UMP (FIG. 6C), the loss of GlcNAc-P-P-Und slows, and there is a slight reduction in the peak of [$^3$H]GalNAc-P-P-Und, suggesting that [$^3$H]GalNAc-P-P-Und is re-equilibrating with the [$^3$H]GlcNAc-P-P-Und pool by reversal of the epimerase reaction (see Example 7).

Example 7: Interconversion of Exogenous, Purified [$^3$H]GlcNAc-P-P-Und and [$^3$H]GalNAc-P-P-Und Catalyzed by Membranes from E. Coli Cells Expressing Z3206

To provide direct evidence that GlcNAc-P-P-Und and GalNAc-P-P-Und can be directly interconverted by membrane fractions from E. coli cells expressing Z3260, purified [$^3$H]GlcNAc-P-P-Und and [$^3$H]GalNAc-P-P-Und were tested as exogenous substrates.

Purified [$^3$H]GlcNAc-P-P-Und/[$^3$H]GalNAc-P-P-Und were prepared as in Example 4 (Metabolic Labeling of Bacterial Cells and Purification of GlcNAc-P-P-Und and GalNAc-P-P-Und). [$^3$H]HexNAc-P-P-undecaprenols (2000 dpm/pmol, dispersed in 1% Triton X-100, final concentration 0.1%) were incubated with E. coli membranes as in Example 2 in Assay For the Biosynthesis of [$^3$H]GlcNAc-P-P-Und and [$^3$H]GalNAc-P-P-Und in E. coli Membranes In Vitro.

Figure 7A:
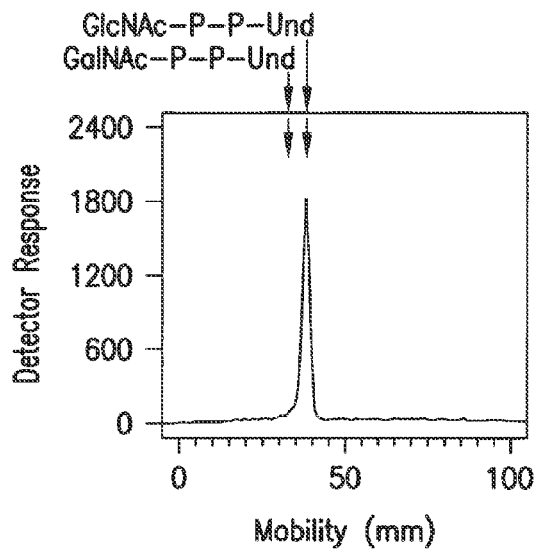
FIGS. 7A, 7B, 7C, 7D, 7E, and 7F shows conversion of exogenous [$^3$H]GlcNAc-P-P-Und and [$^3$H]GalNAc-P-P-Und to the pertinent [$^3$H]HexNAc-P-P-Und product catalyzed by membranes from strain 21546 expressing Z3206. Membrane fractions from E. coli strain 21546 (FIG. 7B and FIG. 7E) and 215461:pMLBAD/Z3206 (FIG. 7C and FIG. 7F) were incubated with purified [$^3$H]GlcNAc-P-P-Und (FIG. 7A, FIG. 7B, and FIG. 7C) or [$^3$H]GalNAc-P-P-Und (panels at FIG. 7D, FIG. 7E, and FIG. 7F) (dispersed ultrasonically in 1% Triton X-100) for 1 min at 37° C. [$^3$H]GlcNAc/GalNAc-P-P-Und were extracted, resolved by thin layer chromatography on borate-impregnated silica gel plates (Baker Si250) and detected with a Bioscan AR2000 radiochromatoscanner as described in Example 3.
Figure 7B:
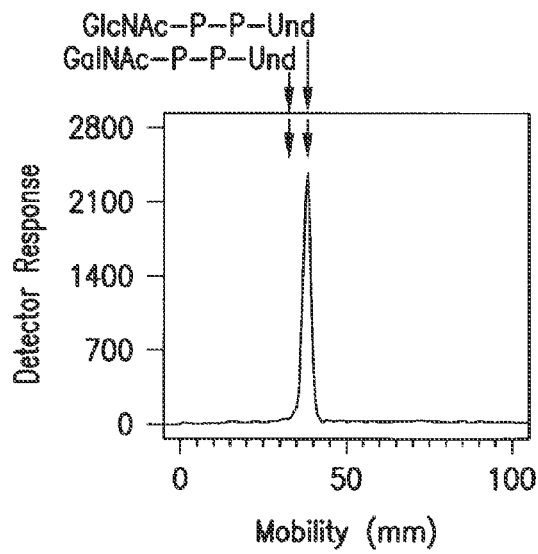
Figure 7C:
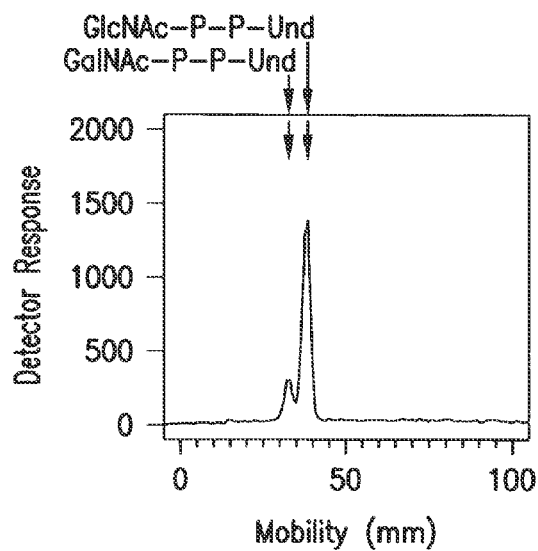
Figure 7D:
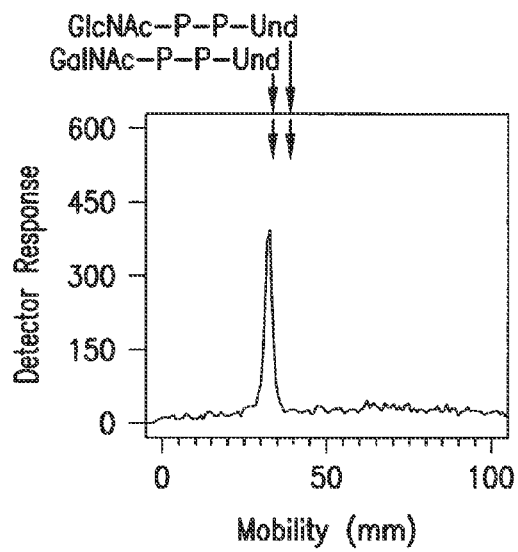
Figure 7E:
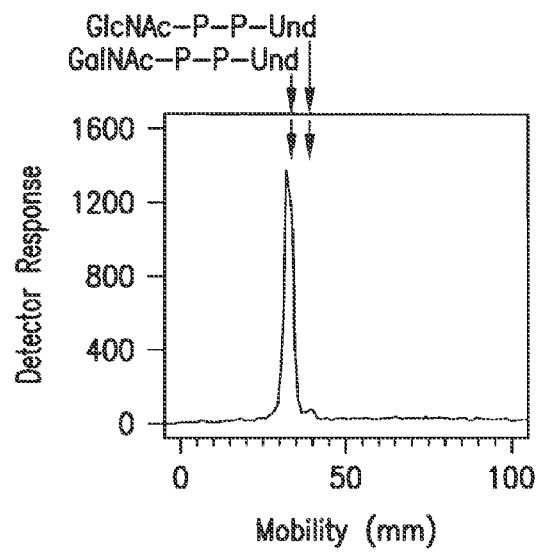
Figure 7F:
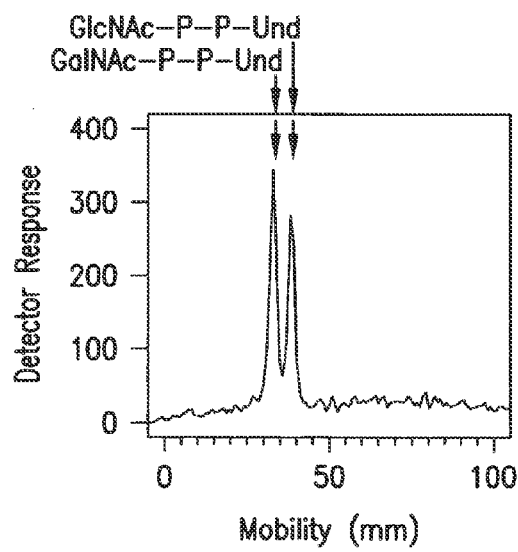

Preliminary experiments showed that the epimerase was active when exogenous [$^3$H]GalNAc-P-P-Und was added to the reaction mixtures dispersed in Triton X-100, CHAPS (3-[(3-cholamidopropyl)dimethylammonio]-1-propanesulfonic acid), Nonidet P-40, or octylglucoside and exhibited a pH optimum in the range 7-8.5. The chromatographic mobility of the purified [$^3$H]GlcNAc-P-P-Und and [$^3$H]GalNAc-P-P-Und before incubation with membrane fractions is shown in FIG. 7A and FIG. 7D. As seen in FIG. 7B and FIG. 7E, the glycolipids are unaffected by incubation with membrane fractions from E. coli 21546. However, incubation of the purified glycolipids with membrane fractions from E. coli 21546 expressing Z3206 catalyzes the conversion of exogenous [$^3$H]GlcNAc-P-P-Und to [$^3$H]GalNAc-P-P-Und (FIG. 7C) and the conversion of [$^3$H]GalNAc-P-P-Und to [$^3$H]GlcNAc-P-P-Und (FIG. 7F). These results demonstrate directly that GlcNAc-P-P-Und and GalNAc-P-P-Und can be enzymatically interconverted in E. coli strains expressing the Z3206.

Example 8: E. coli Z3206 is not a UDP-GlcNAc 4-Epimerase

To determine if Z3206 can catalyze the formation of UDP-GalNAc, the N-glycosylation apparatus from C. jejuni was expressed in E. coli. In this reporter system, glycosylation of the target protein AcrA is dependent on the presence of the pgl locus (Wacker, M., Linton, D., Hitchen, P. G., Nita-Lazar, M., Haslam, S. M., North, S. J., Panico, M., Morris, H. R., Dell, A., Wrenn, B. W., Aebi, M. (2002) Science 298, 1790-1793), including a functional Gne UDP-Glc/UDP-GlcNAc epimerase (Bernatchez, S., Szymanski, C. M., Ishiyama, N., Li, J., Jarrell, H. C., Lau, P. C., Berghuis, A. M., Young, N. M., Wakarchuk, W. W. (2005) J. Biol. Chem. 280, 4792-4802). Glycosylation of AcrA is lost if the pgl cluster contains a deletion of gne (Linton, D., Dorrell, N., Hitchen, P. G., Amber, S., Karlyshev, A. V., Morris, H. R., Dell, A., Valvano, M. A., Aebi, M. and Wren, B. W. (2005) Mol Microbiol. 55, 1695-1703). The ability of Z3206 to restore AcrA-glycosylation in the presence of the pgl operon Δgne was investigated in vivo by expressing AcrA (pWA2) together with the pgl locus Δgne complemented by either Gne (pMLBAD:gne) or Z3206 (pMLBAD:Z3206).

Total E. coli cell extracts were prepared for immunodetection analysis using cells at a concentration equivalent to 1 A$_{600}$ unit that were resuspended in 100 µl of SDS loading buffer (Laemmli, U. (1970) Nature 227, 680-685). Aliquots of 10 µl were loaded on 10% SDS-PAGE. Periplasmic extracts of E. coli cells were prepared by lysozyme treatment (Feldman, M. F., Wacker, M., Hernandez, M., Hitchen, P. G., Marolda, C. L., Kowarik, M., Morris, H. R., Dell, A., Valvano, M. A., Aebi, M. (2005) Proc Natl Acad Sci USA 102, 3016-3021), and 10 µl of the final sample (corresponding to 0.2 A$_{600}$ units of cells) was analyzed by SDS-PAGE. After being blotted on nitrocellulose membrane, sample was immunostained with the specific antiserum (Aebi, M., Gassenhuber, J., Domdey, H., and te Heesen, S. (1996) Glycobiology 6, 439-444). Anti-AcrA (Wacker, M., Linton, D., Hitchen, P. G., Nita-Lazar, M., Haslam, S. M., North, S. J., Panico, M., Morris, H. R., Dell, A., Wrenn, B. W., Aebi, M. (2002) Science 298, 1790-1793) antibodies were used. Anti-rabbit IgG-HRP (Bio-Rad) was used as secondary antibody. Detection was carried out with ECL™ Western blotting detection reagents (Amersham Biosciences).

As shown in FIG. 8, the glycosylated protein, which migrates slower than the unglycosylated form, was formed only when cells expressing pgl locus Δgne were complemented by One (lane 2). Z3206 was unable to restore glycosylation of the reporter glycoprotein (FIG. 8, lane 1). Accordingly, Z3206 does not complement glycosylation of AcrA in a Gne dependent glycosylation system. Expression of Gne and membrane-associated Z3206 were confirmed by immunodetection.

Example 9: Analysis of S. flexneri 6+/− Z3206 LPS

Figure 9:
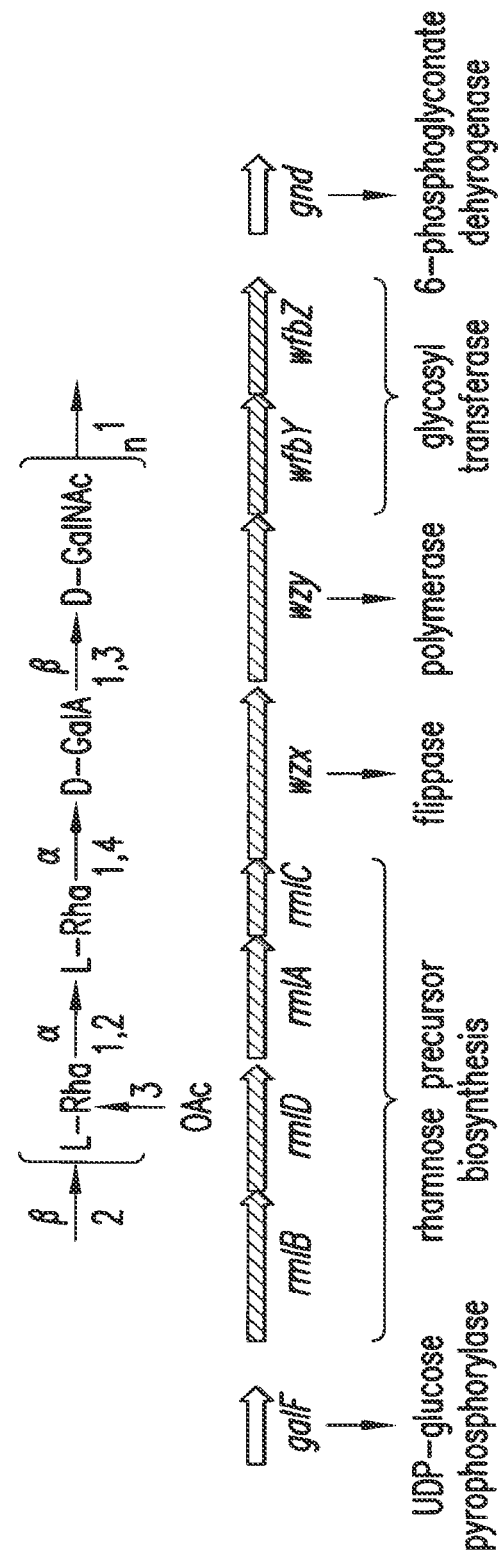
FIG. 9 shows the genes that have been identified by Liu B et al. (*Structure and genetics of Shigella O antigens* FEMS Microbiology Review, 2008. 32: p. 27).

In FIG. 9 are depicted some of the genes required for the biosynthesis of the Shigella flexneri 6 O-antigen: genes encoding enzymes for biosynthesis of nucleotide sugar precursors; genes encoding glycosyltransferases; genes encoding O antigen processing proteins; and genes encoding proteins responsible for the O-acetylation. The structure of the O antigen has been elucidated by Dmitriev, B. A. et al (Dmitriev. B. A., et al Somatic Antigens of Shigella Eur J Biochem, 1979. 98: p. 8; Liu B et al Structure and genetics of Shigella O antigens FEMS Microbiology Review, 2008. 32: p. 27).

To identify all the genes required for the biosynthesis of the Shigella flexneri 6 O-antigen a genomic library was constructed.

Cloning of S. flexneri 6 genomic DNA

S. flexneri 6 genomic DNA was isolated using a Macherey-Nagel NucleoSpin® Tissue Kit following the protocol for DNA isolation from bacteria. DNA was isolated from five S. flexneri 6 overnight cultures at 2 ml each and final elution was done with 100 µl elution buffer (5 mM Tris/HCl, pH 8.5). The eluted fractions were pooled, precipitated by isopropanol and the final pellet was resuspended in 52 µl TE buffer of which the total volume was subjected to end-repair according to the protocol given by CopyControl™ Fosmid Library Production Kit (EPICENTRE). End-repaired DNA was purified on a 1% low melting point agarose gel run with 1×TAE buffer, recovered and precipitated by ethanol as described in the kit protocol. Resuspension of the precipitated DNA was done in 7 μl TE buffer of which 0.15 μl DNA was ligated into pCC1FOS (SEQ ID NO: 27) according to the EPICENTRE protocol. Packaging of the ligation product into phage was performed according to protocol and the packaged phage was diluted 1:1 in phage dilution buffer of which 10 μl were used to infect 100 μl EPI300-T1 cells that were previous grown as described by EPICENTRE. Cells (110 μl) were plated six times with approximately 100 colonies per plate such that the six plates contain the entire S. flexneri 6 genomic library. Plates were developed by colony blotting and positive/negative colonies were western blotted and silver stained.

Colony Blotting

For colony blots a nitrocellulose membrane was laid over the solid agar plate, removed, washed three times in 1×PBST and treated in the same manner. The membrane was first blocked in 10% milk for one hour at room temperature after which it was incubated for one hour at room temperature in 2 ml 1% milk (in PBST) with the anti-type VI antiserum (primary antibody). After three washes in PBST at 10 minutes each, the membrane was incubated for another hour at room temperature in the secondary antibody, 1:20000 peroxidase conjugated goat-anti-rabbit IgG (Bio-Rad) in 2 ml 1% milk (in PBST). After a final three washes with PBST (10 minutes each) the membrane was developed in a UVP Chemi Doc Imaging System with a 1:1 mix of luminol and peroxide buffer provided by the SuperSignal® West Dura Extended Duration Substrate Kit (Thermo Scientific).

Figure 10:
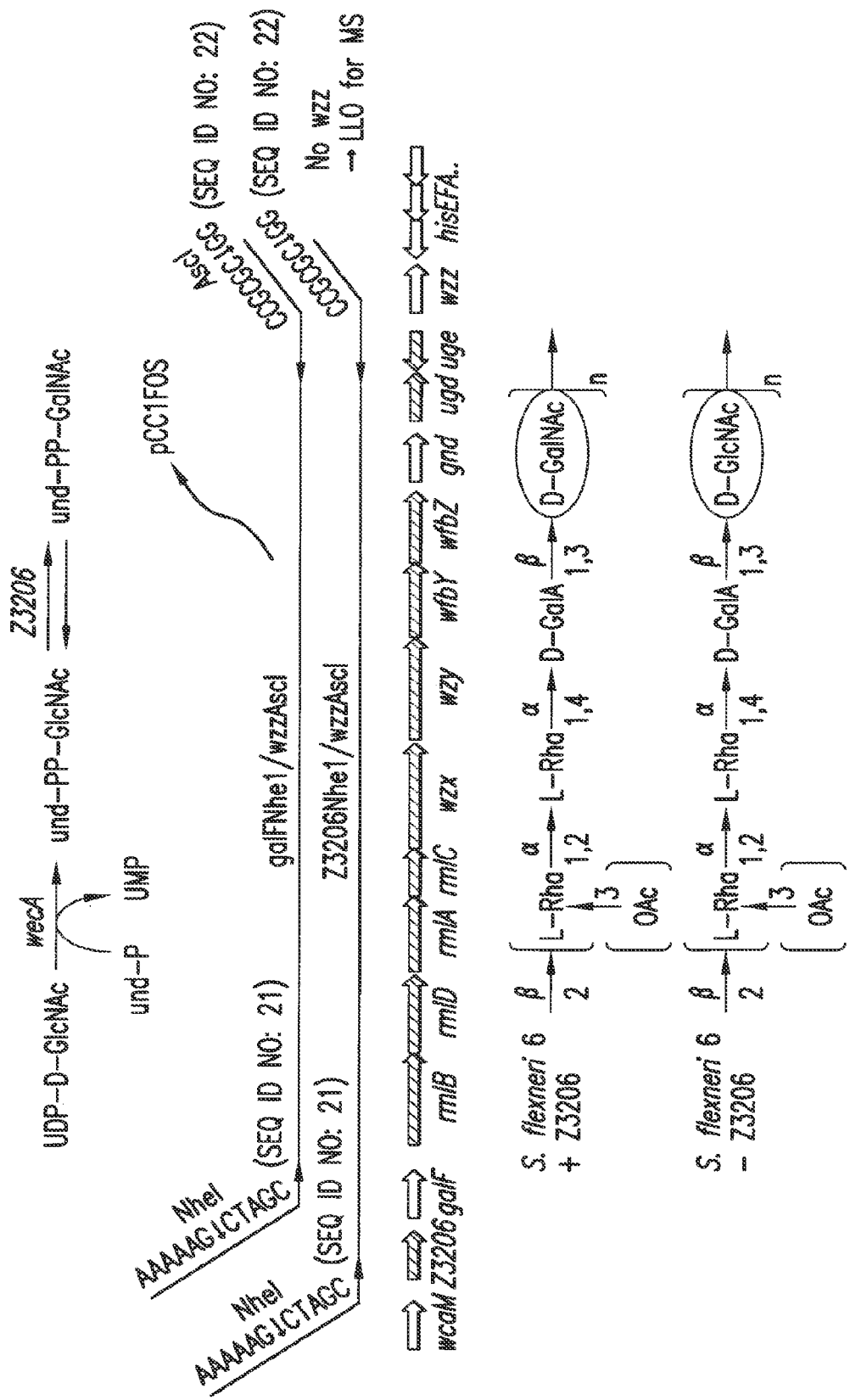
FIG. 10 is a scheme showing the DNA region containing the genes required to synthesize the *S. flexneri* 6 O antigen.

The clone reacting with S. flexneri 6 antiserum following production of a S. flexneri 6 genomic library was sequenced by primer walking out of the region previously sequenced by Liu et al. (Liu et al., 2008) reaching from rmlB to wtbZ (FIG. 9). Primers rmlB_rev and wfbZ_fwd (S. flexneri—Z3206) annealed in rmlB and wfbZ and were used to sequence the insert of the clone until wcaM and hisI/F were reached (S. flexneri+Z3206), respectively (FIG. 10).

In order to establish whether O antigen synthesis is maintained in clones lacking Z3206 (thus hindering epimerization of und-GlcNAc to und-GalNAc), two plasmids were constructed (SEQ ID NO. 28 and SEQ ID NO. 29) (FIG. 10), transformed into E. coli cells and analyzed by silver staining and western blot.

Figure 11:
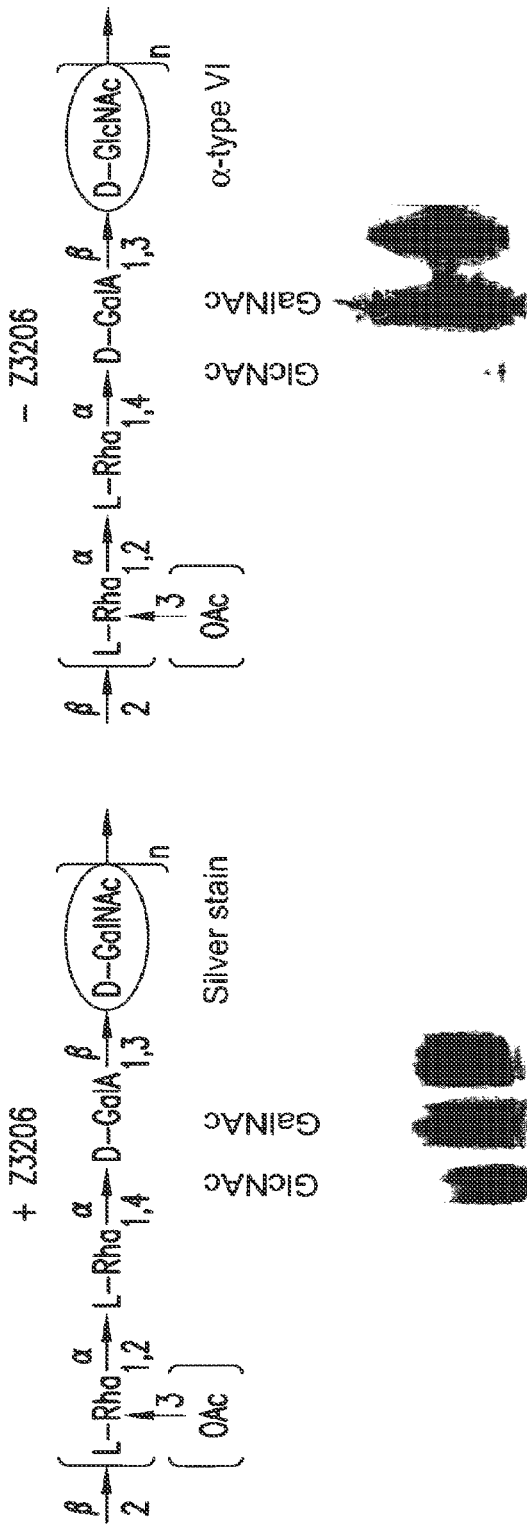
FIG. 11 shows expression of the *S. flexneri* 6 O antigen in *E. coli*. LPS was visualized by either silver staining or by transfer to nitrocellulose membranes and detection by antibodies directed against *S. flexneri* 6.

As shown in FIG. 11, LPS is produced in E. coli cells + or −Z3206. The O antigen can be produced without Z3206 however with lower production yield, which indicates that the efficiency of polysaccharide production without the epimerase (Z3206) is lower.

Example 10: Analysis of S. flexneri 6+/− Z3206 LLO

Purification of Undecaprenol-PP-O Antigen by C18 Column Chromatography

E. coli cells expressing S. flexeneri antigen+/− Z3206 were pelleted, washed once in 50 ml 0.9% NaCl and the final pellets were lyophilized overnight. The pellets were washed once in 30 ml 85-95% methanol, reextracted with 10:10:3 chloroform-methanol-water (v/v/v) and the extracts were converted to a two-phase Bligh/Dyer system by addition of water, resulting in a final ratio of 10:10:9 (C:M:W). Phases were separated by centrifugation and the upper aqueous phases were loaded each on a C18 Sep-Pak cartridge conditioned with 10 ml methanol and equilibrated with 10 ml 3:48:47 (C:M:W). Following loading, the cartridges were washed with 10 ml 3:48:47 (C:M:W) and eluted with 5 ml 10:10:3 (C:M:W). 20 OD samples of the loads, flow-throughs, washes and elutions of the C18 column were dried in an Eppendorf Concentrator Plus, washed with 250 μl methanol, reevaporated and washed a further three times with 30 μl ddH2O.

Glycolipid Hydrolysis

The glycolipid samples from the wash of the C18 column were hydrolysed by dissolving the dried samples in 2 ml n-propanol:2 M trifluoroacetic acid (1:1), heating to 50° C. for 15 minutes and evaporating to dryness under N2.

Oligosaccharide Labeling with 2-Aminobenzoate and HPLC

Labeling was done according to Bigge et al. (Bigge, 1995) and glycan cleanup was performed using the paper disk method described in Merry et al. (2002) (Merry et al., 2002). Separation of 2-AB labeled glycans was performed by HPLC using a GlycoSep-N normal phase column according to Royle et al. (Royle, 2002) but modified to a three solvent system. Solvent A was 10 mM ammonium formate pH 4.4 in 80% acetonitrole. Solvent B was 30 mM ammonium formate pH 4.4. in 40% acetonitrile. Solvent C was 0.5% formic acid. The column temperature was 30° C. and 2-AB labeled glycans were detected by fluorescence ($\lambda$ex=330 nm, $\lambda$em=420 nm). Gradient conditions were a linear gradient of 100% A to 100% B over 160 minutes at a flow rate of 0.4 ml/min, followed by 2 minutes 100% B to 100% C, increasing the flow rate to 1 ml/min. The column was washed for 5 minutes with 100% C, returning to 100% A over 2 minutes and running for 15 minutes at 100% A at a flow rate of 1 ml/min, then returning the flow rate to 0.4 ml/min for 5 minutes. All samples were injected in water.

Figure 12:
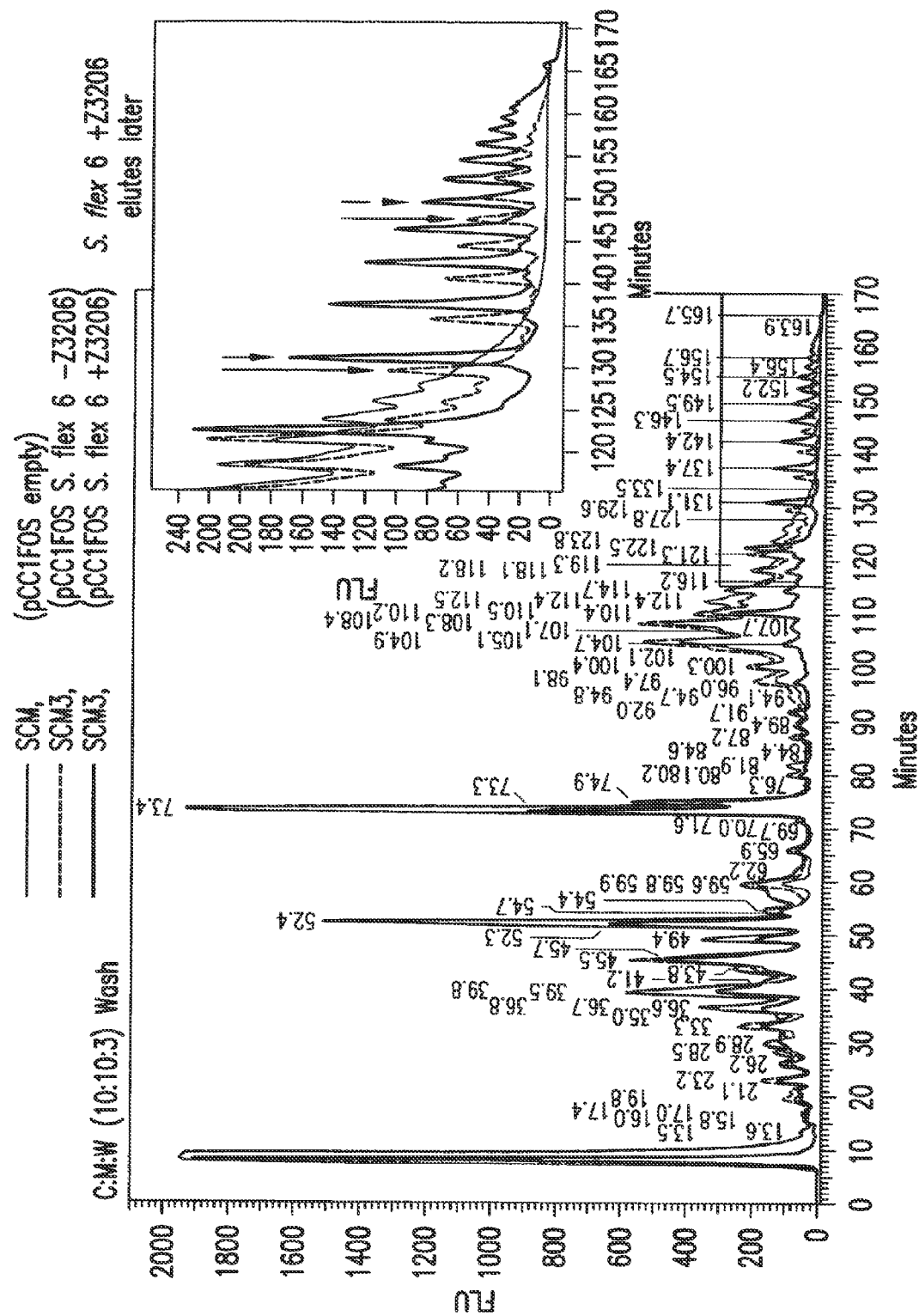
FIG. 12 shows HPLC of O antigen. LLO analysis of *E. coli* cells (SCM3) containing *S. flexneri*—Z3206, *E. coli* cells (SCM3) containing *S. flexneri*+Z3206 or empty *E. coli* (SCM3) cells.

The plasmids expressing the S. flexneri O-antigen with (SEQ ID NO: 29) or without (SEQ ID NO: 28) Z3206 were transformed into SCM3 cells (FIG. 10). Traces at late elution volumes shows a difference between the curves of the two samples containing the S. flexneri O antigen+/−Z3206 (FIG. 12). This difference in the elution pattern can be explained by a different oligosaccharide structure carrying a different monosaccharide at the reducing end: GlcNAc or GalNAc depending on the presence of the epimerase (Z3206).

Example 11: Analysis of pglB Specificity by Production and Characterization of Bioconjugate Produced from S. flexneri 6+/−Z3206

Figure 13:
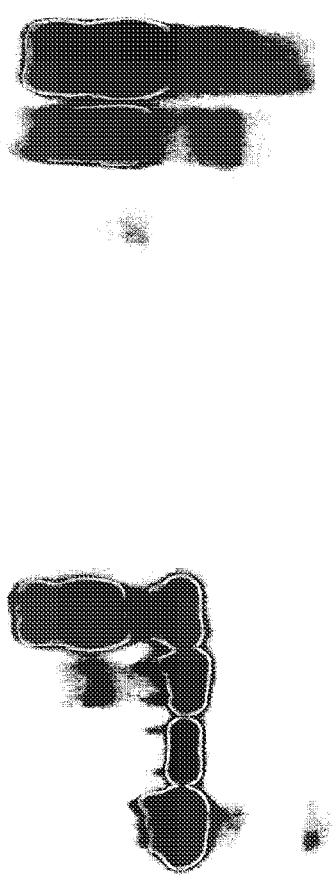
FIG. 13 shows Western blot of Nickel purified proteins from *E. coli* cells expressing EPA, pglB and *S. flexneri* 6 O-antigen+/−Z3206.

To assess whether pglB can transfer oligosaccharides having GlcNAc (S. flexneri 6 O-antigen) at the reducing end to the carrier protein EPA Nickel purified extracts from E. coli cells expressing EPA (SEQ ID NO: 25), PglB (SEQ ID NO: 26) and S. flexneri 6 O-antigen+/−Z3206 (SEQ ID NO: 29/SEQ ID NO: 28) were analyzed by western blot using anti EPA and anti type VI antibodies. The S. flexneri O6 antigen with and without GalNAc at the reducing end was transferred to EPA by PglB as detected by antiEPA and anti VI antisera (FIG. 13).

The O antigen is still produced and detected, but with lower production yield, which indicates that the efficiency of polysaccharide production without the epimerase is lower.

While this invention has been particularly shown and described with references to embodiments thereof, it will be understood by those skilled in the art that various changes in form and detail may be made therein without departing from the scope of the invention encompassed by the claims. Such various changes that will be understood by those skilled in the art as covered within the scope of the invention include, in particular, N-glycosylated proteins and bioconjugates comprising a glycan other than those from E. coli and S. flexneri with GalNAc at the reducing terminus.

Sequence Listing

Applicant: GlycoVaxyn AG
Title: Biosynthetic System That Produces Immunogenic
Polysaccharides In Prokaryotic Cells
Number of SEQ ID NOs: 29

Nucleotide Sequence for E. coli O157 Z3206
Length: 993
Type: DNA
Organism: E. coli O157
Sequence:

SEQ ID NO: 1

ATGAACGATAACGTTTTGCTCATAGGAGCTTCCGGATTCGTAGGAACCCGACTACTTGAAACGG

CAATTGCTGACTTTAATATCAAGAAGCTGGACAAACAGCAGAGCCACTTTTATCCAGAAATCAC

ACAGATTGGCGATGTTCGCCATCAACAGGCACTGGACCAGGCGTTAGTCGGTTTTGACACTGTT

GTACTACTGGCAGCGGAACACCGCGATGACGTCAGCCCTACTTCTCTCTATTATGATGTCAACG

TTCAGGGTAGCCGCAATGTGCTGGCGGCCATGGAAAAAATGGCGTTAAAAATATCATCTTTAC

CAGTTCCGTTGCTGTTTATGGTTTGAACAAACACAACCCTGACGAAAACCATCCACACGACCCT

TTGAACCACTACGGCAAAAGTAAGTGGCAGGCAGAGGAAGTGCTGCGTGAATGGTATAACAAAG

CACCAACAGAACGTTCATTAACCATCATCCGTGCTACCGTTATCTTCGGTGAACGCAACCGCGG

TAACGTCTATAACTTGCTGAAACAGATCGGTGGCGGCAAGTTTATGATGGTGGGCGCAGGGACT

AACTATAAGTCCATGGCTTATGTTGGAAACATTGTTGAGTTTATGAAGTACAAACTGAAGAATG

TTGCCGCAGGTTATGAGGTTTATAACTACGTTGATAAGCCAGACCTGAACATGAACCAGTTGGT

TGCTGAAGTTGAACAAAGCCTGAACAAAAAGATCCCTTCTATGCACTTGCCTTACCCACTAGGA

ATGCTGGGTGGATATTGCTTTGATATCCTGAGCAAAATTACGGGCAAAAAATACGCTGTCAGCT

CAGTGCGCGTGAAAAAATTCTGCGCAACAACACAGTTTGACGCAACGAAAGTGCATTCTTCAGG

TTTTGTGGCACCGTATACGCTGTCGCAAGGTCTGGATCGAAGACTGCAGTATGAATTCGTTCAT

GCCAAAAAGACGACATAACGTTTGTTTCTGAG

Amino Acid Sequence for Z3206
Length: 331
Type: PRT
Organism: E coli O157
Sequence:

SEQ ID NO: 2

MNDNVLLIGASGFVGTRLLETAIADFNIKNLDKQQSHFYPEITQIGDVRDQQALDQALVGFDTV

VLLAAEHRDDVSPTSLYYDVNVQGTRNVLAAMEKNGVKNIIFTSSVAVYGLNKHNPDENHPHDP

FNHYGKSKWQAEEVLREWYNKAPTERSLTIIRPTVIFGERNRGNVYNLLKQIAGGKFMMVGAGT

NYKSMAYVGNIVEFIKYKLKNVAAGYEVYNYVDKPDLNMNQLVAEVEQSLNKKIPSMHLPYPLG

MLGGYCFDILSKITGKKYAVSSVRVKKFCATTQFDATKVHSSGFVAPYTLSQGLDRTLQYEFVH

AKKDDITFVSE

Nucleotide Sequence for E. coli O55 gne
Locus AF461121_1 BCT 2 May 2002
Definition (UDP-GlcNAc 4-epimerase Gne [Escherichia coil])
Accession AAL67550
Length: 993
Type: DNA
Organism: E. coli O55
Sequence:

SEQ ID NO: 3

ATGAACGATA ACGTTTTGCT CATAGGAGCT TCCGGATTCG TAGGAACCCG

ACTACTTGAA ACGGCAATTG CTGACTTTAA TATCAAGAAC CTGGACAAAC

AGCAGAGCCA CTTTTATCCA GAAATCACAC AGATTGGTGA TGTTCGTGAT

CAACAGGCAC TCGACCAGGC GTTAGCCGGT TTTGACACTG TTGTGCTACT

GGCAGCGGAA CACCGCGATG ACGTCAGCCC TACTTCTCTC TATTATGATG

```
                                    -continued
_____
                              Sequence Listing
_____

TCAACGTTCA GGGTACCCGC AATGTGCTGG CGGCCATGGA AAAAAATGGC

GTTAAAAATA TCATCTTTAC CAGTTCCGTT GCTGTTTATG GTTTGAACAA

ACACAACCCT GACGAAAACC ATCCACACGA TCCTTTCAAC CACTACGGCA

AAAGTAAGTG GCAGGCAGAG GAAGTGCTGC GTGAATGGTA TAACAAAGCA

CCAACAGAAC GTTCATTAAC CATCATCCGT CCTACCGTTA TCTTCGGTGA

ACGGAACCGC GGTAACGTCT ATAACTTGCT GAAACAGATC GCTGGCGGCA

AGTTTATGAT GGTGGGCGCA GGGACTAACT ATAAGTCCAT GGCTTATGTT

GGAAACATTG TTGAGTTTAT CAAGTACAAA CTGAAGAATG TTGCCGCAGG

TTACGAGGTT TATAACTACG TTGATAAGCC AGACCTGAAC ATGAACCAGT

TGGTTGCTGA AGTTGAACAA AGCCTGAACA AAAGATCCC TTCTATGCAC

TTGCCTTACC CACTAGGAAT GCTGGGTGGA TATTGCTTTG ATATCCTGAG

CAAAATTACG GGCAAAAAAT ACGCTGTCAG CTCTGTGCGC GTGAAAAAAT

TCTGCGCAAC AACACAGTTT GACGCAACGA NAGTGCATTC TTCAGGTTTT

GTGGCACCGT ATACGCTGTC GCAAGGTCTG GATCGAACTC TGCAGTATGA

ATTCGTCCAT GCCAAAAAAG ACGACATAAC GTTTGTTTCT GAG
```

Amino Acid Sequence for E. coli O55 UDP-GlcNAc 4-epimerase Gne
Locus AF461121_1
Definition (UDP-GlcNAc 4-epimerase Gne [Escherichia coli])
Accession AAL67550
Length: 331 aa linear
Type: PRT
Organism: E. coli O55
Sequence:

SEQ ID NO: 4

```
mndnvlliga sgfvgtrlle taiadfnikn ldkqqshfyp eitqigdvrd qqaldqalag fdtvvllaae hrddvsptsl yydvnvqgtr nvlaamekng vkniiftssv avyglnkhnp denhphdpfn hygkskwqae evirewynka ptersltiir ptvifgernr gnvynllkqi aggkfmmvga gtnyksmayv gnivefikyk lknvaagyev ynyvdkpdln mnqlvaeveq sinkkipsmh lpyplgmlgg ycfdilskit gkkyayssvr vkkfcattqf datkvhssgf vapytlsqgl drtlqyefvh akkdditfvs e
```

Nucleotide Sequence for E. coli O86 gne1
Locus AAO37706 BCT 6 Dec. 2005
Definition UDP-GlcNAc C4-epimerase [Escherichia coli O86].
Accession AAO37706
Length: 993
Type: DNA
Organism: E. coli O86
Sequence:

SEQ ID NO. 5

```
ATGAACGATA ACGTTTTGCT CATAGGAGCT TCCGGATTCG TAGGAACCCG

ACTACTTGAA ACGGCAATTG CTGACTTTAA TATCAAGAAC CTGGACAAAC

AGCAGAGCCA CTTTTATCCA GAAATCACAC AGATTGGTGA TGTTCGTGAT

CAACAGGCAC TCGACCAGGC GTTAGCCGGT TTTGACACTG TTGTACTACT

GGCAGCGGAA CACCGCGATG ACGTCAGCCC TACTTCTCTC TATTATGATG

TCAACGTTCA GGGTACCCGC AATGTGCTGG CGGCCATGGA AAAAAATGGC

GTTAAAAATA TCATCTTTAC CAGTTCCGTT GCTGTTTATG GTTTGAACAA
```

```
ACACAACCCT GACGAAAACC ATCCACACGA CCCTTTCAAC CACTACGGCA

AAAGCAAGTG GCAGGCGGAG GAAGTGCTGC GTGAATGGTA TAACAAAGCA

CCAACAGAAC GTTCATTAAC TATCATCCGT CCTACCGTTA TCTTCGGTGA

ACGCAACCGC GGTAACGTCT ATAACTTGCT GAAACAGATC GCTGGCGGCA

AGTTTATGAT GGTGGGCGCA GGGACTAACT ATAAGTCCAT GGCTTATGTT

GGAAACATTG TTGAGTTTAT CAAGTACAAA CTGAAGAATG TTGCCGCAGG

TTACGAGGTT TATAACTACG TTGATAAGCC AGACCTGAAC ATGAACCAGT

TGGTTGCTGA AGTTGAACAA AGCCTGAACA AAAGATCCC TTCTATGCAC

TTGCCTTACC CACTAGGAAT GCTGGGTGGA TATTGCTTTG ATATCCTGAG

CAAAATTACG GGCAAAAAT ACGCTGTCAG CTCTGTGCGC GTGAAAAAAT

TCTGCGCAAC AACACAGTTT GACGCAACGA AAGTGCATTC TTCAGGTTTT

GTGGCACCGT ATACGCTGTC GCAAGGTCTG GATCGAACTC TGCAGTATGA

ATTCGTCCAT GCCAAAAAAG ACGACATAAC GTTTGTTTCT GAG
```

Amino Acid Sequence for E. coli O86 UDP-GlcNAc C4-epimerase
Locus AAO37706
Definition UDP-GlcNAc C4-epimerase [Escherichia coli O86].
Accession AAO37706
Length: 331 aa linear
Type: PRT
Organism: E. coli O86
Sequence:                                                                        SEQ ID NO: 6

```
mndnvlliga sgfvgtrlle taiadfnikn ldkqqshfyp eitqigdvrd qqaldqalag fdtvvllaae hrddvsptsl yydvnvqgtr nvlaamekng vkniiftssv avyglnkhnp denhphdpfn hygkskwqae evlrewynka ptersltiir ptvifgernr gnvynllkqi aggkfmmvga gtnyksmayv gnivefikyk lknvaagyev ynyvdkpdln mnqlvaeveq slnkkipsmh lpyplgmlgg ycfdilskit gkkyayssvr vkkfcattqf datkvhssgf vapytlsqgl drtlqyefvh akkdditfvs e
```

Nucleotide Sequence for Shigella boydii O18 gne
Locus ACD09753 BCT 5 May 2008
Definition UDP-N-acetylglucosamine 4-epimerase
[Shigella boydii CDC 3083-94].
Accession ACD09753
Length: 993
Type: DNA
Organism: Shigella boydii O18
Sequence:                                                                        SEQ ID NO: 7

```
ATGAACGATA ACGTTTTGCT CATAGGAGCT TCCGGATTCG TAGGAACCCG

ACTACTTGAA ACGGCAATTG CTGACTTTAA TATCAAGAAC CTGGACAAAC

AGCAGAGCCA TTTTTATCCA GCAATCACAC AGATTGGCGA TGTTCGTGAT

CAACAGGCAC TCGACCAGGC GTTAGCCGGT TTTGACACTG TTGTACTACT

GGCAGCGGAA CACCGCGATG ACGTCAGCCC TACTTCTCTC TATTATGATG

TCAACGTTCA GGGTACCCGC AATGTGCTGG CGGCCATGGA AAAAAATGGC

GTTAAAAATA TCATCTTTAC CAGTTCCGTT GCTGTTTATG GTTTGAACAA

ACACAACCCT GACGAAAACC ATCCACACGA CCCTTTCAAC CACTACGGCA

AAAGTAAGTG GCAGGCAGAG GAAGTGCTGC GTGAATGGTA TAACAAAGCA
```

-continued

Sequence Listing

```
CCAACAGAAC GTTCATTAAC CATCATCCGT CCTACCGTTA TCTTCGGTGA

ACGCAACCGC GGTAACGTCT ATAACTTGCT GAAACAGATC GCTGGCGGCA

AGTTTATGAT GGTGGGCGCA GGGACTAACT ATAAGTCCAT GGCTTATGTT

GGAAACATTG TTGAGTTTAT CAAGTACAAA CTGAAGAATG TTGCCGCAGG

TTATGAGGTT TATAACTATG TTGATAAGCC AGACCTGAAC ATGAACCAGT

TGGTTGCTGA AGTTGAACAA AGCCTGAACA AAAGATCCC TTCTATGCAC

TTGCCTTACC CACTAGGAAT GCTGGGTGGA TATTGCTTTG ATATCCTGAG

CAAAATTACG GGCAAAAAAT ACGCTGTCAG CTCTGTGCGC GTGAAAAAAT

TCTGCGCAAC AACACAGTTT GACGCAACGA AAGTGCATTC TTCAGGTTTT

GTGGCACCGT ATACGCTGTC GCAAGGTCTG GATCGAACTC TGCAGTATGA

ATTCGTCCAT GCCAAAAAAG ACGACATAAC GTTTGTTTCT GAG
```

Amino Acid Sequence for Shigella boydii O18 UDP-N-
acetylglucosamine 4-epimerase
Locus ACD09753
Definition UDP-N-acetylglucosamine 4-epimerase [*Shigella boydii* CDC 3083-94].
Accession ACD09753
Length: 331 aa linear
Type: PRT
Organism: *Shigella boydii* O18
Sequence:

SEQ ID NO: 8 mndnvlliga sgfvgtrile taiadfnikn ldkggshfyp aitqigdvrd qqaldqalag fdtvvliaae hrddvsptsi yydvnvqgtr nvlaamekng vkniiftssv avyglnkhnp denhphdpfn hygkskwqae evirewynka ptersltiir ptvifgernr gnvynllkqi aggkfmmvga gtnyksmayv gnivefikyk lknvaagyev ynyvdkpdln mnqlvaeveq sinkkipsmh lpyplgmlgg ycfdilskit gkkyayssvr vkkfcattqf datkvhssgf vapytlsggl drtlqyefvh akkdditfvs Nucleotide Sequence for *Salmonella enterica* O30 gne
Locus AAV34516 BCT 25 Oct. 2004
Definition UDP-GlcNAc 4-epimerase [*Salmonella enterica* subsp. *salamae serovar* Greenside].
Accession AAV34516
Length: 993
Type: DNA
Organism: *Salmonella enterica* O30
Sequence:

SEQ ID NO: 9

ATGAACGATA ACGTTTTGCT CATTGGTGCT TCCGGATTCG TAGGAACCCG

ACTCCTTGAA ACGGCAGTGG ATGATTTTAA TATCAAGAAC CTGGATAAAC

AGCAAAGCCA TTTCTACCCA GAGATTACAC ACATTGGCGA TGTTCGTGAC

CAACAAATCC TTGACCAGAC GTTGGTGGGT TTTGACACCG TAGTACTATT

GGCTGCGGAG CATCGTGATG ATGTTAGTCC TACCTCGCTT TATTATGATG

TCAACGTCCA GGGAACGCGT AATGTACTGG CGGCGATGGA AAAAAATGGT

GTAAAAAATA TCATTTTTAC CAGTTCCGTT GCAGTTTATG GACTCAACAA

GAAAAATCCT GACGAAACGC ACCCTCACGA TCCCTTTAAT CATTACGGAA

AAAGTAAATG GCAAGCAGAA GAAGTTCTGC GTGAGTGGCA TGCTAAAGCG

CCGAATGAGC GTTCTTTGAC CATAATTCGT CCTACCGTTA TTTTCGGGGA

```
GCGTAACCGC GGTAATGTAT ACAATCTCTT GAAACAGATC GCTGGTGGTA

AATTTGCGAT GGTTGGTCCG GGAACTAACT ATAAATCAAT GGCTTATGTT

GGTAATATCG TTGAGTTTAT CAAATTCAAA CTCAAGAATG TTACGGCGGG

CTATGAAGTT TATAATTATG TTGATAAACC TGATCTGAAT ATGAATCAAT

TGGTTGCTGA AGTAGAGCAG AGCCTGGGCA AAAAAATACC ATCGATGCAC

CTTCCATATC CATTAGGTAT GCTGGGGGGT TACTGTTTCG ATATCCTGAG

CAAAGTAACG GGCAAGAAGT ACGCTGTAAG TTCGGTTCGT GTTAAAAAAT

TCTGTGCGAC AACGCAGTTT GATGCAACAA AAGTGCATTC TTCTGGTTTT

GTTGCGCCAT ACACCTTATC TCAGGGGTTG GATCGTACAC TGCAATATGA

ATTTGTTCAT GCAAGAAAG ATGACATTAC ATTCGTTTCA GAG
```

Amino Acid Sequence for *Salmonella enterica* O30 UDP-GlcNAc 4-epimerase
Locus AAV34516
Definition UDP-GlcNAc 4-epimerase
[*Salmonella enterica* subsp. *salamae* serovar Greenside].
Accession AAV34516
Length: 331 aa linear
Type: PRT
Organism: *Salmonella enterica* O30
Sequence:

SEQ ID NO: 10

```
mndnviliga sgfvgtrlle tavddfnikn ldkggshfyp eithigdvrd ggildgtivg fdtvvilaae hrddvsptsl yydvnvqgtr nvlaamekng vkniiftssv avyglnkknp dethphdpfn hygkskwgae evlrewhaka pnersltiir ptvifgernr gnvyralkgi aggkfamvgp gtnyksmayv gnivefikfk lknvtagyev ynywdkpdln mnglvaeveg slgkkipsmh lpyplgmlgg ycfdilskvt gkkyayssvr vkkfcattqf datkvhssgf vapytlsggl drtlgyefvh akkdditfvs e
```

Nucleotide Sequence for *C. jejuni* gne
Locus YP_002344524 BCT 14 Sep. 2010
Definition UDP-GlcNAc/Glc 4-epimerase
[*Campylobacter jejuni* subsp. *jejuni*
Accession YP_002344524
Length: 987
Type: DNA
Organism: *C. jejuni*
Sequence:

SEQ ID NO: 11

```
ATGAAAATTCTTATTAGCGGTGGTGCAGGTTATATAGGTTCTCATACTTTAAGACAATT

TTTAAAAACAGATCATGAAATTTGTGTTTTAGATAATCTTTCTAAGGGTTCTAAAATCG

CAATAGAAGATTTGCAAAAAACAAGAGCTTTTAAATTTTTCGAACAAGATTTAAGTGAT

TTTCAAGGCGTAAAAGCATTGTTTGAGAGAGAAAAATTTGACGCTATTGTGCATTTTGC

AGCAAGCATTGAAGTTTTTGAAAGTATGCAAAATCCTTTAAAATATTATATGAACAACA

CTGTTAATACGACAAATCTCATCGAAACTTGTTTGCAAACTGGAGTGAATAAATTTATA

TTTTCTTCAACGGCGGCCACTTATGGCGAACCACAAACTCCCGTTGTGAGCGAAACAAG

TCCTTTAGCACCTATTAATCCTTATGGGCGTAGTAAGCTTATGAGTGAAGAAGTTTTGC

GTGATGCAAGTATGGCAAATCCTGAATTTAAGCATTGTATTTTAAGATATTTTAATGTT

GCAGGTGCTTGTATGGATTATACTTTAGGACAACGCTATCCAAAAGCGACTTTGCTTAT

AAAAGTTGCAGCTGAATGTGCCGCAGGAAAACGTGATAAACTTTTCATATTTGGCGATG
```

Sequence Listing

```
ATTATGATACAAAAGATGGTACTTGCATAAGAGATTTTATCCATGTAGATGATATTTCA

AGTGCACATTTAGCGGCTTTGGATTATTTAAAAGAGAATGAAAGCAATGTTTTTAATGT

AGGTTATGGACATGGTTTTAGCGTAAAAGAAGTGATTGAAGCGATGAAAAAAGTTAGCG

GAGTGGATTTTAAAGTAGAACTTGCCCCACGCCGTGCGGGTGATCCTAGTGTATTGATT

TCTGATGCAAGTAAAATCAGAAATCTTACTTCTTGGCAGCCTAAATATGATGATTTAGA

GCTTATTTGTAAATCTGCTTTTGATTGGGAAAAACAGTGTTAA
```

Amino Acid Sequence for *C. jejuni* UDP-GlcNAc/Glc 4-epimerase
Locus YP_002344524
Definition UDP-GlcNAc/Glc 4-epimerase
[*Campylobacter jejuni* subsp. *jejuni*
Accession YP_002344524
Length: 328 aa linear
Type: PRT
Organism: *C. jejuni*
Sequence:
SEQ ID NO: 12

```
mkilisggag yigshtlrqf lktdheicvl dnlskgskia iedlqktraf kffeqdlsdf qgvkalfere kfdaivhfaa sievfesmqn plkyymnntv nttnlietcl gtgvnkfifs staatygepq tpvvsetspl apinpygrsk imseevirda smanpefkhc ilryfnvaga cmdytlaqry pkatllikva aecaagkrdk ififgddydt kdgtcirdfi hvddissahi aaldylkene snvfnvgygh gfsvkeviea mkkvsgvdfk velaprragd psvlisdask irnltswqpk yddlelicks afdwekqc
```

Nucleotide Sequence for *E. coli* K12 galE
Locus AP_001390 BCT 30 Apr. 2010
Definition UDP-galactose-4-epimerase
[*Escherichia coli* str. K-12 substr. W3110].
Accession AP_001390
Length: 1,017
Type: DNA
Organism: *E. coli* K12
Sequence:
SEQ ID NO: 13

```
ATGAGAGTTCTGGTTACCGGTGGTAGCGGTTACATTGGAAGTCATACCTGTGTGCAA

TTACTGCAAAACGGTCATGATGTCATCATTCTTGATAACCTCTGTAACAGTAAGCGC

AGCGTACTGCCTGTTATCGAGCCTTTTAGGCGGCAAACATCCAACGTTTGTTGAAGG

CGATATTCGTAACGAAGCGTTGATGACCGAGATCCTGCACGATCACGCTATCGACAC

CGTGATCCACTTCGCCGGGCTGAAAGCCGTGGGCGAATCGGTACAAAAACCGCTGGA

ATATTACGACAACAATGTCAACGGCACTCTGCGCCTGATTAGCGCCATGCGCGCCGC

TAACGTCAAAAACTTTATTTTTAGCTCCTCCGCCACCGTTTATGGCGATCAGCCCAA

AATTCCATACGTTGAAAGCTTCCCGACCGGCACACCGCAAAGCCCTTACGGCAAAAG

CAAGCTGATGGTGGAACAGATCCTCACCGATCTGCAAAAAGCCCAGCCGGACTGGAG

CATTGCCCTGCTGCGCTACTTCAACCCGGTTGGCGCGCATCCGTCGGGCGATATGGG

CGAAGATCCGCAAGGCATTCCGAATAACCTGATGCCATACATCGCCCAGGTTGCTGT

AGGCCGTCGCGACTCGCTGGCGATTTTTGGTAACGATTATCCGACCGAAGATGGTAC

TGGCGTACGCGATTACATCCACGTAATGGATCTGGCGGACGGTCACGTCGTGGCGAT

GGAAAAACTGGCGAACAAGCCAGGCGTACACATCTACAACCTCGGCGCTGGCGTAGG

CAACAGCGTGCTGGACGTGGTTAATGCCTTCAGCAAAGCCTGCGGCAAACCGGTTAA

TTATCATTTTGCACCGCGTCGCGAGGGCGACCTTCCGGCCTACTGGGCGGACGCCAG
```

```
CAAAGCCGACCGTGAACTGAACTGGCGCGTAACGCGCACACTCGATGAAATGGCGCA

GGACACCTGGCACTGGCAGTCACGCCATCCACAGGGATATCCCGATTAA
```

Amino Acid Sequence for *E. coli* K12 UDP-galactose-4-epimerase
Locus AP_001390
Definition UDP-galactose-4-epimerase
[*Escherichia coli* str. K-12 substr. W3110].
Accession AP_001390
Length: 338 aa linear
Type: PRT
Organism: *E. coli* K12
Sequence:

SEQ ID NO: 14

```
mrvlvtqgsgyigshtcvqllqnghdviildnlcnskrsvlpvierlggkhptfvegdi rnealmteilhdhaidtvihfaglkavgesvqkpleyydnnvngtlrlisamraanvkn fifsssatvygdqpkipyvesfptgtpqspygksklmveqiltdlqkaqpdwsiallry fnpvgahpsgdmgedpqgipnnlmpyiaqvavgrrdslaifgndyptedgtgvrdyihv mdladghvvameklankpgvhiynigagvgnsvldvvnafskacgkpvnyhfaprregd lpaywadaskadrelnwrvtrtldemaqdtwhwqsrhpqgypd
```

Nucleotide Sequence for *E. coli* O86 gne2
Locus AAV85952 BCT 27 Mar. 2005
Definition Gne [*Escherichia coli* O86[.
Accession AAV85952
Length: 1,020
Type: DNA
Organism: *E. coli* O86
Sequence:

SEQ ID NO: 15

```
ATGGTGATTT TCGTAACAGG CGGTGCAGGA TATATTGGAT CCCATACCAT

ACTTGAGTTA CTTAATAATC GTCATGATGT CGTTTCGATA GATAATTTTG

TCAATTCCTC TATAGAATCA TTAAAAAGAC TAGAGCAAAT AACTAATAAG

AAAATTATTT CTTATCAAGG TGATATCCGT GATAAAAATC TACTTGATGA

GATTTTTTCA AGACACCATA TCCATGCTGT AATTCACTTT GCATCGTTAA

AATCTGTAGG TGAGTCTAAG TTAAAGCCCT TAGAGTATTA TTCTAATAAT

GTTGGTGGAA CTTTAGTATT ACTTCAATGC ATGAAGAGAT ATAACATTAA

TAAAATGATA TTTAGCTCTT CTGCTACTGT TTATGGGAGT AACAGTATCC

CTCCCCATAC GGAAGATAGA CGAATTGGTG AAACTACAAA CCCATATGGG

ACATCGAAAT TTATAATAGA AATAATTTTG AGTGATTATT GTGATAGTGA

TAATAATAAA TCAGTAATTG CACTGCGTTA CTTTAATCCA ATCGGAGCAC

ATAAGTCCGG GATGATTGGT GAAAATCCTA ACGGGATCCC TAATAATCTG

GTTCCTTATA TATCTAAAGT TGCACAAAAT CAACTTCCTG TATTAAATAT

TTATGGCAAC GATTATCCAA CTAAAGATGG TACAGGAGTA AGAGACTATA

TACATGTCTG TGATTTGGCT AAAGGGCATG TTAAAGCATT AGAATATATG

TTTTTAAATG ATGTCAATTA TGAAGCTTTT AATTTAGGTA CTGGTCAAGG

TTATTCTGTT TTAGAGATTG TAAAAATGTT TGAGATAGTC ACTAAAAAGA

GTATACCTGT TGCTATTTGT AATAGACGTG AGGGGGATGT TGCGGAGTCA

TGGGCGTCTG CTGATTTGGC ACATAAAAAG CTTTCCTGGA AAGCGCAAAA

AAATTTGAAA GAAATGATCG AAGATGTATG GCGTTGGCAA ACAACAATC

CAAATGGATA TAAAAAATAA
```

Sequence Listing

Amino Acid Sequence for E. coli O86 Gne
Locus AAV85952
Definition Gne [Escherichia coli O86].
Accession AAV85952
Length: 339 aa (gne2) linear
Type: PRT
Organism: E. coli O86
Sequence:

SEQ ID NO: 16 mvifvtggag yigshtilel innghdvvsi dnfvnssies lkrvegitnk kiisyggdir dknlldeifs rhhidavihf aslksvgesk lkpleyysnn vgctivllec mkryninkmi fsssatvygs nsipphtedr rigettnpyg tskfiieiil sdycdsdnnk svialryfnp igahksgmig enpngipnnl vpyiskvaqn qlpviniygn dyptkdgtgv rdyihvcdla kghvkaleym findvnyeaf nlgtgqgysv leivkmfeiv tkksipvaic nrregdvaes wasadlahkk lswkaeknlk emiedvwrwq tnnpngykk Nucleotide Sequence for synthetic oligonucleotide Z3206-
Fw (primer) encoding an end of Z3206; restriction sites underlined
Length: 30
Type: DNA
Sequence:

SEQ ID NO: 17

AAA<u>CCCGGG</u>ATGAACGATAACGTTTTGCTC

Nucleotide Sequence for synthetic oligonucleotide Z3206-
RvHA (primer) encoding an end of Z3206 with a hemoaglutinin
tag (HA tag); restriction sites underlined
Length: 60
Type: DNA
Organism:
Sequence:

SEQ ID NO: 18

AAA<u>TCTAGA</u>TTAAGCGTAATCTGGAACATCGTATGGGTACTCAGAAACAAACGTTATGTC

Nucleotide Sequence for synthetic oligonucleotide gne-Fw
(primer) with restriction sites underlined
Length: 29
Type: DNA
Organism:
Sequence:

SEQ ID NO: 19

AAA<u>CCATGG</u>ATGAAAATTCTTATTAGCGG

Nucleotide Sequence for synthetic oligonucleotide gne-RV
(primer) with restriction sites underlined
Length: 57
Type: DNA
Organism:
Sequence:

SEQ ID NO: 20

AAA<u>TCTAGA</u>TTAAGCGTAATCTGGAACATCGTATGGGTAGCACTGTTTTTCCCAATC

Nucleotide Sequence for oligonucleotide containing
restriction sites for NheI restriction enzyme
Length: 11
Type: DNA
Organism:
Sequence:

SEQ ID NO: 21

AAAAAGCTAGC

Nucleotide Sequence for oligonucleotide containing
restriction sites for AscI restriction enzyme
Length: 8
Type: DNA
Organism:
Sequence:

SEQ ID NO: 22

CCGCGCGG

Nucleotide Sequence for plasmid pMLBAD: Z3206 (E. coli O157
insert in plasmid) encoding Z3206 with a C-terminal hemagglutinin tag
Definition Ligation of product into Z3206-pMLBAD*
Features        Location/Qualifiers
CDS             2105..3098
                /label=Z3206
CDS             3098..3127
                /label=HA
Length: 7794 bp
Type: DNA circular UNA
Sequence:

SEQ ID NO: 23

```
   1 TCTACGGGGT CTGACGCTCA GTGGAACGAA ATCGATGAGC TCGCACGAAC CCAGTTGACA
  61 TAAGCCTGTT CGGTTCGTAA ACTGTAATGC AAGTAGCGTA TGCGCTCACG CAACTGGTCC
 121 AGAACCTTGA CCGAACGCAG CGGTGGTAAC GGCGCAGTGG CGGTTTTCAT GGCTTGTTAT
 181 GACTGTTTTT TTGTACAGTC TAGCCTCGGG CATCCAAGCT AGCTAAGCGC GTTACGCCGT
 241 GGGTCGATGT TTGATGTTAT GGAACAGCAA CGATGTTACG CAGCAGGGTA GTCGCCCTAA
 301 AACAAAGTTA GGCAGCCGTT GTGCTGGTGC TTTCTAGTAG TTGTTGTGGG GTAGGCAGTC
 361 AGAGCTCGAT TTGCTTGTCG CCATAATAGA TTCACAAGAA GGATTCGACA TGGGTCAAAG
 421 TAGCGATGAA GCCAACGCTC CCGTTGCAGG GCAGTTTGCG CTTCCCCTGA GTGCCACCTT
 481 TGGCTTAGGG GATCGCGTAC GCAAGAAATC TGGTGCCGCT TGGCAGGGTC AAGTCGTCGG
 541 TTGGTATTGC ACAAAACTCA CTCCTGAAGG CTATGCGGTC GAGTCCGAAT CCCACCCAGG
 601 CTCAGTGCAA ATTTATCCTG TGGCTGCACT TGAACGTGTG GCCTAAGCGA TATCTTAGGA
 661 TCTCCCATCG GTGATGTCGG CGATATAGGC GCCAGCAACC GCACCTGTGG CGCCGGTGAT
 721 GCCGGCCACG ATGCGTCCGG CGTAGAGGAT CTGCTCATGT TTGACAGCTT ATCATCGATG
 781 CATAATGTGC CTGTCAAATG GACGAAGCAG GGATTCTGCA AACCCTATGC TACTCCGTCA
 841 AGCCGTCAAT TGTCTGAATC GTTACCAATT ATGCAACTT GACGGCTACA TCATTCACTT
 901 TTTCTTCACA ACCGGCACGG AACTCGCTCG GGCTGGCCCC GGTGCATTTT TTAAATACCC
 961 GCGAGAAATA GAGTTGATCG TCAAAACCAA CATTGCGACC GACGGTGGCG ATAGGCATCC
1021 GGGTGGTGCT CAAAAGCAGC TTCGCCTGGC TGATACGTTG GTCCTCGCGC CAGCTTAAGA
1081 CGCTAATCCC TAACTGCTGG CGGAAAAGAT GTGACAGACG CGACGGCGAC AAGCAAACAT
1141 GCTGTGCGAC GCTGGCGATA TCAAAATTGC TGTCTGCCAG GTGATCGCTG ATGTACTGAC
1201 AAGCCTCGCG TACCCGATTA TCCATCGGTG GATGGAGCGA CTCGTTAATC GCTTCCATGC
1261 GCCGCAGTAA CAATTGCTCA AGCAGATTTA TCGCCAGCAG CTCCGAATAG CGCCCTTCCC
1321 CTTGCCCGGC GTTAATGATT TGCCCAAACA GGTCGCTGAA ATGCGGCTGG TGCGCTTCAT
1381 CCGGGCGAAA GAACCCCGTA TTGGCAAATA TTGACGGCCA GTTAAGCCAT TCATGCCAGT
1441 AGGCGCGCGG ACGAAAGTAA ACCCACTGGT GATACCATTC GCGAGCCTCC GGATGACGAC
1501 CGTAGTGATG AATCTCTCCT GGCGGGAACA GCAAAATATC ACCCGGTCGG CAAACAAATT
1561 CTCGTCCCTG ATTTTTCACC ACCCCCTGAC CGCGAATGGT GAGATTGAGA ATATAACCTT
1621 TCATTCCCAG CGGTCGGTCG ATAAAAAAAT CGAGATAACC GTTGGCCTCA ATCGGCGTTA
1681 AACCCGCCAC CAGATGGGCA TTAAACGAGT ATCCCGGCAG CAGGGGATCA TTTTGCGCTT
1741 CAGCCATACT TTTCATACTC CCGCCATTCA GAGAAGAAAC CAATTGTCCA TATTGCATCA
1301 GACATTGCCG TCACTGCGTC TTTTACTGGC TCTTCTGCT AACCAAACCG GTAACCCCGC
1861 TTATTAAAAG CATTCTGTAA CAAAGCGGGA CCAAAGCCAT GACAAAACG CGTAACAAAA
```

```
                              Sequence Listing

1921   GTGTCTATAA TCACGGCAGA AAAGTCCACA TTGATTATTT GCACGGCGTC ACACTTTGCT
1981   ATGCCATAGC ATTTTTATCC ATAAGATTAG CGGATCCTAC CTGACGCTTT TTATCGCAAC
2041   TCTCTACTGT TTCTCCATAC CCGTTTTTTT GGGCTAGCAG GAGGAATTCA CCATGGTACC
2101   CGGGATGAAC GATAACGTTT TGCTCATAGG AGCTTCCGGA TTCGTAGGAA CCCGACTACT
2161   TGAAACGGCA ATTGCTGACT TTAATATCAA GAACCTGGAC AAACAGCAGA GCCACTTTTA
2221   TCCAGAAATC ACACAGATTG GCGATGTTCG CGATCAACAG GCACTCGACC AGGCGTTAGT
2281   CGGTTTTGAC ACTGTTGTAC TACTGGCAGC GGAACACCGC GATGACGTCA GCCCTACTTC
2341   TCTCTATTAT GATGTCAACG TTCAGGGTAC CCGCAATGTG CTGGCGGCCA TGGAAAAAAA
2401   TGGCGTTAAA AATATCATCT TTACCAGTTC CGTTGCTGTT TATGGTTTGA ACAAACACAA
2461   CCCTGACGAA AACCATCCAC ACGACCCTTT CAACCACTAC GGCAAAAGTA AGTGGCAGGC
2521   AGAGGAAGTG CTGCGTGAAT GGTATAACAA AGCACCAACA GAACGTTCAT TAACCATCAT
2581   CCGTCCTACC GTTATCTTCG GTGAACGCAA CCGCGGTAAC GTCTATAACT TGCTGAAACA
2641   GATCGCTGGC GGCAAGTTTA TGATGGTGGG CGCAGGGACT AACTATAAGT CCATGGCTTA
2701   TGTTGGAAAC ATTGTTGAGT TTATCAAGTA CAAACTGAAG AATGTTGCCG CAGGTTATGA
2761   GGTTTATAAC TACGTTGATA AGCCAGACCT GAACATGAAC CAGTTGGTTG CTGAAGTTGA
2821   ACAAAGCCTG AACAAAAGA TCCCTTCTAT GCACTTGCCT TACCCACTAG GAATGCTGGG
2881   TGGATATTGC TTTGATATCC TGAGCAAAAT TACGGGCAAA AATACGCTG TCAGCTCAGT
2941   GCGCGTGAAA AAATTCTGCG CAACAACACA GTTTGACGCA ACGAAAGTGC ATTCTTCAGG
3001   TTTTGTGGCA CCGTATACGC TGTCGCAAGG TCTGGATCGA ACACTGCAGT ATGAATTCGT
3061   TCATGCCAAA AAAGACGACA TAACGTTTGT TTCTGAGTAC CCATACGATG TTCCAGATTA
3121   CGCTTAATCT AGAGTCGACC TGCAGGCATG CAAGCTTGGC TGTTTTGGCG GATGAGAGAA
3181   GATTTTCAGC CTGATACAGA TTAAATCAGA ACGCAGAAGC GGTCTGATAA ACAGAATTT
3241   GCCTGGCGGC AGTAGCGCGG TGGTCCCACC TGACCCCATG CCGAACTCAG AAGTGAAACG
3301   CCGTAGCGCC GATGGTAGTG TGGGGTCTCC CCATGCGAGA GTAGGGAACT GCCAGGCATC
3361   AAATAAAACG AAAGGCTCAG TCGAAAGACT GGGCCTTTCG TTTTATCTGT TGTTTGTCGG
3421   TGAACGCTCT CCTGAGTAGG ACAAATCCGC CGGGAGCGGA TTTGAACGTT GCGAAGCAAC
3481   GGCCCGGAGG GTGGCGGGCA GGACGCCCGC CATAAACTGC CAGGCATCAA ATTAAGCAGA
3541   AGGCCATCCT GACGGATGGC CTTTTTGCGT TTCTACAAAC TCTTCCACTC ACTACAGCAG
3601   AGCCATTTAA ACAACATCCC CTCCCCCTTT CCACCGCGTC AGACGCCCGT AGCAGCCCGC
3661   TACGGGCTTT TTCATGCCCT GCCCTAGCGT CCAAGCCTCA CGGCCGCGCT CGGCCTCTCT
3721   GGCGGCCTTC TGGCGCTGAG GTCTGCCTCG TGAAGAAGGT GTTGCTGACT CATACCAGGC
3781   CTGAATCGCC CCATCATCCA GCCAGAAAGT GAGGGAGCCA CGGTTGATGA GAGCTTTGTT
3841   GTAGGTGGAC CAGTTGGTGA TTTTGAACTT TGCTTTGCC ACGGAACGGT CTGCGTTGTC
3901   GGGAAGATGC GTGATCTGAT CCTTCAACTC AGCAAAAGTT CGATTTATTC AACAAAGCCG
3961   CCGTCCCGTC AAGTCAGCGT AATGCTCTGC CAGTGTTACA ACCAATTAAC CAATTCTGAT
4021   TAGAAAAACT CATCGAGCAT CAAATGAAAC TGCAATTTAT TCATATCAGG ATTATCAATA
4081   CCATATTTTT GAAAAGCCG TTTCTGTAAT GAAGGAGAAA ACTCACCGAG GCAGTTCCAT
4141   AGGATGGCAA GATCCTGGTA TCGGTCTGCG ATTCCGACTC GTCCAACATC AATACAACCT
4201   ATTAATTTCC CCTCGTCAAA AATAAGGTTA TCAAGCGAGA AATCACCATG AGTGACGACT
```

```
4261  GAATCCGGTG AGAATGGCAA AAGCTAAAAA GGCCGTAATA TCCAGCTGAA CGGTCTGGTT

4321  ATAGGTACAT TGAGCAACTG ACTGAAATGC CTCAAAATGT TCTTTACGAT GCCATTGGGA

4381  TATATCAACG GTGGTATATC CAGTGATTTT TTTCTCCATT TTAGCTTCCT TAGCTCCTGA

4441  AAATCTCGAT AACTCAAAAA ATACGCCCGG TAGTGATCTT ATTTCATTAT GGTGAAAGTT

4501  GGAACCTCTT ACGTGCCGAT CAACGTCTCA TTTTCGCCAA AAGTTGGCCC AGGGCTTCCC

4561  GGTATCAACA GGGACACCAG GATTTATTTA TTCTGCGAAG TGATCTTCCG TCACAGGTAT

4621  TTATTCGAAG ACGAAAGGGC CTCGTGATAC GCCTATTTTT ATAGGTTAAT GTCATGATAA

4681  TAATGGTTTC TTAGACGTCA GGTGGCACTT TTCGGGGAAA TGTGCGCGCC CGCGTTCCTG

4741  CTGGCGCTGG GCCTGTTTCT GGCGCTGGAC TTCCCGCTGT TCCGTCAGCA GCTTTTCGCC

4801  CACGGCCTTG ATGATCGCGG CGGCCTTGGC CTGCATATCC CGATTCAACG GCCCCAGGGC

4861  GTCCAGAACG GGCTTCAGGC GCTCCCGAAG GTCTCGGGCC GTCTCTTGGG CTTGATCGGC

4921  CTTCTTGCGC ATCTCACGCG CTCCTGCGGC GGCCTGTAGG GCAGGCTCAT ACCCCTGCCG

4981  AACCGCTTTT GTCAGCCGGT CGGCCACGGC TTCCGGCGTC TCAACGCGCT TGAGATTCC

5041  CAGCTTTTCG GCCAATCCCT GCGGTGCATA GGCGCGTGGC TCGACCGCTT GCGGGCTGAT

5101  GGTGACGTGG CCCACTGGTG GCCGCTCCAG GGCCTCGTAG AACGCCTGAA TGCGCGTGTG

5161  ACGTGCCTTG CTGCCCTCGA TGCCCCGTTG CAGCCCTAGA TCGGCCACAG CGGCCGCAAA

5221  CGTGGTCTGG TCGCGGGTCA TCTGCGCTTT GTTGCCGATG AACTCCTTGG CCGACAGCCT

5281  GCCGTCCTGC GTCAGCGGCA CCACGAACGC GGTCATGTGC GGGCTGGTTT CGTCACGGTG

5341  GATGCTGGCC GTCACGATGC GATCCGCCCC GTACTTGTCC GCCAGCCACT TGTGCGCCTT

5401  CTCGAAGAAC GCCGCCTGCT GTTCTTGGCT GGCCGACTTC CACCATTCCG GCTGGCCGT

5461  CATGACGTAC TCGACCGCCA ACACAGCGTC CTTGCGCCGC TTCTCTGGCA GCAACTCGCG

5521  CAGTCGGCCC ATCGCTTCAT CGGTGCTGCT GGCCGCCCAG TGCTCGTTCT CTGGCGTCCT

5581  GCTGGCGTCA GCGTTGGGCG TCTCGCGCTC GCGGTAGGCG TGCTTGAGAC TGGCCGCCAC

5641  GTTGCCCATT TTCGCCAGCT TCTTGCATCG CATGATCGCG TATGCCGCCA TGCCTGCCCC

5701  TCCCTTTTGG TGTCCAACCG GCTCGACGGG GGCAGCGCAA GGCGGTGCCT CCGGCGGGCC

5761  ACTCAATGCT TGAGTATACT CACTAGACTT TGCTTCGCAA AGTCGTGACC GCCTACGGCG

5821  GCTGCGGCGC CCTACGGGCT TGCTCTCCGG GCTTCGCCCT GCGCGGTCGC TGCGCTCCCT

5881  TGCCAGCCCG TGGATATGTG GACGATGGCC GCGAGCGGCC ACCGGCTGGC TCGCTTCGCT

5941  CGGCCCGTGG ACAACCCTGC TGGACAAGCT GATGGACAGG CTGCGCCTGC CCACGAGCTT

6001  GACCACAGGG ATTGCCCACC GGCTACCCAG CCTTCGACCA CATACCCACC GGCTCCAACT

6061  GCGCGGCCTG CGGCCTTGCC CCATCAATTT TTTTAATTTT CTCTGGGGAA AAGCCTCCGG

6121  CCTGCGGCCT GCGCGCTTCG CTTGCCGGTT GGACACCAAG TGGAAGGCGG GTCAAGGCTC

6181  GCGCAGCGAC CGCGCAGCGG CTTGGCCTTG ACGCGCCTGG AACGACCCAA GCCTATGCGA

6241  GTGGGGGCAG TCGAAGGCGA AGCCCGCCCG CCTGCCCCCC GAGCCTCACG GCGGCGAGTG

6301  CGGGGGTTCC AAGGGGGCAG CGCCACCTTG GGCAAGGCCG AAGGCCGCGC AGTCGATCAA

6361  CAAGCCCCGG AGGGGCCACT TTTTGCCGGA GGGGGAGCCG CGCCGAAGGC GTGGGGGAAC

6421  CCCGCAGGGG TGCCCTTCTT TGGGCACCAA AGAACTAGAT ATAGGGCGAA ATGCGAAAGA

6481  CTTAAAAATC AACAACTTAA AAAGGGGGG TACGCAACAG CTCATTGCGG CACCCCCGC
```

-continued

| | | | | | |
|---|---|---|---|---|---|
| 6541 | AATAGCTCAT | TGCGTAGGTT | AAAGAAAATC | TGTAATTGAC | TGCCACTTTT | ACGCAACGCA |
| 6601 | TAATTGTTGT | CGCGCTGCCG | AAAAGTTGCA | GCTGATTGCG | CATGGTGCCG | CAACCGTGCG |
| 6661 | GCACCCTACC | GCATGGAGAT | AAGCATGGCC | ACGCAGTCCA | GAGAAATCGG | CATTCAAGCC |
| 6721 | AAGAACAAGC | CCGGTCACTG | GGTGCAAACG | AACGCAAAG | CGCATGAGGC | GTGGGCCGGG |
| 6781 | CTTATTGCGA | GGAAACCCAC | GGCGGCAATG | CTGCTGCATC | ACCTCGTGGC | GCAGATGGGC |
| 6841 | CACCAGAACG | CCGTGGTGGT | CAGCCAGAAG | ACACTTTCCA | AGCTCATCGG | ACGTTCTTTG |
| 6901 | CGGACGGTCC | AATACGCAGT | CAAGGACTTG | GTGGCCGAGC | GCTGGATCTC | CGTCGTGAAG |
| 6961 | CTCAACGGCC | CCGGCACCGT | GTCGGCCTAC | GTGGTCAATG | ACCGCGTGGC | GTGGGGCCAG |
| 7021 | CCCCGCGACC | AGTTGCGCCT | GTCGGTGTTC | AGTGCCGCCG | TGGTGGTTGA | TCACGACGAC |
| 7081 | CAGGACGAAT | CGCTGTTGGG | GCATGGCGAC | CTGCGCCGCA | TCCCGACCCT | GTATCCGGGC |
| 7141 | GAGCAGCAAC | TACCGACCGG | CCCCGGCGAG | GAGCCGCCCA | GCCAGCCCGG | CATTCCGGGC |
| 7201 | ATGGAACCAG | ACCTGCCAGC | CTTGACCGAA | ACGGAGGAAT | GGGAACGGCG | CGGGCAGCAG |
| 7261 | CGCCTGCCGA | TGCCCGATGA | GCCGTGTTTT | CTGGACGATG | GCGAGCCGTT | GGAGCCGCCG |
| 7321 | ACACGGGTCA | CGCTGCCGCG | CCGGTAGCAC | TTGGGTTGCG | CAGCAACCCG | TAAGTGCGCT |
| 7381 | GTTCCAGACT | ATCGGCTGTA | GCCGCCTCGC | CGCCCTATAC | CTTGTCTGCC | TCCCCGCGTT |
| 7441 | GCGTCGCGGT | GCATGGAGCC | GGGCCACCTC | GACCTGAATG | GAAGCCGGCG | GCACCTCGCT |
| 7501 | AACGGATTCA | CCGTTTTTAT | CAGGCTCTGG | GAGGCAGAAT | AAATGATCAT | ATCGTCAATT |
| 7561 | ATTACCTCCA | CGGGGAGAGC | CTGAGCAAAC | TGGCCTCAGG | CATTTGAGAA | GCACACGGTC |
| 7621 | ACACTGCTTC | CGGTAGTCAA | TAAACCGGTA | AACCAGCAAT | AGACATAAGC | GGCTATTTAA |
| 7681 | CGACCCTGCC | CTGAACCGAC | GACCGGGTCG | AATTTGCTTT | CGAATTTCTG | CCATTCATCC |
| 7741 | GCTTATTATC | ACTTATTCAG | GCGTAGCACC | AGGCGTTTAA | GTCGACCAAT | AACC |

Nucleotide Sequence for pMLBAD: gne (E. coli O157 insert
in plasmid) which encodes Gne with a C-terminal hemagglutinin tag
Locus gne-pMLBAD
Definition Ligation of dig galE into pmlbad did (NcoI-XbaI)
Features        Location/Qualifiers
CDS             2097..3080
                /label=galE
CDS             3081..3107
                /label=HA
Region          3108..3110
                /label=stop
Length: 7776 bp
Type: DNA circular UNA
Sequence:
                                                              SEQ ID NO: 24

| | | | | | |
|---|---|---|---|---|---|
| 1 | TCTACGGGGT | CTGACGCTCA | GTGGAACGAA | ATCGATGAGC | TCGCACGAAC | CCAGTTGACA |
| 61 | TAAGCCTGTT | CGGTTCGTAA | ACTGTAATGC | AAGTAGCGTA | TGCGCTCACG | CAACTGGTCC |
| 121 | AGAACCTTGA | CCGAACGCAG | CGGTGGTAAC | GGCGCAGTGG | CGGTTTTCAT | GGCTTGTTAT |
| 181 | GACTGTTTTT | TTGTACAGTC | TAGCCTCGGG | CATCCAAGCT | AGCTAAGCGC | GTTACGCCGT |
| 241 | GGGTCGATGT | TTGATGTTAT | GGAACAGCAA | CGATGTTACG | CAGCAGGGTA | GTCGCCCTAA |
| 301 | AACAAAGTTA | GGCAGCCGTT | GTGCTGGTGC | TTTCTAGTAG | TTGTTGTGGG | GTAGGCAGTC |
| 361 | AGAGCTCGAT | TTGCTTGTCG | CCATAATAGA | TTCACAAGAA | GGATTCGACA | TGGGTCAAAG |
| 421 | TAGCGATGAA | GCCAACGCTC | CCGTTGCAGG | GCAGTTTGCG | CTTCCCCTGA | GTGCCACCTT |
| 481 | TGGCTTAGGG | GATCGCGTAC | GCAAGAAATC | TGGTGCCGCT | TGGCAGGGTC | AAGTCGTCGG |
| 541 | TTGGTATTGC | ACAAAACTCA | CTCCTGAAGG | CTATGCGGTC | GAGTCCGAAT | CCCACCCAGG |

-continued

| | Sequence Listing |
|---|---|
| 601 | CTCAGTGCAA ATTTATCCTG TGGCTGCACT TGAACGTGTG GCCTAAGCGA TATCTTAGGA |
| 661 | TCTCCCATCG GTGATGTCGG CGATATAGGC GCCAGCAACC GCACCTGTGG CGCCGGTGAT |
| 721 | GCCGGCCACG ATGCGTCCGG CGTAGAGGAT CTGCTCATGT TTGACAGCTT ATCATCGATG |
| 781 | CATAATGTGC CTGTCAAATG GACGAAGCAG GGATTCTGCA AACCCTATGC TACTCCGTCA |
| 841 | AGCCGTCAAT TGTCTGATTC GTTACCAATT ATGACAACTT GACGGCTACA TCATTCACTT |
| 901 | TTTCTTCACA ACCGGCACGG AACTCGCTCG GCTGGCCCC GGTGCATTTT TTAAATACCC |
| 961 | GCGAGAAATA GAGTTGATCG TCAAAACCAA CATTGCGACC GACGGTGGCG ATAGGCATCC |
| 1021 | GGGTGGTGCT CAAAAGCAGC TTCGCCTGGC TGATACGTTG GTCCTCGCGC CAGCTTAAGA |
| 1081 | CGCTAATCCC TAACTGCTGG CGGAAAAGAT GTGACAGACG CGACGGCGAC AAGCAAACAT |
| 1141 | GCTGTGCGAC GCTGGCGATA TCAAAATTGC TGTCTGCCAG GTGATCGCTG ATGTACTGAC |
| 1201 | AAGCCTCGCG TACCCGATTA TCCATCGGTG GATGGAGCGA CTCGTTAATC GCTTCCATGC |
| 1261 | GCCGCAGTAA CAATTGCTCA AGCAGATTTA TCGCCAGCAG CTCCGAATAG CGCCCTTCCC |
| 1321 | CTTGCCCGGC GTTAATGATT TGCCCAAACA GGTCGCTGAA ATGCGGCTGG TGCGCTTCAT |
| 1381 | CCGGGCGAAA GAACCCCGTA TTGGCAAATA TTGACGGCCA GTTAAGCCAT TCATGCCAGT |
| 1441 | AGGCGCGCGG ACGAAAGTAA ACCCACTGGT GATACCATTC GCGAGCCTCC GGATGACGAC |
| 1501 | CGTAGTGATG AATCTCTCCT GGCGGGAACA GCAAAATATC ACCCGGTCGG CAAACAAATT |
| 1561 | CTCGTCCCTG ATTTTTCACC ACCCCCTGAC CGCGAATGGT GAGATTGAGA ATATAACCTT |
| 1621 | TCATTCCCAG CGGTCGGTCG ATAAAAAAAT CGAGATAACC CTTGGCCTCA ATCGGCGTTA |
| 1681 | AACCCGCCAC CAGATGGGCA TTAAACGAGT ATCCCGGCAG CAGGGGATCA TTTTGCGCTT |
| 1741 | CAGCCATACT TTTCATACTC CCGCCATTCA GAGAAGAAAC CAATTGTCCA TATTGCATCA |
| 1801 | GACATTGCCG TCACTGCGTC TTTTACTGGC TCTTCTCGCT AACCAAACCG GTAACCCCGC |
| 1861 | TTATTAAAAG CATTCTGTAA CAAAGCGGGA CCAAAGCCAT GACAAAAACG CGTAACAAAA |
| 1921 | GTGTCTATAA TCACGGCAGA AAAGTCCACA TTGATTATTT GCACGGCGTC ACACTTTGCT |
| 1981 | ATGCCATAGC ATTTTTATCC ATAAGATTAG CGGATCCTAC CTGACGCTTT TTATCGCAAC |
| 2041 | TCTCTACTGT TTCTCCATAC CCGTTTTTTT GGGCTAGCAG GAGGAATTCA CCATGGATGA |
| 2101 | AAATTCTTAT TAGCGGTGGT GCAGGTTATA TAGGTTCTCA TACTTTAAGA CAATTTTTAA |
| 2161 | AAACAGATCA TGAAATTTGT GTTTTAGATA ATCTTTCTAA GGGTTCTAAA ATCGCAATAG |
| 2221 | AAGATTTGCA AAAAATAAGA ACTTTTAAAT TTTTTGAACA AGATTTAAGT GATTTTCAAG |
| 2281 | GCGTAAAAGC ATTGTTTGAG AGAGAAAAAT TTGACGCTAT TGTGCATTTT GCAGCGAGCA |
| 2341 | TTGAAGTTTT TGAAAGTATG CAAACCCTT TAAAGTATTA TATGAATAAC ACTGTTAATA |
| 2401 | CGACAAATCT CATCGAAACT TGTTTGCAAA CTGGAGTGAA TAAATTTATA TTTTCTTCAA |
| 2461 | CGGCAGCCAC TTATGGCGAA CCACAAACTC CCGTTGTGAG CGAAACAAGT CCTTTAGCAC |
| 2521 | CTATTAATCC TTATGGGCGT AGTAAGCTTA TGAGCGAAGA GGTTTTGCGT GATGCAAGTA |
| 2581 | TGGCAAATCC TGAATTTAAG CATTGTATTT TAAGATATTT TAATGTTGCA GGTGCTTGCA |
| 2641 | TGGATTATAC TTTAGGACAA CGCTATCCAA AAGCGACTTT GCTTATAAAA GTTGCAGCTG |
| 2701 | AATGTGCCGC AGAAAAACGT AATAAACTTT TCATATTTGG CGATGATTAT GATACAAAAG |
| 2761 | ATGGCACTTG CATAAGAGAT TTTATCCATG TGGATGATAT TTCAAGTGCG CATTTATCGG |
| 2821 | CTTTGGATTA TTTAAAAGAG AATGAAAGCA ATGTTTTTAA TGTAGGTTAA GGACATGGTT |
| 2881 | TTAGCGTAAA AGAAGTGATT GAAGCGATGA AAAAAGTTAG CGGAGTGGAT TTTAAAGTAG |

```
2941  AACTTGCCCC ACGCCGTGCG GGTGATCCTA GTGTATTGAT TTCTGATGCA AGTAAAATCA
3001  GAAATCTTAC TTCTTGGCAG CCTAAATATG ATGATTTAGG GCTTATTTGT AAATCTGCTT
3061  TTGATTGGGA AAAACAGTGC TACCCATACG ATGTTCCAGA TTACGCTTAA TCTAGAGTCG
3121  ACCTGCAGGC ATGCAAGCTT GGCTGTTTTG GCGGATGAGA GAAGATTTTC AGCCTGATAC
3181  AGATTAAATC AGAACGCAGA AGCGGTCTGA TAAAACAGAA TTTGCCTGGC GGCAGTAGCG
3241  CGGTGGTCCC ACCTGACCCC ATGCCGAACT CAGAAGTGAA ACGCCGTAGC GCCGATGGTA
3301  GTGTGGGGTC TCCCCATGCG AGAGTAGGGA ACTGCCAGGC ATCAAATAAA ACGAAAGGCT
3361  CAGTCGAAAG ACTGGGCCTT TCGTTTTATC TGTTGTTTGT CGGTGAACGC TCTCCTGAGT
3421  AGGACAAATC CGCCGGGAGC GGATTTGAAC GTTGCGAAGC AACGGCCCGG AGGGTGGCGG
3481  GCAGGACGCC CGCCATAAAC TGCCAGGCAT CAAATTAAGC AGAAGGCCAT CCTGACGGAT
3541  GGCCTTTTTG CGTTTCTACA AACTCTTCCA CTCACTACAG CAGAGCCATT TAAACAACAT
3601  CCCCTCCCCC TTTCCACCGC GTCAGACGCC CGTAGCAGCC CGCTACGGGC TTTTTCATGC
3661  CCTGCCCTAG CGTCCAAGCC TCACGCCGC GCTCGGCCTC TCTGGCGGCC TTCTGGCGCT
3721  GAGGTCTGCC TCGTGAAGAA GGTGTTGCTG ACTCATACCA GGCCTGAATC GCCCCATCAT
3781  CCAGCCAGAA AGTGAGGGAG CCACGGTTGA TGAGAGCTTT GTTGTAGGTG GACCAGTTGG
3841  TGATTTTGAA CTTTTGCTTT GCCACGGAAC GGTCTGCGTT GTCGGGAAGA TGCGTGATCT
3901  GATCCTTCAA CTCAGCAAAA GTTCGATTTA TTCAACAAAG CCGCCGTCCC GTCAAGTCAG
3961  CGTAATGCTC TGCCAGTGTT ACAACCAATT AACCAATTCT GATTAGAAAA ACTCATCGAG
4021  CATCAAATGA AACTGCAATT TATTCATATC AGGATTATCA ATACCATATT TTTGAAAAAG
4081  CCGTTTCTGT AATGAAGGAG AAAACTCACC GAGGCAGTTC CATAGGATGG CAAGATCCTG
4141  GTATCGGTCT GCGATTCCGA CTCGTCCAAC ATCAATACAA CCTATTAATT TCCCCTCGTC
4201  AAAAATAAGG TTATCAAGCG AGAAATCACC ATGAGTGACG ACTGAATCCG GTGAGAATGG
4261  CAAAAGCTAA AAAGGCCGTA ATATCCAGCT GAACGGTCTG GTTATAGGTA CATTGAGCAA
4321  CTGACTGAAA TGCCTCAAAA TGTTCTTTAC GATGCCATTG GGATATATCA ACGGTGGTAT
4381  ATCCAGTGAT TTTTTTCTCC ATTTTAGCTT CCTTAGCTCC TGAAAATCTC GATAACTCAA
4441  AAAATACGCC CGGTAGTGAT CTTATTTCAT TATGGTGAAA GTTGGAACCT CTTACGTGCC
4501  GATCAACGTC TCATTTTCGC CAAAAGTTGG CCCAGGGCTT CCCGGTATCA ACAGGGACAC
4561  CAGGATTTAT TTATTCTGCG AAGTGATCTT CCGTCACAGG TATTTATTCG AAGACGAAAG
4621  GGCCTCGTGA TACGCCTATT TTTATAGGTT AATGTCATGA TAATAATGGT TTCTTAGACG
4681  TCAGGTGGCA CTTTTCGGGG AAATGTGCGC GCCCGCGTTC CTGCTGGCGC TGGGCCTGTT
4741  TCTGGCGCTG GACTTCCCGC TGTTCCGTCA GCAGCTTTTC GCCCACGGCC TTGATGATCG
4801  CGGCGGCCTT GGCCTGCATA TCCCGATTCA ACGGCCCCAG GGCGTCCAGA ACGGGCTTCA
4861  GGCGCTCCCG AAGGTCTCGG GCCGTCTCTT GGGCTTGATC GGCCTTCTTG CGCATCTCAC
4921  GCGCTCCTGC GGCGGCCTGT AGGGCAGGCT CATACCCCTG CCGAACCGCT TTTGTCAGCC
4981  GGTCGGCCAC GGCTTCCGGC GTCTCAACGC GCTTTGAGAT TCCCAGCTTT TCGGCCAATC
5041  CCTGCGGTGC ATAGGCGCGT GGCTCGACCG CTTGCGGGCT GATGGTGACG TGGCCCACTG
5101  GTGGCCGCTC CAGGGCCTCG TAGAACGCCT GAATGCGCGT GTGACGTGCC TTGCTGCCCT
5161  CGATGCCCCG TTGCAGCCCT AGATCGGCCA CAGCGGCCGC AAACGTGGTC TGGTCGCGGG
```

-continued

Sequence Listing

```
5221  TCATCTGCGC TTTGTTGCCG ATGAACTCCT TGGCCGACAG CCTGCCGTCC TGCGTCAGCG
5281  GCACCACGAA CGCGGTCATG TGCGGGCTGG TTTCGTCACG GTGGATGCTG GCCGTCACGA
5341  TGCGATCCGC CCCGTACTTG TCCGCCAGCC ACTTGTGCGC CTTCTCGAAG AACGCCGCCT
5401  GCTGTTCTTG GCTGGCCGAC TTCCACCATT CCGGGCTGGC CGTCATGACG TACTCGACCG
5461  CCAACACAGC GTCCTTGCGC CGCTTCTCTG GCAGCAACTC GCGCAGTCGG CCCATCGCTT
5521  CATCGGTGCT GCTGGCCGCC CAGTGCTCGT TCTCTGGCGT CCTGCTGGCG TCAGCGTTGG
5581  GCGTCTCGCG CTCGCGGTAG GCGTGCTTGA GACTGGCCGC CACGTTGCCC ATTTTCGCCA
5641  GCTTCTTGCA TCGCATGATC GCGTATGCCG CCATGCCTGC CCCTCCCTTT TGGTGTCCAA
5701  CCGGCTCGAC GGGGGCAGCG CAAGGCGGTG CCTCCGGCGG CCACTCAAT GCTTGAGTAT
5761  ACTCACTAGA CTTTGCTTCG CAAAGTCGTG ACCGCCTACG GCGGCTGCGG CGCCCTACGG
5821  GCTTGCTCTC CGGGCTTCGC CCTGCGCGGT CGCTGCGCTC CCTTGCCAGC CCGTGGATAT
5881  GTGGACGATG GCCGCGAGCG GCCACCGGCT GGCTCGCTTC GCTCGGCCCG TGGACAACCC
5941  TGCTGGACAA GCTGATGGAC AGGCTGCGCC TGCCCACGAG CTTGACCACA GGGATTGCCC
6001  ACCGGCTACC CAGCCTTCGA CCACATACCC ACCGGCTCCA ACTGCGCGGC CTGCGGCCTT
6061  GCCCCATCAA TTTTTTTAAT TTTCTCTGGG GAAAAGCCTC CGGCCTGCGG CCTGCGCGCT
6121  TCGCTTGCCG GTTGGACACC AAGTGGAAGG CGGGTCAAGG CTCGCGCAGC GACCGCGCAG
6181  CGGCTTGGCC TTGACGCGCC TGGAACGACC CAAGCCTATG CGAGTGGGGG CAGTCGAAGG
6241  CGAAGCCCGC CCGCCTGCCC CCCGAGCCTC ACGGCGGCGA GTGCGGGGGT TCCAAGGGGG
6301  CAGCGCCACC TTGGGCAAGG CCGAAGGCCG CGCAGTCGAT CAACAAGCCC CGGAGGGGCC
6361  ACTTTTTGCC GGAGGGGGAG CCGCGCCGAA GGCGTGGGGG AACCCCGCAG GGGTGCCCTT
6421  CTTTGGGCAC CAAAGAACTA GATATAGGGC GAAATGCGAA AGACTTAAAA ATCAACAACT
6481  TAAAAAAGGG GGGTACGCAA CAGCTCATTG CGGCACCCCC CGCAATAGCT CATTGCGTAG
6541  GTTAAAGAAA ATCTGTAATT GACTGCCACT TTTACGCAAC GCATAATTGT TGTCGCGCTG
6601  CCGAAAAGTT GCAGCTGATT GCGCATGGTG CCGCAACCGT GCGGCACCCT ACCGCATGGA
6661  GATAAGCATG GCCACGCAGT CCAGAGAAAT CGGCATTCAA GCCAAGAACA AGCCCGGTCA
6721  CTGGGTGCAA ACGGAACGCA AAGCGCATGA GGCGTGGGCC GGGCTTATTG CGAGGAAACC
6781  CACGGCGGCA ATGCTGCTGC ATCACCTCGT GGCGCAGATG GGCCACCAGA ACGCCGTGGT
6841  GGTCAGCCAG AAGACACTTT CCAAGCTCAT CGGACGTTCT TGCGGACGG TCCAATACGC
6901  AGTCAAGGAC TTGGTGGCCG AGCGCTGGAT CTCCGTCGTG AAGCTCAACG GCCCCGGCAC
6961  CGTGTCGGCC TACGTGGTCA ATGACCGCGT GGCGTGGGGC CAGCCCCGCG ACCAGTTGCG
7021  CCTGTCGGTG TTCAGTGCCG CCGTGGTGGT TGATCACGAC GACCAGGACG AATCGCTGTT
7081  GGGGCATGGC GACCTGCGCC GCATCCCGAC CCTGTATCCG GGCGAGCAGC AACTACCGAC
7141  CGGCCCCGGC GAGGAGCCGC CCAGCCAGCC CGGCATTCCG GGCATGGAAC CAGACCTGCC
7201  AGCCTTGACC GAAACGGAGG AATGGGAACG GCGCGGGCAG CAGCGCCTGC CGATGCCCGA
7261  TGAGCCGTGT TTTCTGGACG ATGGCGAGCC GTTGGAGCCG CCGACACGGG TCACGCTGCC
7321  GCGCCGGTAG CACTTGGGTT GCGCAGCAAC CCGTAAGTGC GCTGTTCCAG ACTATCGGCT
7381  GTAGCCGCCT CGCCGCCCTA TACCTTGTCT GCCTCCCCGC GTTGCGTCGC GGTGCATGGA
7441  GCCGGGCCAC CTCGACCTGA ATGGAAGCCG GCGGCACCTC GCTAACGGAT TCACCGTTTT
7501  TATCAGGCTC TGGGAGGCAG AATAAATGAT CATATCGTCA ATTATTACCT CCACGGGGAG
```

```
      7561  AGCCTGAGCA AACTGGCCTC AGGCATTTGA GAAGCACACG GTCACACTGC TTCCGGTAGT

7621  CAATAAACCG GTAAACCAGC AATAGACATA AGCGGCTATT TAACGACCCT GCCCTGAACC

7681  GACGACCGGG TcGAATrTGc ETTCGAATTT CTGCCATTCA TCCGCTTATT ATCACTTATT

7741  CAGGCGTAGC ACCAGGCGTT TAAGTCGACC AATAAC
```

Amino Acid Sequence for modified EPA with signal sequence
Disclosed in WO 2009/104074 (as SEQ ID NO. 6)
Type: PRT
Organism: Artificial
/note="Description of Artificial Sequence: Synthetic polypeptide"
Length: 643
Sequence:

SEQ ID NO: 25

```
Met Lys Lys Ile Trp Leu Ala Leu Ala Gly Leu Val Leu Ala Phe Ser
1               5                  10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
    210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Asp Asn Asn Asn Ser Thr Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Ala Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320
```

Sequence Listing

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
                340                 345                 350

Ala Ile Arg Glu Gln Pre Glu Gln Ala Arg Leu Ala Leu Thr Leu Ala
                355                 360                 365

Ala Ala Glu Ser Glu Arg Phe Val Arg Gln Gly Thr Gly Asn Asp Glu
                370                 375                 380

Ala Gly Ala Ala Ser Ala Asp Val Val Ser Leu Thr Cys Pro Val Ala
385                 390                 395                 400

Lys Asp Gln Asn Arg Thr Lys Gly Glu Cys Ala Gly Pro Ala Asp Ser
                405                 410                 415

Gly Asp Ala Leu Leu Glu Arg Asn Tyr Pro Thr Gly Ala Glu Phe Leu
                420                 425                 430

Gly Asp Gly Gly Asp Val Ser Phe Ser Thr Arg Gly Thr Gln Asn Trp
                435                 440                 445

Thr Val Glu Arg Leu Leu Gln Ala His Arg Gln Leu Glu Glu Arg Gly
                450                 455                 460

Tyr Val Phe Val Gly Tyr His Gly Thr Phe Leu Glu Ala Ala Gln Ser
465                 470                 475                 480

Ile Val Phe Gly Gly Val Arg Ala Arg Ser Gln Asp Leu Asp Ala Ile
                485                 490                 495

Trp Arg Gly Phe Tyr Ile Ala Gly Asp Pro Ala Leu Ala Tyr Gly Tyr
                500                 505                 510

Ala Gln Asp Gln Glu Pro Asp Ala Arg Gly Arg Ile Arg Asn Gly Ala
                515                 520                 525

Leu Leu Arg Val Tyr Val Pro Arg Trp Ser Leu Pro Gly Phe Tyr Arg
                530                 535                 540

Thr Gly Leu Thr Leu Ala Ala Pro Glu Ala Ala Gly Glu Val Glu Arg
545                 550                 555                 560

Leu Ile Gly His Pro Leu Pro Leu Arg Leu Asp Ala Ile Thr Gly Pro
                565                 570                 575

Glu Glu Glu Gly Gly Arg Val Thr Ile Leu Gly Trp Pro Leu Ala Glu
                580                 585                 590

Arg Thr Val Val Ile Pro Ser Ala Ile Pro Thr Asp Pro Arg Asn Val
                595                 600                 605

Gly Gly Asp Leu Asp Pro Ser Ser Ile Pro Asp Lys Glu Gln Ala Ile
                610                 615                 620

Ser Ala Leu Pro Asp Tyr Ala Ser Gln Pro Gly Lys Pro Pro Arg Glu
625                 630                 635                 640

Asp Leu Lys

Amino Acid Sequence for PglB
Disclosed in WO 2009/104074 (as SEQ ID NO. 2)
Length: 722
Type: PRT
Organism: *Campylobacter jejuni*
Sequence:
                                                        SEQ ID NO: 26
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
                20                  25                  30

Val Trp Trp Ala Ser Glu Phe Asn Glu Tyr Phe Phe Asn Asn Gln Leu
                35                  40                  45

-continued

Sequence Listing

Met Ile Ile Ser Asn Asp Gly Tyr Ala Phe Ala Glu Gly Ala Arg Asp
50                    55                    60

Met Ile Ala Gly Phe His Gln Pro Asn Asp Leu Ser Tyr Tyr Gly Ser
65                    70                    75                    80

Ser Leu Ser Ala Leu Thr Tyr Trp Leu Tyr Lys Ile Thr Pro Phe Ser
                85                    90                    95

Phe Glu Ser Ile Ile Leu Tyr Met Ser Thr Phe Leu Ser Ser Leu Val
                100                   105                   110

Val Ile Pro Thr Ile Leu Leu Ala Asn Glu Tyr Lys Arg Pro Leu Met
                115                   120                   125

Gly Phe Val Ala Ala Leu Leu Ala Ser Ile Ala Asn Ser Tyr Tyr Asn
130                   135                   140

Arg Thr Met Ser Gly Tyr Tyr Asp Thr Asp Met Leu Val Ile Val Leu
145                   150                   155                   160

Pro Met Phe Ile Leu Phe Phe Met Val Arg Met Ile Leu Lys Lys Asp
                165                   170                   175

Phe Phe Ser Leu Ile Ala Leu Pro Leu Phe Ile Gly Ile Tyr Leu Trp
                180                   185                   190

Trp Tyr Pro Ser Ser Tyr Thr Leu Asn Val Ala Leu Ile Gly Leu Phe
                195                   200                   205

Leu Ile Tyr Thr Leu Ile Phe His Arg Lys Glu Lys Ile Phe Tyr Ile
                210                   215                   220

Ala Val Ile Leu Ser Ser Leu Thr Leu Ser Asn Ile Ala Trp Phe Tyr
225                   230                   235                   240

Gln Ser Ala Ile Ile Val Ile Leu Phe Ala Leu Phe Ala Leu Glu Gln
                245                   250                   255

Lys Arg Leu Asn Phe Met Ile Ile Gly Ile Leu Gly Ser Ala Thr Leu
                260                   265                   270

Ile Phe Leu Ile Leu Ser Gly Gly Val Asp Pro Ile Leu Tyr Gln Leu
                275                   280                   285

Lys Phe Tyr Ile Phe Arg Ser Asp Glu Ser Ala Asn Leu Thr Gln Gly
                290                   295                   300

Phe Met Tyr Phe Asn Val Asn Gln Thr Ile Gln Glu Val Glu Asn Val
305                   310                   315                   320

Asp Leu Ser Glu Phe Met Arg Arg Ile Ser Gly Ser Glu Ile Val Phe
                325                   330                   335

Leu Phe Ser Leu Phe Gly Phe Val Trp Leu Leu Arg Lys His Lys Ser
                340                   345                   350

Met Ile Met Ala Leu Pro Ile Leu Val Leu Gly Phe Leu Ala Leu Lys
                355                   360                   365

Gly Gly Leu Arg Phe Thr Ile Tyr Ser Val Pro Val Met Ala Leu Gly
                370                   375                   380

Phe Gly Phe Leu Leu Ser Glu Phe Lys Ala Ile Met Val Lys Lys Tyr
385                   390                   395                   400

Ser Gln Leu Thr Ser Asn Val Cys Ile Val Phe Ala Thr Ile Leu Thr
                405                   410                   415

Leu Ala Pro Val Phe Ile His Ile Tyr Asn Tyr Lys Ala Pro Thr Val
                420                   425                   430

Phe Ser Gln Asn Glu Ala Ser Leu Leu Asn Gln Leu Lys Asn Ile Ala
                435                   440                   445

Asn Arg Glu Asp Tyr Val Val Thr Trp Ala Ala Tyr Gly Tyr Pro Val

-continued

Sequence Listing

```
         450            455            460
Arg Tyr Tyr Ser Asp Val Lys Thr Leu Val Asp Gly Gly Lys His Leu
465                 470                475                 480

Gly Lys Asp Asn Phe Phe Pro Ser Phe Ala Leu Ser Lys Asp Glu Gln
            485                 490                495

Ala Ala Ala Asn Met Ala Arg Leu Ser Val Glu Tyr Thr Glu Lys Ser
            500                 505                510

Phe Tyr Ala Pro Gln Asn Asp Ile Leu Lys Thr Asp Ile Leu Gln Ala
            515                 520                525

Met Met Lys Asp Tyr Asn Gln Ser Asn Val Asp Leu Phe Leu Ala Ser
            530                 535                540

Leu Ser Lys Pro Asp Phe Lys Ile Asp Thr Pro Lys Thr Arg Asp Ile
545                 550                555                 560

Tyr Leu Tyr Met Pro Ala Arg Met Ser Leu Ile Phe Ser Thr Val Ala
                565                 570                575

Ser Phe Ser Phe Ile Asn Leu Asp Thr Gly Val Leu Asp Lys Pro Phe
                580                 585                590

Thr Phe Ser Thr Ala Tyr Pro Leu Asp Val Lys Asn Gly Glu Ile Tyr
                595                 600                605

Leu Ser Asn Gly Val Val Leu Ser Asp Phe Arg Ser Phe Lys Ile
            610                 615                 620

Gly Asp Asn Val Val Ser Val Asn Ser Ile Val Glu Ile Asn Ser Ile
625                 630                635                640

Lys Gln Gly Glu Tyr Lys Ile Thr Pro Ile Asp Asp Lys Ala Gln Phe
                645                 650                555

Tyr Ile Phe Tyr Leu Lys Asp Ser Ala Ile Pro Tyr Ala Gln Phe Ile
                660                 665                670

Leu Met Asp Lys Thr Met Phe Asn Ser Ala Tyr Val Gln Met Phe Phe
                675                 680                685

Leu Gly Asn Tyr Asp Lys Asn Leu Phe Asp Leu Val Ile Asn Ser Arg
            690                 695                700

Asp Ala Lys Val Phe Lys Leu Lys Ile Tyr Pro Tyr Asp Val Pro Asp
705                 710                715                 720

Tyr Ala
```

Nucleotide Sequence for pCC1FOS Empty plasmid
Locus pCC1FOS with MCS cassette
Features        Location/Qualifiers
Region          230..256
                /label="pCC1/pEpiFOS fwd"
Region          311..330
                /label="T7 promoter"
Region          complement(504..529)
                /label="pCC1pEpiFOS rv"
CDS             complement(805..1464)
                /label=cat
CDS             1683..2030
                /label=redF
CDS             3425..4180
                /label=repE
CDS             4759..5934
                /label=parA
CDS             5934..6905
                /label=parB
ORIGIN
Length: 8171 bp
Type: DNA circular TNA
Organism: Artificial
Sequence:

SEQ ID NO: 27

```
Sequence Listing

1   GCGGCCGCAA GGGGTTCGCG TCAGCGGGTG TTGGCGGGTG TCGGGCTGG  CTTAACTATG
  61   CGGCATCAGA GCAGATTGTA CTGAGAGTGC ACCATATGCG GTGTGAAATA CCGCACAGAT
 121   GCGTAAGGAG AAAATACCGC ATCAGGCGCC ATTCGCCATT CAGCTGCGCA ACTGTTGGGA
 181   AGGGCGATCG GTGCGGGCCT CTTCGCTATT ACGCCAGCTG GCGAAAGGGG GATGTGCTGC
 241   AAGGCGATTA AGTTGGGTAA CGCCAGGGTT TTCCCAGTCA CGACGTTGTA AAACGACGGC
 301   CAGTGAATTG TAATACGACT CACTATAGGG CGAATTCGAG CTCGGTACCC GGGGATCCCA
 361   CGTGGCGCGC CACTAGTGCT AGCGACGTCG TGGGATCCTC TAGAGTCGAC CTGCAGGCAT
 421   GCAAGCTTGA GTATTCTATA GTCTCACCTA AATAGCTTGG CGTAATCATG GTCATAGCTG
 481   TTTCCTGTGT GAAATTGTTA TCCGCTCACA ATTCCACACA ACATACGAGC CGGAAGCATA
 541   AAGTGTAAAG CCTGGGGTGC CTAATGAGTG AGCTAACTCA CATTAATTGC GTTGCGCTCA
 601   CTGCCCGCTT TCCAGTCGGG AAACCTGTCG TGCCAGCTGC ATTAATGAAT CGGCCAACGC
 661   GAACCCCTTG CGGCCGCCCG GGCCGTCGAC CAATTCTCAT GTTTGACAGC TTATCATCGA
 721   ATTTCTGCCA TTCATCCGCT TATTATCACT TATTCAGGCG TAGCAACCAG GCGTTTAAGG
 781   GCACCAATAA CTGCCTTAAA AAAATTACGC CCCGCCCTGC CACTCATCGC AGTACTGTTG
 841   TAATTCATTA AGCATTCTGC CGACATGGAA GCCATCACAA ACGGCATGAT GAACCTGAAT
 901   CGCCAGCGGC ATCAGCACCT TGTCGCCTTG CGTATAATAT TTGCCCATGG TGAAAACGGG
 961   GGCGAAGAAG TTOTCCATAT TGGCCACGTT TAAATCAAAA CTGGTGAAAC TCACCCAGGG
1021   ATTGGCTGAG ACGAAAAACA TATTCTCAAT AAACCCTTTA GGGAAATAGG CCAGGTTTTC
1081   ACCGTAACAC GCCACATCTT GCGAATATAT GTGTAGAAAC TGCCGGAAAT CGTCGTGGTA
1141   TTCACTCCAG AGCGATGAAA ACGTTTCAGT TTGCTCATGG AAAACGGTGT AACAAGGGTG
1201   AACACTATCC CATATCACCA GCTCACCGTC TTTCATTGCC ATACGAAATT CCGGATGAGC
1261   ATTCATCAGG CGGGCAAGAA TGTGAATAAA GGCCGGATAA AACTTGTGCT TATTTTTCTT
1321   TACGGTCTTT AAAAAGGCCG TAATATCCAG CTGAACGGTC TGGTTATAGG TACATTGAGC
1381   AACTGACTGA AATGCCTCAA AATGTTCTTT ACGATGCCAT TGGGATATAT CAACGGTGGT
1441   ATATCCAGTG ATTTTTTTCT CCATTTTAGC TTCCTTAGCT CCTGAAAATC TCGATAACTC
1501   AAAAAATACG CCCGGTAGTG ATCTTATTTC ATTATGGTGA AAGTTGGAAC CTCTTACGTG
1561   CCGATCAACG TCTCATTTTC GCCAAAAGTT GGCCCAGGGC TTCCCGGTAT CAACAGGGAC
1621   ACCAGGATTT ATTTATTCTG CGAAGTGATC TTCCGTCACA GGTATTTATT CGCGATAAGC
1681   TCATGGAGCG GCGTAACCGT CGCACAGGAA GGACAGAGAA AGCGCGGATC TGGGAAGTGA
1741   CGGACAGAAC GGTCAGGACC TGGATTGGGG AGGCGGTTGC CGCCGCTGCT GCTGACGGTG
1801   TGACGTTCTC TGTTCCGGTC ACACCACATA CGTTCCGCCA TTCCTATGCG ATGCACATGC
1861   TGTATGCCGG TATACCGCTG AAAGTTCTGC AAAGCCTGAT GGGACATAAG TCCATCAGTT
1921   CAACGGAAGT CTACACGAAG GTTTTTGCGC TGGATGTGGC TGCCCGGCAC CGGGTGCAGT
1981   TTGCGATGCC GGAGTCTGAT GCGGTTGCGA TGCTGAAACA ATTATCCTGA GAATAAATGC
2041   CTTGGCCTTT ATATGGAAAT GTGGAACTGA GTGGATATGC TGTTTTTGTC TGTTAAACAG
2101   AGAAGCTGGC TGTTATCCAC TGAGAAGCGA ACGAAACAGT CGGGAAAATC TCCCATTATC
2161   GTAGAGATCC GCATTATTAA TCTCAGGAGC CTGTGTAGCG TTTATAGGAA GTAGTGTTCT
2221   GTCATGATGC CTGCAAGCGG TAACGAAAAC GATTTGAATA TGCCTTCAGG AACAATAGAA
2281   ATCTTCGTGC CGTGTTACGT TGAAGTGGAG CGGATTATGT CAGCAATGGA CAGAACAACC
```

```
2341  TAATGAACAC AGAACCATGA TGTGGTCTGT CCTTTTACAG CCAGTAGTGC TCGCCGCAGT

2401  CGAGCGACAG GGCGAAGCCC TCGGCTGGTT GCCCTCGCCG CTGGGCTGGC GGCCGTCTAT

2461  GGCCCTGCAA ACGCGCCAGA AACGCCGTCG AAGCCGTGTG CGAGACACCG CGGCCGGCCG

2521  CCGGCGTTGT GGATACCTCG CGGAAAACTT GGCCCTCACT GACAGATGAG GGGCGGACGT

2581  TGACACTTGA GGGGCCGACT CACCCGGCGC GGCGTTGACA GATGAGGGGC AGGCTCGATT

2641  TCGGCCGGCG ACGTGGAGCT GGCCAGCCTC GCAAATCGGC GAAAACGCCT GATTTTACGC

2701  GAGTTTCCCA CAGATGATGT GGACAAGCCT GGGGATAAGT GCCCTGCGGT ATTGACACTT

2761  GAGGGGCGCG ACTACTGACA GATGAGGGGC GCGATCCTTG ACACTTGAGG GGCAGAGTGC

2821  TGACAGATGA GGGGCGCACC TATTGACATT TGAGGGGCTG TCCACAGGCA GAAATCCAG

2881  CATTTGCAAG GGTTTCCGCC CGTTTTTCGG CCACCGCTAA CCTGTCTTTT AACCTGCTTT

2941  TAAACCAATA TTTATAAACC TTGTTTTTAA CCAGGGCTGC GCCCTGTGCG CGTGACCGCG

3001  CACGCCGAAG GGGGGTGCCC CCCCTTCTCG AACCCTCCCG GTCGAGTGAG CGAGGAAGCA

3061  CCAGGGAACA GCACTTATAT ATTCTGCTTA CACACGATGC CTGAAAAAAC TTCCCTTGGG

3121  GTTATCCACT TATCCACGGG GATATTTTTA TAATTATTTT TTTTATAGTT TTTAGATCTT

3181  CTTTTTTAGA GCGCCTTGTA GGCCTTTATC CATGCTGGTT CTAGAGAAGG TGTTGTGACA

3241  AATTGCCCTT TCAGTGTGAC AAATCACCCT CAAATGACAG TCCTGTCTGT GACAAATTGC

3301  CCTTAACCCT GTGACAAATT GCCCTCAGAA GAAGCTGTTT TTTCACAAAG TTATCCCTGC

3361  TTATTGACTC TTTTTTATTT AGTGTGACAA TCTAAAAACT TGTCACACTT CACATGGATC

3421  TGTCATGGCG GAAACAGCGG TTATCAATCA CAAGAAACGT AAAAATAGCC CGCGAATCGT

3481  CCAGTCAAAC GACCTCACTG AGGCGGCATA TAGTCTCTCC CGGGATCAAA AACGTATGCT

3541  GTATCTGTTC GTTGACCAGA TCAGAAAATC TGATGGCACC CTACAGGAAC ATGACGGTAT

3601  CTGCGAGATC CATGTTGCTA AATATGCTGA ATATTCGGA TTGACCTCTG CGAAGCCAG

3661  TAAGGATATA CGGCAGGCAT TGAAGAGTTT CGCGGGGAAG GAAGTGGTTT TTTATCGCCC

3721  TGAACAGGAT GCCGGCGATG AAAAAGGCTA TGAATCTTTT CCTTGGTTTA TCAAACGTGC

3781  GCACAGTCCA TCCAGAGGGC TTTACAGTGT ACATATCAAC CCATATCTCA TTCCCTTCTT

3841  TATCGGGTTA CAGAACCGGT TTACGCAGTT CGGCTTAGTG GAAACAAAAG AAATCACCAA

3901  TCCGTATCCC ATGCGTTTAT ACGAATCCCT GTGTCAGTAT CGTAAGCCGG ATGGCTCAGG

3961  CATCGTCTCT CTGAAAATCG ACTGGATCAT AGAGCGTTAC CAGCTGCCTC AAAGTTACCA

4021  GCGTATGCCT GACTTCCGCC GCCGCTTCCT GCAGGTCTGT GTTAATGAGA TCAACAGCAG

4081  AACTCCAATG CGCCTCTCAT ACATTGAGAA AAAGAAAGGC CGCCAGACGA CTCATATCGT

4141  ATTTTCCTTC CGCGATATCA CTTCCATGAC GACAGGATAG TCTGAGGGTT ATCTGTCACA

4201  GATTTGAGGG TGGTTCGTCA CATTTGTTCT GACCTACTGA GGGTAATTTG TCACAGTTTT

4261  GCTGTTTCCT TCAGCCTGCA TGGATTTTCT CATACTTTTT GAACTGTAAT TTTTAAGGAA

4321  GCCAAATTTG AGGGCAGTTT GTCACAGTTG ATTTCCTTCT CTTTCCCTTC GTCATGTGAC

4381  CTGATATCGG GGGTTAGTTC GTCATCATTG ATGAGGGTTG ATTATCACAG TTTATTACTC

4441  TGAATTGGCT ATCCGCGTGT GTACCTCTAC CTGGAGTTTT TCCCACGGTG GATATTTCTT

4501  CTTGCGCTGA GCGTAAGAGC TATCTGACAG AACAGTTCTT CTTTGCTTCC TCGCCAGTTC

4561  GCTCGCTATG CTCGGTTACA CGGCTGCGGC GAGCGCTAGT GATAATAAGT GACTGAGGTA
```

```
4621  TGTGCTCTTC TTATCTCCTT TTGTAGTGTT GCTCTTATTT TAAACAACTT TGCGGTTTTT
4681  TGATGACTTT GCGATTTTGT TGTTGCTTTG CAGTAAATTG CAAGATTTAA TAAAAAAACG
4741  CAAAGCAATG ATTAAAGGAT GTTCAGAATG AAACTCATGG AAACACTTAA CCAGTGCATA
4801  AACGCTGGTC ATGAAATGAC GAAGGCTATC GCCATTGCAC AGTTTAATGA TGACAGCCCG
4861  GAAGCGAGGA AAATAACCCG GCGCTGGAGA ATAGGTGAAG CAGCGGATTT AGTTGGGGTT
4921  TCTTCTCAGG CTATCAGAGA TGCCGAGAAA GCAGGGCGAC TACCGCACCC GGATATGGAA
4981  ATTCGAGGAC GGGTTGAGCA ACGTGTTGGT TATACAATTG AACAAATTAA TCATATGCGT
5041  GATGTGTTTG GTACGCGATT GCGACGTGCT GAAGACGTAT TTCCACCGGT GATCGGGGTT
5101  GCTGCCCATA AAGGTGGCGT TTACAAAACC TCAGTTTCTG TTCATCTTGC TCAGGATCTG
5161  GCTCTGAAGG GGCTACGTGT TTTGCTCGTG GAAGGTAACG ACCCCCAGGG AACAGCCTCA
5221  ATGTATCACG ATGGGTACC AGATCTTCAT ATTCATGCAG AAGACACTCT CCTGCCTTTC
5281  TATCTTGGGG AAAAGGACGA TGTCACTTAT GCAATAAAGC CCACTTGCTG GCCGGGGCTT
5341  GACATTATTC CTTCCTGTCT GGCTCTGCAC CGTATTGAAA CTGAGTTAAT GGGCAAATTT
5401  GATGAAGGTA AACTGCCCAC CGATCCACAC CTGATGCTCC GACTGGCCAT TGAAACTCTT
5461  GCTCATGACT ATGATGTCAT AGTTATTGAC AGCGCGCCTA ACCTGGGTAT CGGCACGATT
5521  AATGTCGTAT GTGCTGCTGA TGTGCTGATT GTTCCCACGC TGCTGAGTT GTTTGACTAC
5581  ACCTCCGCAC TGCAGTTTTT CGATATGCTT CGTGATCTGC TCAAGAACGT TGATCTTAAA
5641  GGGTTCGAGC CTGATGTACG TATTTTGCTT ACCAAATACA GCAATAGTAA TGGCTCTCAG
5701  TCCCCGTGGA TGGAGGAGCA AATTCGGGAT GCCTGGGGAA GCATGGTTCT AAAAAATGTT
5761  GTACGTGAAA CGGATGAAGT TGGTAAAGGT CAGATCCGGA TGAGAACTGT TTTTGAACAG
5821  GCCATTGATC AACGCTCTTC AACTGGTGCC TGGAGAAATG CTCTTTCTAT TTGGGAACCT
5881  GTCTGCAATG AAATTTTCGA TCGTCTGATT AAACCACGCT GGGAGATTAG ATAATGAAGC
5941  GTGCGCCTGT TATTCCAAAA CATACGCTCA ATACTCAACC GGTTGAAGAT ACTTCGTTAT
6001  CGACACCAGC TGCCCCGATG GTGGATTCGT TAATTGCGCG CGTAGGAGTA ATGGCTCGCG
6061  GTAATGCCAT TACTTTGCCT GTATGTGGTC GGGATGTGAA GTTTACTCTT GAAGTGCTCC
6121  GGGGTGATAG TGTTGAGAAG ACCTCTCGGG TATGGTCAGG TAATGAACGT GACCAGGAGC
6181  TGCTTACTGA GGACGCACTG GATGATCTCA TCCCTTCTTT TCTACTGACT GGTCAACAGA
6241  CACCGGCGTT CGGTCGAAGA GTATCTGGTG TCATAGAAAT TGCCGATGGG AGTCGCCGTC
6301  GTAAAGCTGC TGCACTTACC GAAAGTGATT ATCGTGTTCT GGTTGGCGAG CTGGATGATG
6361  AGCAGATGGC TGCATTATCC AGATTGGGTA ACGATTATCG CCCAACAAGT GCTTATGAAC
6421  GTGGTCAGCG TTATGCAAGC CGATTGCAGA ATGAATTTGC TGGAAATATT TCTGCGCTGG
6481  CTGATGCGGA AAATATTTCA CGTAAGATTA TTACCCGCTG TATCAACACC GCCAAATTGC
6541  CTAAATCAGT TGTTGCTCTT TTTTCTCACC CCGGTGAACT ATCTGCCCGG TCAGGTGATG
6601  CACTTCAAAA AGCCTTTACA GATAAAGAGG AATTACTTAA GCAGCAGGCA TCTAACCTTC
6661  ATGAGCAGAA AAAAGCTGGG GTGATATTTG AAGCTGAAGA AGTTATCACT CTTTTAACTT
6721  CTGTGCTTAA AACGTCATCT GCATCAAGAA CTAGTTTAAG CTCACGACAT CACTTTGCTC
6781  CTGGAGCGAC AGTATTGTAT AAGGGCCATA AAATGGTGCT AACCTGGAC AGGTCTCGTG
6841  TTCCAACTGA GTGTATAGAG AAAATTGAGG CCATTCTTAA GGAACTTGAA AAGCCAGCAC
6901  CCTGATGCGA CCACGTTTTA GTTTACTTTT ATCTGTCTTT ACTTAATGTC CTTTGTTACA
```

```
6961  GGCCAGAAAG CATAACTGGC CTGAATATTC TCTCTGGGCC CACTGTTCCA CTTGTATCGT

7021  CGGTCTGATA ATCAGACTGG GACCACGGTC CCACTCGTAT CGTCGGTCTG ATTATTAGTC

7081  TGGGACCACG GTCCCACTCG TATCGTCGGT CTGATTATTA GTCTGGGACC ACGGTCCCAC

7141  TCGTATCGTC GGTCTGATAA TCAGACTGGG ACCACGGTCC CACTCGTATC GTCGGTCTGA

7201  TTATTAGTCT GGGACCATGG TCCCACTCGT ATCGTCGGTC TGATTATTAG TCTGGGACCA

7261  CGGTCCCACT CGTATCGTCG GTCTGATTAT TAGTCTGGAA CCACGGTCCC ACTCGTATCG

7321  TCGGTCTGAT TATTAGTCTG GGACCACGGT CCCACTCGTA TCGTCGGTCT GATTATTAGT

7381  CTGGGACCAC GATCCCACTC GTGTTGTCGG TCTGATTATC GGTCTGGGAC CACGGTCCCA

7441  CTTGTATTGT CGATCAGACT ATCAGCGTGA GACTACGATT CCATCAATGC CTGTCAAGGG

7501  CAAGTATTGA CATGTCGTCG TAACCTGTAG AACGGAGTAA CCTCGGTGTG CGGTTGTATG

7561  CCTGCTGTGG ATTGCTGCTG TGTCCTGCTT ATCCACAACA TTTTGCGCAC GGTTATGTGG

7621  ACAAAATACC TGGTTACCCA GGCCGTGCCG CCACGTTAAC CGGGCTGCAT CCGATGCAAG

7681  TGTGTCGCTG TCGACGAGCT CGCGAGCTCG GACATGAGGT TGCCCCGTAT TCAGTGTCGC

7741  TGATTTGTAT TGTCTGAAGT TGTTTTTACG TTAAGTTGAT GCAGATCAAT TAATACGATA

7801  CCTGCGTCAT AATTGATTAT TTGACGTGGT TGATGGCCT CCACGCACGT TGTGATATGT

7861  AGATGATAAT CATTATCACT TTACGGGTCC TTTCCGGTGA TCCGACAGGT TACGGGCGG

7921  CGACCTCGCG GGTTTTCGCT ATTTATGAAA ATTTTCCGGT TTAAGGCGTT TCCGTTCTTC

7981  TTCGTCATAA CTTAATGTTT TTATTTAAAA TACCCTCTGA AAAGAAAGGA AACGACAGGT

8041  GCTGAAAGCG AGCTTTTTGG CCTCTGTCGT TTCCTTTCTC TGTTTTGTC CGTGGAATGA

8101  ACAATGGAAG TCCGAGCTCA TCGCTAATAA CTTCGTATAG CATACATTAT ACGAAGTTAT

8161  ATTCGATCCA C
```

Nucleotide Sequence for pCC1FOS cut (pFOS) and  
S. flexneri 6 O-antigen without Z3206  
Locus pFOS cut and O-antige cut (-Z3206)  
Definition Ligation of inverted pCC1FOS with MCS cassette cut with NheI and into *S. flexneri* 6 O antigen cluster amplified with galFNheI and wzzAscI cut with NheI and AscI

```
FEATURES        Location/Qualifiers
CDS             3..411
           /label='galF
CDS             784..1869
           /label=rmlB
CDS             1869..2768
           /label=rmlD
CDS             2826..3704
           /label=rmlA
CDS             3709..4266
           /label=rmlC
CDS             4263..5495
           /label=wzx
CDS             5551..6738
           /label=wzy
CDS             6755..7624
           /label=wfbY
CDS             7621..8454
           /label=wfbZ
CDS             8559..9965
           /label=gnd
CDS             10187..11380
           /label=ugd
CDS             complement(11416..12450)
           /label=uge
CDS             12802..12828
           /label=wzz'
Region          complement(12868..12887)
```

|     |                                |
| --- | ------------------------------ |
|     | /label="T7 promoter"           |
| Region | complement(12942..12968)     |
|     | /label="pCC1/pEpiRDS fwd"      |
| CDS | complement(14460..15431)       |
|     | /label=parB                    |
| CDS | complement(15431..16606)       |
|     | /label=parA                    |
| CDS | complement(7185..17940)        |
|     | /label=repE                    |
| CDS | complement(19335..19682)       |
|     | /label=redF                    |
| CDS | 19901..20560                   |
|     | /label=cat                     |
| Region | 20836..20861                |
|     | /label="pCC1pEpiFOS rv"        |

Length: 20982 bp
Type: DNA circular UNA
Sequence:

SEQ ID NO: 28

```
   1 CTAGCGGCAA AACGTATGCC GGGTGACCTC TCTGAATACT CCGTCATCCA GACCAAAGAA
  61 CCGCTGGATC GCGAAGGTAA AGTCAGCCGC ATTGTTGAAT TTATCGAAAA ACCGGATCAG
 121 CCGCAGACGC TGGACTCAGA CATCATGGCC GTTGGTCGCT ATGTGCTTTC TGCCGATATT
 181 TGGCCGGAAC TTGAACGTAC TCAGCCTGGT GCATGGGGAC GTATTCAGCT GACTGATGCC
 241 ATTGCCGAGC TGGCGAAAAA ACAGTCCGTT GATGCAATGC TGATGACCGG CGACAGCTAC
 301 GACTGCGGTA AAAAATGGG CTATATGCAG GCGTTTGTGA AGTATGGGCT GCGCAACCTG
 361 AAAGAAGGGG CGAAGTTCCG TAAAGGTATT GAGAAGCTGT TAAGCGAATA ATGAAAATCT
 421 GACCGGATGT AACGGTTGAT AAGAAAATTA TAACGGCAGT GAAGATTCGT GGTGAAAGTA
 481 ATTTGTTGCG AATATTCCTG CCGTTGTTTT ATATAAACAA TCAGAATAAC AACGAGTTAG
 541 CAATAGGATT TTAGTCAAAG TTTTCCAGGA TTTTCCTTGT TTCCAGAGCG GATTGGTAAG
 601 ACAATTAGCT TTTGAATTTT TCGGGTTTAG CGCGAGTGGG TAACGCTCGT CACATCGTAG
 661 GCATGCATGC AGTGCTCTGG TAGCTGTAAA GCCAGGGGCG GTAGCGTGCA TTAATACTTC
 721 TATTAATCAA ACTGAGAGCC GCTTATTTCA CAGCATGCTC TGAAGCAATA TGGAATAAAT
 781 TAGGTGAAAA TACTTGTTAC TGGTGGCGCA GGATTTATTG GTTTTGCTGT AGTTCGTCAC
 841 ATTATAAATA ATACGCAGGA TAGTGTTGTT AATGTCGATA AATTAACGTA CGCCGGAAAC
 901 CTGGAATCAC TTGCTGATGT TTCTGATTCT GAACGCTATG TTTTTGAACA TGCGGATATT
 961 TGCGATGCAG CTGCAATGGC ACGGATTTTT GCTCAGCATC AGCCAGATGC AGTGATGCAC
1021 CTGGCTGCTG AAAGCCATGT TGACCGTTCA ATTACAGGTC CTGCGGCATT TATTGAAACC
1081 AATATTGTTG GTACATATGT CCTTTTGGAA GCCGCTCGCA ATTATTGGTC TGCTCTTGAT
1141 AGCGACAAGA AAACTAGATT CCGTTTTCAT CATATTTCTA CTGACGAAGT CTATGGTGAT
1201 TTGCCTCATC CTGACGAGGT AAATAATACA GAAGAATTAC CCTTATTTAC AGAGACAACA
1261 GCTTACGCGC AAGCAGCCC TTATTCCGCT TCAAAAGCAT CCAGCGATCA TTTAGTCCGC
1321 GCGTGGAAAC GTACCTATGG TTTACCAACC ATTGTGACTA ATTGCTCTAA TAATTATGGT
1381 CCTTATCATT TCCCGGAAAA ATTGATTCCA TTGGTTATTC TGAATGCTCT GGAAGGTAAG
1441 GCATTACCTA TTTATGGCAA AGGGGATCAA ATTCGTGACT GGCTGTATGT TGAAGATCAT
1501 GCGCGTGCGT TATATACCGT CGTAACCGAA GGTAAAGCGG GTGAAACTTA ACATTGGT
1561 GGACACAACG AAAGAAAAA CATCGATGTA GTGCTCACTA TTTGTGATTT GCTGGATGAG
1621 ATTGTACCGA AAGAGAAATC TTACCGCGAG CAAATTACTT ATGTTGCCGA TCGCCCGGGA
1681 CACGATCGCC GTTATGCGAT TGATGCAGAG AAGATTAGCC GCGAATTGGG CTGGAAACCG
```

```
1741  CAGGAAACGT TTGAGAGCGG GATTCGGAAG ACATTGGAAT GGTACCTGTC CAATACAAAA
1801  TGGGTTGATA ATGTGAAAAG TGGTGCTTAT CAATCGTGGA TTGAACAGAA CTATGAGGGC
1861  CGCCAGTAAT GAATATCCTC CTTTTCGGCA AAACAGGGCA GGTAGGTTGG GAACTACAGC
1921  GTGCTCTGGC ACCTTTGGGT AATTTGATTG CTCTTGATGT TCACTCCACT GATTATTGTG
1981  GTGATTTTAG TAATCCTGAA GGTGTAGCTG AAACAGTCAA AAGAATTCGA CCTGATGTTA
2041  TTGTTAATGC TGCGGCTCAC ACCGCAGTAG ATAAGGCTGA GTCAGAACCC GAATTTGCAC
2101  AATTACTCAA TGCGACTAGT GTTGAATCAA TTGCAAAAGA GGCTAATGAA GTTGGGGCTT
2161  GGGTAATTCA TTACTCAACT GACTACGTAT TCCCTGGAAA TGGCGACACG CCATGGCTGG
2221  AGACGGATGC AACCGCACCG CTAAATGTTT ACGGTGAAAC CAAGTTAGCC GGAGAAAAAG
2281  CGTTACAGGA ACATTGCGCG AAGCATCTTA TTTTCCGTAC CAGCTGGGTA TACGCAGCTA
2341  AAGGAAATAA CTTCGCCAAA ACGATGTTGC GTCTGGCAAA AGAGCGCGAA GAACTGGCTG
2401  TGATAAATGA TCAATTTGGT GCGCCAACAG GTGCTGAGCT GCTGGCTGAT TGTACGGCAC
2461  ATGCTATTCG TGTGGCACTG AATAAACCGG AAGTCGCAGG TTTGTACCAT CTGGTAGCCA
2521  GTGGTACCAC AACCTGGCAC GATTATGCTG CGCTGGTTTT TGAAGAGGCG CGCAAAGCAG
2581  GTATTCCCCT TGCACTCAAC AAGCTCAACG CAGTACCAAC AACAGCCTAT CCTACACCAG
2641  CTCGTCGTCC ACATAACTCT CGCCTTAATA CAGAAAAATT TCAGCAGAAC TTTGCGCTTG
2701  TCTTGCCTGA CTGGCAGGTT GGTGTGAAAC GAATGCTCAA CGAATTAATT ACGACTACAG
2761  CAATTTAATA GTTTTTGCAT CTTGTTCGTG ATGGTGGAGC AAGATGAATT AAAAGGAATG
2821  ATGAAATGAA AACGCGTAAA GGTATTATTT TAGCGGGTGG TTCTGGTACA CGTCTTTATC
2881  CTGTGACTAT GGCTGTCAGT AAACAGCTAT TACCTATTTA TGATAAGCCG ATGATCTATT
2941  ACCCGCTCTC TACACTGATG TTGGCGGGTA TTCGCGATAT TCTGATTATT AGTACGCCAC
3001  AGGATACTCC TCGTTTTCAA CAACTGCTAG GTGACGGTAG CCAGTGGGGG CTAAATCTTC
3061  AGTACAAAGT GCAACCGACT CCAGATGGGC TTGCGCAGGC GTTTATTATC GGTGAAGAGT
3121  TTATCGGTGG TGATGATTGT GCTTTGGTTC TTGGTGATAA TATCTTCTAC GGTCATGATC
3181  TGCCGAAGTT AATGGATGTC GCTGTTAACA AGAAAGTGG TGCAACGGTA TTTGCCTATC
3241  ACGTTAATGA TCCTGAACGC TACGGCGTCG TTGAGTTTGA TAAAAACGGT ACGGCAATAA
3301  GCCTGGAAGA AAAACCGCTA CAACCAAAAA GTAATTATGC GGTAACCGGG CTTTATTTCT
3361  ATGATAACGA CGTTGTCGAA ATGGCGAAAA ACCTTAAGCC TTCTGCCCGT GGTGAACTGG
3421  AAATTACCGA TATTAACCGT ATTTATATGG AACAGGGGCG TTTATCCGTT GCCATGATGG
3481  GGCGTGGTTA TGCATGGCTG GATACGGGGA CACATCGAG TCTTATTGAA GCAAGCAACT
3541  TCATTGCCAC CATTGAAGAG CGCCAGGGAC TAAAGGTTTC CTGCCCAGAA GAAATTGCTT
3601  ACCGTAAAGG GTTTATTGAT GCTGAACAGG TGAAAGCATT AGCGGAGCCG CTGAAAAAAA
3661  ATGCTTATGG ACAGTATCTG CTGAAAATGA TTAAAGGTTA TTAATAAAAT GAACGTAATT
3721  AAAACAGAAA TTCCTGATGT GTTAATTTTC GAGCCGAAAG TTTTTGGTGA TGAGCGTGGT
3781  TTCTTTATGG AAAGCTTTAA TCAGAAAGTT TTCGAAGAAG CTGTAGGACG TAAGGTTGAA
3841  TTTGTTCAGG ATAACCATTC GAAGTCTAGT AAAGGTGTTT TACGCGGGCT GCATTATCAG
3901  TTAGAACCTT ATGCGCAAGG GAAACTGGTA CGTTGCGTTG TTGGTGAGGT TTTTGATGTA
3961  GCTGTTGATA TTCGTAAATC GTCGCCTACC TTTGGTAAAT GGGTTGGGGT GAATTTATCT
4021  GCTGAGAATA AGCGGCAATT GTGGATCCCT GAGGGATTTG CACATGGTTT TTTGGTGCTG
```

```
4081  AGCGAGACTG CGGAATTTTT ATATAAAACG ACGAACTATT ATCATCCTGA TAGTGATAGA
4141  GGGATTGTAT GGAATGATCC TATTCTGAGC ATAAAATGGC CGACGATAGA ACATAATAAT
4201  TATATTTTAT CGATTAAAGA TGCAAGGGCT AAAGAATTGC ATAACATGAA GGAATTATTT
4261  TTGTGAGTAT TGTAAAGAAT ACTTTATGGA ATATAAGTGG GTATATTATA CCATCATTAA
4321  TAGCAATTCC TGCGTTAGGT ATACTGTCTA GAATTCTAGG GACCCGAGCAA TTTGGCCTTT
4381  TTACGTTAGC TATTGCCTTA GTTGGATATG CAAGTATTTT TGATGCTGGA TTGACCAGAG
4441  CTGTTATAAG AGAAGTATCA ATATATAAAA ATGTTCATAA AGAATTAAGA GCGATCATTT
4501  CAACTTCAAC GGTAATTCTA ACTATATTGG GCTTGATTGG CGGTAGTGTA CTATTTTTGA
4561  GTAGCAATGT AATTGTTAAA TTATTAAACA TTAACGCGAA TCATGTTGTA GAATCTGTCA
4621  AAGCAATATA TATTATTTCA GCTACCATAC CCTTATACTT GTTAAACCAA GTCTGGTTGG
4681  GGATTTTTGA GGGGATGGAA AAGTTCAGAA AAGTAAATTT AATAAAATCA ATTAACAACT
4741  CTTTTGTGGC TGGATTACCA GTGATTTTCT GTTTTTTTCA TGGAGGATTA CTAAGTGCTA
4801  TATATGGTTT AGTTATGGCA AGAGTCTTAT CACTTATAGT GACCTTTATA TTTAGTCGAA
4861  AACTAATAAT ATCATCTGGG CTGTCTGTAA AAATTGTAAC AGTTAAAAGA TTAATCGGCT
4921  TTGGAAGCTG GATAACAGTT AGCAATATTA TTAGCCCTAT TATGACATAT ATGGATCGTT
4981  TTATTCTTTC ACACATTGTG GGGGCTGATA AGTTTCTTT TTATACTGCT CCGTCTGAAG
5041  GTATACAACG CTTAACGATA TTACCAAGTG CGTTGTCCAG AGCTATTTTT CCAAGATTAA
5101  GTTCAGAATT GCAATCGGTA AAGCAAACTA AAATATTATC ATATTTATA ATGGTTATTG
5161  GTATACTTCC AATTGTAATG TTGATAATTA TTTTATCAGA TTTTATAATG TCCGCTTGGA
5221  TGGGACCTAC ATATCATGGG ACGCCAGGTA TAGTATTAAA AATTCTTGCA ATAGGTTTCT
5281  TTTTTAATTG CATTGCACAA ATCCCATTTG TTTCAGTTCA GGCTAGTGGA AGATCAAAAA
5341  TTACAGCTAT TATTCATTTG CTCGAAGTTA TCCCATATTT ATGCATATTA TATATTTTA
5401  TTTATCATTG GGGAATTGTT GGAGCCGCAA TAGCATGGTC TGTAAGAACA TCGTTAGATT
5461  TTTTGATATT ATTATTAATT GATACGAAAT ATTAATAGCG AATTGATTTT AGGGATTACT
5521  TCCTCAAGCC CATCTAATTA GAGTGCAAAC ATGACTTCTG ATTTTTATAA CTCAAAAGAC
5581  AAAAGTTTAA GTGTTCTTTT GTTTTTTGGG TTTATATTTT TCCTTACACG TAGCTTTCCA
5641  TTTATTCAAT ATAGTTCGAT TATGGAGGGG TTTTTATGTC TTTGTATCAT GTCATTTACA
5701  AAGAAAATTG CAAACGGAAT ATATCACTAT CCTGTTATTT TAATATTTCT ATTAGCTCTT
5761  TTTATAAATT TTATTTATTC CTATATCAAG GGTAACGATA TAGCGATAAT AATTAGGTTT
5821  TATATTATCA TATTATTTAT ATTATGTGCT TATTTCTGCT CTTATGGAAC CATCTCGATT
5881  GTTAAAATAT TTTTATATTT AATGGTATTA CAGGCGGTTA TTATATCCAT CATTAGTATT
5941  TATATGACAA AAACATATGG TATTGGTGAT TATTCAGCAC TAAGACATTA TTTTTTGGAG
6001  AATGATTATG GTGATGTTTA TACATATGGA AGTGGTTTCT ATAGAGTTCA AATTAAAGGA
6061  AATGCTCTCA TTCCATTTGC CTTTATGTTG CATATAGTCA TAAAAGATTA TTTCTATTAT
6121  CGATTCAAAA ATACAATAAC CGTTATTCTG GCTATAGGTA CTATAGTGGC TGGTAATTTT
6181  GCATATTTTG TTTCGATATG CTTGTTTTTT ATGTATATTA TACTATGTTC TAAATCTAAC
6241  TCACGATACG CTAAATTAAG GAAAATTATT TTTGGGGTTT TTCTTACTGT GATTCTCCCT
6301  TTTTTTATTA CATATTCAAT TGAGTTGATA ATCATGAAAT CAAATGGAGC TGATTCTTCT
```

```
6361  TTAGGAGTTA GATGGGATCA GTTTACTGTA TTAATTAATG ATCTTACAGA GTCTGTATCA
6421  AATTTTGTTA TAGGTTCTGG TTTGGGTAAT GTCATCAAAA TTCAAACTCC TATCCGTGAT
6481  TATAGTGCAT ATATATATTA TGAATTGCAG TCAGTTTATT TTTTAAATCA ACTTGGCGTT
6541  ATTTTATTTA CTTTGTTTTT ATTAATTAAT CTCCTTCTCA CGATTAAAAT CATAAAATAC
6601  AGTGAGTTGT GTGTGCTATA TTTTCTATAT GTTTCTTATG CAATTACTAA TCCTTATATT
6661  TTAGACTCTA ACCATGTTGC TGTAATAATT GTATTAGTGA CATTAAGTAA TGTTCTAAAA
6721  AAGATGAAAG CTAAATGAAG GTTTTAAGGT GAAGATGGAC ACTGTATATG CCGTTTTGGT
6781  TGCTTACAAC CCAGAACATA ATGATTTAAA AAATGCGGTT GAATTATTGT TGAGACAAGT
6841  TACTAAAGTT GTCGTTTGCA ATAACTCTAC AAATGGTTAT AAATATGCTG AAAATTCTTC
6901  AGGCGATGTA AAAATATTCA ATTTCAATGA TAATTTAGGC ATAGCAGAAG CCCAAAGTAT
6961  AGGAATGAAA TGGGCTTTTG AAAATGGCGC TGATTTTATA TTGCAAATGG ATCAGGATAG
7021  TATTCCTGAT CCTAAGATGG TAGAGCAGTT ACTTACTTGT TACAAAAAAT TGCTTAAACA
7081  AAATGTCAAT GTTGGTTTAG TTGGTTCACA AGATTTTGAT AAAGTAACTG GTGAATTAAA
7141  TAAAGCAAGG GTAAAAAAAG GGAAACCACT TACAGAAGTT TATTATGAGG TAGATAGTAC
7201  A1TAAGTTCT GGCAGTCTAA TACCAAAAAA TAGTTGGTTG ATTGTTGGAG AATGAAAGA
7261  TGAGCTTTTT ATCGATGCGG TAGACCATGA ATATTGTTGG AGATTAAGAG CTGCTGGGTT
7321  TAAAGTAATT AGGAATAAAA ATGCGTTACT TGCACATAGA CTTGGAGATG GGCGATTTAA
7381  GATCTTAAAT ATTCTTTCTG TCGGTTTGCC AAGCCCATTT CGTCATTATT ATGCTACTCG
7441  AAATATCTTT CTTTTATTAA ATAAAAATTA TGTACCCATC TACTGGAAAA TTTCTAGTCT
7501  GGTTAAATTA ATTGGAAAGG TTTTTTTATA TCCTATTTTC CTTCCAAATG GTAATAAAAG
7561  GTTATATTTT TTTTTAAAAG GCATTAATGA CGGTTTAATG GGTCGAAGTG GTAAAATGAA
7621  ATGAATCATA GATTAGAAAA ATTCTCAGTT TTAATTAGCA TTTATAAAAA TGATCTACCG
7681  CAATTTTTTG AGGTGGCTCT ACGCTCTATT TTTCACGATC AAACACTTAA GCCAGATCAA
7741  ATAGTAATTG TTGCAGATGG AGAACTCCAT CAAACACACA TCGATATTAT AAATTCATTC
7801  ATTGATGATG TTGGCAATAA AATAGTAACA TTTGTACCTT TACCTAGAAA TGTTGGATTG
7861  GCTAATGCCT TAAATGAAGG ATTAAAGGCT TGTAGGAATG AGTTAGTGGC AAGAATGGAT
7921  GCTGATGATA TTTCTTTGCC TCATCGGTTT GAGAAACAAA TTTCTTTTAT GATTAATAAT
7981  TCAGAAATAG ATGTATGTGG CAGTTTTATT GATGAAATTG AAACTGTTAC TGAGGAGTTT
8041  ATTTCAACAC GCAAAGTGCC TCTCGAACAT AGAGAAATAG TTAAATTCGC GAGGAAACGA
8101  AGCGCAGTTA GCCATCCTTC TGTAATTTTT AGAAAGAATA CAGTATTAGC TGTTGGTGGT
8161  TATCCTCCAT TCAGAAAATC TCAAGATTTT GCATTGTGGA GCCTATTAAT TGTACATAAT
8221  GCAAGATTTG CAAATCTTCC AGATATTTTA TTAAAAATGC GAACTGGTCG TAATCTTATG
8281  GCTCGACGTG GATTGTCATA TTTATTGTAC GAGTATAAAG TATTGTATTA TCAATATAAA
8341  ATTGGTTTTA TTCGAAAAAA TGAATTAATA AGTAATGCTA TGTTGAGAAC ATTTTTTCGT
8401  ATAATGCCAT CTAAATTAAA GGAGCTGATG TATTCAATCG TTAGGAATCG ATAATAATAA
8461  TTTTCTGATT AAGTGTTATG GATTTATTTT TATTAGGCAT ATTCTATAAT TAAGCATAAC
8521  CCGCATACCA CCCAGCGGTA TCCTGACAGG AGTAAACAAT GTCAAAGCAA CAGATCGGCG
8581  TCGTCGGTAT GGCAGTGATG GGGCGCAACC TTGCGCTCAA TATCGAAAGC CGTGGTTATA
8641  CCGTCTCTAT TTTCAACCGT TCCCGTGAAA AGACCGAAGA AGTGATTACC GAAAATCCAG
```

```
 8701  GCAAGAAACT GGTTCCTTAC TATACGGTGA AAGAATTTGT TGAATCTCTG GAAACGCCTC
 8761  GTCGCATCCT GTTAATGGTG AAAGCAGGTG CTGGCACGGA TGCTGCTATT GATTCCCTCA
 8821  AGCCATACCT CGATAAAGGT GACATCATCA TTGATGGTGG TAACACCTTC TTCCATGACA
 8881  CCATTCGTCG TAACCGTGAG CTTTCTGCAG AAGGCTTTAA CTTTATCGGT ACCGGTGTTT
 8941  CCGGTGGTGA AGAAGGTGCG CTGAAAGGTC CTTCCATTAT GCCTGGTGGG CAGAAAGAAG
 9001  CTTATGAACT GATTGCGCCG ATCCTGACCA AAATCGCCGC TGTGGCTGAA GACGGCGAAC
 9061  CGTGCGTTAC CTATATTGGT GCCGATGGTG CAGGTCATTA TGTGAAGATG GTTCACAACG
 9121  GTATTGAATA CGGTGATATG CAGCTGATTG CTGAAGCCTA TTCTCTGCTT AAAGGTGGCT
 9181  TGAACCTCAC CAACGAAGAA CTGGCGCAGA CCTTTACCGA GTGGAATAAC GGTGAACTGA
 9241  GCAGCTACCT GATCGACATC ACCAAAGATA TCTTCACCAA AAAAGATGAA GAGGGTAACT
 9301  ACCTGGTTGA TGTGATTCTG GATGAAGCAG CAAACAAAGG TACGGGCAAA TGGACCAGCC
 9361  AGAGCGCGCT GGATCTCGGC GAACCGCTGT CGCTGATTAC CGAGTCTGTG TTTGCACGTT
 9421  ATATCTCTTC TCTGAAAGAG CAGCGTGTTG CCGCATCTAA AGTTCTCTCT GGCCCGCAAG
 9481  CGCAGCCAGC TGGCGACAAT GCTGAGTTCA TCGAAAAAGT TCGCCGTGCG CTGTATCTGG
 9541  GCAAAATCGT TTCTTACGCT CAGGGCTTCT CTCAGCTACG CGCTGCGTCT GAAGAGTACA
 9601  ACTGGGATCT GAACTACGGT GAAATCGCGA AGATTTTCCG TGCTGGCTCC ATCATCCGTG
 9661  CGCAGTTCCT GCAGAAAATC ACCGATGCTT ATGCCGAAAA TCCGCAGATC GCTAACCTGT
 9721  TGCTGGCTCC TTACTTCAAG CAAATTGCCG ATGACTACCA GCAGGCGCTG CGCGATGTCG
 9781  TCGCTTACGC AGTACAGAAC GGTATCCCGG TGCCCTACCT CGCCGCTGCG GTTGCCTATT
 9841  ACGACAGCTA CCGCGCCGCT GTTCTGCCTG CGAACCTGAT CCAGGCACAG CGTGACTATT
 9901  TCGGTGCGCA TACTTATAAG CGCATTGATA AAGAAGGTGT GTTCCATACC GAATGGCTGG
 9961  ATTAATCTGA TTTAAATCAA TTAATCAAAG CAAGGCCCGG AGAAACCCTC CGGGCTTTTT
10021  TATTATACAA AGCGGCAGGT TAGGGCCTTT TTTTATAATT TATAGTTAAA AACGCGATAT
10081  AATACAGCGC CGCACAGCAG GATCGCTGCC TTGACAGTTC ATCTACATCA GCGTTAAAAA
10141  TCCCGCAGTA GATGAAGCTG TGGTGGTGGA TTAATGACCA CTCTAAATGT TAACCGGAA
10201  GAAGTCAGAG CTAATGAAAA TAACAATTTC AGGAACAGGT TATGTTGGTC TTTCAAATGG
10261  TATTCTGATT GCGCAAAACC ACGAAGTGGT TGCACTGGAT ATCGTTCAGG CCAAAGTGGA
10321  CATGCTTAAC AAGAGGCAGT CACCGCTTGT TGATAAGGAG ATTGAAGAGT ATCTGGCGAC
10381  TAAAGATCTC AATTTCCGCG CTACGACAGA TAAGTATGAC GCGTATAAAA ATGCCGATTA
10441  CGTTATTATT GCCACACCTA CCGATTATGA TCCGAAAACA AATTACTTTA ATACCTCAAG
10501  CGTGGAAGCG GTCATTCGTG ATGTGACAGA AATTAATCCC AACGCGGTAA TGATTATAAA
10561  ATCAACTATC CCTGTTGGTT TTACAGAGTC CATTAAAGAA CGTTTTGGTA TTGAAAATGT
10621  GATCTTTTCG CCTGAGTTTT TGCGTGAAGG TAAAGCACTT TATGATAACT TACACCCATC
10681  ACGCATTGTG ATTGGCGAGC AGTCTGAACG CGCTAAACGT TTTGCTGCGT TATTACAGGA
10741  AGGCGCCATT AAGCAAGACA TACCAACATT GTTTACTGAC TCAACCGAGG CTGAGGCGAT
10801  TAAACTTTTT GCGAACACTT ATCTGGCGAT GCGTGTAGCG TATTTCAATG AACTTGATAG
10861  TTATGCTGAA AGCCTGGGAC TTAATTCACG CCAGATTATT GAGGGCGTAT GCCTTGACCC
10921  GCGTATCGGT AATCACTACA ACACCCGTCA TTCGGTTAT GGTGGTTATT GTCTGCCGAA
```

```
10981  AGATACTAAG CAGTTACTGG CAAATTACCA GTCTGTGCCG AATAACCTGA TCTCGGCAAT
11041  TGTTGACGCC AACCGCACGC GCAAAGATTT TATTGCCGAT TCTATCCTTG CACGTAAACC
11101  GAAAGTTGTT GGCGTCTATC GTTTGATTAT GAAGAATGGT TCAGACAATT TCGTGCTTC
11161  CTCGATTCAG GGTATTATGA AGCGAATCAA GGCGAAAGGT GTGCCTGTAA TCGTTTATGA
11221  GCCAGCTATG AAAGAGGACG ATTTTTTCCG GTCGCGCGTG GTACGTGATC TGGATGCGTT
11281  CAAACAAGAA GCTGATGTTA TTATTTCTAA CCGTATGTCT GCCGATCTGG CTGATGTAGC
11341  AGATAAAGTT TATACGCGCG ACTTGTTTGG CAATGATTAA TTATTTTGTT TCATTCTAAG
11401  AAAAGGCCCT AATAAATTAG GGCCTTTTCT TATGGTTTTG TAAAATCAAA CTTTATAGAA
11461  GTTACGATAC CATTCTACAA AGTTCTTTAC CCCTTCTTTA ACTGACGTTT CAGGTTTGAA
11521  TCCTATTACG TCATACAGTG CTTTTGTATC AGCACTGGTT TCCAGTACAT CACCGGGTTG
11581  GAGAGGCATC ATATTTTTGT TGGCTTCAAT ACCCAGAGCC TCTTCTAACG CATTGATATA
11641  GTCCATCAAC TCCACAGGCG AACTATTACC AATGTTATAG ACACGATATG GTGCTGAACT
11701  TGTTGCAGGC GAGCCTGTTT CTACAGCCCA CTGTGGGTTT TTTTCTGGAA TAACATCCTG
11761  TAAGCGAATA ATAGCTTCGG CAATATCATC AATGTAAGTA AAGTCACGCT TCATTTTGCC
11821  GAAGTTGTAA ACATCAATGC TTTTACCTTC CAGCATGGCT TTAGTGAATT TAAATAATGC
11881  CATATCCGGA CGTCCCCATG GACCATAAAC CGTAAAGAAA CGCAGCCCTG TGGTCGGTAA
11941  GCCATACAAA TGAGAATATG TATGGGCCAT GAGTTCATTC GCTTTTTTAG TTGCTGCATA
12001  AAGCGAAACA GGATGATCTA CAGAGTCATC TGTAGAGAAA GGCATCTTGC GGTTCATGCC
12061  ATAAACAGAA CTGGAGGAAG CGTAAAGTAG ATGCTGAACA TTATTATGGC GACATCCTTC
12121  TAGTATGTTC AGGAATCCAA TCAGGTTTGC ATCTGCATAT GCATTGGGAT TTTCAAGAGA
12181  GTAACGTACA CCGGCTTGCG CAGCGAGGTT TATTACGCGT TCGAACCGCT CGTCTGCAAA
12241  CAGTGCCGCC ATTTTCTCAC GATCGGCCAG GTCAATTTTA TAAAAACTGA AGTTGTCGTG
12301  CTTGAGTAAA TCAAGTCGTG CTTGTTTGAG GTTGACATCG TAATAATCAT TTAAGTTGTC
12361  AATGCCTACA ACCTGATGAC CAGCTGCAAG AAGCCGTTTA CTTAGATAGA AACCGATAAA
12421  GCCAGCAGCT CCCGTAACCA GAAATTTCAT TTATAATCCT CGCTCAGGCT AGAATATAGC
12481  CAATCTTCAT CTGGCATAAC TGAAAGTTAA ATTATACCGT TAGACAAGAA AAAAGATAA
12541  TCGGTATCAG TTCTAAACTT GGCTGTTTTT TCTGGTAACG TGCTCATTTT ACAATCAAAG
12601  CTGTTCTAAG CTGACTATAC AAGCCGACGT CATTATCTCC AACCGTATGG CAGAAGAGCT
12661  TAAGGATGTG GCAGACAAAG TCTACACCCG CGATCTCTTT GGCAGTGACT AACATCCTGT
12721  TATCATGGCG ATTTTCGCCC TGATTCTCTT ATGTTCCCTT TGTAATAATT CATTATTTTT
12781  ATCATTTATC CTATAGCATT CATGGCGATT ATCGCTAAAC TATGGCGGCG CGCCACGTGG
12841  GATCCCCGGG TACCGAGCTC GAATTCGCCC TATAGTGAGT CGTATTACAA TTCACTGGCC
12901  GTCGTTTTAC AACGTCGTGA CTGGGAAAAC CCTGGCGTTA CCCAACTTAA TCGCCTTGCA
12961  GCACATCCCC CTTTCGCCAG CTGGCGTAAT AGCGAAGAGG CCCGCACCGA TCGCCCTTCC
13021  CAACAGTTGC GCAGCTGAAT GGCGAATGGC GCCTGATGCG GTATTTTCTC CTTACGCATC
13081  TGTGCGGTAT TTCACACCGC ATATGGTGCA CTCTCAGTAC AATCTGCTCT GATGCCGCAT
13141  AGTTAAGCCA GCCCCGACAC CCGCCAACAC CCGCTGACGC GAACCCCTTG CGGCCGCATC
13201  GAATATAACT TCGTATAATG TATGCTATAC GAAGTTATTA GCGATGAGCT CGGACTTCCA
13261  TTGTTCATTC CACGGACAAA AACAGAGAAA GGAAACGACA GAGGCCAAAA AGCTCGCTTT
```

```
13321  CAGCACCTGT CGTTTCCTTT CTTTTCAGAG GGTATTTTAA ATAAAAACAT TAAGTTATGA

13381  CGAAGAAGAA CGGAAACGCC TTAAACCGGA AAATTTTCAT AAATAGCGAA AACCCGCGAG

13441  GTCGCCGCCC CGTAACCTGT CGGATCACCG GAAAGGACCC GTAAAGTGAT AATGATTATC

13501  ATCTACATAT CACAACGTGC GTGGAGGCCA TCAAACCACG TCAAATAATC AATTATGACG

13561  CAGGTATCGT ATTAATTGAT CTGCATCAAC TTAACGTAAA AACAACTTCA GACAATACAA

13621  ATCAGCGACA CTGAATACGG GGCAACCTCA TGTCCGAGCT CGCGAGCTCG TCGACAGCGA

13681  CACACTTGCA TCGGATGCAG CCCGGTTAAC GTGCCGGCAC GGCCTGGGTA ACCAGGTATT

13741  TTGTCCACAT AACCGTGCGC AAAATGTTGT GGATAAGCAG GACACAGCAG CAATCCACAG

13801  CAGGCATACA ACCGCACACC GAGGTTACTC CGTTCTACAG GTTACGACGA CATGTCAATA

13861  CTTGCCCTTG ACAGGCATTG ATGGAATCGT AGTCTCACGC TGATAGTCTG ATCGACAATA

13921  CAAGTGGGAC CGTGGTCCCA GACCGATAAT CAGACCGACA ACACGAGTGG GATCGTGGTC

13981  CCAGACTAAT AATCAGACCG ACGATACGAG TGGGACCGTG GTCCCAGACT AATAATCAGA

14041  CCGACGATAC GAGTGGGACC GTGGTTCCAG ACTAATAATC AGACCGACGA TACGAGTGGG

14101  ACCGTGGTCC CAGACTAATA ATCAGACCGA CGATACGAGT GGGACCATGG TCCCAGACTA

14161  ATAATCAGAC CGACGATACG AGTGGGACCG TGGTCCCAGT CTGATTATCA GACCGACGAT

14221  ACGAGTGGGA CCGTGGTCCC AGACTAATAA TCAGACCGAC GATACGAGTG GGACCGTGGT

14281  CCCAGACTAA TAATCAGACC GACGATACGA GTGGGACCGT GGTCCCAGTC TGATTATCAG

14341  ACCGACGATA CAAGTGGAAC AGTGGGCCCA GAGAGAATAT TCAGGCCAGT TATGCTTTCT

14401  GGCCTGTAAC AAAGGACATT AAGTAAAGAC AGATAAACGT AGACTAAAAC GTGGTCGCAT

14461  CAGGGTGCTG CCTTTTCAAG TTCCTTAAGA ATGGCCTCAA TTTTCTCTAT ACACTCAGTT

14521  GGAACACGAG ACCTGTCCAG GTTAAGCACC ATTTTATCGC CCTTATACAA TACTGTCGCT

14581  CCAGGAGCAA ACTGATGTCG TGAGCTTAAA CTAGTTCTTG ATGCAGATGA CGTTTTAAGC

14641  ACAGAAGTTA AAAGAGTGAT AACTTCTTCA GCTTCAAATA TCACCCCAGC TTTTTTCTGC

14701  TCATGAAGGT TAGATGCCTG CTGCTTAAGT AATTCCTCTT TATCTGTAAA TTTTTTTTGA

14761  AGTGCATCAC CTGACCGGGC AGATAGTTCA CCGGGGTGAG AAAAAAGAGC AACAACTGAT

14821  TTAGGCAATT TGGCGGTGTT GATACAGCGG GTAATAATCT TACGTGAAAT ATTTTCCGCA

14881  TCAGCCAGCG CAGAAATATT TCCAGCAAAT TCATTCTGCA ATCGGCTTGC ATAACGCTGA

14941  CCACGTTCAT AAGCACTTGT TGGGCGATAA TCGTTACCCA ATCTGGATAA TGCAGCCATC

15001  TGCTCATCAT CCAGCTCGCC AACCAGAACA CGATAATCAC TTTCGGTAAG TGCAGCAGCT

15061  TTACGACGGC GACTCCCATC GGCAATTTCT ATGACACCAG ATACTCTTCG ACCGAACGCC

15121  GGTGTCTGTT GACCAGTCAG TAGAAAAGAA GGGATGAGAT CATCCAGTGC GTCCTCAGTA

15181  AGCAGCTCCT GGTCACGTTC ATTACCTGAC CATACCCGAG AGGTCTTCTC AACACTATCA

15241  CCCCGGAGCA CTTCAAGAGT AAACTTCACA TCCCGACCAC ATACAGGCAA AGTAATGGCA

15301  TTACCGCGAG CCATTACTCC TACGCGCGCA ATTAACGAAT CCACCATCGG GGCAGCTGGT

15361  GTCGATAACG AAGTATCTTC AACCGGTTGA GTATTGAGCG TATGTTTTGG AATAACAGGC

15421  GCACGCTTCA TTATCTAATC TCCCAGCGTG GTTTAATCAG ACGATCGAAA ATTTCATTGC

15481  AGACAGGTTC CCAAATAGAA AGAGCATTTC TCCAGGCACC AGTTGAAGAG CGTTGATCAA

15541  TGGCCTGTTC AAAAACAGTT CTCATCCGGA TCTGACCTTT ACCAACTTCA TCCGTTTCAC
```

```
15601  GTACAACATT TTTTAGAACC ATGCTTCCCC AGGCATCCCG AATTTGCTCC TCCATCCACG
15661  GGGACTGAGA GCCATTACTA TTGCTGTATT TGGTAAGCAA AATACGTACA TCAGGCTCGA
15721  ACCCTTTAAG ATCAACGTTC TTGAGCAGAT CACGAAGCAT ATCGAAAAAC TGCAGTGCGG
15781  AGGTGTAGTC AAACAACTCA GCAGGCGTGG GAACAATCAG CACATCAGCA GCACATACGA
15841  CATTAATCGT GCCGATACCC AGGTTAGGCG CGCTGTCAAT AACTATGACA TCATAGTCAT
15901  GAGCAACAGT TTCAATGGCC AGTCGGAGCA TCAGGTGTGG ATCGGTGGGC AGTTTACCTT
15961  CATCAAATTT GCCCATTAAC TCAGTTTCAA TACGGTGCAG AGCCAGACAG GAAGGAATAA
16021  TGTCAAGCCC CGGCCAGCAA GTGGGCTTTA TTGCATAAGT GACATCGTCC TTTTCCCCAA
16081  GATAGAAAGG CAGGAGAGTG TCTTCTGCAT GAATATGAAG ATCTGGTACC CATCCGTGAT
16141  ACATTGAGGC TGTTCCCTGG GGGTCGTTAC CTTCCACGAG CAAACACGT AGCCCCTTCA
16201  GAGCCAGATC CTGAGCAAGA TGAACAGAAA CTGAGGTTTT GTAAACGCCA CCTTTATGGG
16261  CAGCAACCCC GATCACCGGT GGAAATACGT CTTCAGCACG TCGCAATCGC GTACCAAACA
16321  CATCACGCAT ATGATTAATT TGTTCAATTG TATAACCAAC ACGTTGCTCA ACCCGTCCTC
16381  GAATTTCCAT ATCCGGGTGC GGTAGTCGCC CTGCTTTCTC GGCATCTCTG ATAGCCTGAG
16441  AAGAAACCCC AACTAAATCC GCTGCTTCAC CTATTCTCCA GCGCCGGGTT ATTTTCCTCG
16501  CTTCCGGGCT GTCATCATTA AACTGTGCAA TGGCGATAGC CTTCGTCATT TCATGACCAG
16561  CGTTTATGCA CTGGTTAAGT GTTTCCATGA GTTTCATTCT GAACATCCTT TAATCATTGC
16621  TTTGCGTTTT TTTATTAAAT CTTGCAATTT ACTGCAAAGC AACAACAAAA TCGCAAAGTC
16681  ATCAAAAAAC CGCAAAGTTG TTTAAAATAA GAGCAACACT ACAAAAGGAG ATAAGAAGAG
16741  CACATACCTC AGTCACTTAT TATCACTAGC GCTCGCCGCA GCCGTGTAAC CGAGCATAGC
16801  GAGCGAACTG GCGAGGAAGC AAAGAAGAAC TGTTCTGTCA GATAGCTCTT ACGCTCAGCG
16861  CAAGAAGAAA TATCCACCGT GGGAAAAACT CCAGGTAGAG GTACACACGC GGATAGCCAA
16921  TTCAGAGTAA TAAACTGTGA TAATCAACCC TCATCAATGA TGACGAACTA ACCCCCGATA
16981  TCAGGTCACA TGACGAAGGG AAAGAGAAGG AAATCAACTG TGACAAACTG CCCTCAAATT
17041  TGGCTTCCTT AAAAATTACA GTTCAAAAAG TATGAGAAAA TCCATGCAGG CTGAAGGAAA
17101  CAGCAAAACT GTGACAAATT ACCCTCAGTA GGTCAGAACA AATGTGACGA ACCACCCTCA
17161  AATCTGTGAC AGATAACCCT CAGACTATCC TGTCGTCATG GAAGTGATAT CGCGGAAGGA
17221  AAATACGATA TGAGTCGTCT GGCGGCCTTT CTTTTTCTCA ATGTATGAGA GGCGCATTGG
17281  AGTTCTGCTG TTGATCTCAT TAACACAGAC CTGCAGGAAG CGGCGGCGGA AGTCAGGCAT
17341  ACGCTGGTAA CTTTGAGGCA GCTGGTAACG CTCTATGATC CAGTCGATTT TCAGAGAGAC
17401  GATGCCTGAG CCATCCGGCT TACGATACTG ACACAGGGAT TCGTATAAAC GCATGGCATA
17461  CGGATTGGTG ATTTCTTTTG TTTCACTAAG CCGAAACTGC GTAAACCGGT TCTGTAACCC
17521  GATAAAGAAG GGAATGAGAT ATGGGTTGAT ATGTACACTG TAAAGCCCTC TGGATGGACT
17581  GTGCGCACGT TTGATAAACC AAGGAAAAGA TTCATAGCCT TTTTCATCGC CGGCATCCTC
17641  TTCAGGGCGA TAAAAAACCA CTTCCTTCCC CGCGAAACTC TTCAATGCCT GCCGTATATC
17701  CTTACTGGCT TCCGCAGAGG TCAATCCGAA TATTTCAGCA TATTTAGCAA CATGGATCTC
17761  GCAGATACCG TCATGTTCCT GTAGGGTGCC ATCAGATTTT CTGATCTGGT CAACGAACAG
17821  ATACAGCATA CGTTTTTGAT CCCGGGAGAG ACTATATGCC GCCTCAGTGA GGTCGTTTGA
17881  CTGGACGATT CGCGGGCTAT TTTTACGTTT CTTGTGATTG ATAACCGCTG TTTCCGCCAT
```

```
17941  GACAGATCCA TGTGAAGTGT GACAAGTTTT TAGATTGTCA CACTAAATAA AAAAGAGTCA

18001  ATAAGCAGGG ATAACTTTGT GAAAAAACAG CTTCTTCTGA GGGCAATTTG TCACAGGGTT

18061  AAGGGCAATT TGTCACAGAC AGGACTGTCA TTTGAGGGTG ATTTGTCACA CTGAAAGGGC

18121  AATTTGTCAC AACACCTTCT CTAGAACCAG CATGGATAAA GGCCTACAAG GCGCTCTAAA

18181  AAAGAAGATC TAAAAACTAT AAAAAAAATA ATTATAAAAA TATCCCGTGA GATAAGTGGA

18241  TAACCCCAAG GGAAGTTTTT TCAGGCATCG TGTGTAAGCA GAATATATAA GTGCTGTTCC

18301  CTGGTGCTTC CTCGCTCACT CGACCGGGAG GGTTCGAAGA GGGGGGGCAC CCCCCTTCGG

18361  CGTGCGCGGT CACGCGCACA GGGCGCAGCC CTGGTTAAAA ACAAGGTTTA TAAATATTGG

18421  TTTAAAAGCA GGTTAAAAGA CAGGTTAGCG GTGGCCGAAA ACGGGCGGA AACCCTTGCA

18481  AATGCTGGAT TTTCTGCCTG TGGACAGCCC CTCAAATGTC AATAGGTGCG CCCCTCATCT

18541  GTCAGCACTC TGCCCCTCAA GTGTCAAGGA TCGCGCCCCT CATCTGTCAG TAGTCGCGCC

13601  CCTCAAGTGT CAATACCGCA GGGCACTTAT CCCCAGGCTT GTCCACATCA TCTGTGGGAA

18661  ACTCGCGTAA AATCAGGCGT TTTCGCCGAT TTGCGAGGCT GGCCAGCTCC ACGTCGCCGG

18721  CCGAAATCGA GCCTGCCCCT CATCTGTCAA CGCCGCGCCG GGTGAGTCGG CCCCTCAAGT

18781  GTCAACGTCC GCCCCTCATC TGTCAGTGAG GGCCAAGTTT TCCGCGAGGT ATCCACAACG

18841  CCGGCGGCCG GCCGCGGTGT CTCGCACACG GCTTCGACGG CGTTTCTGGC GCGTTTGCAG

18901  GGCCATAGAC GGCCGCCAGC CCAGCGGCGA GGGCAACCAG CCGAGGGCTT CGCCCTGTCG

18961  CTCGACTGCG GCGAGCACTA CTGGCTGTAA AAGGACAGAC CACATCATGG TTCTGTGTTC

19021  ATTAGGTTGT TCTGTCCATT GCTGACATAA TCCGCTCCAC TTCAACGTAA CACCGCACGA

19081  AGATTTCTAT TGTTCCTGAA GGCATATTCA AATCGTTTTC GTTACCGCTT GCAGGCATCA

19141  TGACAGAACA CTACTTCCTA TAAACGCTAC ACAGGCTCCT GAGATTAATA ATGCGGATCT

19201  CTACGATAAT GGGAGATTTT CCCGACTGTT TCGTTCGCTT CTCAGTGGAT AACAGCCAGC

19261  TTCTCTGTTT AACAGACAAA AACAGCATAT CCACTCAGTT CCACATTTCC ATATAAAGGC

19321  CAAGGCATTT ATTCTCAGGA TAATTGTTTC AGCATCGCAA CCGCATCAGA CTCCGGCATC

19381  GCAAACTGCA CCCGGTGCCG GGCAGCCACA TCCAGCGCAA AAACCTTCGT GTAGACTTCC

19441  GTTGAACTGA TGGACTTATG TCCCATCAGG CTTTGCAGAA CTATCAGCGG TATACCGGCA

19501  TACAGCATGT GCATCGCATA GGAATGGCGG AACGTATGTG GTGTGACCGG AACAGAGAAC

19561  GTCACACCGT CAGCAGCAGC GGCGGCAACC GCCTCCCCAA TCCAGGTCCT GACCGTTCTG

19621  TCCGTCACTT CCCAGATCCG CGCTTTCTCT GTCCTTCCTG TGCGACGGTT ACGCCGCTCC

19681  ATGAGCTTAT CGCGAATAAA TACCTGTGAC GGAAGATCAC TTCGCAGAAT AAATAAATCC

19741  TGGTGTCCCT GTTGATACCG GGAAGCCCTG GGCCAACTTT TGGCGAAAAT GAGACGTTGA

19801  TCGGCACGTA AGAGGTTCCA ACTTTCACCA TAATGAAATA AGATCACTAC CGGGCGTATT

19861  TTTTGAGTTA TCGAGATTTT CAGGAGCTAA GGAAGCTAAA ATGGAGAAAA AAATCACTGG

19921  ATATACCACC GTTGATATAT CCCAATGGCA TCGTAACTAA CATTTTGAGG CATTTCAGTC

19981  AGTTGCTCAA TGTACCTATA ACCAGACCGT TCAGCTGGAT ATTACGGCCT TTTTAAAGAC

20041  CGTAAAGAAA AATAAGCACA AGTTTTATCC GGCCTTTATT CACATTCTTG CCCGCCTGAT

20101  GAATGCTCAT CCGGAATTTC GTATGGCAAT GAAAGACGGT GAGCTGGTGA TATGGGATAG

20161  TGTTCACCCT TGTTACACCG TTTTCCATGA GCAAACTGAA ACGTTTTCAT CGCTCTGGAG
```

-continued

Sequence Listing

```
20221  TGAATACCAC GACGATTTCC GGCAGTTTCT ACACATATAT TCGCAAGATG TGGCGTGTTA

20281  CGGTGAAAAC CTGGCCTATT TCCCTAAAGG GTTTATTGAG AATATGTTTT TCGTCTCAGC

20341  CAATCCCTGG GTGAGTTTCA CCAGTTTTGA TTTAAACGTG GCCAATATGG ACAACTTCTT

20401  CGCCCCCGTT TTCACCATGG GCAAATATTA TACGCAAGGC GACAAGGTGC TGATGCCGCT

20461  GGCGATTCAG GTTCATCATG CCCTTTGTGA TGGCTTCCAT GTCGGCAGAA TGCTTAATGA

20521  ATTACAACAG TACTGCGATG AGTGGCAGGG CGGGGCGTAA TTTTTTTAAG GCAGTTATTG

20581  GTGCCCTTAA ACGCCTGGTT GCTACGCCTG AATAAGTGAT AATAAGCGGA TGAATGGCAG

20641  AAATTCGATG ATAAGCTGTC AAACATGAGA ATTGGTCGAC GGCCCGGGCG GCCGCAAGGG

20701  GTTCGCGTTG GCCGATTCAT TAATGCAGCT GGCACGACAG GTTTCCCGAC TGGAAAGCGG

20761  GCAGTGAGCG CAACGCAATT AATGTGAGTT AGCTCACTCA TTAGGCACCC CAGGCTTTAC

20821  ACTTTATGCT TCCGGCTCGT ATGTTGTGTG GAATTGTGAG CGGATAACAA TTTCACACAG

20881  GAAACAGCTA TGACCATGAT TACGCCAAGC TATTTAGGTG AGACTATAGA ATACTCAAGC

20941  TTGCATGCCT GCAGGTCGAC TCTAGAGGAT CCCACGACGT CG
```

```
Nucleotide Sequence for pCC1FOS cut (pFOS)
and S. flexneri 6 O-antigen with Z3206
Locus pFOS cut and O-antigen cut (Z3206+)
Definition Ligation of inverted S. flexneri 6 O antigen cluster
amplified with Z3206Nhe and wzzAscI cut with NheI and AscI into
pCC1FOS with MCS cassette cut with NheI and AscI
Features        Location/Qualifiers
CDS             complement(370..396)
                /label=wzz'
CDS             748..1752
                /label=uge
CDS             complement(1818..3011)
                /label=ugd
CDS             complement(3233..4639)
                /label=gnd
CDS             complement(4744..5577)
                /label=wfbZ
CDS             complement(5574..6443)
                /label=wfbY
CDS             complement(6460..7647)
                /label=wzy
CDS             complement(7703..8935)
                /label=wzx
CDS             complement(8932..9489)
                /label=rmlC
CDS             complement(9494..10372)
                /label=rmlA
CDS             complement(10430..11329)
                /label=rmlD
CDS             complement(11329..12414)
                /label=rmlB
CDS             complement(12787..13680)
                /label=galF
CDS             complement(13912..14907)
                /label=Z3206
CDS             complement(15065..15097)
                /label='weaM
CDS             complement(15525..16184)
                /label=cat
CDS             16403..16750
                /label=redF
CDS             18145..18900
                /label=repE
CDS             19479..20654
                /label=parA
CDS             20654..21625
                /label=parB
Length: 22887 bp
Type: DNA circular UNA
Sequence:
```

SEQ ID NO: 29

```
   1 GCGGCCGCAA GGGGTTCGCG TCAGCGGGTG TTGGCGGGTG TCGGGCTGG  CTTAACTATG
  61 CGGCATCAGA GCAGATTGTA CTGAGAGTGC ACCATATGCG GTGTGAAATA CCGCACAGAT
 121 GCGTAAGGAG AAAATACCGC ATCAGGCGCC ATTCGCCATT CAGCTGCGCA ACTGTTGGGA
 181 AGGGCGATCG GTGCGGGCCT CTTCGCTATT ACGCCAGCTG GCGAAAGGGG GATGTGCTGC
 241 AAGGCGATTA AGTTGGGTAA CGCCAGGGTT TTCCCAGTCA CGACGTTGTA AAACGACGGC
 301 CAGTGAATTG TAATACGACT CACTATAGGG CGAATTCGAG CTCGGTACCC GGGGATCCCA
 361 CGTGGCGCGC CGCCATAGTT TAGCGATAAT CGCCATGAAT GCTATAGGAT AAATGATAAA
 421 AATAATGAAT TATTACAAAG GAACATAAG  AGAATCAGGG CGAAAATCGC CATGATAACA
 481 GGATGTTAGT CACTGCCAAA GAGATCGCGG GTGTAGACTT TGTCTGCCAC ATCCTTAAGC
 541 TCTTCTGCCA TACGGTTGGA GATAATGACG TCGGCTTGTA TAGTCAGCTT AGAACAGCTT
 601 TGATTGTAAA ATGAGCACGT TACCAGAAAA AACAGCCAAG TTTAGAACTG ATACCGATTA
 661 TCTTTTTTTC TTGTCTAACG GTATAATTTA ACTTTCAGTT ATGCCAGATG AAGATTGGCT
 721 ATATTCTAGC CTGAGCGAGG ATTATAAATG AAATTTCTGG TTACGGGAGC TGCTGGCTTT
 781 ATCGGTTTCT ATCTAAGTAA ACGGCTTCTT GCAGCTGGTC ATCAGGTTGT AGGCATTGAC
 841 AACTTAAATG ATTATTACGA TGTCAACCTC AAACAAGCAC GACTTGATTT ACTCAAGCAC
 901 GACAACTTCA GTTTTTATAA AATTGACCTG GCCGATCGTG AGAAAATGGC GGCACTGTTT
 961 GCAGACGAGC GGTTCGAACG CGTAATAAAC CTCGCTGCGC AAGCCGGTGT ACGTTACTCT
1021 CTTGAAAATC CCAATGCATA TGCAGATGCA AACCTGATTG GATTCCTGAA CATACTAGAA
1081 GGATGTCGCC ATAATAATGT TCAGCATCTA CTTTACGCTT CCTCCAGTTC TGTTTATGGC
1141 ATGAACCGCA AGATGCCTTT CTCTACAGAT GACTCTGTAG ATCATCCTGT TTCGCTTTAT
1201 GCAGCAACTA AAAAAGCGAA TGAACTCATG GCCCATACAT ATTCTCATTT GTATGGCTTA
1261 CCGACCACAG GGCTGCGTTT CTTTACGGTT TATGGTCCAT GGGGACGTCC GGATATGGCA
1321 TTATTTAAAT TCACTAAAGC CATGCTGGAA GGTAAAAGCA TTGATGTTTA CAACTTCGGC
1381 AAAATGAAGC GTGACTTTAC TTACATTGAT GATATTGCCG AAGCTATTAT TCGCTTACAG
1441 GATGTTATTC CAGAAAAAAA CCCACAGTGG GCTGTAGAAA CAGGCTCGCC TGCAACAAGT
1501 TCAGCACCAT ATCGTGTCTA TAACATTGGT AATAGTTCGC CTGTGGAGTT GATGGACTAT
1561 ATCAATGCGT TAGAAGAGGC TCTGGGTATT GAAGCCAACA AAAATATGAT GCCTCTCCAA
1621 CCCGGTGATG TACTGGAAAC CAGTGCTGAT ACAAAAGCAC TGTATGACGT AATAGGATTC
1681 AAACCTGAAA CGTCAGTTAA AGAAGGGGTA AGAACTTTG  TAGAATGGTA TCGTAACTTC
1741 TATAAAGTTT GATTTTACAA AACCATAAGA AAAGGCCCTA ATTTATTAGG GCCTTTTCTT
1801 AGAATGAAAC AAAATAATTA ATCATTGCCA AACAAGTCGC GCGTATAAAC TTTATCTGCT
1861 ACATCAGCCA GATCGGCAGA CATACGGTTA GAAATAATAA CATCAGCTTC TTGTTTGAAC
1921 GCATCCAGAT CACGTACCAC GCGCGACCGG AAAAAATCGT CCTCTTTCAT AGCTGGCTCA
1981 TAAACGATTA CAGGCACACC TTTCGCCTTG ATTCGCTTCA TAATACCCTG AATCGAGGAA
2041 GCACGAAAAT TGTCTGAACC ATTCTTCATA ATCAAACGAT AGACGCCAAC AACTTTCGGT
2101 TTACGTGCAA GGATAGAATC GGCAATAAAA TCTTTGCGCG TGCGGTTGGC GTCAACAATT
2161 GCCGAGATCA GGTTATTCGG CACAGACTGG TAATTTGCCA GTAACTGCTT AGTATCTTTC
2221 GGCAGACAAT AACCACCATA ACCGAATGAC GGGTTGTTGT AGTGATTACC GATACGCGGG
2281 TCAAGGCATA CGCCCTCAAT AATCTGGCGT GAATTAAGTC CCAGGCTTTC AGCATAACTA
```

```
2341  TCAAGTTCAT TGAAATACGC TACACGCATC GCCAGATAAG TGTTCGCAAA AAGTTTAATC
2401  GCCTCAGCCT CGGTTGAGTC AGTAAACAAT GTTGGTATGT CTTGCTTAAT GGCGCCTTCC
2461  TGTAATAACG CAGCAAAACG TTTAGCGCGT TCAGACTGCT CGCCAATCAC AATGCGTGAT
2521  GGGTGTAAGT TATCATAAAG TGCTTTACCT TCACGCAAAA ACTCAGGCGA AAAGATCACA
2581  TTTTCAATAC CAAAACGTTC TTTAATGGAC TCTGTAAAAC CAACAGGGAT AGTTGATTTT
2641  ATAATCATTA CCGCGTTGGG ATTAATTTCT GTCACATCAC GAATGACCGC TTCCACGCTT
2701  GAGGTATTAA AATAATTTGT TTTCGGATCA TAATCGGTAG GTGTGGCAAT AATAACGTAA
2761  TCGGCATTTT TATACGCGTC ATACTTATCT GTCGTAGCGC GGAAATTGAG ATCTTTAGTC
2821  GCCAGATACT CTTCAATCTC CTTATCAACA AGCGGTGACT GCCTCTTGTT AAGCATGTCC
2881  ACTTTGGCCT GAACGATATC CAGTGCAACC ACTTCGTGGT TTTGCGCAAT CAGAATACCA
2941  TTTGAAAGAC CAACATAACC TGTTCCTGAA ATTGTTATTT TCATTAGCTC TGACTTCTTC
3001  CGGTTAAACA TTTAGAGTGG TCATTAATCC ACCACCACAG CTTCATCTAC TGCGGGATTT
3061  TTAACGCTGA TGTAGATGAA CTGTCAAGGC AGCGATCCTG CTGTGCGGCG CTGTATTATA
3121  TCGCGTTTTT AACTATAAAT TATAAAAAAA GGCCCTAACC TGCCGCTTTG TATAATAAAA
3181  AAGCCCGGAG GGTTTCTCCG GGCCTTGCTT TGATTAATTG ATTTAAATCA GATTAATCCA
3241  GCCATTCGGT ATGGAACACA CCTTCTTTAT CAATGCGCTT ATAAGTATGC GCACCGAAAT
3301  AGTCACGCTG TGCCTGGATC AGGTTCGCAG GCAGAACAGC GGCGCGGTAG CTGTCGTAAT
3361  AGGCAACCGC AGCGGCGAAG GTCGGCACCG GGATACCGTT CTGTACTGCG TAAGCGACGA
3421  CATCGCGCAG CGCCTGCTGG TAGTCATCGG CAATTTGCTT GAAGTAAGGA GCCAGCAACA
3481  GGTTAGCGAT CTGCGGATTT TCGGCATAAG CATCGGTGAT TTTCTGCAGG AACTGCGCAC
3541  GGATGATGCA GCCAGCACGG AAAATCTTCG CGATTTCACC GTAGTTCAGA TCCCAGTTGT
3601  ACTCTTCAGA CGCAGCGCGT AGCTGAGAGA AGCCCTGAGC GTAAGAAACG ATTTTGCCCA
3661  GATACAGCGC ACGGCGAACT TTTTCGATGA ACTCAGCATT GTCGCCAGCT GGCTGCGCTT
3721  GCGGGCCAGA GAGAACTTTA GATGCGGCAA CACGCTGCTC TTTCAGAGAA GAGATATAAC
3781  GTGCAAACAC AGACTCGGTA ATCAGCGACA GCGGTTCGCC GAGATCCAGC GCGCTCTGGC
3841  TGGTCCATTT GCCCGTACCT TTGTTTGCTG CTTCATCCAG AATCACATCA ACCAGGTAGT
3901  TACCCTCTTC ATCTTTTTTG GTGAAGATAT CTTTGGTGAT GTCGATCAGG TAGCTGCTCA
3961  GTTCACCGTT ATTCCACTCG GTAAAGGTCT GCGCCAGTTC TTCGTTGGTG AGGTTCAAGC
4021  CACCTTTAAG CAGAGAATAG GCTTCAGCAA TCAGCTGCAT ATCACCGTAT TCAATACCGT
4081  TGTGAACCAT CTTCACATAA TGACCTGCAC CATCGGCACC AATATAGGTA ACGACGGTT
4141  CGCCGTCTTC AGCCACAGCG GCGATTTTGG TCAGGATCGG CGCAATCAGT TCATAAGCTT
4201  CTTTCTGCCC ACCAGGCATA ATGGAAGGAC CTTTCAGCGC ACCTTCTTCA CCACCGGAAA
4261  CACCGGTACC GATAAAGTTA AAGCCTTCTG CAGAAAGCTC ACGGTTACGA CGAATGGTGT
4321  CATGGAAGAA GGTGTTACCA CCATCAATGA TGATGTCACC TTTATCGAGG TATGGCTTGA
4381  GGGAATCAAT AGCAGCATCC GTGCCAGCAC CTGCTTTCAC CATTAACAGG ATGCGACGAG
4441  GCGTTTCCAG AGATTCAACA AATTCTTTCA CCGTATAGTA AGGAACCAGT TCTTGCCTG
4501  GATTTTCGGT AATCACTTCT TCGGTCTTTT CACGGGAACG GTTGAAAATA GAGACGGTAT
4561  AACCACGGCT TTCGATATTG AGCGCAAGGT TGCGCCCCAT CACTGCCATA CCGACGACGC
```

```
4621  CGATCTGTTG CTTTGACATT GTTTACTCCT GTCAGGATAC CGCTGGGTGG TATGCGGGTT
4681  ATGCTTAATT ATAGAATATG CCTAATAAAA ATAAATCCAT AACACTTAAT CAGAAAATTA
4741  TTATTATCGA TTCCTAACGA TTGAATACAT CAGCTCCTTT AATTTAGATG GCATTATACG
4801  AAAAAATGTT CTCAACATAG CATTACTTAT TAATTCATTT TTTCGAATAA AACCAATTTT
4861  ATATTGATAA TACAATACTT TATACTCGTA CAATAAATAT GACAATCCAC GTCGAGCCAT
4921  AAGATTACGA CCAGTTCGCA TTTTTAATAA AATATCTGGA AGATTTGCAA ATCTTGCATT
4981  ATGTACAATT AATAGGCTCC ACAATGCAAA ATCTTGAGAT TTTCTGAATG GAGGATAACC
5041  ACCAACAGCT AATACTGTAT TCTTTCTAAA AATTACAGAA GGATGGCTAA CTGCGCTTCG
5101  TTTCCTCGCG AATTTAACTA TTTCTCTATG TTCGAGAGGC ACTTTGCGTG TTGAAATAAA
5161  CTCCTCAGTA ACAGTTTCAA TTTCATCAAT AAAACTGCCA CATACATCTA TTTCTGAATT
5221  ATTAATCATA AAAGAAATTT GTTTCTCAAA CCGATGAGGC AAAGAAATAT CATCAGCATC
5281  CATTCTTGCC ACTAACTCAT TCCTACAAGC CTTTAATCCT TCATTTAAGG CATTAGCCAA
5341  TCCAACATTT CTAGGTAAAG GTACAAATGT TACTATTTTA TTGCCAACAT CATCAATGAA
5401  TGAATTTATA ATATCGATGT GTGTTTGATG GAGTTCTCCA TCTGCAACAA TTACTATTTG
5461  ATCTGGCTTA AGTGTTTGAT CGTGAAAAAT AGAGCGTAGA GCCACCTCAA AAAATTGCGG
5521  TAGATCATTT TTATAAATGC TAATTAAAAC TGAGAATTTT TCTAATCTAT GATTCATTTC
5581  ATTTTACCAC TTCGACCCAT TAAACCGTCA TTAATGCCTT TTAAAAAAAA ATATAACCTT
5641  TTATTACCAT TTGGAAGGAA AATAGGATAT AAAAAAACCT TTCCAATTAA TTTAACCAGA
5701  CTAGAAATTT TCCAGTAGAT GGGTACATAA TTTTTATTTA ATAAAAGAAA GATATTTCGA
5761  GTAGCATAAT AATGACGAAA TGGGCTTGGC AAACCGACAG AAAGAATATT TAAGATCTTA
5821  AATCGCCCAT CTCCAAGTCT ATGTGCAAGT AACGCATTTT TATTCCTAAT TACTTTAAAC
5881  CCAGCAGCTC TTAATCTCCA ACAATATTCA TGGTCTACCG CATCGATAAA AAGCTCATCT
5941  TTCATTCCTC CAACAATCAA CCAACTATTT TTTGGTATTA GACTGCCAGA ACTTAATGTA
6001  CTATCTACCT CATAATAAAC TTCTGTAAGT GGTTTCCCTT TTTTTACCCT TGCTTTATTT
6061  AATTCACCAG TTACTTTATC AAAATCTTGT GAACCAACTA AACCAACATT GACATTTTGT
6121  TTAAGCAATT TTTTGTAACA AGTAAGTAAC TGCTCTACCA TCTTAGGATC AGGAATACTA
6181  TCCTGATCCA TTTGCAATAT AAAATCAGCG CCATTTTCAA AAGCCCATTT CATTCCTATA
6241  CTTTGGGCTT CTGCTATGCC TAAATTATCA TTGAAATTGA ATATTTTTAC ATCGCCTGAA
6301  GAATTTTCAG CATATTTATA ACCATTTGTA GAGTTATTGC AAACGACAAC TTTAGTAACT
6361  TGTCTCAACA ATAATTCAAC CGCATTTTTT AAATCATTAT GTTCTGGGTT GTAAGCAACC
6421  AAAACGGCAT ATACAGTGTC CATCTTCACC TTAAAACCTT CATTTAGCTT TCATCTTTTT
6481  TAGAACATTA CTTAATGTCA CTAATACAAT TATTACAGCA ACATGGTTAG AGTCTAAAAT
6541  ATAAGGATTA GTAATTGCAT AAGAAACATA TAGAAAATAT AGCACACACA ACTCACTGTA
6601  TTTTATGATT TTAATCGTGA GAAGGAGATT AATTAATAAA AACAAGTAA ATAAAATAAC
6661  GCCAAGTTGA TTTAAAAAAT AAACTGACTG CAATTCATAA TATATATATG CACTATAATC
6721  ACGGATAGGA GTTTGAATTT TGATGACATT ACCCAAACCA GAACCTATAA CAAAATTTGA
6781  TACAGACTCT GTAAGATCAT TAATTAATAC AGTAAACTGA TCCCATCTAA CTCCTAAAGA
6841  AGAATCAGCT CCATTTGATT TCATGATTAT CAACTCAATT GAATATGTAA TAAAAAAAGG
6901  GAGAATCACA GTAAGAAAAA CCCCAAAAAT AATTTTCCTT AATTTAGCGT ATCGTGAGTT
```

```
6961  AGATTTAGAA CATAGTATAA TATACATAAA AAACAAGCAT ATCGAAACAA AATATGCAAA

7021  ATTACCAGCC ACTATAGTAC CTATAGCCAG AATAACGGTT ATTGTATTTT TGAATCGATA

7081  ATAGAAATAA TCTTTTATGA CTATATGCAA CATAAAGGCA AATGGAATGA GAGCATTTCC

7141  TTTAATTTGA ACTCTATAGA AACCACTTCC ATATGTATAA ACATCACCAT AATCATTCTC

7201  CAAAAAATAA TGTCTTAGTG CTGAATAATC ACCAATACCA TATGTTTTTG TCATATAAAT

7261  ACTAATGATG GATATAATAA CCGCCTGTAA TACCATTAAA TATAAAAATA TTTTAACAAT

7321  CGAGATGGTT CCATAAGAGC AGAAATAAGC ACATAATATA AATAATATGA TAATATAAAA

7381  CCTAATTATT ATCGCTATAT CGTTACCCTT GATATAGGAA TAAATAAAAT TTATAAAAAG

7441  AGCTAATAGA AATATTAAAA TAACAGGATA GTGATATATT CCGTTTGCAA TTTTCTTTGT

7501  AAATGACATG ATACAAAGAC ATAAAAACCC CTCCATAATC CAACTATATT GAATAAATGG

7561  AAAGCTACGT GTAAGGAAAA ATATAAACCC AAAAAACAAA AGAACACTTA AACTTTTGTC

7621  TTTTGAGTTA TAAAAATCAG AAGTCATGTT TGCACTCTAA TTAGATGGGC TTGAGGAAGT

7681  AATCCCTAAA ATCAATTCGC TATTAATATT TCGTATCAAT TAATAATAAT ATCAAAAAAT

7741  CTAACGATGT TCTTACAGAC CATGCTATTG CGGCTCCAAC AATTCCCCAA TGATAAATAA

7801  AAATATATAA TATGCATAAA TATGGGATAA CTTCGAGCAA ATGAATAATA GCTGTAATTT

7861  TTGATCTTCC ACTAGCCTGA ACTGAAACAA ATGGGATTTG TGCAATGCAA TTAAAAAAGA

7921  AACCTATTGC AAGAATTTTT AATACTATAC CTGGCGTCCC ATGATATGTA GGTCCCATCC

7981  AAGCGGACAT TATAAAATCT GATAAAATAA TTATCAACAT TACAATTGGA AGTATACCAA

8041  TAACCATTAT AAAATATGAT AATATTTTAG TTTGCTTTAC CGATTGCAAT TCTGAACTTA

8101  ATCTTGGAAA AATAGCTCTG GACAACGCAC TTGGTAATAT CGTTAAGCGT TGTATACCTT

8161  CAGACGGAGC AGTATAAAAA GAAACTTTAT CAGCCCCCAC AATGTGTGAA AGAATAAAAC

8221  GATCCATATA TGTCATAATA GGGCTAATAA TATTGCTAAC TGTTATCCAG CTTCCAAAGC

8281  CGATTAATCT TTTAACTGTT ACAATTTTTA CAGACAGCCC AGATGATATT ATTAGTTTTC

8341  GACTAAATAT AAAGGTCACT ATAAGTGATA AGACTCTTGC CATAACTAAA CCATATATAG

8401  CACTTAGTAA TCCTCCATGA AAAAAACAGA AAATCACTGG TAATCCAGCC ACAAAAGAGT

8461  TGTTAATTGA TTTTATTAAA TTTACTTTTC TGAACTTTTC CATCCCCTCA AAAATCCCCA

8521  ACCAGACTTG GTTTAACAAG TATAAGGGTA TGGTAGCTGA AATAATATAT ATTGCTTTGA

8581  CAGATTCTAC AACATGATTC GCGTTAATGT TTAATAATTT AACAATTACA TTGCTACTCA

8641  AAAATAGTAC ACTACCGCCA ATCAAGCCCA ATATAGTTAG AATTACCGTT GAAGTTGAAA

8701  TGATCGCTCT TAATTCTTTA TGAACATTTT TATATATTGA TACTTCTCTT ATAACAGCTC

8761  TGGTCAATCC AGCATCAAAA ATACTTGCAT ATCCAACTAA GGCAATAGCT AACGTAAAAA

8821  GGCCAAATTG CTCGGTCCCT AGAATTCTAG ACAGTATACC TAACGCAGGA ATTGCTATTA

8881  ATGATGGTAT AATATACCCA CTTATATTCC ATAAAGTATT CTTTACAATA CTCACAAAAA

8941  TAATTCCTTC ATGTTATGCA ATTCTTTAGC CCTTGCATCT TTAATCGATA AAATATAATT

9001  ATTATGTTCT ATCGTCGGCC ATTTTATGCT CAGAATAGGA TCATTCCATA CAATCCCTCT

9061  ATCACTATCA GGATGATAAT AGTTCGTCGT TTTATATAAA AATTCCGCAG TCTCGCTCAG

9121  CACCAAAAAA CCATGTGCAA ATCCCTCAGG GATCCACAAT TGCCGCTTAT TCTCAGCAGA

9181  TAAATTCACC CCAACCCATT TACCAAAGGT AGGCGACGAT TTACGAATAT CAACAGCTAC
```

-continued

Sequence Listing

```
 9241  ATCAAAAACC TCACCAACAA CGCAACGTAC CAGTTTCCCT TGCGCATAAG GTTCTAACTG
 9301  ATAATGCAGC CCGCGTAAAA CACCTTTACT AGACTTCGAA TGGTTATCCT GAACAAATTC
 9361  AACCTTACGT CCTACAGCTT CTTCGAAAAC TTTCTGATTA AAGCTTTCCA TAAAGAAACC
 9421  ACGCTCATCA CCAAAAACTT TCGGCTCGAA AATTAACACA TCAGGAATTT CTGTTTTAAT
 9481  TACGTTCATT TTATTAATAA CCTTTAATCA TTTTCAGCAG ATACTGTCCA TAAGCATTTT
 9541  TTTTCAGCGC CTCCGCTAAT GCTTTCACCT GTTCAGCATC AATAAACCCT TTACGGTAAG
 9601  CAATTTCTTC TGGGCAGGAA ACCTTTAGTC CCTGGCGCTC TTCAATGGTG GCAATGAAGT
 9661  TGCTTGCTTC AATAAGACTC TGATGTGTCC CCGTATCCAG CCATGCATAA CCACGCCCCA
 9721  TCATGGCAAC GGATAAACGC CCCTGTTCCA TATAAATACG GTTAATATCG GTAATTTCCA
 9781  GTTCACCACG GGCAGAAGGC TTAAGGTTTT TCGCCATTTC GACAACGTCG TTATCATAGA
 9841  AATAAAGCCC GGTTACCGCA TAATTACTTT TTGGTTGTAG CGGTTTTTCT TCCAGGCTTA
 9901  TTGCCGTACC GTTTTTATCA AACTCAACGA CGCCGTAGCG TTCAGGATCA TTAACGTGAT
 9961  AGGCAAATAC CGTTGCACCA CTTTCTTTGT TAACAGCGAC ATCCATTAAC TTCGGCAGAT
10021  CATGACCGTA GAAGATATTA TCACCAAGAA CCAAAGCACA ATCATCACCA CCGATAAACT
10081  CTTCACCGAT AATAAACGCC TGCGCAAGCC CATCTGGAGT CGGTTGCACT TTGTACTGAA
10141  GATTTAGCCC CCACTGGCTA CCGTCACCTA GCAGTTGTTG AAAACGAGGA GTATCCTGTG
10201  GCGTACTAAT AATCAGAATA TCGCGAATAC CCGCCAACAT CAGTGTAGAG AGCGGGTAAT
10261  AGATCATCGG CTTATCATAA ATAGGTAATA GCTGTTTACT GACAGCCATA GTCACAGGAT
10321  AAAGACGTGT ACCAGAACCA CCCGCTAAAA TAATACCTTT ACGCGTTTTC ATTTCATCAT
10381  TCCTTTTAAT TCATCTTGCT CCACCATCAC GAACAAGATG CAAAAACTAT TAAATTGCTG
10441  TAGTCGTAAT TAATTCGTTG AGCATTCGTT TCACACCAAC CTGCCAGTCA GGCAAGACAA
10501  GCGCAAAGTT CTGCTGAAAT TTTTCTGTAT TAAGGCGAGA GTTATGTGGA CGACGAGCTG
10561  GTGTAGGATA GGCTGTTGTT GGTACTGCGT TGAGCTTGTT GAGTGCAAGG GGAATACCTG
10621  CTTTGCGCGC CTCTTCAAAA ACCAGCGCAG CATAATCGTG CCAGGTTGTG GTACCACTGG
10681  CTACCAGATG GTACAAACCT GCGACTTCCG GTTTATTCAG TGCCACACGA ATAGCATGTG
10741  CCGTACAATC AGCCAGCAGC TCAGCACCTG TTGGCGCACC AAATTGATCA TTTATCACAG
10801  CCAGTTCTTC GCGCTCTTTT GCCAGACGCA ACATCGTTTT GGCGAAGTTA TTTCCTTTAG
10861  CTGCGTATAC CCAGCTGGTA CGGAAAATAA GATGCTTCGC GCAATGTTCC TGTAACGCTT
10921  TTTCTCCGGC TAACTTGGTT TCACCGTAAA CATTTAGCGG TGCGGTTGCA TCCGTCTCCA
10981  GCCATGGCGT GTCGCCATTT CCAGGGAATA CGTAGTCAGT TGAGTAATGA ATTACCCAAG
11041  CCCCAACTTC ATTAGCCTCT TTTGCAATTG ATTCAACACT AGTCGCATTG AGTAATTGTG
11101  CAAATTCGGG TTCTGACTCA GCCTTATCTA CTGCGGTGTG AGCCGCAGCA TTAACAATAA
11161  CATCAGGTCG AATTCTTTTG ACTGTTTCAG CTACACCTTC AGGATTACTA AAATCACCAC
11221  AATAATCAGT GGAGTGAACA TCAAGAGCAA TCAAATTACC CAAAGGTGCC AGAGCACGCT
11281  GTAGTTCCCA ACCTACCTGC CCTGTTTTGC CGAAAAGGAG GATATTCATT ACTGGCGGCC
11341  CTCATAGTTC TGTTCAATCC ACGATTGATA AGCACCACTT TTCACATTAT CAACCCATTT
11401  TGTATTGGAC AGGTACCATT CCAATGTCTT CCGAATCCCG CTCTCAAACG TTTCCTGCGG
11461  TTTCCAGCCC AATTCGCGGC TAATCTTCTC TGCATCAATC GCATAACGGC GATCGTGTCC
11521  CGGGCGATCG GCAACATAAG TAATTTGCTC GCGGTAAGAT TTCTCTTTCG GTACAATCTC
```

```
11581  ATCCAGCAAA TCACAAATAG TGAGCACTAC ATCGATGTTT TTCTTTTCGT TGTGTCCACC

11641  AATGTTATAA GTTTCACCCG CTTTACCTTC GGTTACGACG GTATATAACG CACGCGCATG

11701  ATCTTCAACA TACAGCCAGT CACGAATTTG ATCCCCTTTG CCATAAATAG GTAATGCCTT

11761  ACCTTCCAGA GCATTCAGAA TAACCAATGG AATCAATTTT TCCGGGAAAT GATAAGGACC

11821  ATAATTATTA GAGCAATTAG TCACAATGGT TGGTAAACCA TAGGTACGTT TCCACGCGCG

11881  GACTAAATGA TCGCTGGATG CTTTTGAAGC GGAATAAGGG CTGCTTGGCG CGTAAGCTGT

11941  TGTCTCTGTA AATAAGGGTA ATTCTTCTGT ATTATTTACC TCGTCAGGAT GAGGCAAATC

12001  ACCATAGACT TCGTCAGTAG AAATATGATG AAAACGGAAT CTAGTTTTCT TGTCGCTATC

12061  AAGAGCAGAC CAATAATTGC GAGCGGCTTC CAAAAGGACA TATGTACCAA CAATATTGGT

12121  TTCAATAAAT GCCGCAGGAC CTGTAATTGA ACGGTCAACA TGGCTTTCAG CAGCCAGGTG

12181  CATCACTGCA TCTGGCTGAT GCTGAGCAAA AATCCGTGCC ATTGCAGCTG CATCGCAAAT

12241  ATCCGCATGT TCAAAAACAT AGCGTTCAGA ATCAGAAACA TCAGCAAGTG ATTCCAGGTT

12301  TCCGGCGTAC GTTAATTTAT CGACATTAAC AACACTATCC TGCGTATTAT TTATAATGTG

12361  ACGAACTACA GCAAAACCAA TAAATCCTGC GCCACCAGTA ACAAGTATTT TCACCTAATT

12421  TATTCCATAT TGCTTCAGAG CATGCTGTGA ATAAGCGGC TCTCAGTTTG ATTAATAGAA

12481  GTATTAATGC ACGCTACCGC CCCTGGCTTT ACAGCTACCA GAGCACTGCA TGCATGCCTA

12541  CGATGTGACG AGCGTTACCC ACTCGCGCTA AACCCGAAAA ATTCAAAAGC TAATTGTCTT

12601  ACCAATCCGC TCTGGAAACA AGGAAAATCC TGGAAAACTT TGACTAAAAT CCTATTGCTA

12661  ACTCGTTGTT ATTCTGATTG TTTATATAAA ACAACGGCAG GAATATTCGC AACAAATTAC

12721  TTTCACCACG AATCTTCACT GCCGTTATAA TTTTCTTATC AACCGTTACA TCCGGTCAGA

12781  TTTTCATTAT TCGCTTAACA GCTTCTCAAT ACCTTTACGG AACTTCGCCC CTTCTTTCAG

12841  GTTGCGCAGC CCATACTTCA CAAACGCCTG CATATAGCCC ATTTTTTTAC CGCAGTCGTA

12901  GCTGTCGCCG GTCATCAGCA TTGCATCAAC GGACTGTTTT TTCGCCAGCT CGGCAATGGC

12961  ATCAGTCAGC TGAATACGTC CCCATGCACC AGGCTGAGTA CGTTCAAGTT CCGGCCAAAT

13021  ATCGGCAGAA AGCACATAGC GACCAACGGC CATGATGTCT GAGTCCAGCG TCTGCGGCTG

13081  ATCCGGTTTT TCGATAAATT CAACAATGCG GCTGACTTTA CCTTCGCGAT CCAGCGGTTC

13141  TTTGGTCTGG ATGACGGAGT ATTCAGAGAG GTCACCCGGC ATACGTTTTG CCAGCACCTG

13201  GCTACGGCCC GTTTCATTGA AGCGCGCAAT CATGGCAGCA AGGTTGTAGC GTAGCGGGTC

13261  GGCGCTGGCG TCGTCGATCA CAACGTCTGG CAGCACCACG ACAAATGGAT TGTCACCAAT

13321  GGCGGGTCGT GCACACAAAA TGGAGTGACC TAAACCTAAA GGTTCGCCCT GACGCACGTT

13381  CATAATAGTC ACGCCCGGCG GGCAGATAGA TTGCACTTCC GCCAGTAGTT GACGCTTCAC

13441  GCGCTGCTCA AGGAGAGATT CTAATTCATA AGAGGTGTCG AAGTGGTTTT CGACCGCGTT

13501  CTTGGACGCA TGAGTTACCA GGAGGATTTC TTTGATCCCT GCAGCCACAA TCTCGTCAAC

13561  AATGTACTGA ATCATTGGCT TGTCGACGAT CGGTAGCATC TCTTTGGGTA TCGCCTTAGT

13621  GGCAGGCAAC ATATGCATCC CAAGACCCGC TACCGGTATA ACTGCTTTTA AATTCGTCAT

13681  TATTTTCCTA CCTCTAAGGG GCTGATAGTG CGTAAATTAT TGTCATAGGT TAGCCAAACG

13741  GTATGGCTAT ATACCAAGCA TAACTTTGAT TAAACCTTAC GATAACACTA CACACCATCA

13801  GCATCTGGGT TACTCGGATT ACTCGGAAAT CCACATACTG ATAATTTAAT CAGTACCTCT
```

```
13861  TTCCGAATAA TCGTAGTCCA ACCTGGTCCT TTTTTCTCTG ACTCGTCTGC ATTACTCAGA

13921  AACAAACGTT ATGTCGTCTT TTTTGGCATG GACGAATTCA TACTGCAGAG TTCGATCCAG

13981  ACCTTGCGAC AGCGTATACG GTGCAACAAA ACCTGAAGAA TGCACTTTCG TTGCGTCAAA

14041  CTGTGTTGTT GCGCAGAATT TTTTCACGCG CACAGAGCTG ACAGCGTATT TTTTGCCCGT

14101  AATTTTGCTC AGGATATCAA AGCAATATCC ACCCAGCATT CCTAGTGGGT AAGGCAAGTG

14161  CATAGAAGGG ATCTTTTTGT TCAGGCTTTG TTCAACTTCA GCAACCAACT GGTTCATGTT

14221  CAGGTCTGGC TTATCAACAT AGTTATAAAC CTCATAACCT GCGGCAACAT TCTTCAGTTT

14281  GTACTTGATA AACTCAACAA TGTTTCCAAC ATAAGCCATG GACTTATAGT TAGTCCCTGC

14341  GCCCACCATC ATAAACTTGC CGCCAGCGAT CTGTTTCAGC AAGTTATAGA CGTTACCGCG

14401  GTTGCGTTCA CCGAAGATAA CGGTAGGACG GATGATGGTT AATGAACGTT CTGTTGGTGC

14461  TTTGTTATAC CATTCACGCA GCACTTCCTC TGCCTGCCAC TTACTTTTGC CGTAGTGGTT

14521  GAAAGGGTCG TGTGGATGGT TTTCGTCAGG GTTGTGTTTG TTCAAACCAT AAACAGCAAC

14581  GGAACTGGTA AAGATGATAT TTTTAACGCC ATTTTTTTCC ATGGCCGCCA GCACATTGCG

14641  GGTACCCTGA ACGTTGACAT CATAATAGAG AGAAGTAGGG CTGACGTCAT CGCGGTGTTC

14701  CGCTGCCAGT AGTACAACAG TGTCAAAACC GGCTAACGCC TGGTCGAGTG CCTGTTGATC

14761  ACGAACATCA CCAATCTGTG TGATTTCTGG ATAAAAGTGG CTCTGCCGTT TGTCCAGGTT

14821  CTTGATATTA AAGTCAGCAA TTGCCGTTTC AAGTAGTCGG GTTCCTACGA ATCCGGAAGC

14881  TCCTATGAGC AAAACGTTAT TGTTCATAAA TCACTTTAGT CTGGTTGTTA CGTAAGAAAC

14941  ACAAGATAAA GATGAGTACC TTCCCTGAGT AGTCAATGCT GCCCAGCCCC AGCTTTAACA

15001  GTTAGTGTGA GGATTATAAT CTTTTAGAAC ATTATATCCA GTAAGTTTAT GAATGGTCGC

15061  AAATCTACTC TCTCCGTTCC GGCAATCTAA AGTTAATGCT AGCGACGTCG TGGGATCCTC

15121  TAGAGTCGAC CTGCAGGCAT GCAAGCTTGA GTATTCTATA GTCTCACCTA AATAGCTTGG

15181  CGTAATCATG GTCATAGCTG TTTCCTGTGT GAAATTGTTA TCCGCTCACA ATTCCACACA

15241  ACATACGAGC CGGAAGCATA AAGTGTAAAG CCTGGGGTGC CTAATGAGTG AGCTAACTCA

15301  CATTAATTGC GTTGCGCTCA CTGCCCGCTT TCCAGTCGGG AAACCTGTCG TGCCAGCTGC

15361  ATTAATGAAT CGGCCAACGC GAACCCCTTG CGGCCGCCCG GGCCGTCGAC CAATTCTCAT

15421  GTTTGACAGC TTATCATCGA ATTTCTGCCA TTCATCCGCT TATTATCACT TATTCAGGCG

15481  TAGCAACCAG GCGTTTAAGG GCACCAATAA CTGCCTTAAA AAAATTACGC CCCGCCCTGC

15541  CACTCATCGC AGTACTGTTG TAATTCATTA AGCATTCTGC CGACATGGAA GCCATCACAA

15601  ACGGCATGAT GAACCTGAAT CGCCAGCGGC ATCAGCACCT TGTCGCCTTG CGTATAATAT

15661  TTGCCCATGG TGAAAACGGG GGCGAAGAAG TTGTCCATAT TGGCCACGTT TAAATCAAAA

15721  CTGGTGAAAC TCACCCAGGG ATTGGCTGAG ACGAAAAACA TATTCTCAAT AAACCCTTTA

15781  GGGAAATAGG CCAGGTTTTC ACCGTAACAC GCCACATCTT GCGAATATAT GTGTAGAAAC

15841  TGCCGGAAAT CGTCGTGGTA TTCACTCCAG AGCGATGAAA ACGTTTCAGT TTGCTCATGG

15901  AAAACGGTGT AACAAGGGTG AACACTATCC CATATCACCA GCTCACCGTC TTTCATTGCC

15961  ATACGAAATT CCGGATGAGC ATTCATCAGG CGGGCAAGAA TGTGAATAAA GGCCGGATAA

16021  AACTTGTGCT TATTTTTCTT TACGGTCTTT AAAAAGGCCG TAATATCCAG CTGAACGGTC

16081  TGGTTATAGG TACATTGAGC AACTGACTGA AATGCCTCAA ATGTTCTTT ACGATGCCAT

16141  TGGGATATAT CAACGGTGGT ATATCCAGTG ATTTTTTTCT CCATTTTAGC TTCCTTAGCT
```

```
16201  CCTGAAAATC TCGATAACTC AAAAAATACG CCCGGTAGTG ATCTTATTTC ATTATGGTGA

16261  AAGTTGGAAC CTCTTACGTG CCGATCAACG TCTCATTTTC GCCAAAAGTT GGCCCAGGGC

16321  TTCCCGGTAT CAACAGGGAC ACCAGGATTT ATTTATTCTG CGAAGTGATC TTCCGTCACA

16381  GGTATTTATT CGCGATAAGC TCATGGAGCG GCGTAACCGT CGCACAGGAA GGACAGAGAA

16441  AGCGCGGATC TGGGAAGTGA CGGACAGAAC GGTCAGGACC TGGATTGGGG AGGCGGTTGC

16501  CGCCGCTGCT GCTGACGGTG TGACGTTCTC TGTTCCGGTC ACACCACATA CGTTCCGCCA

16561  TTCCTATGCG ATGCACATGC TGTATGCCGG TATACCGCTG AAAGTTCTGC AAAGCCTGAT

16621  GGGACATAAG TCCATCAGTT CAACGGAAGT CTACACGAAG GTTTTTGCGC TGGATGTGGC

16681  TGCCCGGCAC CGGGTGCAGT TTGCGATGCC GGAGTCTGAT GCGGTTGCGA TGCTGAAACA

16741  ATTATCCTGA GAATAAATGC CTTGGCCTTT ATATGGAAAT GTGGAACTGA GTGGATATGC

16801  TGTTTTTGTC TGTTAAACAG AGAAGCTGGC TGTTATCCAC TGAGAAGCGA ACGAAACAGT

16861  CGGGAAAATC TCCCATTATC GTAGAGATCC GCATTATTAA TCTCAGGAGC CTGTGTAGCG

16921  TTTATAGGAA GTAGTGTTCT GTCATGATGC CTGCAAGCGG TAACGAAAAC GATTTGAATA

16981  TGCCTTCAGG AACAATAGAA ATCTTCGTGC GGTGTTACGT TGAAGTGGAG CGGATTATGT

17041  CAGCAATGGA CAGAACAACC TAATGAACAC AGAACCATGA TGTGGTCTGT CCTTTTACAG

17101  CCAGTAGTGC TCGCCGCAGT CGAGCGACAG GGCGAAGCCC TCGGCTGGTT GCCCTCGCCG

17161  CTGGGCTGGC GGCCGTCTAT GGCCCTGCAA ACGCGCCAGA AACGCCGTCG AAGCCGTGTG

17221  CGAGACACCG CGGCCGGCCG CCGGCGTTGT GGATACCTCG CGGAAAACTT GGCCCTCACT

17281  GACAGATGAG GGGCGGACGT TGACACTTGA GGGGCCGACT CACCCGGCGC GGCGTTGACA

17341  GATGAGGGGC AGGCTCGATT TCGCCGGCG ACGTGGAGCT GGCCAGCCTC GCAAATCGGC

17401  GAAAACGCCT GATTTTACGC GAGTTTCCCA CAGATGATGT GGACAAGCCT GGGGATAAGT

17461  GCCCTGCGGT ATTGACACTT GAGGGGCGCG ACTACTGACA GATGAGGGGC GCGATCCTTG

17521  ACACTTGAGG GGCAGAGTGC TGACAGATGA GGGGCGCACC TATTGACATT TGAGGGGCTG

17581  TCCACAGGCA GAAAATCCAG CATTTGCAAG GGTTTCCGCC CGTTTTTCGG CCACCGCTAA

17641  CCTGTCTTTT AACCTGCTTT TAAACCAATA TTTATAAACC TTGTTTTTAA CCAGGGCTGC

17701  GCCCTGTGCG CGTGACCGCG CACGCCGAAG GGGGGTGCCC CCCCTTCTCG AACCCTCCCG

17761  GTCGAGTGAG CGAGGAAGCA CCAGGGAACA GCACTTATAT ATTCTGCTTA CACACGATGC

17821  CTGAAAAAAC TTCCCTTGGG GTTATCCACT TATCCACGGG GATATTTTTA TAATTATTTT

17881  TTTTATAGTT TTTAGATCTT CTTTTTTAGA GCGCCTTGTA GGCCTTTATC CATGCTGGTT

17941  CTAGAGAAGG TGTTGTGACA AATTGCCCTT TCAGTGTGAC AAATCACCCT CAAATGACAG

18001  TCCTGTCTGT GACAAATTGC CCTTAACCCT GTGACAAATT GCCCTCAGAA GAAGCTGTTT

18061  TTTCACAAAG TTATCCCTGC TTATTGACTC TTTTTTATTT AGTGTGACAA TCTAAAAACT

18121  TGTCACACTT CACATGGATC TGTCATGGCG GAAACAGCGG TTATCAATCA CAAGAAACGT

18181  AAAAATAGCC CGCGAATCGT CCAGTCAAAC GACCTCACTG AGGCGGCATA TAGTCTCTCC

18241  CGGGATCAAA AACGTATGCT GTATCTGTTC GTTGACCAGA TCAGAAAATC TGATGGCACC

18301  CTACAGGAAC ATGACGGTAT CTGCGAGATC CATGTTGCTA AATATGCTGA ATATTCGGA

18361  TTGACCTCTG CGGAAGCCAG TAAGGATATA CGGCAGGCAT TGAGAGTTT CGCGGGGAAG

18421  GAAGTGGTTT TTTATCGCCC TGAAGAGGAT GCCGGCGATG AAAAAGGCTA TGAATCTTTT
```

```
18481  CCTTGGTTTA TCAAACGTGC GCACAGTCCA TCCAGAGGGC TTTACAGTGT ACATATCAAC

18541  CCATATCTCA TTCCCTTCTT TATCGGGTTA CAGAACCGGT TTACGCAGTT TCGGCTTAGT

18601  GAAACAAAAG AAATCACCAA TCCGTATGCC ATGCGTTTAT ACGAATCCCT GTGTCAGTAT

18661  CGTAAGCCGG ATGGCTCAGG CATCGTCTCT CTGAAAATCG ACTGGATCAT AGAGCGTTAC

18721  CAGCTGCCTC AAAGTTACCA GCGTATGCCT GACTTCCGCC GCCGCTTCCT GCAGGTCTGT

18781  GTTAATGAGA TCAACAGCAG AACTCCAATG CGCCTCTCAT ACATTGAGAA AAAGAAAGGC

18841  CGCCAGACGA CTCATATCGT ATTTTCCTTC CGCGATATCA CTTCCATGAC GACAGGATAG

18901  TCTGAGGGTT ATCTGTCACA GATTTGAGGG TGGTTCGTCA CATTTGTTCT GACCTACTGA

18961  GGGTAATTTG TCACAGTTTT GCTGTTTCCT TCAGCCTGCA TGGATTTTCT CATACTTTTT

19021  GAACTGTAAT TTTTAAGGAA GCCAAATTTG AGGGCAGTTT GTCACAGTTG ATTTCCTTCT

19081  CTTTCCCTTC GTCATGTGAC CTGATATCGG GGTTAGTTC GTCATCATTG ATGAGGGTTG

19141  ATTATCACAG TTTATTACTC TGAATTGGCT ATCCGCGTGT GTACCTCTAC CTGGAGTTTT

19201  TCCCACGGTG GATATTTCTT CTTGCGCTGA GCGTAAGAGC TATCTGACAG AACAGTTCTT

19261  CTTTGCTTCC TCGCCAGTTC GCTCGCTATG CTCGGTTACA CGGCTGCGGC GAGCGCTAGT

19321  GATAATAAGT GACTGAGGTA TGTGCTCTTC TTATCTCCTT TTGTAGTGTT GCTCTTATTT

19381  TAAACAACTT TGCGGTTTTT TGATGACTTT GCGATTTTGT TGTTGCTTTG CAGTAAATTG

19441  CAAGATTTAA TAAAAAAACG CAAAGCAATG ATTAAAGGAT GTTCAGAATG AAACTCATGG

19501  AAACACTTAA CCAGTGCATA AACGCTGGTC ATGAAATGAC GAAGGCTATC GCCATTGCAC

19561  AGTTTAATGA TGACAGCCCG GAAGCGAGGA AAATAACCCG CGCTGGAGA ATAGGTGAAG

19621  CAGCGGATTT AGTTGGGGTT TCTTCTCAGG CTATCAGAGA TGCCGAGAAA GCAGGGCGAC

19681  TACCGCACCC GGATATGGAA ATTCGAGGAC GGGTTGAGCA ACGTGTTGGT TATACAATTG

19741  AACAAATTAA TCATATGCGT GATGTGTTTG GTACGCGATT GCGACGTGCT GAAGACGTAT

19801  TTCCACCGGT GATCGGGGTT GCTGCCCATA AGGTGGCGT TTACAAAACC TCAGTTTCTG

19861  TTCATCTTGC TCAGGATCTG GCTCTGAAGG GGCTACGTGT TTTGCTCGTG GAAGGTAACG

19921  ACCCCCAGGG AACAGCCTCA ATGTATCACG GATGGGTACC AGATCTTCAT ATTCATGCAG

19981  AAGACACTCT CCTGCCTTTC TATCTTGGGG AAAAGGACGA TGTCACTTAT GCAATAAAGC

20041  CCACTTGCTG GCCGGGGCTT GACATTATTC CTTCCTGTCT GGCTCTGCAC CGTATTGAAA

20101  CTGAGTTAAT GGGCAAATTT GATGAAGGTA AACTGCCCAC CGATCCACAC CTGATGCTCC

20161  GACTGGCCAT TGAAACTGTT GCTCATGACT ATGATGTCAT AGTTATTGAC AGCGCGCCTA

20221  ACCTGGGTAT CGGCACGATT AATGTCGTAT GTGCTGCTGA TGTGCTGATT GTTCCCACGC

20281  CTGCTGAGTT GTTTGACTAC ACCTCCGCAC TGCAGTTTTT CGATATGCTT CGTGATCTGC

20341  TCAAGAACGT TGATCTTAAA GGGTTCGAGC CTGATGTACG TATTTTGCTT ACCAAATACA

20401  GCAATAGTAA TGGCTCTCAG TCCCCGTGGA TGGAGGAGCA AATTCGGGAT GCCTGGGGAA

20461  GCATGGTTCT AAAAAATGTT GTACGTGAAA CGGATGAAGT TGGTAAAGGT CAGATCCGGA

20521  TGAGAACTGT TTTTGAACAG GCCATTGATC AACGCTCTTC AACTGGTGCC TGGAGAAATG

20581  CTCTTTCTAT TTGGGAACCT GTCTGCAATG AAATTTTCGA TCGTCTGATT AAACCACGCT

20641  GGGAGATTAG ATAATGAAGC GTGCGCCTGT TATTCCAAAA CATACGCTCA ATACTCAACC

20701  GGTTGAAGAT ACTTCGTTAT CGACACCAGC TGCCCCGATG GTGGATTCGT TAATTGCGCG

20761  CGTAGGAGTA ATGGCTCGCG GTAATGCCAT TACTTTGCCT GTATGTGGTC GGGATGTGAA
```

```
20821  GTTTACTCTT GAAGTGCTCC GGGGTGATAG TGTTGAGAAG ACCTCTCGGG TATGGTCAGG

20881  TAATGAACGT GACCAGGAGC TGCTTACTGA GGACGCACTG GATGATCTCA TCCCTTCTTT

20941  TCTACTGACT GGTCAACAGA CACCGGCGTT CGGTCGAAGA GTATCTGGTG TCATAGAAAT

21001  TGCCGATGGG AGTCGCCGTC GTAAAGCTGC TGCACTTACC GAAAGTGATT ATCGTGTTCT

21061  GGTTGGCGAG CTGGATGATG AGCAGATGGC TGCATTATCC AGATTGGGTA ACGATTATCG

21121  CCCAACAAGT GCTTATGAAC GTGGTCAGCG TTATGCAAGC CGATTGCAGA ATGAATTTGC

21181  TGGAAATATT TCTGCGCTGG CTGATGCGGA AAATATTTCA CGTAAGATTA TTACCCGCTG

21241  TATCAACACC GCCAAATTGC CTAAATCAGT TGTTGCTCTT TTTTCTCACC CCGGTGAACT

21301  ATCTGCCCGG TCAGGTGATG CACTTCAAAA AGCCTTTACA GATAAAGAGG AATTACTTAA

21361  GCAGCAGGCA TCTAACCTTC ATGAGCAGAA AAAGCTGGG GTGATATTTG AAGCTGAAGA

21421  AGTTATCACT CTTTTAACTT CTGTGCTTAA AACGTCATCT GCATCAAGAA CTAGTTTAAG

21481  CTCACGACAT CAGTTTGCTC CTGGAGCGAC AGTATTGTAT AAGGGCGATA AAATGGTGCT

21541  TAACCTGGAC AGGTCTCGTG TTCCAACTGA GTGTATAGAG AAAATTGAGG CCATTCTTAA

21601  GGAACTTGAA AAGCCAGCAC CCTGATGCGA CCACGTTTTA GTCTACGTTT ATCTGTCTTT

21661  ACTTAATGTC CTTTGTTACA GGCCAGAAAG CATAACTGGC CTGAATATTC TCTCTGGGCC

21721  CACTGTTCCA CTTGTATCGT CGGTCTGATA ATCAGACTGG GACCACGGTC CCACTCGTAT

21781  CGTCGGTCTG ATTATTAGTC TGGGACCACG GTCCCACTCG TATCGTCGGT CTGATTATTA

21841  GTCTGGGACC ACGGTCCCAC TCGTATCGTC GGTCTGATAA TCAGACTGGG ACCACGGTCC

21901  CACTCGTATC GTCGGTCTGA TTATTAGTCT GGGACCATGG TCCCACTCGT ATCGTCGGTC

21961  TGATTATTAG TCTGGGACCA CGGTCCCACT CGTATCGTCG GTCTGATTAT TAGTCTGGAA

22021  CCACGGTCCC ACTCGTATCG TCGGTCTGAT TATTAGTCTG GACCACGGT CCCACTCGTA

22081  TCGTCGGTCT GATTATTAGT CTGGGACCAC GATCCCACTC GTGTTGTCGG TCTGATTATC

22141  GGTCTGGGAC CACGGTCCCA CTTGTATTGT CGATCAGACT ATCAGCGTGA GACTACGATT

22201  CCATCAATGC CTGTCAAGGG CAAGTATTGA CATGTCGTCG TAACCTGTAG AACGGAGTAA

22261  CCTCGGTGTG CGGTTGTATG CCTGCTGTGG ATTGCTGCTG TGTCCTGCTT ATCCACAACA

22321  TTTTGCGCAC GGTTATGTGG ACAAAATACC TGGTTACCCA GGCCGTGCCG GCACGTTAAC

22381  CGGGCTGCAT CCGATGCAAG TGTGTCGCTG TCGACGAGCT CGCGAGCTCG GACATGAGGT

22441  TGCCCCGTAT TCAGTGTCGC TGATTTGTAT TGTCTGAAGT TGTTTTTACG TTAAGTTGAT

22501  GCAGATCAAT TAATACGATA CCTGCGTCAT AATTGATTAT TTGACGTGGT TTGATGGCCT

22561  CCACGCACGT TGTGATATGT AGATGATAAT CATTATCACT TTACGGGTCC TTTCCGGTGA

22621  TCCGACAGGT TACGGGCGG CGACCTCGCG GGTTTTCGCT ATTTATGAAA ATTTTCCGGT

22681  TTAAGGCGTT TCCGTTCTTC TTCGTCATAA CTTAATGTTT TTATTTAAAA TACCCTCTGA

22741  AAAGAAAGGA AACGACAGGT GCTGAAAGCG AGCTTTTTGG CCTCTGTCGT TTCCTTTCTC

22801  TGTTTTTGTC CGTGGAATGA ACAATGGAAG TCCGAGCTCA TCGCTAATAA CTTCGTATAG

22861  CATACATTAT ACGAAGTTAT ATTCGAT
```

<160> NUMBER OF SEQ ID NOS: 31

<210> SEQ ID NO 1
<211> LENGTH: 993
<212> TYPE: DNA
<213> ORGANISM: Escherichia coli

<400> SEQUENCE: 1

```
atgaacgata acgttttgct cataggagct tccggattcg taggaacccg actacttgaa      60
acggcaattg ctgactttaa tatcaagaac ctggacaaac agcagagcca cttttatcca     120
gaaatcacac agattggcga tgttcgcgat caacaggcac tcgaccaggc gttagtcggt     180
tttgacactg ttgtactact ggcagcggaa caccgcgatg acgtcagccc tacttctctc     240
tattatgatg tcaacgttca gggtacccgc aatgtgctgg cggccatgga aaaaaatggc     300
gttaaaaata tcatctttac cagttccgtt gctgtttatg gtttgaacaa acacaaccct     360
gacgaaaacc atccacacga ccctttcaac cactacggca aaagtaagtg gcaggcagag     420
gaagtgctgc gtgaatggta taacaaagca ccaacagaac gttcattaac catcatccgt     480
cctaccgtta tcttcggtga acgcaaccgc ggtaacgtct ataacttgct gaaacagatc     540
gctggcggca gtttatgat ggtgggcgca gggactaact ataagtccat ggcttatgtt      600
ggaaacattg ttgagtttat caagtacaaa ctgaagaatg ttgccgcagg ttatgaggtt     660
tataactacg ttgataagcc agacctgaac atgaaccagt tggttgctga agttgaacaa     720
agcctgaaca aaagatccc ttctatgcac ttgccttacc cactaggaat gctgggtgga      780
tattgctttg atatcctgag caaaattacg ggcaaaaaat acgctgtcag ctcagtgcgc     840
gtgaaaaaat tctgcgcaac aacacagttt gacgcaacga aagtgcattc ttcaggtttt     900
gtggcaccgt atacgctgtc gcaaggtctg gatcgaacac tgcagtatga attcgttcat     960
gccaaaaaag acgacataac gtttgtttct gag                                  993
```

<210> SEQ ID NO 2
<211> LENGTH: 331
<212> TYPE: PRT
<213> ORGANISM: Escherichia coli

<400> SEQUENCE: 2

```
Met Asn Asp Asn Val Leu Leu Ile Gly Ala Ser Gly Phe Val Gly Thr
  1               5                  10                  15

Arg Leu Leu Glu Thr Ala Ile Ala Asp Phe Asn Ile Lys Asn Leu Asp
             20                  25                  30

Lys Gln Gln Ser His Phe Tyr Pro Glu Ile Thr Gln Ile Gly Asp Val
         35                  40                  45

Arg Asp Gln Gln Ala Leu Asp Gln Ala Leu Val Gly Phe Asp Thr Val
     50                  55                  60

Val Leu Leu Ala Ala Glu His Arg Asp Asp Val Ser Pro Thr Ser Leu
 65                  70                  75                  80

Tyr Tyr Asp Val Asn Val Gln Gly Thr Arg Asn Val Leu Ala Ala Met
                 85                  90                  95

Glu Lys Asn Gly Val Lys Asn Ile Ile Phe Thr Ser Ser Val Ala Val
            100                 105                 110

Tyr Gly Leu Asn Lys His Asn Pro Asp Glu Asn His Pro His Asp Pro
        115                 120                 125

Phe Asn His Tyr Gly Lys Ser Lys Trp Gln Ala Glu Glu Val Leu Arg
    130                 135                 140

Glu Trp Tyr Asn Lys Ala Pro Thr Glu Arg Ser Leu Thr Ile Ile Arg
```

| | | | | 145 | | | | 150 | | | | 155 | | | | 160 | |
|---|---|---|---|---|---|---|---|---|---|---|---|---|---|---|---|---|---|

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
        195                 200                 205

Tyr Lys Leu Lys Asn Val Ala Ala Gly Tyr Glu Val Tyr Asn Tyr Val
    210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
            245                 250                 255

Met Leu Gly Gly Tyr Cys Phe Asp Ile Leu Ser Lys Ile Thr Gly Lys
        260                 265                 270

Lys Tyr Ala Val Ser Ser Val Arg Val Lys Lys Phe Cys Ala Thr Thr
    275                 280                 285

Gln Phe Asp Ala Thr Lys Val His Ser Ser Gly Phe Val Ala Pro Tyr
290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
            325                 330

<210> SEQ ID NO 3
<211> LENGTH: 993
<212> TYPE: DNA
<213> ORGANISM: Escherichia coli

<400> SEQUENCE: 3

| atgaacgata acgttttgct cataggagct tccggattcg taggaacccg actacttgaa | 60 |
|---|---|
| acggcaattg ctgactttaa tatcaagaac ctggacaaac agcagagcca ctttttatcca | 120 |
| gaaatcacac agattggtga tgttcgtgat caacaggcac tcgaccaggc gttagccggt | 180 |
| tttgacactg ttgtgctact ggcagcggaa caccgcgatg acgtcagccc tacttctctc | 240 |
| tattatgatg tcaacgttca gggtacccgc aatgtgctgg cggccatgga aaaaaatggc | 300 |
| gttaaaaata tcatctttac cagttccgtt gctgtttatg gtttgaacaa acacaaccct | 360 |
| gacgaaaacc atccacacga tcctttcaac cactacggca aaagtaagtg gcaggcagag | 420 |
| gaagtgctgc gtgaatggta taacaaagca ccaacagaac gttcattaac catcatccgt | 480 |
| cctaccgtta tcttcggtga acggaaccgc ggtaacgtct ataacttgct gaaacagatc | 540 |
| gctggcggca gtttatgat ggtgggcgca gggactaact ataagtccat ggcttatgtt | 600 |
| ggaaacattg ttgagtttat caagtacaaa ctgaagaatg ttgccgcagg ttacgaggtt | 660 |
| tataactacg ttgataagcc agacctgaac atgaaccagt tggttgctga agttgaacaa | 720 |
| agcctgaaca aaaagatccc ttctatgcac ttgccttacc cactaggaat gctgggtgga | 780 |
| tattgctttg atatcctgag caaaattacg ggcaaaaaat acgctgtcag ctctgtgcgc | 840 |
| gtgaaaaaat tctgcgcaac aacacagttt gacgcaacga agtgcattc ttcaggtttt | 900 |
| gtggcaccgt atacgctgtc gcaaggtctg gatcgaactc tgcagtatga attcgtccat | 960 |
| gccaaaaaag acgacataac gtttgtttct gag | 993 |

<210> SEQ ID NO 4

```
<211> LENGTH: 331
<212> TYPE: PRT
<213> ORGANISM: Escherichia coli

<400> SEQUENCE: 4

Met Asn Asp Asn Val Leu Leu Ile Gly Ala Ser Gly Phe Val Gly Thr
1               5                   10                  15

Arg Leu Leu Glu Thr Ala Ile Ala Asp Phe Asn Ile Lys Asn Leu Asp
            20                  25                  30

Lys Gln Gln Ser His Phe Tyr Pro Glu Ile Thr Gln Ile Gly Asp Val
        35                  40                  45

Arg Asp Gln Gln Ala Leu Asp Gln Ala Leu Ala Gly Phe Asp Thr Val
    50                  55                  60

Val Leu Leu Ala Ala Glu His Arg Asp Asp Val Ser Pro Thr Ser Leu
65                  70                  75                  80

Tyr Tyr Asp Val Asn Val Gln Gly Thr Arg Asn Val Leu Ala Ala Met
                85                  90                  95

Glu Lys Asn Gly Val Lys Asn Ile Ile Phe Thr Ser Ser Val Ala Val
            100                 105                 110

Tyr Gly Leu Asn Lys His Asn Pro Asp Glu Asn His Pro His Asp Pro
        115                 120                 125

Phe Asn His Tyr Gly Lys Ser Lys Trp Gln Ala Glu Glu Val Leu Arg
    130                 135                 140

Glu Trp Tyr Asn Lys Ala Pro Thr Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
        195                 200                 205

Tyr Lys Leu Lys Asn Val Ala Ala Gly Tyr Glu Val Tyr Asn Tyr Val
    210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
                245                 250                 255

Met Leu Gly Gly Tyr Cys Phe Asp Ile Leu Ser Lys Ile Thr Gly Lys
            260                 265                 270

Lys Tyr Ala Val Ser Ser Val Arg Val Lys Phe Cys Ala Thr Thr
        275                 280                 285

Gln Phe Asp Ala Thr Lys Val His Ser Ser Gly Phe Val Ala Pro Tyr
    290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
                325                 330

<210> SEQ ID NO 5
<211> LENGTH: 993
<212> TYPE: DNA
<213> ORGANISM: Escherichia coli

<400> SEQUENCE: 5
atgaacgata acgttttgct cataggagct tccggattcg taggaacccg actacttgaa      60
```

```
acggcaattg ctgactttaa tatcaagaac ctggacaaac agcagagcca cttttatcca    120
gaaatcacac agattggtga tgttcgtgat caacaggcac tcgaccaggc gttagccggt    180
tttgacactg ttgtactact ggcagcggaa caccgcgatg acgtcagccc tacttctctc    240
tattatgatg tcaacgttca gggtacccgc aatgtgctgg cggccatgga aaaaaatggc    300
gttaaaaata tcatctttac cagttccgtt gctgtttatg gtttgaacaa acacaaccct    360
gacgaaaacc atccacacga cccttcaac cactacggca aaagcaagtg gcaggcggag    420
gaagtgctgc gtgaatggta taacaaagca ccaacagaac gttcattaac tatcatccgt    480
cctaccgtta tcttcggtga acgcaaccgc ggtaacgtct ataacttgct gaaacagatc    540
gctggcggca gtttatgat ggtgggcgca gggactaact ataagtccat ggcttatgtt    600
ggaaacattg ttgagtttat caagtacaaa ctgaagaatg ttgccgcagg ttacgaggtt    660
tataactacg ttgataagcc agacctgaac atgaaccagt tggttgctga agttgaacaa    720
agcctgaaca aaaagatccc ttctatgcac ttgccttacc cactaggaat gctgggtgga    780
tattgctttg atatcctgag caaaattacg ggcaaaaaat acgctgtcag ctctgtgcgc    840
gtgaaaaaat tctgcgcaac aacacagttt gacgcaacga agtgcattc ttcaggtttt    900 gtggcaccgt atacgctgtc gcaaggtctg gatcgaactc tgcagtatga attcgtccat    960
gccaaaaaag acgacataac gtttgtttct gag                                993

<210> SEQ ID NO 6
<211> LENGTH: 331
<212> TYPE: PRT
<213> ORGANISM: Escherichia coli

<400> SEQUENCE: 6

Met Asn Asp Asn Val Leu Leu Ile Gly Ala Ser Gly Phe Val Gly Thr
1               5                   10                  15

Arg Leu Leu Glu Thr Ala Ile Ala Asp Phe Asn Ile Lys Asn Leu Asp
                20                  25                  30

Lys Gln Gln Ser His Phe Tyr Pro Glu Ile Thr Gln Ile Gly Asp Val
            35                  40                  45

Arg Asp Gln Gln Ala Leu Asp Gln Ala Leu Ala Gly Phe Asp Thr Val
        50                  55                  60

Val Leu Ala Ala Glu His Arg Asp Asp Val Ser Pro Thr Ser Leu
65                  70                  75                  80

Tyr Tyr Asp Val Asn Val Gln Gly Thr Arg Asn Val Leu Ala Ala Met
                85                  90                  95

Glu Lys Asn Gly Val Lys Asn Ile Ile Phe Thr Ser Ser Val Ala Val
                100                 105                 110

Tyr Gly Leu Asn Lys His Asn Pro Asp Glu Asn His Pro His Asp Pro
            115                 120                 125

Phe Asn His Tyr Gly Lys Ser Lys Trp Gln Ala Glu Glu Val Leu Arg
        130                 135                 140

Glu Trp Tyr Asn Lys Ala Pro Thr Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
        195                 200                 205
```

Tyr Lys Leu Lys Asn Val Ala Ala Gly Tyr Glu Val Tyr Asn Tyr Val
    210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
                245                 250                 255

Met Leu Gly Gly Tyr Cys Phe Asp Ile Leu Ser Lys Ile Thr Gly Lys
            260                 265                 270

Lys Tyr Ala Val Ser Ser Val Arg Val Lys Lys Phe Cys Ala Thr Thr
        275                 280                 285

Gln Phe Asp Ala Thr Lys Val His Ser Ser Gly Phe Val Ala Pro Tyr
    290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
                325                 330

<210> SEQ ID NO 7
<211> LENGTH: 993
<212> TYPE: DNA
<213> ORGANISM: Shigella boydii

<400> SEQUENCE: 7

| | | | | |
|---|---|---|---|---|
| atgaacgata | acgttttgct | cataggagct | tccggattcg | taggaacccg actacttgaa | 60 |
| acggcaattg | ctgactttaa | tatcaagaac | ctggacaaac | agcagagcca tttttatcca | 120 |
| gcaatcacac | agattggcga | tgttcgtgat | caacaggcac | tcgaccaggc gttagccggt | 180 |
| tttgacactg | ttgtactact | ggcagcggaa | caccgcgatg | acgtcagccc tacttctctc | 240 |
| tattatgatg | tcaacgttca | gggtacccgc | aatgtgctgg | cggccatgga aaaaaatggc | 300 |
| gttaaaaata | tcatctttac | cagttccgtt | gctgtttatg | gtttgaacaa cacaacccct | 360 |
| gacgaaaacc | atccacacga | ccctttcaac | cactacggca | aaagtaagtg gcaggcagag | 420 |
| gaagtgctgc | gtgaatggta | taacaaagca | ccaacagaac | gttcattaac catcatccgt | 480 |
| cctaccgtta | tcttcggtga | acgcaaccgc | ggtaacgtct | ataacttgct gaaacagatc | 540 |
| gctggcggca | gtttatgat | ggtgggcgca | gggactaact | ataagtccat ggcttatgtt | 600 |
| ggaaacattg | ttgagtttat | caagtacaaa | ctgaagaatg | ttgccgcagg ttatgaggtt | 660 |
| tataactatg | ttgataagcc | agacctgaac | atgaaccagt | tggttgctga agttgaacaa | 720 |
| agcctgaaca | aaaagatccc | ttctatgcac | ttgccttacc | cactaggaat gctgggtgga | 780 |
| tattgctttg | atatcctgag | caaaattacg | ggcaaaaaat | acgctgtcag ctctgtgcgc | 840 |
| gtgaaaaaat | tctgcgcaac | aacacagttt | gacgcaacga | aagtgcattc ttcaggtttt | 900 |
| gtggcaccgt | atacgctgtc | gcaaggtctg | gatcgaactc | tgcagtatga attcgtccat | 960 |
| gccaaaaaag | acgacataac | gtttgtttct | gag | | 993 |

<210> SEQ ID NO 8
<211> LENGTH: 331
<212> TYPE: PRT
<213> ORGANISM: Shigella boydii

<400> SEQUENCE: 8

Met Asn Asp Asn Val Leu Leu Ile Gly Ala Ser Gly Phe Val Gly Thr
1               5                   10                  15

Arg Leu Leu Glu Thr Ala Ile Ala Asp Phe Asn Ile Lys Asn Leu Asp
            20                  25                  30

```
Lys Gln Gln Ser His Phe Tyr Pro Ala Ile Thr Gln Ile Gly Asp Val
            35                  40                  45

Arg Asp Gln Gln Ala Leu Asp Gln Ala Leu Ala Gly Phe Asp Thr Val
 50                  55                  60

Val Leu Leu Ala Ala Glu His Arg Asp Val Ser Pro Thr Ser Leu
 65                  70                  75                  80

Tyr Tyr Asp Val Asn Val Gln Gly Thr Arg Asn Val Leu Ala Ala Met
                    85                  90                  95

Glu Lys Asn Gly Val Lys Asn Ile Ile Phe Thr Ser Ser Val Ala Val
                100                 105                 110

Tyr Gly Leu Asn Lys His Asn Pro Asp Glu Asn His Pro His Asp Pro
            115                 120                 125

Phe Asn His Tyr Gly Lys Ser Lys Trp Gln Ala Glu Glu Val Leu Arg
            130                 135                 140

Glu Trp Tyr Asn Lys Ala Pro Thr Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
            195                 200                 205

Tyr Lys Leu Lys Asn Val Ala Ala Gly Tyr Glu Val Tyr Asn Tyr Val
            210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
                245                 250                 255

Met Leu Gly Gly Tyr Cys Phe Asp Ile Leu Ser Lys Ile Thr Gly Lys
            260                 265                 270

Lys Tyr Ala Val Ser Ser Val Arg Val Lys Lys Phe Cys Ala Thr Thr
            275                 280                 285

Gln Phe Asp Ala Thr Lys Val His Ser Ser Gly Phe Val Ala Pro Tyr
            290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
            325                 330
```

<210> SEQ ID NO 9
<211> LENGTH: 993
<212> TYPE: DNA
<213> ORGANISM: Salmonella enterica

<400> SEQUENCE: 9

```
atgaacgata acgttttgct cattggtgct tccggattcg taggaacccg actccttgaa        60
acggcagtgg atgattttaa tatcaagaac ctggataaac agcaaagcca tttctaccca       120
gagattacac acattggcga tgttcgtgac caacaaatcc ttgaccagac gttggtgggt       180
tttgacaccg tagtactatt ggctgcggag catcgtgatg atgttagtcc tacctcgctt       240
tattatgatg tcaacgtcca gggaacgcgt aatgtactgg cggcgatgga aaaaaatggt       300
gtaaaaaata tcattttttac cagttccgtt gcagtttatg gactcaacaa gaaaaatcct       360
gacgaaacgc accctcacga tcccttttaat cattacggaa aaagtaaatg gcaagcagaa       420
```

-continued

```
gaagttctgc gtgagtggca tgctaaagcg ccgaatgagc gttctttgac cataattcgt    480
cctaccgtta ttttcgggga gcgtaaccgc ggtaatgtat acaatctctt gaaacagatc    540
gctggtggta aatttgcgat ggttggtccg ggaactaact ataaatcaat ggcttatgtt    600
ggtaatatcg ttgagtttat caaattcaaa ctcaagaatg ttacggcggg ctatgaagtt    660
tataattatg ttgataaacc tgatctgaat atgaatcaat tggttgctga agtagagcag    720
agcctgggca aaaaaatacc atcgatgcac cttccatatc cattaggtat gctgggggggt   780 tactgtttcg atatcctgag caaagtaacg ggcaagaagt acgctgtaag ttcggttcgt    840
gttaaaaaat tctgtgcgac aacgcagttt gatgcaacaa aagtgcattc ttctggtttt    900
gttgcgccat acaccttatc tcaggggttg gatcgtacac tgcaatatga atttgttcat    960
gcaaagaaag atgacattac attcgtttca gag                                 993
```

<210> SEQ ID NO 10
<211> LENGTH: 331
<212> TYPE: PRT
<213> ORGANISM: Salmonella enterica

<400> SEQUENCE: 10

```
Met Asn Asp Asn Val Leu Leu Ile Gly Ala Ser Gly Phe Val Gly Thr
1               5                   10                  15

Arg Leu Leu Glu Thr Ala Val Asp Asp Phe Asn Ile Lys Asn Leu Asp
            20                  25                  30

Lys Gln Gln Ser His Phe Tyr Pro Glu Ile Thr His Ile Gly Asp Val
        35                  40                  45

Arg Asp Gln Gln Ile Leu Asp Gln Thr Leu Val Gly Phe Asp Thr Val
    50                  55                  60

Val Leu Leu Ala Ala Glu His Arg Asp Asp Val Ser Pro Thr Ser Leu
65                  70                  75                  80

Tyr Tyr Asp Val Asn Val Gln Gly Thr Arg Asn Val Leu Ala Ala Met
                85                  90                  95

Glu Lys Asn Gly Val Lys Asn Ile Ile Phe Thr Ser Ser Val Ala Val
            100                 105                 110

Tyr Gly Leu Asn Lys Lys Asn Pro Asp Glu Thr His Pro His Asp Pro
        115                 120                 125

Phe Asn His Tyr Gly Lys Ser Lys Trp Gln Ala Glu Glu Val Leu Arg
    130                 135                 140

Glu Trp His Ala Lys Ala Pro Asn Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Ala Met Val Gly Pro Gly Thr
            180                 185                 190

Asn Tyr Lys Ser Met Ala Tyr Val Gly Asn Ile Val Glu Phe Ile Lys
        195                 200                 205

Phe Lys Leu Lys Asn Val Thr Ala Gly Tyr Glu Val Tyr Asn Tyr Val
    210                 215                 220

Asp Lys Pro Asp Leu Asn Met Asn Gln Leu Val Ala Glu Val Glu Gln
225                 230                 235                 240

Ser Leu Gly Lys Lys Ile Pro Ser Met His Leu Pro Tyr Pro Leu Gly
                245                 250                 255

Met Leu Gly Gly Tyr Cys Phe Asp Ile Leu Ser Lys Val Thr Gly Lys
            260                 265                 270
```

```
Lys Tyr Ala Val Ser Ser Val Arg Val Lys Lys Phe Cys Ala Thr Thr
            275                 280                 285

Gln Phe Asp Ala Thr Lys Val His Ser Ser Gly Phe Val Ala Pro Tyr
        290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
                325                 330

<210> SEQ ID NO 11
<211> LENGTH: 987
<212> TYPE: DNA
<213> ORGANISM: Campylobacter jejuni

<400> SEQUENCE: 11
atgaaaattc ttattagcgg tggtgcaggt tatataggtt ctcatacttt aagacaattt      60
ttaaaaacag atcatgaaat tgtgttttta gataatcttt ctaagggttc taaaatcgca     120
atagaagatt tgcaaaaaac aagagctttt aaattttcg aacaagattt aagtgatttt     180
caaggcgtaa aagcattgtt tgagagagaa aaatttgacg ctattgtgca ttttgcagca     240
agcattgaag tttttgaaag tatgcaaaat cctttaaaat attatatgaa caacactgtt     300
aatacgacaa atctcatcga aacttgtttg caaactggag tgaataaatt tatatttct    360 tcaacggcgg ccacttatgg cgaaccacaa actcccgttg tgagcgaaac aagtccttta     420
gcacctatta atccttatgg cgtagtaag cttatgagtg aagaagtttt gcgtgatgca     480
agtatggcaa atcctgaatt taagcattgt attttaagat attttaatgt tgcaggtgct     540
tgtatggatt atacttagg acaacgctat ccaaaagcga ctttgcttat aaaagttgca     600
gctgaatgtg ccgcaggaaa acgtgataaa cttttcatat ttggcgatga ttatgataca     660
aaagatggta cttgcataag agattttatc catgtagatg atatttcaag tgcacattta     720
gcggctttgg attatttaaa agagaatgaa agcaatgttt taatgtagg ttatggacat     780 ggttttagcg taaaagaagt gattgaagcg atgaaaaaag ttagcggagt ggattttaaa     840
gtagaacttg ccccacgccg tgcgggtgat cctagtgtat tgatttctga tgcaagtaaa     900
atcagaaatc ttacttcttg gcagcctaaa tatgatgatt tagagcttat ttgtaaatct     960
gcttttgatt gggaaaaaca gtgttaa                                        987

<210> SEQ ID NO 12
<211> LENGTH: 328
<212> TYPE: PRT
<213> ORGANISM: Campylobacter jejuni

<400> SEQUENCE: 12

Met Lys Ile Leu Ile Ser Gly Gly Ala Gly Tyr Ile Gly Ser His Thr
1               5                   10                  15

Leu Arg Gln Phe Leu Lys Thr Asp His Glu Ile Cys Val Leu Asp Asn
            20                  25                  30

Leu Ser Lys Gly Ser Lys Ile Ala Ile Glu Asp Leu Gln Lys Thr Arg
        35                  40                  45

Ala Phe Lys Phe Phe Glu Gln Asp Leu Ser Asp Phe Gln Gly Val Lys
    50                  55                  60

Ala Leu Phe Glu Arg Glu Lys Phe Asp Ala Ile Val His Phe Ala Ala
65                  70                  75                  80

Ser Ile Glu Val Phe Glu Ser Met Gln Asn Pro Leu Lys Tyr Tyr Met
```

```
                    85                  90                  95
Asn Asn Thr Val Asn Thr Thr Asn Leu Ile Glu Thr Cys Leu Gln Thr
            100                 105                 110

Gly Val Asn Lys Phe Ile Phe Ser Thr Ala Ala Thr Tyr Gly Glu
        115                 120                 125

Pro Gln Thr Pro Val Val Ser Glu Thr Ser Pro Leu Ala Pro Ile Asn
            130                 135                 140

Pro Tyr Gly Arg Ser Lys Leu Met Ser Glu Val Leu Arg Asp Ala
145                 150                 155                 160

Ser Met Ala Asn Pro Glu Phe Lys His Cys Ile Leu Arg Tyr Phe Asn
                165                 170                 175

Val Ala Gly Ala Cys Met Asp Tyr Thr Leu Gly Gln Arg Tyr Pro Lys
            180                 185                 190

Ala Thr Leu Leu Ile Lys Val Ala Ala Glu Cys Ala Ala Gly Lys Arg
            195                 200                 205

Asp Lys Leu Phe Ile Phe Gly Asp Asp Tyr Asp Thr Lys Asp Gly Thr
        210                 215                 220

Cys Ile Arg Asp Phe Ile His Val Asp Asp Ile Ser Ser Ala His Leu
225                 230                 235                 240

Ala Ala Leu Asp Tyr Leu Lys Glu Asn Glu Ser Asn Val Phe Asn Val
                245                 250                 255

Gly Tyr Gly His Gly Phe Ser Val Lys Glu Val Ile Glu Ala Met Lys
            260                 265                 270

Lys Val Ser Gly Val Asp Phe Lys Val Glu Leu Ala Pro Arg Arg Ala
        275                 280                 285

Gly Asp Pro Ser Val Leu Ile Ser Asp Ala Ser Lys Ile Arg Asn Leu
    290                 295                 300

Thr Ser Trp Gln Pro Lys Tyr Asp Leu Glu Leu Ile Cys Lys Ser
305                 310                 315                 320

Ala Phe Asp Trp Glu Lys Gln Cys
            325

<210> SEQ ID NO 13
<211> LENGTH: 1017
<212> TYPE: DNA
<213> ORGANISM: Escherichia coli

<400> SEQUENCE: 13
atgagagttc tggttaccgg tggtagcggt tacattggaa gtcataccctg tgtgcaatta      60
ctgcaaaacg tcatgatgt catcattctt gataacctct gtaacagtaa gcgcagcgta     120
ctgcctgtta tcgagcgttt aggcggcaaa catccaacgt tgttgaagg cgatattcgt     180
aacgaagcgt tgatgaccga gatcctgcac gatcacgcta tcgacaccgt gatccacttc     240
gccgggctga agccgtgggc gaatcggta caaaaaccgc tggaatatta cgacaacaat     300
gtcaacggca ctctgcgcct gattagcgcc atgcgcgccg ctaacgtcaa aaactttatt     360
tttagctcct ccgccaccgt ttatggcgat cagcccaaaa ttccatacgt tgaaagcttc     420
ccgaccggca caccgcaaag cccttacggc aaaagcaagc tgatggtgga acagatcctc     480
accgatctgc aaaaagccca gcggactgg agcattgccc tgctgcgcta cttcaacccg     540
gttggcgcgc atccgtcggg cgatatgggc gaagatccgc aaggcattcc gaataacctg     600
atgccataca tcgcccaggt tgctgtaggc cgtcgcgact cgctggcgat ttttggtaac     660
gattatccga ccgaagatgg tactggcgta cgcgattaca tccacgtaat ggatctggcg     720
```

-continued

```
gacggtcacg tcgtggcgat ggaaaaactg gcgaacaagc caggcgtaca catctacaac    780
ctcggcgctg gcgtaggcaa cagcgtgctg gacgtggtta atgccttcag caaagcctgc    840
ggcaaaccgg ttaattatca ttttgcaccg cgtcgcgagg gcgaccttcc ggcctactgg    900
gcggacgcca gcaaagccga ccgtgaactg aactggcgcg taacgcgcac actcgatgaa    960
atggcgcagg acacctggca ctggcagtca cgccatccac agggatatcc cgattaa     1017
```

<210> SEQ ID NO 14
<211> LENGTH: 338
<212> TYPE: PRT
<213> ORGANISM: Escherichia coli

<400> SEQUENCE: 14

```
Met Arg Val Leu Val Thr Gly Gly Ser Gly Tyr Ile Gly Ser His Thr
1               5                   10                  15

Cys Val Gln Leu Leu Gln Asn Gly His Asp Val Ile Leu Asp Asn
            20                  25                  30

Leu Cys Asn Ser Lys Arg Ser Val Leu Pro Val Ile Glu Arg Leu Gly
        35                  40                  45

Gly Lys His Pro Thr Phe Val Glu Gly Asp Ile Arg Asn Glu Ala Leu
    50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
            100                 105                 110

Ala Ala Asn Val Lys Asn Phe Ile Phe Ser Ser Ser Ala Thr Val Tyr
        115                 120                 125

Gly Asp Gln Pro Lys Ile Pro Tyr Val Glu Ser Phe Pro Thr Gly Thr
    130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
            180                 185                 190

Pro Gln Gly Ile Pro Asn Asn Leu Met Pro Tyr Ile Ala Gln Val Ala
        195                 200                 205

Val Gly Arg Arg Asp Ser Leu Ala Ile Phe Gly Asn Asp Tyr Pro Thr
    210                 215                 220

Glu Asp Gly Thr Gly Val Arg Asp Tyr Ile His Val Met Asp Leu Ala
225                 230                 235                 240

Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270

Val Asn Ala Phe Ser Lys Ala Cys Gly Lys Pro Val Asn Tyr His Phe
        275                 280                 285

Ala Pro Arg Arg Glu Gly Asp Leu Pro Ala Tyr Trp Ala Asp Ala Ser
    290                 295                 300

Lys Ala Asp Arg Glu Leu Asn Trp Arg Val Thr Arg Thr Leu Asp Glu
305                 310                 315                 320

Met Ala Gln Asp Thr Trp His Trp Gln Ser Arg His Pro Gln Gly Tyr
```

Pro Asp

<210> SEQ ID NO 15
<211> LENGTH: 1020
<212> TYPE: DNA
<213> ORGANISM: Escherichia coli

<400> SEQUENCE: 15

```
atggtgattt tcgtaacagg cggtgcagga tatattggat cccataccat acttgagtta      60
cttaataatg gtcatgatgt cgtttcgata gataattttg tcaattcctc tatagaatca     120
ttaaaaagag tagagcaaat aactaataag aaaattattt cttatcaagg tgatatccgt     180
gataaaaatc tacttgatga gattttttca agacaccata tcgatgctgt aattcacttt     240
gcatcgttaa atctgtaggt tgagtctaag ttaaagccct tagagtatta ttctaataat     300
gttggtggaa ctttagtatt acttgaatgc atgaagagat ataacattaa taaaatgata     360
tttagctctt ctgctactgt ttatgggagt aacagtatcc ctccccatac ggaagataga     420
cgaattggtg aaactacaaa cccatatggg acatcgaaat ttataataga ataaattttg     480
agtgattatt gtgatagtga taataataaa tcagtaattg cactgcgtta ctttaatcca     540
atcggagcac ataagtccgg gatgattggt gaaaatccta acgggatccc taataatctg     600
gttccttata tatctaaagt tgcacaaaat caacttcctg tattaaatat ttatggcaac     660
gattatccaa ctaaagatgg tacaggagta agagactata tacatgtctg tgatttggct     720
aaagggcatg ttaaagcatt agaatatatg tttttaaatg atgtcaatta tgaagctttt     780
aatttaggta ctggtcaagg ttattctgtt ttagagattg taaaaatgtt tgagatagtc     840
actaaaaaga gtatacctgt tgctatttgt aatagacgtg aggggatgt tgcggagtca     900
tgggcgtctg ctgatttggc acataaaaag cttttcctgga agcggaaaa aaatttgaaa     960
gaaatgatcg aagatgtatg gcgttggcaa acaaacaatc caaatggata taaaaataa    1020
```

<210> SEQ ID NO 16
<211> LENGTH: 339
<212> TYPE: PRT
<213> ORGANISM: Escherichia coli

<400> SEQUENCE: 16

```
Met Val Ile Phe Val Thr Gly Gly Ala Gly Tyr Ile Gly Ser His Thr
1               5                   10                  15

Ile Leu Glu Leu Leu Asn Asn Gly His Asp Val Val Ser Ile Asp Asn
            20                  25                  30

Phe Val Asn Ser Ser Ile Glu Ser Leu Lys Arg Val Glu Gln Ile Thr
        35                  40                  45

Asn Lys Lys Ile Ile Ser Tyr Gln Gly Asp Ile Arg Asp Lys Asn Leu
    50                  55                  60

Leu Asp Glu Ile Phe Ser Arg His His Ile Asp Ala Val Ile His Phe
65                  70                  75                  80

Ala Ser Leu Lys Ser Val Gly Glu Ser Lys Leu Lys Pro Leu Glu Tyr
                85                  90                  95

Tyr Ser Asn Asn Val Gly Gly Thr Leu Val Leu Leu Glu Cys Met Lys
            100                 105                 110

Arg Tyr Asn Ile Asn Lys Met Ile Phe Ser Ser Ser Ala Thr Val Tyr
        115                 120                 125

Gly Ser Asn Ser Ile Pro Pro His Thr Glu Asp Arg Arg Ile Gly Glu
```

```
                130                 135                 140
Thr Thr Asn Pro Tyr Gly Thr Ser Lys Phe Ile Ile Glu Ile Ile Leu
145                 150                 155                 160

Ser Asp Tyr Cys Asp Ser Asp Asn Asn Lys Ser Val Ile Ala Leu Arg
                165                 170                 175

Tyr Phe Asn Pro Ile Gly Ala His Lys Ser Gly Met Ile Gly Glu Asn
                180                 185                 190

Pro Asn Gly Ile Pro Asn Asn Leu Val Pro Tyr Ile Ser Lys Val Ala
                195                 200                 205

Gln Asn Gln Leu Pro Val Leu Asn Ile Tyr Gly Asn Asp Tyr Pro Thr
                210                 215                 220

Lys Asp Gly Thr Gly Val Arg Asp Tyr Ile His Val Cys Asp Leu Ala
225                 230                 235                 240

Lys Gly His Val Lys Ala Leu Glu Tyr Met Phe Leu Asn Asp Val Asn
                245                 250                 255

Tyr Glu Ala Phe Asn Leu Gly Thr Gly Gln Gly Tyr Ser Val Leu Glu
                260                 265                 270

Ile Val Lys Met Phe Glu Ile Val Thr Lys Lys Ser Ile Pro Val Ala
                275                 280                 285

Ile Cys Asn Arg Arg Glu Gly Asp Val Ala Glu Ser Trp Ala Ser Ala
                290                 295                 300

Asp Leu Ala His Lys Lys Leu Ser Trp Lys Ala Glu Lys Asn Leu Lys
305                 310                 315                 320

Glu Met Ile Glu Asp Val Trp Arg Trp Gln Thr Asn Asn Pro Asn Gly
                325                 330                 335

Tyr Lys Lys

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaacccggga tgaacgataa cgttttgctc                                        30

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaatctagat taagcgtaat ctggaacatc gtatgggtac tcagaaacaa acgttatgtc      60

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaaccatgga tgaaaattct tattagcgg                                         29
```

<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaatctagat taagcgtaat ctggaacatc gtatgggtag cactgttttt cccaatc     57

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaaagctag c                                                        11

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 ccgcgcgg                                                             8

<210> SEQ ID NO 23
<211> LENGTH: 7794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tctacggggt ctgacgctca gtggaacgaa atcgatgagc tcgcacgaac ccagttgaca    60
taagcctgtt cggttcgtaa actgtaatgc aagtagcgta tgcgctcacg caactggtcc   120
agaaccttga ccgaacgcag cggtggtaac ggcgcagtgg cggttttcat ggcttgttat   180
gactgttttt ttgtacagtc tagcctcggg catccaagct agctaagcgc gttacgccgt   240
gggtcgatgt ttgatgttat ggaacagcaa cgatgttacg cagcagggta gtcgccctaa   300
aacaaagtta ggcagccgtt gtgctggtgc tttctagtag ttgttgtggg gtaggcagtc   360
agagctcgat ttgcttgtcg ccataataga ttcacaagaa ggattcgaca tgggtcaaag   420
tagcgatgaa gccaacgctc ccgttgcagg gcagtttgcg cttcccctga gtgccaccttt  480 tggcttaggg gatcgcgtac gcaagaaatc tggtgccgct tggcagggtc aagtcgtcgg   540
ttggtattgc acaaaactca ctcctgaagg ctatgcggtc gagtccgaat cccacccagg   600
ctcagtgcaa atttatcctg tggctgcact tgaacgtgtg gcctaagcga tatcttagga   660
tctcccatcg gtgatgtcgg cgatataggc gccagcaacc gcacctgtgg cgccggtgat   720
gccggccacg atgcgtccgg cgtagaggat ctgctcatgt ttgacagctt atcatcgatg   780
cataatgtgc ctgtcaaatg gacgaagcag ggattctgca aacccatgc tactccgtca    840 agccgtcaat tgtctgattc gttaccaatt atgacaactt gacggctaca tcattcactt   900

```
tttcttcaca accggcacgg aactcgctcg ggctggcccc ggtgcatttt ttaaatacccc      960
gcgagaaata gagttgatcg tcaaaaccaa cattgcgacc gacggtggcg ataggcatcc     1020
gggtggtgct caaaagcagc ttcgcctggc tgatacgttg gtcctcgcgc cagcttaaga     1080
cgctaatccc taactgctgg cggaaaagat gtgacgacg cgacggcgac aagcaaacat      1140
gctgtgcgac gctggcgata tcaaaattgc tgtctgccag gtgatcgctg atgtactgac     1200
aagcctcgcg tacccgatta tccatcggtg gatggagcga ctcgttaatc gcttccatgc     1260
gccgcagtaa caattgctca agcagattta tcgccagcag ctccgaatag cgcccttccc     1320
cttgcccggc gttaatgatt tgcccaaaca ggtcgctgaa atgcggctgg tgcgcttcat     1380
ccgggcgaaa gaacccccgta ttggcaaata ttgacggcca gttaagccat tcatgccagt    1440
aggcgcgcgg acgaaagtaa acccactggt gataccattc gcgagcctcc ggatgacgac    1500
cgtagtgatg aatctctcct ggcgggaaca gcaaaatatc acccggtcgg caaacaaatt    1560
ctcgtccctg atttttcacc accccctgac cgcgaatggt gagattgaga atataacctt    1620
tcattcccag cggtcggtcg ataaaaaaat cgagataacc gttggcctca atcggcgtta    1680
aacccgccac cagatgggca ttaaacgagt atcccggcag caggggatca ttttgcgctt    1740
cagccatact tttcatactc ccgccattca gagaagaaac caattgtcca tattgcatca    1800
gacattgccg tcactgcgtc ttttactggc tcttctcgct aaccaaaccg gtaaccccgc    1860
ttattaaaag cattctgtaa caaagcggga ccaaagccat gacaaaaacg cgtaacaaaa    1920
gtgtctataa tcacggcaga aaagtccaca ttgattattt gcacggcgtc acactttgct    1980
atgccatagc attttatcc ataagattag cggatcctac ctgacgcttt ttatcgcaac     2040
tctctactgt ttctccatac ccgttttttt gggctagcag gaggaattca ccatggtacc   2100
cgggatgaac gataacgttt tgctcatagg agcttccgga ttcgtaggaa cccgactact   2160
tgaaacggca attgctgact ttaatatcaa gaacctggac aaacagcaga gccactttta    2220
tccagaaatc acacagattg cgatgttcg cgatcaacag gcactcgacc aggcgttagt     2280
cggttttgac actgttgtac tactggcagc ggaacaccgc gatgacgtca gccctacttc    2340
tctctattat gatgtcaacg ttcagggtac ccgcaatgtg ctggcggcca tggaaaaaaa    2400
tggcgttaaa aatatcatct ttaccagttc cgttgctgtt tatggtttga caaacacaa     2460
ccctgacgaa aaccatccac acgacccttt caaccactac ggcaaagta agtggcaggc     2520
agaggaagtg ctgcgtgaat ggtataacaa agcaccaaca gaacgttcat taaccatcat    2580
ccgtcctacc gttatcttcg gtgaacgcaa ccgcggtaac gtctataact tgctgaaaca    2640
gatcgctggc ggcaagttta tgatggtggg cgcagggact aactataagt ccatggctta    2700
tgttggaaac attgttgagt ttatcaagta caaactgaag aatgttgccg caggttatga    2760
ggtttataac tacgttgata agccagacct gaacatgaac cagttggttg ctgaagttga    2820
acaaagcctg aacaaaaaga tcccttctat gcacttgcct tacccactag gaatgctggg    2880
tggatattgc tttgatatcc tgagcaaaat tacgggcaaa aaatacgctg tcagctcagt    2940
gcgcgtgaaa aaattctgcg caacaacaca gtttgacgca acgaaagtgc attcttcagg    3000
ttttgtggca ccgtatacgc tgtcgcaagg tctggatcga acactgcagt atgaattcgt     3060
tcatgccaaa aagacgaca taacgtttgt ttctgagtac ccatacgatg ttccagatta     3120
cgcttaatct agagtcgacc tgcaggcatg caagcttggc tgttttggcg gatgagagaa    3180
gattttcagc ctgatacaga ttaaatcaga acgcagaagc ggtctgataa aacagaattt    3240
```

```
gcctggcggc agtagcgcgg tggtcccacc tgacccccatg ccgaactcag aagtgaaacg    3300
ccgtagcgcc gatggtagtg tggggtctcc ccatgcgaga gtagggaact gccaggcatc    3360
aaataaaacg aaaggctcag tcgaaagact gggcctttcg ttttatctgt tgtttgtcgg    3420
tgaacgctct cctgagtagg acaaatccgc cgggagcgga tttgaacgtt gcgaagcaac    3480
ggcccggagg gtggcgggca ggacgcccgc cataaactgc caggcatcaa attaagcaga    3540
aggccatcct gacggatggc cttttttgcgt ttctacaaac tcttccactc actacagcag    3600
agccatttaa caacatccc ctcccccttt ccaccgcgtc agacgcccgt agcagcccgc    3660
tacgggcttt ttcatgccct gccctagcgt ccaagcctca cggccgcgct cggcctctct    3720
ggcggccttc tggcgctgag gtctgcctcg tgaagaaggt gttgctgact cataccaggc    3780
ctgaatcgcc ccatcatcca gccagaaagt gagggagcca cggttgatga gagctttgtt    3840
gtaggtggac cagttggtga ttttgaactt ttgctttgcc acggaacggt ctgcgttgtc    3900
gggaagatgc gtgatctgat ccttcaactc agcaaaagtt cgatttattc aacaaagccg    3960
ccgtcccgtc aagtcagcgt aatgctctgc cagtgttaca accaattaac caattctgat    4020
tagaaaaact catcgagcat caaatgaaac tgcaatttat tcatatcagg attatcaata    4080
ccatattttt gaaaaagccg tttctgtaat gaaggagaaa actcaccgag gcagttccat    4140
aggatggcaa gatcctggta tcggtctgcg attccgactc gtccaacatc aatacaacct    4200
attaatttcc cctcgtcaaa aataaggtta tcaagcgaga atcaccatg agtgacgact    4260
gaatccggtg agaatggcaa aagctaaaaa ggccgtaata tccagctgaa cggtctggtt    4320
ataggtacat tgagcaactg actgaaatgc ctcaaaatgt tctttacgat gccattggga    4380
tatatcaacg gtggtatatc cagtgatttt tttctccatt ttagcttcct agctcctga    4440
aaatctcgat aactcaaaaa atacgcccgg tagtgatctt atttcattat ggtgaaagtt    4500
ggaacctctt acgtgccgat caacgtctca ttttcgccaa aagttggccc agggcttccc    4560
ggtatcaaca gggacaccag gatttattta ttctgcgaag tgatcttccg tcacaggtat    4620
ttattcgaag acgaaagggc ctcgtgatac gcctattttt ataggttaat gtcatgataa    4680
taatggtttc ttagacgtca ggtggcactt ttcggggaaa tgtgcgcgcc cgcgttcctg    4740
ctggcgctgg gcctgtttct ggcgctggac ttcccgctgt ccgtcagca gcttttcgcc    4800
cacgccttg atgatcgcgg cggccttggc ctgcatatcc cgattcaacg gccccagggc    4860
gtccagaacg ggcttcaggc gctcccgaag gtctcgggcc gtctcttggg cttgatcggc    4920
cttcttgcgc atctcacgcg ctcctgcgg ggcctgtagg gcaggctcat accctgccg    4980
aaccgctttt gtcagccggt cggccacggc ttccggcgtc tcaacgcgct ttgagattcc    5040
cagcttttcg gccaatccct gcggtgcata ggcgcgtggc tcgaccgctt gcgggctgat    5100
ggtgacgtgg cccactggtg gccgctccag ggcctcgtag aacgcctgaa tgcgcgtgtg    5160
acgtgccttg ctgccctcga tgcccgttg cagcccctaga tcggcacag cggccgcaaa    5220
cgtggtctgg tcgcgggtca tctgcgcttt gttgccgatg aactccttgg ccgacagcct    5280
gccgtcctgc gtcagcggca ccacgaacgc ggtcatgtgc gggctggttt cgtcacggtg    5340
gatgctggcc gtcacgatgc gatccgcccc gtacttgtcc gccagccact tgtgcgcctt    5400
ctcgaagaac gccgcctgct gttcttggct ggccgacttc caccattccg ggctggccgt    5460
catgacgtac tcgaccgcca acacagcgtc cttgcgccgc ttctctggca gcaactcgcg    5520
cagtcggccc atcgcttcat cggtgctgct ggccgcccag tgctcgttct ctggcgtcct    5580
gctggcgtca gcgttgggcg tctcgcgctc gcggtaggcg tgcttgagac tggccgccac    5640
```

```
gttgcccatt ttcgccagct tcttgcatcg catgatcgcg tatgccgcca tgcctgcccc   5700
tcccttttgg tgtccaaccg gctcgacggg ggcagcgcaa ggcggtgcct ccggcgggcc   5760
actcaatgct tgagtatact cactagactt tgcttcgcaa agtcgtgacc gcctacggcg   5820
gctgcggcgc cctacgggct tgctctccgg gcttcgccct gcgcggtcgc tgcgctccct   5880
tgccagcccg tggatatgtg gacgatggcc gcgagcggcc accggctggc tcgcttcgct   5940
cggcccgtgg acaaccctgc tggacaagct gatggacagg ctgcgcctgc ccacgagctt   6000
gaccacaggg attgcccacc ggctacccag ccttcgacca catacccacc ggctccaact   6060
gcgcggcctg cggccttgcc ccatcaattt ttttaatttt ctctggggaa aagcctccgg   6120
cctgcggcct gcgcgcttcg cttgccggtt ggacaccaag tggaaggcgg gtcaaggctc   6180
gcgcagcgac cgcgcagcgg cttggccttg acgcgcctgg aacgacccaa gcctatgcga   6240
gtgggggcag tcgaaggcga agcccgcccg cctgccccc gagcctcacg gcggcgagtg   6300
cgggggttcc aaggggcag cgccaccttg gcaaggccg aaggccgcgc agtcgatcaa   6360
caagccccgg aggggccact ttttgccgga gggggagccg cgccgaaggc gtggggaac   6420 cccgcagggg tgcccttctt tgggcaccaa agaactagat ataggcgaa atgcgaaaga   6480 cttaaaaatc aacaacttaa aaaggggggg tacgcaacag ctcattgcgg cacccccgc   6540 aatagctcat tgcgtaggtt aaagaaaatc tgtaattgac tgccactttt acgcaacgca   6600
taattgttgt cgcgctgccg aaaagttgca gctgattgcg catggtgccg caaccgtgcg   6660
gcaccctacc gcatggagat aagcatggcc acgcagtcca gagaaatcgg cattcaagcc   6720
aagaacaagc ccggtcactg ggtgcaaacg gaacgcaaag cgcatgaggc gtgggccggg   6780
cttattgcga ggaaacccac ggcggcaatg ctgctgcatc acctcgtggc gcagatgggc   6840
caccagaacg ccgtggtggt cagccagaag acactttcca agctcatcgg acgttctttg   6900
cggacggtcc aatacgcagt caaggacttg gtggccgagc gctggatctc cgtcgtgaag   6960
ctcaacggcc ccgcaccgt gtcggcctac gtggtcaatg accgcgtggc gtggggccag   7020
ccccgcgacc agttgcgcct gtcggtgttc agtgccgccg tggtggttga tcacgacgac   7080
caggacgaat cgctgttggg gcatggcgac ctgcgccgca tcccgaccct gtatccgggc   7140
gagcagcaac taccgaccgg ccccggcgag gagccgccca gccagcccgg cattccgggc   7200
atggaaccag acctgccagc cttgaccgaa acggaggaat gggaacggcg cgggcagcag   7260
cgcctgccga tgcccgatga gccgtgtttt ctggacgatg gcgagccgtt ggagccgccg   7320
acacgggtca cgctgccgcg ccggtagcac ttgggttgcg cagcaacccg taagtgcgct   7380
gttccagact atcggctgta gccgcctcgc cgccctatac cttgtctgcc tccccgcgtt   7440
gcgtcgcggt gcatggagcc gggccacctc gacctgaatg gaagccggcg gcacctcgct   7500
aacggattca ccgttttat caggctctgg gaggcagaat aaatgatcat atcgtcaatt   7560
attacctcca cggggagagc ctgagcaaac tggcctcagg catttgagaa gcacacggtc   7620
acactgcttc cggtagtcaa taaaccggta aaccagcaat agacataagc ggctatttaa   7680 cgacccctgcc ctgaaccgac gaccgggtcg aatttgcttt cgaatttctg ccattcatcc   7740
gcttattatc acttattcag gcgtagcacc aggcgtttaa gtcgaccaat aacc          7794
```

<210> SEQ ID NO 24
<211> LENGTH: 7776
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 24

```
tctacgggt ctgacgctca gtggaacgaa atcgatgagc tcgcacgaac ccagttgaca      60
taagcctgtt cggttcgtaa actgtaatgc aagtagcgta tgcgctcacg caactggtcc     120
agaaccttga ccgaacgcag cggtggtaac ggcgcagtgg cggttttcat ggcttgttat     180
gactgttttt ttgtacagtc tagcctcggg catccaagct agctaagcgc gttacgccgt     240
gggtcgatgt ttgatgttat ggaacagcaa cgatgttacg cagcagggta gtcgccctaa     300
aacaaagtta ggcagccgtt gtgctggtgc tttctagtag ttgttgtggg gtaggcagtc     360
agagctcgat ttgcttgtcg ccataataga ttcacaagaa ggattcgaca tgggtcaaag     420
tagcgatgaa gccaacgctc ccgttgcagg gcagtttgcg cttccctga gtgccacctt      480
tggcttaggg gatcgcgtac gcaagaaatc tggtgccgct tggcagggtc aagtcgtcgg     540
ttggtattgc acaaaactca ctcctgaagg ctatgcggtc gagtccgaat cccacccagg     600
ctcagtgcaa atttatcctg tggctgcact tgaacgtgtg gcctaagcga tatcttagga     660
tctcccatcg gtgatgtcgg cgatataggc gccagcaacc gcacctgtgg cgccggtgat     720
gccggccacg atgcgtccgg cgtagaggat ctgctcatgt ttgacagctt atcatcgatg     780
cataatgtgc ctgtcaaatg gacgaagcag ggattctgca aaccctatgc tactccgtca     840
agccgtcaat tgtctgattc gttaccaatt atgacaactt gacggctaca tcattcactt     900
tttcttcaca accggcacgg aactcgctcg gctggcccc ggtgcatttt ttaaataccc       960
gcgagaaata gagttgatcg tcaaaaccaa cattgcgacc gacggtggcg ataggcatcc    1020
gggtggtgct caaaagcagc ttcgcctggc tgatacgttg gtcctcgcgc cagcttaaga    1080
cgctaatccc taactgctgg cggaaaagat gtgacagacg cgacggcgac aagcaaacat    1140
gctgtgcgac gctggcgata tcaaaattgc tgtctgccag gtgatcgctg atgtactgac    1200
aagcctcgcg tacccgatta tccatcggtg gatggagcga ctcgttaatc gcttccatgc    1260
gccgcagtaa caattgctca agcagattta tcgccagcag ctccgaatag cgccttccc     1320
cttgcccggc gttaatgatt tgcccaaaca ggtcgctgaa atgcggctgg tgcgcttcat    1380
ccgggcgaaa gaaccccgta ttggcaaata ttgacggcca gttaagccat tcatgccagt    1440
aggcgcgcgg acgaaagtaa acccactggt gataccattc gcgagcctcc ggatgacgac    1500
cgtagtgatg aatctctcct ggcgggaaca gcaaaatatc acccggtcgg caaacaaatt    1560
ctcgtccctg attttcacc accccctgac cgcgaatggt gagattgaga ataataacctt    1620
tcattcccag cggtcggtcg ataaaaaat cgagataacc gttggcctca atcggcgtta     1680
aacccgccac cagatgggca ttaaacgagt atcccggcag caggggatca ttttgcgctt    1740
cagccatact tttcatactc ccgccattca gagaagaaac caattgtcca tattgcatca    1800
gacattgccg tcactgcgtc ttttactggc tcttctcgct aaccaaaccg gtaaccccgc    1860
ttattaaaag cattctgtaa caaagcggga ccaaagccat gacaaaaacg cgtaacaaaa    1920
gtgtctataa tcacggcaga aaagtccaca ttgattattt gcacggcgtc acactttgct    1980
atgccatagc attttttatcc ataagattag cggatcctac ctgacgcttt ttatcgcaac    2040
tctctactgt ttctccatac ccgttttttt gggctagcag gaggaattca ccatggatga    2100
aaattcttat tagcggtggt gcaggttata taggttctca tactttaaga caattttaa    2160
aaacagatca tgaaatttgt gttttagata atctttctaa gggttctaaa atcgcaatag    2220
```

```
aagatttgca aaaataaga acttttaaat tttttgaaca agatttaagt gattttcaag    2280
gcgtaaaagc attgtttgag agagaaaaat ttgacgctat tgtgcatttt gcagcgagca    2340
ttgaagtttt tgaaagtatg caaaaccctt taaagtatta tatgaataac actgttaata    2400
cgacaaatct catcgaaact tgtttgcaaa ctggagtgaa taaatttata ttttcttcaa    2460
cggcagccac ttatggcgaa ccacaaactc ccgttgtgag cgaaacaagt cctttagcac    2520
ctattaatcc ttatgggcgt agtaagctta tgagcgaaga ggttttgcgt gatgcaagta    2580
tggcaaatcc tgaatttaag cattgtatttt aagatatttt taatgttgca ggtgcttgca    2640
tggattatac tttaggacaa cgctatccaa aagcgacttt gcttataaaa gttgcagctg    2700
aatgtgccgc agaaaaacgt aataaacttt tcatatttgg cgatgattat gatacaaaag    2760
atggcacttg cataagagat tttatccatg tggatgatat ttcaagtgcg catttatcgg    2820 cttttggatta tttaaaagag aatgaaagca atgttttttaa tgtaggttat ggacatggtt    2880
ttagcgtaaa agaagtgatt gaagcgatga aaaaagttag cggagtggat tttaaagtag    2940
aacttgcccc acgccgtgcg ggtgatccta gtgtattgat ttctgatgca agtaaaatca    3000
gaaatcttac ttcttggcag cctaaatatg atgatttagg gcttatttgt aaatctgctt    3060
ttgattggga aaaacagtgc tacccatacg atgttccaga ttacgcttaa tctagagtcg    3120
acctgcaggc atgcaagctt ggctgttttg gcggatgaga aagattttc agcctgatac    3180 agattaaatc agaacgcaga agcggtctga taaaacagaa tttgcctggc ggcagtagcg    3240
cggtggtccc acctgacccc atgccgaact cagaagtgaa acgccgtagc gccgatggta    3300
gtgtggggtc tccccatgcg agagtaggga actgccaggc atcaaataaa acgaaaggct    3360
cagtcgaaag actgggcctt tcgttttatc tgttgtttgt cggtgaacgc tctcctgagt    3420
aggacaaatc cgccgggagc ggatttgaac gttgcgaagc aacggcccgg agggtggcgg    3480
gcaggacgcc cgccataaac tgccaggcat caaattaagc agaaggccat cctgacggat    3540
ggcctttttg cgtttctaca aactcttcca ctcactacag cagagccatt taaacaacat    3600
cccctccccc tttccaccgc gtcagacgcc cgtagcagcc cgctacgggc ttttttcatgc    3660 cctgccctag cgtccaagcc tcacggccgc gctcggcctc tctggcggcc ttctggcgct    3720
gaggtctgcc tcgtgaagaa ggtgttgctg actcatacca ggcctgaatc gccccatcat    3780
ccagccagaa agtgagggag ccacggttga tgagagcttt gttgtaggtg gaccagttgg    3840
tgattttgaa cttttgcttt gccacggaac ggtctgcgtt gtcgggaaga tgcgtgatct    3900
gatccttcaa ctcagcaaaa gttcgattta ttcaacaaag ccgccgtccc gtcaagtcag    3960
cgtaatgctc tgccagtgtt acaaccaatt aaccaattct gattagaaaa actcatcgag    4020
catcaaatga aactgcaatt tattcatatc aggattatca ataccatatt tttgaaaaag    4080
ccgtttctgt aatgaaggag aaaactcacc gaggcagttc cataggatgg caagatcctg    4140
gtatcggtct gcgattccga ctcgtccaac atcaatacaa cctattaatt tcccctcgtc    4200
aaaaataagg ttatcaagcg agaaatcacc atgagtgacg actgaatccg gtgagaatgg    4260
caaaagctaa aaggccgta atatccagct gaacggtctg gttataggta cattgagcaa    4320
ctgactgaaa tgcctcaaaa tgttctttac gatgccattg ggatatatca acggtggtat    4380
atccagtgat ttttttctcc attttagctt ccttagctcc tgaaaatctc gataactcaa    4440
aaaatacgcc cggtagtgat cttatttcat tatggtgaaa gttggaacct cttacgtgcc    4500
gatcaacgtc tcattttcgc caaaagttgg cccagggctt cccggtatca acagggacac    4560
caggatttat ttattctgcg aagtgatctt ccgtcacagg tatttattcg aagacgaaag    4620
```

```
ggcctcgtga tacgcctatt tttataggtt aatgtcatga taataatggt ttcttagacg    4680
tcaggtggca cttttcgggg aaatgtgcgc gcccgcgttc ctgctggcgc tgggcctgtt    4740
tctggcgctg gacttccgc tgttccgtca gcagcttttc gcccacggcc ttgatgatcg     4800
cggcggcctt ggcctgcata tcccgattca acggccccag ggcgtccaga acgggcttca    4860
ggcgctcccg aaggtctcgg gccgtctctt gggcttgatc ggccttcttg cgcatctcac    4920
gcgctcctgc ggcggcctgt agggcaggct catacccctg ccgaaccgct tttgtcagcc    4980
ggtcggccac ggcttccggc gtctcaacgc gctttgagat tcccagcttt tcggccaatc    5040
cctgcggtgc ataggcgcgt ggctcgaccg cttgcgggct gatggtgacg tggcccactg    5100
gtggccgctc cagggcctcg tagaacgcct gaatgcgcgt gtgacgtgcc ttgctgccct    5160
cgatgccccg ttgcagccct agatcggcca cagcggccgc aaacgtggtc tggtcgcggg    5220
tcatctgcgc tttgttgccg atgaactcct ggccgacag cctgccgtcc tgcgtcagcg     5280
gcaccacgaa cgcggtcatg tgcgggctgg tttcgtcacg gtggatgctg gccgtcacga    5340
tgcgatccgc cccgtacttg tccgccagcc acttgtgcgc cttctcgaag aacgccgcct    5400
gctgttcttg gctggccgac ttccaccatt ccgggctggc cgtcatgacg tactcgaccg    5460
ccaacacagc gtccttgcgc cgcttctctg gcagcaactc gcgcagtcgg cccatcgctt    5520
catcggtgct gctggccgcc cagtgctcgt tctctggcgt cctgctggcg tcagcgttgg    5580
gcgtctcgcg ctcgcggtag gcgtgcttga gactggccgc cacgttgccc attttcgcca    5640
gcttcttgca tcgcatgatc gcgtatgccg ccatgcctgc ccctccctt tggtgtccaa     5700 ccggctcgac gggggcagcg caaggcggtg cctccggcgg gccactcaat gcttgagtat    5760
actcactaga ctttgcttcg caaagtcgtg accgcctacg gcggctgcgg cgccctacgg    5820
gcttgctctc cgggcttcgc cctgcgcggt cgctgcgctc ccttgccagc ccgtggatat    5880
gtggacgatg gccgcgagcg gccaccggct ggctcgcttc gctcggcccg tggacaaccc    5940
tgctggacaa gctgatggac aggctgcgcc tgcccacgag cttgaccaca gggattgccc    6000
accggctacc cagccttcga ccacataccc accggctcca actgcgcggc ctgcggcctt    6060
gccccatcaa ttttttttaat tttctctggg gaaaagcctc cggcctgcgg cctgcgcgct   6120
tcgcttgccg gttggacacc aagtggaagg cgggtcaagg ctcgcgcagc gaccgcgcag    6180
cggcttggcc ttgacgcgcc tggaacgacc caagcctatg cgagtggggg cagtcgaagg    6240
cgaagcccgc ccgcctgccc cccgagcctc acggcggcga gtgcgggggt tccaaggggg    6300
cagcgccacc ttgggcaagg ccgaaggccg cgcagtcgat caacaagccc cggaggggcc    6360 acttttttgcc ggagggggag ccgcgccgaa ggcgtggggg aaccccgcag gggtgcccttt  6420 ctttgggcac caaagaacta gatatagggc gaaatgcgaa agacttaaaa atcaacaact    6480
taaaaagggg gggtacgcaa cagctcattg cggcaccccc cgcaatagct cattgcgtag    6540
gttaaagaaa atctgtaatt gactgccact tttacgcaac gcataattgt tgtcgcgctg    6600
ccgaaaagtt gcagctgatt gcgcatggtg ccgcaaccgt gcggcaccct accgcatgga    6660
gataagcatg ccacgcagt ccagagaaat cggcattcaa gccaagaaca agcccggtca     6720
ctgggtgcaa acgaacgca aagcgcatga ggcgtgggcc gggcttattg cgaggaaacc     6780
cacggcggca atgctgctgc atcacctcgt ggcgcagatg gccaccagaa cgccgtggt     6840 ggtcagccaa aagacacttt ccaagctcat cggacgttct ttgcggacgg tccaatacgc    6900
agtcaaggac ttggtggccg agcgctggat ctccgtcgtg aagctcaacg gccccggcac    6960
```

-continued

```
cgtgtcggcc tacgtggtca atgaccgcgt ggcgtggggc cagccccgcg accagttgcg    7020
cctgtcggtg ttcagtgccg ccgtggtggt tgatcacgac gaccaggacg aatcgctgtt    7080
ggggcatggc gacctgcgcc gcatcccgac cctgtatccg ggcgagcagc aactaccgac    7140
cggccccggc gaggagccgc ccagccagcc cggcattccg ggcatggaac cagacctgcc    7200
agccttgacc gaaacggagg aatgggaacg gcgcgggcag cagcgcctgc cgatgcccga    7260
tgagccgtgt tttctggacg atggcgagcc gttggagccg ccgacacggg tcacgctgcc    7320
gcgccggtag cacttgggtt gcgcagcaac ccgtaagtgc gctgttccag actatcggct    7380
gtagccgcct cgccgcccta taccttgtct gcctccccgc gttgcgtcgc ggtgcatgga    7440
gccgggccac ctcgacctga atggaagccg gcggcacctc gctaacggat tcaccgtttt    7500
tatcaggctc tgggaggcag aataaatgat catatcgtca attattacct ccacggggag    7560
agcctgagca aactggcctc aggcatttga gaagcacacg gtcacactgc ttccggtagt    7620
caataaaccg gtaaccagc aatagacata agcggctatt taacgaccct gccctgaacc    7680
gacgaccggg tcgaatttgc tttcgaattt ctgccattca tccgcttatt atcacttatt    7740
caggcgtagc accaggcgtt taagtcgacc aataac                              7776
```

<210> SEQ ID NO 25
<211> LENGTH: 643
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 25

```
Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
```

```
            210                 215                 220
Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Asp Asn Asn Ser Thr Pro Thr Val Ile Ser His Arg
            260                 265                 270

Leu His Phe Pro Glu Gly Gly Ser Leu Ala Ala Leu Thr Ala His Gln
            275                 280                 285

Ala Cys His Leu Pro Leu Glu Ala Phe Thr Arg His Arg Gln Pro Arg
290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
370                 375                 380

Ala Gly Ala Ala Ser Ala Asp Val Val Ser Leu Thr Cys Pro Val Ala
385                 390                 395                 400

Lys Asp Gln Asn Arg Thr Lys Gly Glu Cys Ala Gly Pro Ala Asp Ser
                405                 410                 415

Gly Asp Ala Leu Leu Glu Arg Asn Tyr Pro Thr Gly Ala Glu Phe Leu
            420                 425                 430

Gly Asp Gly Gly Asp Val Ser Phe Ser Thr Arg Gly Thr Gln Asn Trp
            435                 440                 445

Thr Val Glu Arg Leu Leu Gln Ala His Arg Gln Leu Glu Glu Arg Gly
            450                 455                 460

Tyr Val Phe Val Gly Tyr His Gly Thr Phe Leu Glu Ala Ala Gln Ser
465                 470                 475                 480

Ile Val Phe Gly Gly Val Arg Ala Arg Ser Gln Asp Leu Asp Ala Ile
                485                 490                 495

Trp Arg Gly Phe Tyr Ile Ala Gly Asp Pro Ala Leu Ala Tyr Gly Tyr
                500                 505                 510

Ala Gln Asp Gln Glu Pro Asp Ala Arg Gly Arg Ile Arg Asn Gly Ala
            515                 520                 525

Leu Leu Arg Val Tyr Val Pro Arg Trp Ser Leu Pro Gly Phe Tyr Arg
530                 535                 540

Thr Gly Leu Thr Leu Ala Ala Pro Glu Ala Ala Gly Glu Val Glu Arg
545                 550                 555                 560

Leu Ile Gly His Pro Leu Pro Leu Arg Leu Asp Ala Ile Thr Gly Pro
                565                 570                 575

Glu Glu Glu Gly Gly Arg Val Thr Ile Leu Gly Trp Pro Leu Ala Glu
            580                 585                 590

Arg Thr Val Val Ile Pro Ser Ala Ile Pro Thr Asp Pro Arg Asn Val
            595                 600                 605

Gly Gly Asp Leu Asp Pro Ser Ser Ile Pro Asp Lys Glu Gln Ala Ile
            610                 615                 620

Ser Ala Leu Pro Asp Tyr Ala Ser Gln Pro Gly Lys Pro Pro Arg Glu
625                 630                 635                 640
```

```
<210> SEQ ID NO 26
<211> LENGTH: 722
<212> TYPE: PRT
<213> ORGANISM: Campylobacter jejuni

<400> SEQUENCE: 26
```

Asp Leu Lys

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
            370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Ala Ala Tyr Gly Tyr Pro Val
450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
            610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
            690                 695                 700

Asp Ala Lys Val Phe Lys Leu Lys Ile Tyr Pro Tyr Asp Val Pro Asp
705                 710                 715                 720

Tyr Ala

<210> SEQ ID NO 27
<211> LENGTH: 8171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gcggccgcaa ggggttcgcg tcagcgggtg ttggcgggtg tcggggctgg cttaactatg    60
cggcatcaga gcagattgta ctgagagtgc accatatgcg gtgtgaaata ccgcacagat   120
gcgtaaggag aaaataccgc atcaggcgcc attcgccatt cagctgcgca actgttggga   180
agggcgatcg gtgcgggcct cttcgctatt acgccagctg gcgaaagggg gatgtgctgc   240
aaggcgatta agttgggtaa cgccagggtt ttcccagtca cgacgttgta aaacgacggc   300
cagtgaattg taatacgact cactataggg cgaattcgag ctcggtaccc ggggatccca   360
cgtggcgcgc cactagtgct agcgacgtcg tgggatcctc tagagtcgac ctgcaggcat   420
gcaagcttga gtattctata gtctcaccta aatagcttgg cgtaatcatg gtcatagctg   480
tttcctgtgt gaaattgtta tccgctcaca attccacaca acatacgagc cggaagcata   540
aagtgtaaag cctggggtgc ctaatgagtg agctaactca cattaattgc gttgcgctca   600
ctgcccgctt tccagtcggg aaacctgtcg tgccagctgc attaatgaat cggccaacgc   660
gaacccttg cggccgcccg ggccgtcgac caattctcat gtttgacagc ttatcatcga   720
atttctgcca ttcatccgct tattatcact tattcaggcg tagcaaccag gcgtttaagg   780
gcaccaataa ctgccttaaa aaaattacgc cccgccctgc cactcatcgc agtactgttg   840
taattcatta agcattctgc cgacatggaa gccatcacaa acggcatgat gaacctgaat   900
cgccagcggc atcagcacct tgtcgccttg cgtataatat ttgcccatgg tgaaaacggg   960
ggcgaagaag ttgtccatat tggccacgtt taaatcaaaa ctggtgaaac tcacccaggg  1020
attggctgag acgaaaaaca tattctcaat aaacccttta gggaaatagg ccaggttttc  1080
accgtaacac gccacatctt gcgaatatat gtgtagaaac tgccggaaat cgtcgtggta  1140
ttcactccag agcgatgaaa acgtttcagt ttgctcatgg aaaacggtgt aacaagggtg  1200
aacactatcc catatcacca gctcaccgtc tttcattgcc atacgaaatt ccggatgagc  1260
attcatcagg cgggcaagaa tgtgaataaa ggccggataa aacttgtgct tatttttctt  1320
tacggtcttt aaaaaggccg taatatccag ctgaacggtc tggttatagg tacattgagc  1380
aactgactga aatgcctcaa aatgttcttt acgatgccat gggatatat caacggtggt  1440
atatccagtg atttttttct ccattttagc ttccttagct cctgaaaatc tcgataactc  1500
aaaaaatacg cccggtagtg atcttatttc attatggtga agttggaac ctcttacgtg  1560
ccgatcaacg tctcattttc gccaaaagtt ggcccagggc ttcccggtat caacagggac  1620
accaggattt atttattctg cgaagtgatc ttccgtcaca ggtatttatt cgcgataagc  1680
tcatggagcg cgtaaccgt cgcacaggaa ggacagagaa agcgcggatc tgggaagtga  1740
cggacagaac ggtcaggacc tggattgggg aggcggttgc cgccgctgct gctgacggtg  1800
tgacgttctc tgttccggtc acaccacata cgttccgcca ttcctatgcg atgcacatgc  1860
tgtatgccgg tataccgctg aaagttctgc aaagcctgat gggacataag tccatcagtt  1920
caacggaagt ctacacgaag gttttgcgc tggatgtggc tgcccggcac cgggtgcagt  1980
ttgcgatgcc ggagtctgat gcggttgcga tgctgaaaca attatcctga gaataaatgc  2040
cttggccttt atatgaaat gtggaactga gtggatatgc tgttttgtc tgttaaacag  2100
agaagctggc tgttatccac tgagaagcga acgaaacagt cggaaaatc tcccattatc  2160
gtagagatcc gcattattaa tctcaggagc ctgtgtagcg tttataggaa gtagtgttct  2220
gtcatgatgc ctgcaagcgg taacgaaaac gatttgaata tgccttcagg aacaatagaa  2280
atcttcgtgc ggtgttacgt tgaagtggag cggattatgt cagcaatgga cagaacaacc  2340
```

```
taatgaacac agaaccatga tgtggtctgt ccttttacag ccagtagtgc tcgccgcagt    2400
cgagcgacag ggcgaagccc tcggctggtt gccctcgccg ctgggctggc ggccgtctat    2460
ggccctgcaa acgcgccaga aacgccgtcg aagccgtgtg cgagacaccg cggccggccg    2520
ccggcgttgt ggatacctcg cggaaaactt ggccctcact gacagatgag gggcggacgt    2580
tgacacttga ggggccgact cacccggcgc ggcgttgaca gatgaggggc aggctcgatt    2640
tcggccggcg acgtggagct ggccagcctc gcaaatcggc gaaaacgcct gattttacgc    2700
gagtttccca cagatgatgt ggacaagcct ggggataagt gccctgcggt attgacactt    2760
gaggggcgcg actactgaca gatgaggggc gcgatccttg acacttgagg gcagagtgc    2820 tgacagatga ggggcgcacc tattgacatt tgaggggctg tccacaggca gaaaatccag    2880
catttgcaag ggtttccgcc cgttttcgg ccaccgctaa cctgtctttt aacctgcttt     2940
taaaccaata tttataaacc ttgttttaa ccagggctgc gccctgtgcg cgtgaccgcg     3000
cacgccgaag ggggtgccc ccccttctcg aaccctcccg gtcgagtgag cgaggaagca     3060
ccagggaaca gcacttatat attctgctta cacacgatgc ctgaaaaaac ttcccttggg    3120
gttatccact tatccacggg gatattttta taattatttt ttttatagtt tttagatctt    3180
cttttttaga gcgccttgta ggcctttatc catgctggtt ctagagaagg tgttgtgaca    3240
aattgccctt tcagtgtgac aaatcaccct caaatgacag tcctgtctgt gacaaattgc    3300
ccttaaccct gtgacaaatt gccctcagaa gaagctgttt tttcacaaag ttatccctgc    3360
ttattgactc ttttttattt agtgtgacaa tctaaaaact tgtcacactt cacatggatc    3420
tgtcatggcg gaaacagcgg ttatcaatca caagaaacg aaaaatagcc cgcgaatcgt     3480
ccagtcaaac gacctcactg aggcggcata tagtctctcc cgggatcaaa acgtatgct    3540 gtatctgttc gttgaccaga tcagaaaatc tgatggcacc ctacaggaac atgacggtat    3600
ctgcgagatc catgttgcta aatatgctga atattcgga ttgacctctg cggaagccag     3660
taaggatata cggcaggcat tgaagagttt cgcggggaag gaagtggttt ttatcgccc     3720 tgaagaggat gccggcgatg aaaaaggcta tgaatctttt ccttggttta caaacgtgc     3780 gcacagtcca tccagagggc tttacagtgt acatatcaac ccatatctca ttcccttctt    3840
tatcgggtta cagaaccggt ttacgcagtt tcggcttagt gaaacaaaag aaatcaccaa    3900
tccgtatgcc atgcgtttat acgaatccct gtgtcagtat cgtaagccgg atggctcagg    3960
catcgtctct ctgaaaatcg actggatcat agagcgttac cagctgcctc aaagttacca    4020
gcgtatgcct gacttccgcc gccgcttcct gcaggtctgt gttaatgaga tcaacagcag    4080
aactccaatg cgcctctcat acattgagaa aaagaaaggc cgccagacga ctcatatcgt    4140
attttccttc cgcgatatca cttccatgac gacaggatag tctgagggtt atctgtcaca    4200
gatttgaggg tggttcgtca catttgttct gacctactga gggtaatttg tcacagtttt    4260
gctgtttcct tcagcctgca tggattttct catacttttt gaactgtaat ttttaaggaa    4320
gccaaatttg agggcagttt gtcacagttg atttccttct ctttcccttc gtcatgtgac    4380
ctgatatcgg gggttagttc gtcatcattg atgagggttg attatcacag tttattactc    4440
tgaattggct atccgcgtgt gtacctctac ctggagtttt tcccacggtg atatttctt     4500 cttgcgctga gcgtaagagc tatctgacag aacagttctt ctttgcttcc tcgccagttc    4560
gctcgctatg ctcggttaca cggctgcggc gagcgctagt gataataagt gactgaggta    4620
tgtgctcttc ttatctcctt ttgtagtgtt gctcttattt aaacaacttt gcggttttt     4680 tgatgacttt gcgatttgt tgttgctttg cagtaaattg caagatttaa taaaaaaacg    4740
```

```
caaagcaatg attaaaggat gttcagaatg aaactcatgg aaacacttaa ccagtgcata    4800
aacgctggtc atgaaatgac gaaggctatc gccattgcac agtttaatga tgacagcccg    4860
gaagcgagga aaataacccg gcgctggaga ataggtgaag cagcggattt agttggggtt    4920
tcttctcagg ctatcagaga tgccgagaaa gcagggcgac taccgcaccc ggatatggaa    4980
attcgaggac gggttgagca acgtgttggt tatacaattg aacaaattaa tcatatgcgt    5040
gatgtgtttg gtacgcgatt gcgacgtgct gaagacgtat ttccaccggt gatcggggtt    5100
gctgcccata aaggtggcgt ttacaaaacc tcagtttctg ttcatcttgc tcaggatctg    5160
gctctgaagg ggctacgtgt tttgctcgtg gaaggtaacg accccagggg aacagcctca    5220
atgtatcacg gatgggtacc agatcttcat attcatgcag aagacactct cctgcctttc    5280
tatcttgggg aaaaggacga tgtcacttat gcaataaagc ccacttgctg gccgggggctt    5340 gacattattc cttcctgtct ggctctgcac cgtattgaaa ctgagttaat gggcaaattt    5400
gatgaaggta aactgcccac cgatccacac ctgatgctcc gactggccat tgaaactgtt    5460
gctcatgact atgatgtcat agttattgac agcgcgccta acctgggtat cggcacgatt    5520
aatgtcgtat gtgctgctga tgtgctgatt gttcccacgc ctgctgagtt gtttgactac    5580
acctccgcac tgcagttttt cgatatgctt cgtgatctgc tcaagaacgt tgatcttaaa    5640
gggttcgagc ctgatgtacg tattttgctt accaaataca gcaatagtaa tggctctcag    5700
tccccgtgga tggaggagca aattcgggat gcctggggaa gcatggttct aaaaaatgtt    5760
gtacgtgaaa cggatgaagt tggtaaaggt cagatccgga tgagaactgt ttttgaacag    5820
gccattgatc aactgctctt caactggtgcc tggagaaatg ctctttctat ttgggaacct    5880
gtctgcaatg aaattttcga tcgtctgatt aaaccacgct gggagattag ataatgaagc    5940
gtgcgcctgt tattccaaaa catacgctca atactcaacc ggttgaagat acttcgttat    6000
cgacaccagc tgccccgatg gtggattcgt taattgcgcg cgtaggagta atggctcgcg    6060
gtaatgccat tactttgcct gtatgtggtc gggatgtgaa gtttactctt gaagtgctcc    6120
ggggtgatag tgttgagaag acctctcggg tatggtcagg taatgaacgt gaccaggagc    6180
tgcttactga ggacgcactg gatgatctca tcccttcttt tctactgact ggtcaacaga    6240
caccggcgtt cggtcgaaga gtatctggtc tcatagaaat tgccgatggg agtcgccgtc    6300
gtaaagctgc tgcacttacc gaaagtgatt atcgtgttct ggttggcgag ctggatgatg    6360
agcagatggc tgcattatcc agattgggta acgattatcg cccaacaagt gcttatgaac    6420
gtggtcagcg ttatgcaagc cgattgcaga atgaatttgc tggaaatatt tctgcgctgg    6480
ctgatgcgga aaatatttca cgtaagatta ttacccgctg tatcaacacc gccaaattgc    6540
ctaaatcagt tgttgctctt ttttctcacc ccggtgaact atctgcccgg tcaggtgatg    6600
cacttcaaaa agcctttaca gataaagagg aattacttaa gcagcaggca tctaaccttc    6660
atgagcagaa aaaagctggg gtgatatttg aagctgaaga agttatcact cttttaactt    6720
ctgtgcttaa aacgtcatct gcatcaagaa ctagtttaag ctcacgacat cagtttgctc    6780
ctggagcgac agtattgtat aagggcgata aaatggtgct taacctggac aggtctcgtg    6840
ttccaactga gtgtatagag aaaattgagg ccattcttaa ggaacttgaa aagccagcac    6900
cctgatgcga ccacgttta gtctacgttt atctgtcttt acttaatgtc ctttgttaca    6960
ggccagaaag cataactggc ctgaatattc tctctgggcc cactgttcca cttgtatcgt    7020
cggtctgata atcagactgg gaccacggtc ccactcgtat cgtcggtctg attattagtc    7080
```

```
tgggaccacg gtcccactcg tatcgtcggt ctgattatta gtctgggacc acggtccac    7140 tcgtatcgtc ggtctgataa tcagactggg accacggtcc cactcgtatc gtcggtctga    7200
ttattagtct gggaccatgg tcccactcgt atcgtcggtc tgattattag tctgggacca    7260
cggtcccact cgtatcgtcg gtctgattat tagtctggaa ccacggtccc actcgtatcg    7320
tcggtctgat tattagtctg gaccacggt cccactcgta tcgtcggtct gattattagt    7380
ctgggaccac gatcccactc gtgttgtcgg tctgattatc ggtctgggac cacggtccca    7440
cttgtattgt cgatcagact atcagcgtga gactacgatt ccatcaatgc ctgtcaaggg    7500
caagtattga catgtcgtcg taacctgtag aacggagtaa cctcggtgtg cggttgtatg    7560
cctgctgtgg attgctgctg tgtcctgctt atccacaaca ttttgcgcac ggttatgtgg    7620
acaaaatacc tggttaccca ggccgtgccg gcacgttaac cgggctgcat ccgatgcaag    7680
tgtgtcgctg tcgacgagct cgcgagctcg gacatgaggt tgccccgtat tcagtgtcgc    7740
tgatttgtat tgtctgaagt tgtttttacg ttaagttgat gcagatcaat taatacgata    7800
cctgcgtcat aattgattat ttgacgtggt ttgatggcct ccacgcacgt tgtgatatgt    7860
agatgataat cattatcact ttacgggtcc tttccggtga tccgacaggt tacggggcgg    7920
cgacctcgcg ggttttcgct atttatgaaa attttccggt ttaaggcgtt tccgttcttc    7980
ttcgtcataa cttaatgttt ttatttaaaa taccctctga aaagaaagga aacgacaggt    8040
gctgaaagcg agcttttgg cctctgtcgt ttccttttctc tgtttttgtc cgtggaatga    8100
acaatggaag tccgagctca tcgctaataa cttcgtatag catacattat acgaagttat    8160
attcgatcca c                                                          8171
```

<210> SEQ ID NO 28
<211> LENGTH: 20982
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 28

```
ctagcggcaa aacgtatgcc gggtgacctc tctgaatact ccgtcatcca gaccaaagaa     60
ccgctggatc gcgaaggtaa agtcagccgc attgttgaat ttatcgaaaa accggatcag    120
ccgcagacgc tggactcaga catcatggcc gttggtcgct atgtgctttc tgccgatatt    180
tggccggaac ttgaacgtac tcagcctggt gcatgggac gtattcagct gactgatgcc    240
attgccgagc tggcgaaaaa acagtccgtt gatgcaatgc tgatgaccgg cgacagctac    300
gactgcggta aaaaaatggg ctatatgcag gcgtttgtga agtatgggct gcgcaacctg    360
aaagaagggg cgaagttccg taaaggtatt gagaagctgt taagcgaata atgaaaatct    420
gaccggatgt aacggttgat aagaaaatta taacggcagt gaagattcgt ggtgaaagta    480
atttgttgcg aatattcctg ccgttgtttt atataaacaa tcagaataac aacgagttag    540
caataggatt ttagtcaaag ttttccagga ttttccttgt ttccagagcg gattggtaag    600
acaattagct tttgaatttt tcgggtttag cgcgagtggg taacgctcgt cacatcgtag    660
gcatgcatgc agtgctctgg tagctgtaaa gccaggggcg gtagcgtgca ttaatacttc    720
tattaatcaa actgagagcc gcttatttca cagcatgctc tgaagcaata tggaataaat    780
taggtgaaaa tacttgttac tggtggcgca ggatttattg gttttgctgt agttcgtcac    840
attataaata atacgcagga tagtgttgtt aatgtcgata aattaacgta cgccggaaac    900
```

```
ctggaatcac ttgctgatgt ttctgattct gaacgctatg tttttgaaca tgcggatatt    960
tgcgatgcag ctgcaatggc acggattttt gctcagcatc agccagatgc agtgatgcac   1020
ctggctgctg aaagccatgt tgaccgttca attacaggtc ctgcggcatt tattgaaacc   1080
aatattgttg gtacatatgt ccttttggaa gccgctcgca attattggtc tgctcttgat   1140
agcgacaaga aaactagatt ccgttttcat catatttcta ctgacgaagt ctatggtgat   1200
ttgcctcatc ctgacgaggt aaataataca gaagaattac ccttatttac agagacaaca   1260
gcttacgcgc caagcagccc ttattccgct tcaaaagcat ccagcgatca tttagtccgc   1320
gcgtggaaac gtacctatgg tttaccaacc attgtgacta attgctctaa taattatggt   1380
ccttatcatt tcccggaaaa attgattcca ttggttattc tgaatgctct ggaaggtaag   1440
gcattaccta tttatggcaa aggggatcaa attcgtgact ggctgtatgt tgaagatcat   1500
gcgcgtgcgt tatataccgt cgtaaccgaa ggtaaagcgg gtgaaactta acattggt    1560
ggacacaacg aaaagaaaaa catcgatgta gtgctcacta tttgtgattt gctggatgag   1620
attgtaccga aagagaaatc ttaccgcgag caaattactt atgttccga tcgcccggga   1680
cacgatcgcc gttatgcgat tgatgcagag aagattagcc gcgaattggg ctggaaaccg   1740
caggaaacgt ttgagagcgg gattcggaag acattggaat ggtacctgtc caatacaaaa   1800
tgggttgata tgtgaaaag tggtgcttat caatcgtgga ttgaacagaa ctatgagggc   1860
cgccagtaat gaatatcctc cttttcggca aaacagggca ggtaggttgg gaactacagc   1920
gtgctctggc acctttgggt aatttgattg ctcttgatgt tcactccact gattattgtg   1980
gtgattttag taatcctgaa ggtgtagctg aaacagtcaa aagaattcga cctgatgtta   2040
ttgttaatgc tgcggctcac accgcagtag ataaggctga gtcagaaccc gaatttgcac   2100
aattactcaa tgcgactagt gttgaatcaa ttgcaaaaga ggctaatgaa gttgggggctt   2160
gggtaattca ttactcaact gactacgtat tccctggaaa tggcgacacg ccatggctgg   2220
agacggatgc aaccgcaccg ctaaatgttt acggtgaaac caagttagcc ggagaaaaag   2280
cgttacagga acattgcgcg aagcatctta ttttccgtac cagctgggta tacgcagcta   2340
aaggaaataa cttcgccaaa acgatgttgc gtctggcaaa agagcgcgaa gaactggctg   2400
tgataaatga tcaatttggt gcgccaacag gtgctgagct gctggctgat tgtacggcac   2460
atgctattcg tgtggcactg aataaaccgg aagtcgcagg tttgtaccat ctggtagcca   2520
gtggtaccac aacctggcac gattatgctg cgctggtttt tgaagaggcg cgcaaagcag   2580
gtattcccct tgcactcaac aagctcaacg cagtaccaac aacagcctat cctacaccag   2640
ctcgtcgtcc acataactct cgccttaata cagaaaaatt tcagcagaac tttgcgcttg   2700
tcttgcctga ctggcaggtt ggtgtgaaac gaatgctcaa cgaattaatt acgactacag   2760
caatttaata gttttttgcat cttgttcgtg atggtggagc aagatgaatt aaaaggaatg   2820
atgaaatgaa aacgcgtaaa ggtattattt tagcgggtgg ttctggtaca cgtctttatc   2880
ctgtgactat ggctgtcagt aaacagctat tacctatttta tgataagccg atgatctatt   2940
acccgctctc tacactgatg ttggcgggta ttcgcgatat tctgattatt agtacgccac   3000
aggatactcc tcgttttcaa caactgctag gtgacggtag ccagtggggg ctaaatcttc   3060
agtacaaagt gcaaccgact ccagatgggc ttgcgcaggc gtttattatc ggtgaagagt   3120
ttatcggtgg tgatgattgt gctttggttc ttggtgataa tatcttctac ggtcatgatc   3180
tgccgaagtt aatggatgtc gctgttaaca aagaaagtgg tgcaacggta tttgcctatc   3240
acgttaatga tcctgaacgc tacggcgtcg ttgagtttga taaaaacggt acggcaataa   3300
```

-continued

```
gcctggaaga aaaaccgcta caaccaaaaa gtaattatgc ggtaaccggg ctttatttct    3360
atgataacga cgttgtcgaa atggcgaaaa accttaagcc ttctgcccgt ggtgaactgg    3420
aaattaccga tattaaccgt atttatatgg aacaggggcg tttatccgtt gccatgatgg    3480
ggcgtggtta tgcatggctg atacggggga cacatcagag tcttattgaa gcaagcaact    3540
tcattgccac cattgaagag cgccagggac taaaggtttc ctgcccagaa gaaattgctt    3600
accgtaaagg gtttattgat gctgaacagg tgaaagcatt agcggagccg ctgaaaaaaa    3660
atgcttatgg acagtatctg ctgaaaatga ttaaaggtta ttaataaaat gaacgtaatt    3720
aaaacagaaa ttcctgatgt gttaattttc gagccgaaag tttttggtga tgagcgtggt    3780
ttctttatgg aaagctttaa tcagaaagtt ttcgaagaag ctgtaggacg taaggttgaa    3840
tttgttcagg ataaccattc gaagtctagt aaaggtgttt tacgcgggct gcattatcag    3900
ttagaacctt atgcgcaagg gaaactggta cgttgcgttg ttggtgaggt ttttgatgta    3960
gctgttgata ttcgtaaatc gtcgcctacc tttggtaaat gggttggggt gaatttatct    4020
gctgagaata agcggcaatt gtggatccct gagggatttg cacatggttt tttggtgctg    4080
agcgagactg cggaattttt atataaaacg acgaactatt atcatcctga tagtgataga    4140
gggattgtat ggaatgatcc tattctgagc ataaaatggc cgacgataga acataataat    4200
tatattttat cgattaaaga tgcaagggct aaagaattgc ataacatgaa ggaattattt    4260
ttgtgagtat tgtaaagaat actttatgga atataagtgg gtatattata ccatcattaa    4320
tagcaattcc tgcgttaggt atactgtcta gaattctagg gaccgagcaa tttggccttt    4380
ttacgttagc tattgcctta gttggatatg caagtatttt tgatgctgga ttgaccagag    4440
ctgttataag agaagtatca atatataaaa atgttcataa agaattaaga gcgatcattt    4500
caacttcaac ggtaattcta actatattgg gcttgattgg cggtagtgta ctattttttga    4560 gtagcaatgt aattgttaaa ttattaaaca ttaacgcgaa tcatgttgta gaatctgtca    4620
aagcaatata tattatttca gctaccatac ccttatactt gttaaaccaa gtctggttgg    4680 ggattttttga ggggatggaa aagttcagaa aagtaaattt aataaaatca attaacaact    4740
cttttgtggc tggattacca gtgatttttct gtttttttca tggaggatta ctaagtgcta    4800
tatatggttt agttatggca agagtcttat cacttatagt gacctttata tttagtcgaa    4860
aactaataat atcatctggg ctgtctgtaa aaattgtaac agttaaaaga ttaatcggct    4920
ttggaagctg ataacagtt agcaatatta ttagccctat tatgacatat atggatcgtt    4980
ttattctttc acacattgtg ggggctgata agtttctttt ttatactgct ccgtctgaag    5040
gtatacaacg cttaacgata ttaccaagtg cgttgtccag agctatttttt ccaagattaa    5100 gttcagaatt gcaatcggta aagcaaacta aaatattatc atatttttata atggttattg    5160 gtatacttcc aattgtaatg ttgataatta ttttatcaga ttttataatg tccgcttgga    5220
tgggacctac atatcatggg acgccaggta tagtattaaa aattcttgca ataggttttct    5280 tttttaattg cattgcacaa atcccatttg tttcagttca ggctagtgga agatcaaaaa    5340
ttacagctat tattcatttg ctcgaagtta tcccatattt atgcatatta tatatttttta    5400 tttatcattg gggaattgtt ggagccgcaa tagcatggtc tgtaagaaca tcgttagatt    5460
ttttgatatt attattaatt gatacgaaat attaatagcg aattgattt agggattact    5520 tcctcaagcc catctaatta gagtgcaaac atgacttctg attttttataa ctcaaaagac    5580 aaaagtttaa gtgttctttt gttttttggg tttatatttt tccttacacg tagctttcca    5640
```

```
tttattcaat atagttggat tatggagggg tttttatgtc tttgtatcat gtcatttaca       5700
aagaaaattg caaacggaat atatcactat cctgttattt taatatttct attagctctt       5760
tttataaatt ttatttattc ctatatcaag ggtaacgata tagcgataat aattaggttt       5820
tatattatca tattatttat attatgtgct tatttctgct cttatggaac catctcgatt       5880
gttaaaatat ttttatattt aatggtatta caggcggtta ttatatccat cattagtatt       5940
tatatgacaa aaacatatgg tattggtgat tattcagcac taagacatta tttttttggag      6000 aatgattatg gtgatgttta tacatatgga agtggtttct atagagttca aattaaagga       6060
aatgctctca ttccatttgc ctttatgttg catatagtca taaaagatta tttctattat       6120
cgattcaaaa atacaataac cgttattctg gctataggta ctatagtggc tggtaatttt       6180
gcatattttg tttcgatatg cttgtttttt atgtatatta tactatgttc taaatctaac       6240
tcacgatacg ctaaattaag gaaaattatt tttggggttt ttcttactgt gattctccct       6300
tttttattta catattcaat tgagttgata atcatgaaat caaatggagc tgattcttct       6360
ttaggagtta gatgggatca gtttactgta ttaattaatg atcttacaga gtctgtatca       6420
aattttgtta taggttctgg tttgggtaat gtcatcaaaa ttcaaactcc tatccgtgat       6480
tatagtgcat atatatatta tgaattgcag tcagtttatt ttttaaatca acttggcgtt       6540
attttattta ctttgttttt attaattaat ctccttctca cgattaaaat cataaaatac       6600
agtgagttgt gtgtgctata ttttctatat gtttcttatg caattactaa tccttatatt       6660
ttagactcta accatgttgc tgtaataatt gtattagtga cattaagtaa tgttctaaaa       6720
aagatgaaag ctaaatgaag gttttaaggt gaagatggac actgtatatg ccgttttggt       6780
tgcttacaac ccagaacata atgatttaaa aaatgcggtt gaattattgt tgagacaagt       6840
tactaaagtt gtcgtttgca ataactctac aaatggttat aaatatgctg aaaattcttc       6900
aggcgatgta aaaatattca atttcaatga taatttaggc atagcagaag cccaaagtat       6960
aggaatgaaa tgggcttttg aaaatggcgc tgatttttata ttgcaaatgg atcaggatag      7020
tattcctgat cctaagatgg tagagcagtt acttacttgt tacaaaaaat tgcttaaaca       7080
aaatgtcaat gttggtttag ttggttcaca agattttgat aaagtaactg gtgaattaaa       7140
taaagcaagg gtaaaaaaag ggaaaccact tacagaagtt tattatgagg tagatagtac       7200
attaagttct ggcagtctaa taccaaaaaa tagttggttg attgttggag gaatgaaaga       7260 tgagctttt atcgatgcgg tagaccatga atattgttgg agattaagag ctgctgggtt       7320
taaagtaatt aggaataaaa atgcgttact tgcacataga cttggagatg ggcgatttaa       7380
gatcttaaat attctttctg tcggttttgcc aagcccattt cgtcattatt atgctactcg       7440
aaatatcttt cttttattaa ataaaaatta tgtacccatc tactgaaaaa tttctagtct       7500
ggttaaatta attggaaagg tttttttata tcctattttc cttccaaatg gtaataaaag       7560
gttatatttt tttttaaaag gcattaatga cggtttaatg ggtcgaagtg gtaaaatgaa       7620
atgaatcata gattagaaaa attctcagtt ttaattagca tttataaaaa tgatctaccg       7680
caattttttg aggtggctct acgctctatt tttcacgatc aaacacttaa gccagatcaa       7740
atagtaattg ttgcagatgg agaactccat caaacacaca tcgatattat aaattcattc       7800
attgatgatg ttggcaataa aatagtaaca tttgtaccctt tacctagaaa tgttggattg       7860
gctaatgcct taaatgaagg attaaaggct tgtaggaatg agttagtggc aagaatggat       7920
gctgatgata tttcttgcc tcatcggttt gagaaacaaa tttcttttat gattaataat       7980
tcagaaatag atgtatgtgg cagttttatt gatgaaattg aaactgttac tgaggagttt       8040
```

```
atttcaacac gcaaagtgcc tctcgaacat agagaaatag ttaaattcgc gaggaaacga   8100
agcgcagtta gccatccttc tgtaattttt agaaagaata cagtattagc tgttggtggt   8160
tatcctccat tcagaaaatc tcaagatttt gcattgtgga gcctattaat tgtacataat   8220
gcaagatttg caaatcttcc agatatttta ttaaaaatgc gaactggtcg taatcttatg   8280
gctcgacgtg gattgtcata tttattgtac gagtataaag tattgtatta tcaatataaa   8340
attggtttta ttcgaaaaaa tgaattaata agtaatgcta tgttgagaac attttttcgt   8400
ataatgccat ctaaattaaa ggagctgatg tattcaatcg ttaggaatcg ataataataa   8460
ttttctgatt aagtgttatg gatttatttt tattaggcat attctataat taagcataac   8520
ccgcatacca cccagcggta tcctgacagg agtaaacaat gtcaaagcaa cagatcggcg   8580
tcgtcggtat ggcagtgatg gggcgcaacc ttgcgctcaa tatcgaaagc cgtggttata   8640
ccgtctctat tttcaaccgt tcccgtgaaa agaccgaaga agtgattacc gaaaatccag   8700
gcaagaaact ggttccttac tatacggtga agaatttgt tgaatctctg aaacgcctc    8760 gtcgcatcct gttaatggtg aaagcaggtg ctggcacgga tgctgctatt gattccctca   8820
agccatacct cgataaaggt gacatcatca ttgatggtgg taacaccttc ttccatgaca   8880
ccattcgtcg taaccgtgag cttctgcag aaggctttaa ctttatcggt accggtgttt    8940
ccggtggtga agaaggtcgc ctgaaaggtc cttccattat gcctggtggg cagaaagaag   9000
cttatgaact gattgcgccg atcctgacca aaatcgccgc tgtggctgaa gacggcgaac   9060
cgtgcgttac ctatattggt gccgatggtg caggtcatta tgtgaagatg gttcacaacg   9120
gtattgaata cggtgatatg cagctgattg ctgaagccta ttctctgctt aaaggtggct   9180
tgaacctcac caacgaagaa ctggcgcaga cctttaccga gtggaataac ggtgaactga   9240
gcagctacct gatcgacatc accaaagata tcttcaccaa aaaagatgaa gagggtaact   9300
acctggttga tgtgattctg gatgaagcag caaacaaagg tacgggcaaa tggaccagcc   9360
agagcgcgct ggatctcggc gaaccgctgt cgctgattac cgagtctgtg tttgcacgtt   9420
atatctcttc tctgaaagag cagcgtgttg ccgcatctaa agttctctct ggcccgcaag   9480
cgcagccagc tggcgacaat gctgagttca tcgaaaaagt tcgccgtgcg ctgtatctgg   9540
gcaaaatcgt ttcttacgct cagggcttct ctcagctacg cgctgcgtct gaagagtaca   9600
actgggatct gaactacggt gaaatcgcga agatttccg tgctggctgc atcatccgtg    9660
cgcagttcct gcagaaaatc accgatgctt atgccgaaaa tccgcagatc gctaacctgt   9720
tgctggctcc ttacttcaag caaattgccg atgactacca gcaggcgctg cgcgatgtcg   9780
tcgcttacgc agtacagaac ggtatcccgg tgccgacctt cgccgctgcg gttgcctatt   9840
acgacagcta ccgcgccgct gttctgcctg cgaacctgat ccaggcacag cgtgactatt   9900
tcggtgcgca tacttataag cgcattgata agaaggtgt gttccatacc gaatggctgg    9960
attaatctga tttaaatcaa ttaatcaaag caaggcccgg agaaaccctc cgggcttttt   10020
tattatacaa agcggcaggt tagggccttt ttttataatt tatagttaaa aacgcgatat   10080
aatacagcgc cgcacagcag gatcgctgcc ttgacagttc atctacatca gcgttaaaaa   10140
tcccgcagta gatgaagctg tggtggtgga ttaatgacca ctctaaatgt ttaaccggaa   10200
gaagtcagag ctaatgaaaa taacaatttc aggaacaggt tatgttggtc tttcaaatgg   10260
tattctgatt gcgcaaaacc acgaagtggt tgcactggat atcgttcagg ccaaagtgga   10320
catgcttaac aagaggcagt caccgcttgt tgataaggag attgaagagt atctggcgac   10380
```

```
taaagatctc aatttccgcg ctacgacaga taagtatgac gcgtataaaa atgccgatta   10440
cgttattatt gccacaccta ccgattatga tccgaaaaca aattatttta atacctcaag   10500
cgtggaagcg gtcattcgtg atgtgacaga aattaatccc aacgcggtaa tgattataaa   10560
atcaactatc cctgttggtt ttacagagtc cattaaagaa cgttttggta ttgaaaatgt   10620
gatcttttcg cctgagtttt tgcgtgaagg taaagcactt tatgataact tacacccatc   10680
acgcattgtg attggcgagc agtctgaacg cgctaaacgt tttgctgcgt tattacagga   10740
aggcgccatt aagcaagaca taccaacatt gtttactgac tcaaccgagg ctgaggcgat   10800
taaacttttt gcgaacactt atctggcgat gcgtgtagcg tatttcaatg aacttgatag   10860
ttatgctgaa agcctgggac ttaattcacg ccagattatt gagggcgtat gccttgaccc   10920
gcgtatcggt aatcactaca acaacccgtc attcggttat ggtggttatt gtctgccgaa   10980
agatactaag cagttactgg caaattacca gtctgtgccg aataacctga tctcggcaat   11040
tgttgacgcc aaccgcacgc gcaaagattt tattgccgat tctatccttg cacgtaaacc   11100
gaaagttgtt ggcgtctatc gtttgattat gaagaatggt tcagacaatt ttcgtgcttc   11160
ctcgattcag ggtattatga agcgaatcaa ggcgaaaggt gtgcctgtaa tcgtttatga   11220
gccagctatg aaagaggacg atttttttccg gtcgcgcgtg gtacgtgatc tggatgcgtt   11280
caaacaagaa gctgatgtta ttatttctaa ccgtatgtct gccgatctgg ctgatgtagc   11340
agataaagtt tatacgcgcg acttgttttgg caatgattaa ttattttgtt tcattctaag   11400
aaaaggccct aataaattag ggcctttttct tatggttttg taaaatcaaa ctttatagaa   11460
gttacgatac cattctacaa agttctttac cccttcttta actgacgttt caggtttgaa   11520
tcctattacg tcatacagtg cttttgtatc agcactggtt tccagtacat caccgggttg   11580
gagaggcatc atatttttgt tggcttcaat acccagagcc tcttctaacg cattgatata   11640
gtccatcaac tccacaggcg aactattacc aatgttatag acacgatatg gtgctgaact   11700
tgttgcaggc gagcctgttt ctacagccca ctgtgggttt ttttctggaa taacatcctg   11760
taagcgaata atagcttcgg caatatcatc aatgtaagta aagtcacgct tcattttgcc   11820
gaagttgtaa acatcaatgc ttttaccttc cagcatggct ttagtgaatt taaataatgc   11880
catatccgga cgtccccatg gaccataaac cgtaaagaaa cgcagccctg tggtcggtaa   11940
gccatacaaa tgagaatatg tatgggccat gagttcattc gcttttttag ttgctgcata   12000
aagcgaaaca ggatgatcta cagagtcatc tgtagagaaa ggcatcttgc ggttcatgcc   12060
ataaacagaa ctggaggaag cgtaaagtag atgctgaaca ttattatggc gacatccttc   12120
tagtatgttc aggaatccaa tcaggtttgc atctgcatat gcattgggat tttcaagaga   12180
gtaacgtaca ccggcttgcg cagcgaggtt tattacgcgt tcgaaccgct cgtctgcaaa   12240
cagtgccgcc attttctcac gatcggccag gtcaatttta taaaaactga agttgtcgtg   12300
cttgagtaaa tcaagtcgtg cttgtttgag gttgacatcg taataatcat ttaagttgtc   12360
aatgcctaca acctgatgac cagctgcaag aagccgttta cttagataga aaccgataaa   12420
gccagcagct cccgtaacca gaaatttcat ttataatcct cgctcaggct agaatatagc   12480
caatcttcat ctggcataac tgaaagttaa attataccgt tagacaagaa aaaagataa   12540 tcggtatcag ttctaaactt ggctgttttt tctggtaacg tgctcatttt acaatcaaag   12600
ctgttctaag ctgactatac aagccgacgt cattatctcc aaccgtatgg cagaagagct   12660
taaggatgtg gcagacaaag tctacacccg cgatctcttt ggcagtgact aacatcctgt   12720
tatcatggcg attttcgccc tgattctctt atgttccctt tgtaataatt cattatttttt   12780
```

```
atcatttatc ctatagcatt catggcgatt atcgctaaac tatggcggcg cgccacgtgg   12840
gatccccggg taccgagctc gaattcgccc tatagtgagt cgtattacaa ttcactggcc   12900
gtcgttttac aacgtcgtga ctgggaaaac cctggcgtta cccaacttaa tcgccttgca   12960
gcacatcccc ctttcgccag ctggcgtaat agcgaagagg cccgcaccga tcgcccttcc   13020
caacagttgc gcagctgaat ggcgaatggc gcctgatgcg gtattttctc cttacgcatc   13080
tgtgcggtat ttcacaccgc atatggtgca ctctcagtac aatctgctct gatgccgcat   13140
agttaagcca gccccgacac ccgccaacac ccgctgacgc gaaccccttg cggccgcatc   13200
gaatataact tcgtataatg tatgctatac gaagttatta gcgatgagct cggacttcca   13260
ttgttcattc cacggacaaa aacagagaaa ggaaacgaca gaggccaaaa agctcgcttt   13320
cagcacctgt cgtttccttt cttttcgagg ggtattttaa ataaaaacat taagttatga   13380
cgaagaagaa cggaaacgcc ttaaaccgga aaattttcat aaatagcgaa aacccgcgag   13440
gtcgccgccc cgtaacctgt cggatcaccg gaaaggaccc gtaaagtgat aatgattatc   13500
atctacatat cacaacgtgc gtggaggcca tcaaaccacg tcaaataatc aattatgacg   13560
caggtatcgt attaattgat ctgcatcaac ttaacgtaaa aacaacttca gacaatacaa   13620
atcagcgaca ctgaatacgg ggcaacctca tgtccgagct cgcgagctcg tcgacagcga   13680
cacacttgca tcggatgcag cccggttaac gtgccggcac ggcctgggta accaggtatt   13740
ttgtccacat aaccgtgcgc aaaatgttgt ggataagcag gacacagcag caatccacag   13800
caggcataca accgcacacc gaggttactc cgttctacag gttacgacga catgtcaata   13860
cttgcccttg acaggcattg atggaatcgt agtctcacgc tgatagtctg atcgacaata   13920
caagtgggac cgtggtccca gaccgataat cagaccgaca acacgagtgg gatcgtggtc   13980
ccagactaat aatcagaccg acgatacgag tgggaccgtg gtcccagact aataatcaga   14040
ccgacgatac gagtgggacc gtggttccag actaataatc agaccgacga tacgagtggg   14100
accgtggtcc cagactaata atcagaccga cgatacgagt gggaccatgg tcccagacta   14160
ataatcagac cgacgatacg agtgggaccg tggtcccagt ctgattatca gaccgacgat   14220
acgagtggga ccgtggtccc agactaataa tcagaccgac gatacgagtg ggaccgtggt   14280
cccagactaa taatcagacc gacgatacga gtgggaccgt ggtcccagtc tgattatcag   14340
accgacgata caagtggaac agtgggccca gagagaatat tcaggccagt tatgctttct   14400
ggcctgtaac aaaggacatt aagtaaagac agataaacgt agactaaaac gtggtcgcat   14460
cagggtgctg gcttttcaag ttccttaaga atggcctcaa ttttctctat acactcagtt   14520
ggaacacgag acctgtccag gttaagcacc attttatcgc ccttatacaa tactgtcgct   14580
ccaggagcaa actgatgtcg tgagcttaaa ctagttcttg atgcagatga cgttttaagc   14640
acagaagtta aaagagtgat aacttcttca gcttcaaata tcaccccagc ttttttctgc   14700
tcatgaaggt tagatgcctg ctgcttaagt aattcctctt tatctgtaaa ggcttttga   14760 agtgcatcac ctgaccgggc agatagttca ccggggtgag aaaaaagagc aacaactgat   14820
ttaggcaatt tggcggtgtt gatacagcgg gtaataatct tacgtgaaat attttccgca   14880
tcagccagcg cagaaatatt tccagcaaat tcattctgca atcggcttgc ataacgctga   14940
ccacgttcat aagcacttgt tgggcgataa tcgttaccca atctggataa tgcagccatc   15000
tgctcatcat ccagctcgcc aaccagaaca cgataatcac tttcggtaag tgcagcagct   15060
ttacgacggc gactcccatc ggcaatttct atgacaccag atactcttcg accgaacgcc   15120
```

```
ggtgtctgtt gaccagtcag tagaaaagaa gggatgagat catccagtgc gtcctcagta    15180
agcagctcct ggtcacgttc attacctgac catacccgag aggtcttctc aacactatca    15240
ccccggagca cttcaagagt aaacttcaca tcccgaccac atacaggcaa agtaatggca    15300
ttaccgcgag ccattactcc tacgcgcgca attaacgaat ccaccatcgg ggcagctggt    15360
gtcgataacg aagtatcttc aaccggttga gtattgagcg tatgttttgg aataacaggc    15420
gcacgcttca ttatctaatc tcccagcgtg gtttaatcag acgatcgaaa atttcattgc    15480
agacaggttc ccaaatagaa agagcatttc tccaggcacc agttgaagag cgttgatcaa    15540
tggcctgttc aaaaacagtt ctcatccgga tctgaccttt accaacttca tccgtttcac    15600
gtacaacatt ttttagaacc atgcttcccc aggcatcccg aatttgctcc tccatccacg    15660
gggactgaga gccattacta ttgctgtatt tggtaagcaa aatacgtaca tcaggctcga    15720 acccctttaag atcaacgttc ttgagcagat cacgaagcat atcgaaaaac tgcagtgcgg    15780
aggtgtagtc aaacaactca gcaggcgtgg gaacaatcag cacatcagca gcacatacga    15840
cattaatcgt gccgataccc aggttaggcg cgctgtcaat aactatgaca tcatagtcat    15900
gagcaacagt ttcaatggcc agtcggagca tcaggtgtgg atcggtgggc agtttacctt    15960
catcaaattt gcccattaac tcagtttcaa tacggtgcag agccagacag gaaggaataa    16020
tgtcaagccc cggccagcaa gtgggctttt ttgcataagt gacatcgtcc ttttccccaa    16080
gatagaaagg caggagagtg tcttctgcat gaatatgaag atctggtacc catccgtgat    16140
acattgaggc tgttccctgg gggtcgttac cttccacgag caaaacacgt agccccttca    16200
gagccagatc ctgagcaaga tgaacagaaa ctgaggtttt gtaaacgcca cctttatggg    16260
cagcaacccc gatcaccggt ggaaatacgt cttcagcacg tcgcaatcgc gtaccaaaca    16320
catcacgcat atgattaatt tgttcaattg tataaccaac acgttgctca acccgtcctc    16380
gaatttccat atccgggtgc ggtagtcgcc ctgctttctc ggcatctctg atagcctgag    16440
aagaaacccc aactaaatcc gctgcttcac ctattctcca gcgccgggtt attttcctcg    16500
cttccgggct gtcatcatta aactgtgcaa tggcgatagc cttcgtcatt tcatgaccag    16560
cgtttatgca ctggttaagt gttttccatga gtttcattct gaacatcctt taatcattgc    16620
tttgcgtttt tttattaaat cttgcaattt actgcaaagc aacaacaaaa tcgcaaagtc    16680
atcaaaaaac cgcaaagttg tttaaaataa gagcaacact acaaaaggag ataagaagag    16740
cacatacctc agtcacttat tatcactagc gctcgccgca gccgtgtaac cgagcatagc    16800
gagcgaactg gcgaggaagc aaagaagaac tgttctgtca gatagctctt acgctcagcg    16860
caagaagaaa tatccaccgt gggaaaaact ccaggtagag gtacacacgc ggatagccaa    16920
ttcagagtaa taaactgtga taatcaaccc tcatcaatga tgacgaacta accccgata    16980 tcaggtcaca tgacgaaggg aaagagaagg aaatcaactg tgacaaactg ccctcaaatt    17040
tggcttcctt aaaaattaca gttcaaaaag tatgagaaaa tccatgcagg ctgaaggaaa    17100
cagcaaaact gtgacaaatt accctcagta ggtcagaaca aatgtgacga accaccctca    17160
aatctgtgac agataaccct cagactatcc tgtcgtcatg gaagtgatat cgcggaagga    17220
aaatacgata tgagtcgtct ggcggccttt ctttttctca atgtatgaga ggcgcattgg    17280
agttctgctg ttgatctcat taacacagac ctgcaggaag cggcggcgga agtcaggcat    17340
acgctggtaa ctttgaggca gctggtaacg ctctatgatc cagtcgattt tcagagagac    17400
gatgcctgag ccatccggct tacgatactg acacagggat tcgtataaac gcatggcata    17460
cggattggtg atttctttg tttcactaag ccgaaactgc gtaaaccggt tctgtaaccc    17520
```

```
gataaagaag ggaatgagat atgggttgat atgtacactg taaagccctc tggatggact   17580
gtgcgcacgt ttgataaacc aaggaaaaga ttcatagcct ttttcatcgc cggcatcctc   17640
ttcagggcga taaaaaacca cttccttccc cgcgaaactc ttcaatgcct gccgtatatc   17700
cttactggct tccgcagagg tcaatccgaa tatttcagca tatttagcaa catggatctc   17760
gcagataccg tcatgttcct gtagggtgcc atcagatttt ctgatctggt caacgaacag   17820
atacagcata cgttttttgat cccgggagag actatatgcc gcctcagtga ggtcgtttga   17880
ctggacgatt cgcgggctat ttttacgttt cttgtgattg ataaccgctg tttccgccat   17940
gacagatcca tgtgaagtgt gacaagtttt tagattgtca cactaaataa aaaagagtca   18000
ataagcaggg ataactttgt gaaaaaacag cttcttctga gggcaatttg tcacagggtt   18060
aagggcaatt tgtcacagac aggactgtca tttgagggtg atttgtcaca ctgaaagggc   18120
aatttgtcac aacaccttct ctagaaccag catggataaa ggcctacaag gcgctctaaa   18180
aaagaagatc taaaaactat aaaaaaaata attataaaaa tatccccgtg ataagtgga   18240 taaccccaag ggaagttttt tcaggcatcg tgtgtaagca gaatatataa gtgctgttcc   18300
ctggtgcttc ctcgctcact cgaccgggag ggttcgagaa ggggggggcac ccccccttcgg   18360 cgtgcgcggt cacgcgcaca gggcgcagcc ctggttaaaa acaaggttta taaatattgg   18420
tttaaaagca ggttaaaaga caggttagcg gtggccgaaa aacgggcgga aacccttgca   18480
aatgctggat tttctgcctg tggacagccc ctcaaatgtc aataggtgcg cccctcatct   18540
gtcagcactc tgcccctcaa gtgtcaagga tcgcgcccct catctgtcag tagtcgcgcc   18600
cctcaagtgt caataccgca gggcacttat ccccaggctt gtccacatca tctgtgggaa   18660
actcgcgtaa aatcaggcgt tttcgccgat ttgcgaggct ggccagctcc acgtcgccgg   18720
ccgaaatcga gcctgcccct catctgtcaa cgccgcgccg ggtgagtcgg ccctcaagt   18780 gtcaacgtcc gcccctcatc tgtcagtgag ggccaagttt ccgcgaggt atccacaacg   18840 ccggcggccg gccgcggtgt ctcgcacacg gcttcgacgg cgtttctggc gcgtttgcag   18900
ggccatagac ggccgccagc ccagcggcga gggcaaccag ccgagggctt cgccctgtcg   18960
ctcgactgcg gcgagcacta ctggctgtaa aaggacagac cacatcatgg ttctgtgttc   19020
attaggttgt tctgtccatt gctgacataa tccgctccac ttcaacgtaa caccgcacga   19080
agatttctat tgttcctgaa ggcatattca aatcgttttc gttaccgctt gcaggcatca   19140
tgacagaaca ctacttccta taaacgctac acaggctcct gagattaata atgcggatct   19200
ctacgataat gggagatttt cccgactgtt tcgttcgctt ctcagtggat aacagccagc   19260
ttctctgttt aacagacaaa aacagcatat ccactcagtt ccacatttcc atataaaggc   19320
caaggcattt attctcagga taattgtttc agcatcgcaa ccgcatcaga ctccggcatc   19380
gcaaactgca cccggtgccg ggcagccaca tccagcgcaa aaaccttcgt gtagacttcc   19440
gttgaactga tggacttatg tcccatcagg ctttgcagaa cttcagcgg tataccggca   19500 tacagcatgt gcatcgcata ggaatggcgg aacgtatgtg gtgtgaccgg aacagagaac   19560
gtcacaccgt cagcagcagc ggcggcaacc gcctccccaa tccaggtcct gaccgttctg   19620
tccgtcactt cccagatccg cgcttttctct gtccttcctg tgcgacggtt acgccgctcc   19680
atgagcttat cgcgaataaa tacctgtgac ggaagatcac ttcgcagaat aaataaatcc   19740
tggtgtccct gttgataccg ggaagccctg ggccaacttt tggcgaaaat gagacgttga   19800
tcggcacgta agaggttcca actttcacca taatgaaata agatcactac cgggcgtatt   19860
```

| | |
|---|---|
| ttttgagtta tcgagatttt caggagctaa ggaagctaaa atggagaaaa aaatcactgg | 19920 |
| ataaccacc gttgatatat cccaatggca tcgtaaagaa cattttgagg catttcagtc | 19980 |
| agttgctcaa tgtacctata accagaccgt tcagctggat attacggcct ttttaaagac | 20040 |
| cgtaaagaaa aataagcaca agttttatcc ggcctttatt cacattcttg cccgcctgat | 20100 |
| gaatgctcat ccggaatttc gtatggcaat gaaagacggt gagctggtga tatgggatag | 20160 |
| tgttcaccct tgttacaccg ttttccatga gcaaactgaa acgttttcat cgctctggag | 20220 |
| tgaataccac gacgatttcc ggcagtttct acacatatat tcgcaagatg tggcgtgtta | 20280 |
| cggtgaaaac ctggcctatt tccctaaagg gtttattgag aatatgtttt tcgtctcagc | 20340 |
| caatccctgg gtgagtttca ccagttttga tttaaacgtg gccaatatgg acaacttctt | 20400 |
| cgccccccgtt ttcaccatgg gcaaatatta tacgcaaggc gacaaggtgc tgatgccgct | 20460 |
| ggcgattcag gttcatcatg ccgtttgtga tggcttccat gtcggcagaa tgcttaatga | 20520 |
| attacaacag tactgcgatg agtggcaggg cggggcgtaa ttttttttaag gcagttattg | 20580 |
| gtgcccttaa acgcctggtt gctacgcctg aataagtgat aataagcgga tgaatggcag | 20640 |
| aaattcgatg ataagctgtc aaacatgaga attggtcgac ggcccgggcg gccgcaaggg | 20700 |
| gttcgcgttg gccgattcat taatgcagct ggcacgacag gtttcccgac tggaaagcgg | 20760 |
| gcagtgagcg caacgcaatt aatgtgagtt agctcactca ttaggcaccc caggctttac | 20820 |
| actttatgct tccggctcgt atgttgtgtg gaattgtgag cggataacaa tttcacacag | 20880 |
| gaaacagcta tgaccatgat tacgccaagc tatttaggtg agactataga atactcaagc | 20940 |
| ttgcatgcct gcaggtcgac tctagaggat cccacgacgt cg | 20982 |

<210> SEQ ID NO 29
<211> LENGTH: 22887
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

| | |
|---|---|
| gcggccgcaa ggggttcgcg tcagcgggtg ttggcgggtg tcggggctgg cttaactatg | 60 |
| cggcatcaga gcagattgta ctgagagtgc accatatgcg gtgtgaaata ccgcacagat | 120 |
| gcgtaaggag aaaataccgc atcaggcgcc attcgccatt cagctgcgca actgttggga | 180 |
| agggcgatcg gtgcgggcct cttcgctatt acgccagctg gcgaaagggg gatgtgctgc | 240 |
| aaggcgatta agttgggtaa cgccagggtt ttcccagtca cgacgttgta aaacgacggc | 300 |
| cagtgaattg taatacgact cactataggg cgaattcgag ctcggtaccc ggggatccca | 360 |
| cgtggcgcgc cgccatagtt tagcgataat cgccatgaat gctataggat aaatgataaa | 420 |
| aataatgaat tattacaaag ggaacataag agaatcaggg cgaaaatcgc catgataaca | 480 |
| ggatgttagt cactgccaaa gagatcgcgg gtgtagactt tgtctgccac atccttaagc | 540 |
| tcttctgcca tacggttgga gataatgacg tcggcttgta tagtcagctt agaacagctt | 600 |
| tgattgtaaa atgagcacgt taccagaaaa aacagccaag tttagaactg ataccgatta | 660 |
| tctttttttc ttgtctaacg gtataattta actttcagtt atgccagatg aagattggct | 720 |
| atattctagc ctgagcgagg attataaatg aaatttctgg ttacgggagc tgctggcttt | 780 |
| atcggtttct atctaagtaa acggcttctt gcagctggtc atcaggttgt aggcattgac | 840 |
| aacttaaatg attattacga tgtcaacctc aaacaagcac gacttgattt actcaagcac | 900 |

```
gacaacttca gttttatataa aattgacctg gccgatcgtg agaaaatggc ggcactgttt    960
gcagacgagc ggttcgaacg cgtaataaac ctcgctgcgc aagccggtgt acgttactct   1020
cttgaaaatc ccaatgcata tgcagatgca aacctgattg gattcctgaa catactagaa   1080
ggatgtcgcc ataataatgt tcagcatcta ctttacgctt cctccagttc tgtttatggc   1140
atgaaccgca agatgccttt ctctacagat gactctgtag atcatcctgt ttcgctttat   1200
gcagcaacta aaaaagcgaa tgaactcatg gcccatacat attctcattt gtatggctta   1260
ccgaccacag ggctgcgttt ctttacggtt tatggtccat ggggacgtcc ggatatggca   1320
ttatttaaat tcactaaagc catgctggaa ggtaaaagca ttgatgttta caacttcggc   1380
aaaatgaagc gtgactttac ttacattgat gatattgccg aagctattat tcgcttacag   1440
gatgttattc cagaaaaaaa cccacagtgg gctgtagaaa caggctcgcc tgcaacaagt   1500
tcagcaccat atcgtgtcta taacattggt aatagttcgc ctgtggagtt gatggactat   1560
atcaatgcgt tagaagaggc tctgggtatt gaagccaaca aaaatatgat gcctctccaa   1620
cccggtgatg tactggaaac cagtgctgat acaaaagcac tgtatgacgt aataggattc   1680
aaacctgaaa cgtcagttaa agaaggggta agaactttg tagaatggta tcgtaacttc   1740
tataaagttt gattttacaa aaccataaga aaggcccta atttattagg gccttttctt   1800
agaatgaaac aaaataatta atcattgcca acaagtcgc gcgtataaac tttatctgct   1860
acatcagcca gatcggcaga catacggtta gaaataataa catcagcttc ttgtttgaac   1920
gcatccagat cacgtaccac gcgcgaccgg aaaaaatcgt cctctttcat agctggctca   1980
taaacgatta caggcacacc tttcgccttg attcgcttca taatacctg aatcgaggaa   2040
gcacgaaaat tgtctgaacc attcttcata atcaaacgat agacgccaac aactttcggt   2100
ttacgtgcaa ggatagaatc ggcaataaaa tctttgcgcg tgcggttggc gtcaacaatt   2160
gccgagatca ggttattcgg cacagactgg taatttgcca gtaactgctt agtatctttc   2220
ggcagacaat aaccaccata accgaatgac gggttgttgt agtgattacc gatacgcggg   2280
tcaaggcata cgccctcaat aatctggcgt gaattaagtc ccaggctttc agcataacta   2340
tcaagttcat tgaaatacgc tacacgcatc gccagataag tgttcgcaaa agtttaatc    2400
gcctcagcct cggttgagtc agtaaacaat gttggtatgt cttgcttaat ggcgccttcc   2460
tgtaataacg cagcaaaacg tttagcgcgt tcagactgct cgccaatcac aatgcgtgat   2520
gggtgtaagt tatcataaag tgctttacct tcacgcaaaa actcaggcga aaagatcaca   2580
ttttcaatac caaacgttc tttaatggac tctgtaaaac caacagggat agttgatttt   2640
ataatcatta ccgcgttggg attaatttct gtcacatcac gaatgaccgc ttccacgctt   2700
gaggtattaa aataatttgt tttcggatca taatcggtag gtgtggcaat aataacgtaa   2760
tcggcatttt tatacgcgtc atacttatct gtcgtagcgc ggaaattgag atctttagtc   2820
gccagatact cttcaatctc cttatcaaca agcggtgact gcctcttgtt aagcatgtcc   2880
actttggcct gaacgatatc cagtgcaacc acttcgtggt tttgcgcaat cagaatacca   2940
tttgaaagac caacataacc tgttcctgaa attgttattt tcattagctc tgacttcttc   3000
cggttaaaca tttagagtgg tcattaatcc accaccacag cttcatctac tgcgggattt   3060
ttaacgctga tgtagatgaa ctgtcaaggc agcgatcctg ctgtgcggcg ctgtattata   3120
tcgcgttttt aactataaat tataaaaaaa ggccctaacc tgccgctttg tataataaaa   3180
aagcccggag ggtttctccg ggccttgctt tgattaattg atttaaatca gattaatcca   3240
gccattcggt atggaacaca ccttctttat caatgcgctt ataagtatgc gcaccgaaat   3300
```

```
agtcacgctg tgcctggatc aggttcgcag gcagaacagc ggcgcggtag ctgtcgtaat    3360
aggcaaccgc agcggcgaag gtcggcaccg ggataccgtt ctgtactgcg taagcgacga    3420
catcgcgcag cgcctgctgg tagtcatcgg caatttgctt gaagtaagga gccagcaaca    3480
ggttagcgat ctgcggattt tcggcataag catcggtgat tttctgcagg aactgcgcac    3540
ggatgatgca gccagcacgg aaaatcttcg cgatttcacc gtagttcaga tcccagttgt    3600
actcttcaga cgcagcgcgt agctgagaga agccctgagc gtaagaaacg attttgccca    3660
gatacagcgc acggcgaact ttttcgatga actcagcatt gtcgccagct ggctgcgctt    3720
gcgggccaga gagaacttta gatgcggcaa cacgctgctc tttcagagaa gagatataac    3780
gtgcaaacac agactcggta atcagcgaca gcggttcgcc gagatccagc gcgctctggc    3840
tggtccattt gcccgtacct ttgtttgctg cttcatccag aatcacatca accaggtagt    3900
taccctcttc atctttttg gtgaagatat ctttggtgat gtcgatcagg tagctgctca    3960
gttcaccgtt attccactcg gtaaaggtct gcgccagttc ttcgttggtg aggttcaagc    4020
cacctttaag cagagaatag gcttcagcaa tcagctgcat atcaccgtat tcaataccgt    4080
tgtgaaccat cttcacataa tgacctgcac catcggcacc aatataggta acgcacggtt    4140
cgccgtcttc agccacagcg gcgattttgg tcaggatcgg cgcaatcagt tcataagctt    4200
ctttctgccc accaggcata atggaaggac ctttcagcgc accttcttca ccaccggaaa    4260
caccggtacc gataaagtta aagccttctg cagaaagctc acggttacga cgaatggtgt    4320
catggaagaa ggtgttacca ccatcaatga tgatgtcacc tttatcgagg tatggcttga    4380
gggaatcaat agcagcatcc gtgccagcac ctgctttcac cattaacagg atgcgacgag    4440
gcgtttccag agattcaaca aattctttca ccgtatagta aggaaccagt tcttgcctg    4500
gattttcggt aatcacttct tcggtctttt cacgggaacg gttgaaaata gagacggtat    4560
aaccacggct ttcgatattg agcgcaaggt tgcgccccat cactgccata ccgacgacgc    4620
cgatctgttg ctttgacatt gtttactcct gtcaggatac cgctgggtgg tatgcgggtt    4680
atgcttaatt atagaatatg cctaataaaa ataaatccat aacacttaat cagaaaatta    4740
ttattatcga ttcctaacga ttgaatacat cagctccttt aatttagatg gcattatacg    4800
aaaaaatgtt ctcaacatag cattacttat taattcattt tttcgaataa aaccaatttt    4860
atattgataa tacaatactt tatactcgta caataaaat gacaatccac gtcgagccat    4920
aagattacga ccagttcgca tttttaataa aatatctgga agatttgcaa atcttgcatt    4980
atgtacaatt aataggctcc acaatgcaaa atcttgagat tttctgaatg gaggataacc    5040
accaacagct aatactgtat tctttctaaa aattacagaa ggatggctaa ctgcgcttcg    5100
tttcctcgcg aatttaacta tttctctatg ttcgagaggc actttgcgtg ttgaaataaa    5160
ctcctcagta acagtttcaa tttcatcaat aaaactgcca catacatcta tttctgaatt    5220
attaatcata aaagaaattt gtttctcaaa ccgatgagc aaagaaatat catcagcatc    5280
cattcttgcc actaactcat tcctacaagc ctttaatcct tcatttaagg cattagccaa    5340
tccaacattt ctaggtaaag gtacaaatgt tactatttta ttgccaacat catcaatgaa    5400
tgaatttata atatcgatgt gtgtttgatg gagttctcca tctgcaacaa ttactatttg    5460
atctggctta agtgtttgat cgtgaaaaat agagcgtaga gccacctcaa aaaattgcgg    5520
tagatcattt ttataaatgc taattaaaac tgagaatttt tctaatctat gattcatttc    5580
attttaccac ttcgacccat taaaccgtca ttaatgcctt ttaaaaaaaa atataacctt    5640
```

```
ttattaccat ttggaaggaa aataggatat aaaaaaacct ttccaattaa tttaaccaga      5700
ctagaaattt tccagtagat gggtacataa ttttttattta ataaaagaaa gatatttcga     5760
gtagcataat aatgacgaaa tgggcttggc aaaccgacag aaagaatatt taagatctta     5820
aatcgcccat ctccaagtct atgtgcaagt aacgcatttt tattcctaat tactttaaac     5880
ccagcagctc ttaatctcca acaatattca tggtctaccg catcgataaa aagctcatct     5940
ttcattcctc caacaatcaa ccaactatttt tttggtatta gactgccaga acttaatgta    6000
ctatctacct cataataaac ttctgtaagt ggtttccctt ttttacccct tgctttattt     6060
aattcaccag ttactttatc aaaatcttgt gaaccaacta aaccaacatt gacattttgt     6120
ttaagcaatt ttttgtaaca agtaagtaac tgctctacca tcttaggatc aggaatacta     6180
tcctgatcca tttgcaatat aaaatcagcg ccattttcaa aagcccattt cattcctata    6240
ctttgggctt ctgctatgcc taaattatca ttgaaattga atattttttac atcgcctgaa    6300 gaattttcag catatttata accatttgta gagttattgc aaacgacaac tttagtaact    6360
tgtctcaaca ataattcaac cgcattttttt aaatcattat gttctgggtt gtaagcaacc   6420
aaaacggcat atacagtgtc catcttcacc ttaaaacctt catttagctt tcatcttttt     6480
tagaacatta cttaatgtca ctaatacaat tattacagca acatggttag agtctaaaat     6540
ataaggatta gtaattgcat aagaaacata tagaaaatat agcacacaca actcactgta    6600
ttttatgatt ttaatcgtga gaaggagatt aattaataaa aacaaagtaa ataaaataac    6660
gccaagttga ttttaaaaat aaactgactg caattcataa tatatatatg cactataatc    6720
acggatagga gtttgaattt tgatgacatt acccaaacca gaacctataa caaaatttga    6780
tacagactct gtaagatcat taattaatac agtaaactga tcccatctaa ctcctaaaga    6840
agaatcagct ccatttgatt tcatgattat caactcaatt gaatatgtaa taaaaaaagg    6900
gagaatcaca gtaagaaaaa ccccaaaaat aatttttcctt aatttagcgt atcgtgagtt   6960
agatttagaa catagtataa tatacataaa aaacaagcat atcgaaacaa atatgcaaa    7020 attaccagcc actatagtac ctatagccag aataacggtt attgtatttt tgaatcgata    7080 atagaaaataa tcttttatga ctatatgcaa cataaaggca aatggaatga gagcatttcc   7140
tttaatttga actctataga aaccacttcc atatgtataa acatcaccat aatcattctc    7200
caaaaaataa tgtcttagtg ctgaataatc accaatacca tatgttttttg tcatataaat   7260 actaatgatg gatataataa ccgcctgtaa taccattaaa tataaaaata ttttaacaat    7320
cgagatggtt ccataagagc agaaataagc acataatata aataatatga taatataaaa    7380
cctaattatt atcgctatat cgttacccctt gatataggaa taaataaaat ttataaaaag   7440
agctaataga aatattaaaa taacaggata gtgatatatt ccgtttgcaa ttttctttgt    7500
aaatgacatg atacaaagac ataaaaaccc ctccataatc caactatatt gaataaatgg    7560
aaagctacgt gtaaggaaaa atataaaccc aaaaacaaa gaacactta aacttttgtc     7620 ttttgagtta taaaaatcag aagtcatgtt tgcactctaa ttagatgggc ttgaggaagt   7680
aatccctaaa atcaattcgc tattaatatt tcgtatcaat taataataat atcaaaaaat  7740
ctaacgatgt tcttcagac catgctattg cggctccaac aattccccaa tgataaataa    7800
aaatatataa tatgcataaa tatgggataa cttcgagcaa atgaataata gctgtaattt    7860
ttgatcttcc actagcctga actgaaacaa atgggatttg tgcaatgcaa ttaaaaagaa    7920
aacctattgc aagaattttt aatactatac ctggcgtccc atgatatgta ggtcccatcc    7980
aagcggacat tataaaatct gataaaataa ttatcaacat tacaattgga agtataccaa    8040
```

```
taaccattat aaaatatgat aatattttag tttgctttac cgattgcaat tctgaactta    8100
atcttggaaa aatagctctg gacaacgcac ttggtaatat cgttaagcgt tgtataccct    8160
cagacggagc agtataaaaa gaaactttat cagcccccac aatgtgtgaa agaataaaac    8220
gatccatata tgtcataata gggctaataa tattgctaac tgttatccag cttccaaagc    8280
cgattaatct tttaactgtt acaattttta cagacagccc agatgatatt attagttttc    8340
gactaaatat aaaggtcact ataagtgata agactcttgc cataactaaa ccatatatag    8400
cacttagtaa tcctccatga aaaaacaga aaatcactgg taatccagcc acaaaagagt    8460
tgttaattga ttttattaaa tttactttc tgaactttc catccctca aaaatcccca      8520 accagacttg gtttaacaag tataagggta tggtagctga ataatatat attgctttga    8580 cagattctac aacatgattc gcgttaatgt ttaataattt aacaattaca ttgctactca    8640
aaaatagtac actaccgcca atcaagccca atatagttag aattaccgtt gaagttgaaa    8700
tgatcgctct taattctta tgaacatttt tatatattga tacttctctt ataacagctc     8760
tggtcaatcc agcatcaaaa atacttgcat atccaactaa ggcaatagct aacgtaaaaa    8820
ggccaaattg ctcggtccct agaattctag acagtatacc taacgcagga attgctatta    8880
atgatggtat aatataccca cttatattcc ataaagtatt ctttacaata ctcacaaaaa    8940
taattccttc atgttatgca attctttagc ccttgcatct ttaatcgata aaatataatt    9000
attatgttct atcgtcggcc attttatgct cagaatagga tcattccata caatccctct    9060
atcactatca ggatgataat agttcgtcgt tttatataaa aattccgcag tctcgctcag    9120
caccaaaaaa ccatgtgcaa atccctcagg gatccacaat tgccgcttat tctcagcaga    9180
taaattcacc ccaacccatt taccaaaggt aggcgacgat ttacgaatat caacagctac    9240
atcaaaaacc tcaccaacaa cgcaacgtac cagtttccct tgcgcataag gttctaactg    9300
ataatgcagc ccgcgtaaaa caccttact agacttcgaa tggttatcct gaacaaattc     9360
aaccttacgt cctacagctt cttcgaaaac tttctgatta agctttccca taaagaaacc    9420
acgctcatca ccaaaaactt tcggctcgaa aattaacaca tcaggaattt ctgttttaat    9480
tacgttcatt ttattaataa ccttaatca ttttcagcag atactgtcca taagcatttt    9540
ttttcagcgg ctccgctaat gctttcacct gttcagcatc aataaaccct ttacggtaag    9600
caatttcttc tgggcaggaa acctttagtc cctggcgctc ttcaatggtg gcaatgaagt    9660
tgcttgcttc aataagactc tgatgtgtcc ccgtatccag ccatgcataa ccacgcccca    9720
tcatggcaac ggataaacgc ccctgttcca tataaatacg gttaatatcg gtaatttcca    9780
gttcaccacg ggcagaaggc ttaaggtttt tcgccatttc gacaacgtcg ttatcataga    9840
aataaagccc ggttaccgca taattacttt ttggttgtag cggttttct tccaggctta     9900 ttgccgtacc gttttatca aactcaacga cgccgtagcg ttcaggatca ttaacgtgat     9960
aggcaaatac cgttgcacca ctttctttgt taacagcgac atccattaac ttcggcagat   10020
catgaccgta gaagatatta tcaccaagaa ccaaagcaca atcatcacca ccgataaact   10080
cttcaccgat aataaacgcc tgcgcaagcc catctggagt cggttgcact ttgtactgaa   10140
gatttagccc ccactggcta ccgtcaccta gcagttgttg aaaacgagga gtatcctgtg   10200
gcgtactaat aatcagaata tcgcgaatac ccgccaacat cagtgtagag agcgggtaat   10260
agatcatcgg cttatcataa ataggtaata gctgtttact gacagccata gtcacaggat   10320
aaagacgtgt accagaacca cccgctaaaa taataccttt acgcgttttc atttcatcat   10380
```

```
tccttttaat tcatcttgct ccaccatcac gaacaagatg caaaaactat taaattgctg   10440
tagtcgtaat taattcgttg agcattcgtt tcacaccaac ctgccagtca ggcaagacaa   10500
gcgcaaagtt ctgctgaaat ttttctgtat taaggcgaga gttatgtgga cgacgagctg   10560
gtgtaggata ggctgttgtt ggtactgcgt tgagcttgtt gagtgcaagg ggaatacctg   10620
ctttgcgcgc ctcttcaaaa accagcgcag cataatcgtg ccaggttgtg gtaccactgg   10680
ctaccagatg gtacaaacct gcgacttccg gtttattcag tgccacacga atagcatgtg   10740
ccgtacaatc agccagcagc tcagcacctg ttggcgcacc aaattgatca tttatcacag   10800
ccagttcttc gcgctctttt gccagacgca acatcgtttt ggcgaagtta tttcctttag   10860
ctgcgtatac ccagctggta cggaaaataa gatgcttcgc gcaatgttcc tgtaacgctt   10920
tttctccggc taacttggtt tcaccgtaaa catttagcgg tgcggttgca tccgtctcca   10980
gccatggcgt gtcgccattt ccagggaata cgtagtcagt tgagtaatga attacccaag   11040
ccccaacttc attagcctct tttgcaattg attcaacact agtcgcattg agtaattgtg   11100
caaattcggg ttctgactca gccttatcta ctgcggtgtg agccgcagca ttaacaataa   11160
catcaggtcg aattcttttg actgtttcag ctacaccttc aggattacta aaatcaccac   11220
aataatcagt ggagtgaaca tcaagagcaa tcaaattacc caaaggtgcc agagcacgct   11280
gtagttccca acctacctgc cctgttttgc cgaaaaggag gatattcatt actggcggcc   11340
ctcatagttc tgttcaatcc acgattgata agcaccactt ttcacattat caacccattt   11400
tgtattggac aggtaccatt ccaatgtctt ccgaatcccg ctctcaaacg tttcctgcgg   11460
tttccagccc aattcgcggc taatcttctc tgcatcaatc gcataacggc gatcgtgtcc   11520
cgggcgatcg gcaacataag taatttgctc gcggtaagat ttctcttcg gtacaatctc   11580 atccagcaaa tcacaaatag tgagcactac atcgatgttt ttcttttcgt tgtgtccacc   11640
aatgttataa gtttcacccg ctttaccttc ggttacgacg gtatataacg cacgcgcatg   11700
atcttcaaca tacagccagt cacgaatttg atcccctttg ccataaatag gtaatgcctt   11760
accttccaga gcattcagaa taaccaatgg aatcaatttt tccgggaaat gataaggacc   11820
ataattatta gagcaattag tcacaatggt tggtaaacca taggtacgtt tccacgcgcg   11880
gactaaatga tcgctggatg cttttgaagc ggaataaggg ctgcttggcg cgtaagctgt   11940
tgtctctgta aataagggta attcttctgt attatttacc tcgtcaggat gaggcaaatc   12000
accatagact tcgtcagtag aaatatgatg aaaacggaat ctagttttct tgtcgctatc   12060
aagagcagac caataattgc gagcggcttc caaaaggaca tatgtaccaa caatattggt   12120
ttcaataaat gccgcaggac ctgtaattga acggtcaaca tggctttcag cagccaggtg   12180
catcactgca tctggctgat gctgagcaaa aatccgtgcc attgcagctg catcgcaaat   12240
atccgcatgt tcaaaaacat agcgttcaga atcagaaaca tcagcaagtg attccaggtt   12300
tccggcgtac gttaatttat cgacattaac aacactatcc tgcgtattat ttataatgtg   12360
acgaactaca gcaaaaccaa taatcctgc gccaccagta acaagtattt tcacctaatt   12420
tattccatat tgcttcagag catgctgtga aataagcggc tctcagtttg attaatagaa   12480
gtattaatgc acgctaccgc ccctggcttt acagctacca gagcactgca tgcatgccta   12540
cgatgtgacg agcgttaccc actcgcgcta aacccgaaaa attcaaaagc taattgtctt   12600
accaatccgc tctggaaaca aggaaaatcc tggaaaactt tgactaaaat cctattgcta   12660
actcgttgtt attctgattg tttatataaa acaacggcag gaatattcgc aacaaattac   12720
tttcaccacg aatcttcact gccgttataa ttttcttatc aaccgttaca tccggtcaga   12780
```

```
ttttcattat tcgcttaaca gcttctcaat acctttacgg aacttcgccc cttctttcag   12840
gttgcgcagc ccatacttca caaacgcctg catatagccc attttttttac cgcagtcgta   12900
gctgtcgccg gtcatcagca ttgcatcaac ggactgtttt ttcgccagct cggcaatggc   12960
atcagtcagc tgaatacgtc cccatgcacc aggctgagta cgttcaagtt ccggccaaat   13020
atcggcagaa agcacatagc gaccaacggc catgatgtct gagtccagcg tctgcggctg   13080
atccggtttt tcgataaatt caacaatgcg gctgacttta ccttcgcgat ccagcggttc   13140
tttggtctgg atgacggagt attcagagag gtcacccggc atacgttttg ccagcacctg   13200
gctacggccc gtttcattga agcgcgcaat catggcagca aggttgtagc gtagcgggtc   13260
ggcgctggcg tcgtcgatca caacgtctgg cagcaccacg acaaatggat tgtcaccaat   13320
ggcgggtcgt gcacacaaaa tggagtgacc taaacctaaa ggttcgccct gacgcacgtt   13380
cataatagtc acgcccggcg ggcagataga ttgcacttcc gccagtagtt gacgcttcac   13440
gcgctgctca aggagagatt ctaattcata agaggtgtcg aagtggtttt cgaccgcgtt   13500
cttggacgca tgagttacca ggaggatttc tttgatccct gcagccacaa tctcgtcaac   13560
aatgtactga atcattggct tgtcgacgat cggtagcatc tctttgggta tcgccttagt   13620
ggcaggcaac atatgcatcc caagacccgc taccggtata actgctttta aattcgtcat   13680
tattttccta cctctaaggg gctgatagtg cgtaaattat tgtcataggt tagccaaacg   13740
gtatggctat ataccaagca taactttgat taaaccttac gataacacta cacaccatca   13800
gcatctgggt tactcggatt actcggaaat ccacatactg ataatttaat cagtaccctct   13860
ttccgaataa tcgtagtcca acctggtcct tttttctctg actcgtctgc attactcaga   13920
aacaaacgtt atgtcgtctt ttttggcatg gacgaattca tactgcagag ttcgatccag   13980
accttgcgac agcgtatacg gtgcaacaaa acctgaagaa tgcactttcg ttgcgtcaaa   14040
ctgtgttgtt gcgcagaatt ttttcacgcg cacagagctg acagcgtatt ttttgcccgt   14100
aattttgctc aggatatcaa agcaatatcc acccagcatt cctagtgggt aaggcaagtg   14160
catagaaggg atctttttgt tcaggctttg ttcaacttca gcaaccaact ggttcatgtt   14220
caggtctggc ttatcaacat agttataaac ctcataacct gcggcaacat tcttcagttt   14280
gtacttgata aactcaacaa tgtttccaac ataagccatg gacttatagt tagtccctgc   14340
gcccaccatc ataaacttgc cgccagcgat ctgtttcagc aagttataga cgttaccgcg   14400
gttgcgttca ccgaagataa cggtaggacg gatgatggtt aatgaacgtt ctgttggtgc   14460
tttgttatac cattcacgca gcacttcctc tgcctgccac ttacttttgc cgtagtggtt   14520
gaaagggtcg tgtggatggt tttcgtcagg gttgtgtttg ttcaaaccat aaacagcaac   14580
ggaactggta aagatgatat ttttaacgcc atttttttcc atggccgcca gcacattgcg   14640
ggtaccctga acgttgacat cataatagag agaagtaggg ctgacgtcat cgcggtgttc   14700
cgctgccagt agtacaacag tgtcaaaacc ggctaacgcc tggtcgagtg cctgttgatc   14760
acgaacatca ccaatctgtg tgatttctgg ataaaagtgg ctctgccgtt tgtccaggtt   14820
cttgatatta aagtcagcaa ttgccgtttc aagtagtcgg gttcctacga atccggaagc   14880
tcctatgagc aaaacgttat tgttcataaa tcactttagt ctggttgtta cgtaagaaac   14940
acaagataaa gatgagtacc ttccctgagt agtcaatgct gcccagcccc agctttaaca   15000
gttagtgtga ggattataat cttttagaac attatatcca gtaagtttat gaatggtcgc   15060
aaatctactc tctccgttcc ggcaatctaa agttaatgct agcgacgtcg tgggatcctc   15120
```

```
tagagtcgac ctgcaggcat gcaagcttga gtattctata gtctcaccta aatagcttgg   15180
cgtaatcatg gtcatagctg tttcctgtgt gaaattgtta ccgctcaca attccacaca   15240 acatacgagc cggaagcata agtgtaaag cctggggtgc ctaatgagtg agctaactca   15300
cattaattgc gttgcgctca ctgcccgctt tccagtcggg aaacctgtcg tgccagctgc   15360
attaatgaat cggccaacgc gaaccccttg cggccgcccg ggccgtcgac caattctcat   15420
gtttgacagc ttatcatcga atttctgcca ttcatccgct tattatcact tattcaggcg   15480
tagcaaccag gcgtttaagg gcaccaataa ctgccttaaa aaattacgc cccgccctgc   15540 cactcatcgc agtactgttg taattcatta agcattctgc cgacatggaa gccatcacaa   15600
acggcatgat gaacctgaat cgccagcggc atcagcacct tgtcgccttg cgtataatat   15660
ttgcccatgg tgaaaacggg ggcgaagaag ttgtccatat tggccacgtt aaatcaaaa   15720 ctggtgaaac tcacccaggg attggctgag acgaaaaaca tattctcaat aaacccttta   15780
gggaaatagg ccaggttttc accgtaacac gccacatctt gcgaatatat gtgtagaaac   15840
tgccggaaat cgtcgtggta ttcactccag agcgatgaaa acgtttcagt ttgctcatgg   15900
aaaacggtgt aacaagggtg aacactatcc catatcacca gctcaccgtc tttcattgcc   15960
atacgaaatt ccggatgagc attcatcagg cgggcaagaa tgtgaataaa ggccggataa   16020
aacttgtgct tatttttctt tacggtcttt aaaaaggccg taatatccag ctgaacggtc   16080
tggttatagg tacattgagc aactgactga aatgcctcaa aatgttcttt acgatgccat   16140
tgggatatat caacggtggt atatccagtg attttttct ccatttagc ttccttagct   16200 cctgaaaatc tcgataactc aaaaaatacg cccggtagtg atcttatttc attatggtga   16260
aagttggaac ctcttacgtg ccgatcaacg tctcattttc gccaaaagtt ggcccagggc   16320
ttcccggtat caacagggac accaggattt atttattctg cgaagtgatc ttccgtcaca   16380
ggtatttatt cgcgataagc tcatggagcg gcgtaaccgt cgcacaggaa ggacagagaa   16440
agcgcggatc tgggaagtga cggacagaac ggtcaggacc tggattgggg aggcggttgc   16500
cgccgctgct gctgacggtg tgacgttctc tgttccggtc acaccacata cgttccgcca   16560
ttcctatgcg atgcacatgc tgtatgccgg tataccgctg aaagttctgc aaagcctgat   16620
gggacataag tccatcagtt caacggaagt ctacacgaag gttttgcgc tggatgtggc   16680 tgcccggcac cgggtgcagt ttgcgatgcc ggagtctgat gcggttgcga tgctgaaaca   16740
attatcctga gaataaatgc cttggccttt atatggaaat gtggaactga gtggatatgc   16800 tgttttgtc tgttaaacag agaagctggc tgttatccac tgagaagcga acgaaacagt   16860
cgggaaaatc tcccattatc gtagagatcc gcattattaa tctcaggagc ctgtgtagcg   16920
tttataggaa gtagtgttct gtcatgatgc ctgcaagcgg taacgaaaac gatttgaata   16980
tgccttcagg aacaatagaa atcttcgtgc ggtgttacgt tgaagtggag cggattatgt   17040
cagcaatgga cagaacaacc taatgaacac agaaccatga tgtggtctgt cctttttacag   17100 ccagtagtgc tcgccgcagt cgagcgacag ggcgaagccc tcggctggtt gccctcgccg   17160
ctgggctggc ggccgtctat ggccctgcaa acgcgccaga aacgccgtcg aagccgtgtg   17220
cgagacaccg cggccggccg ccggcgttgt ggatacctcg cggaaaactt ggccctcact   17280
gacagatgag gggcggacgt tgacacttga ggggccgact cacccggcgc ggcgttgaca   17340
gatgaggggc aggctcgatt tcggccggcg acgtggagct ggccagcctc gcaaatcggc   17400
gaaaacgcct gattttacgc gagtttccca cagatgatgt ggacaagcct ggggataagt   17460
gccctgcggt attgacactt gaggggcgcg actactgaca gatgaggggc gcgatccttg   17520
```

```
acacttgagg ggcagagtgc tgacagatga ggggcgcacc tattgacatt tgaggggctg    17580
tccacaggca gaaaatccag catttgcaag ggtttccgcc cgttttcgg ccaccgctaa    17640 cctgtctttt aacctgcttt taaaccaata tttataaacc ttgttttaa ccagggctgc    17700 gccctgtgcg cgtgaccgcg cacgccaag ggggtgccc cccttctcg aaccctcccg    17760 gtcgagtgag cgaggaagca ccagggaaca gcacttatat attctgctta cacacgatgc    17820
ctgaaaaaac ttcccttggg gttatccact tatccacggg gatattttta taattatttt    17880
ttttatagtt tttagatctt ctttttaga gcgccttgta ggcctttatc catgctggtt    17940
ctagagaagg tgttgtgaca aattgccctt tcagtgtgac aaatcaccct caaatgacag    18000
tcctgtctgt gacaaattgc ccttaaccct gtgacaaatt gccctcagaa gaagctgttt    18060
tttcacaaag ttatccctgc ttattgactc tttttttattt agtgtgacaa tctaaaaact    18120
tgtcacactt cacatggatc tgtcatggcg gaaacagcgg ttatcaatca caagaaacgt    18180
aaaaatagcc cgcgaatcgt ccagtcaaac gacctcactg aggcggcata tagtctctcc    18240
cgggatcaaa aacgtatgct gtatctgttc gttgaccaga tcagaaaatc tgatggcacc    18300
ctacaggaac atgacggtat ctgcgagatc catgttgcta aatatgctga aatattcgga    18360
ttgacctctg cggaagccag taaggatata cggcaggcat tgaagagttt cgcggggaag    18420
gaagtggttt tttatcgccc tgaagaggat gccggcgatg aaaaaggcta tgaatctttt    18480
ccttggttta tcaaacgtgc gcacagtcca tccagagggc tttacagtgt acatatcaac    18540
ccatatctca ttcccttctt tatcgggtta cagaaccggt ttacgcagtt tcggcttagt    18600
gaaacaaaag aaatcaccaa tccgtatgcc atgcgtttat acgaatccct gtgtcagtat    18660
cgtaagccgg atggctcagg catcgtctct ctgaaaatcg actggatcat agagcgttac    18720
cagctgcctc aaagttacca gcgtatgcct gacttccgcc gccgcttcct gcaggtctgt    18780
gttaatgaga tcaacagcag aactccaatg cgcctctcat acattgagaa aaagaaaggc    18840
cgccagacga ctcatatcgt attttccttc cgcgatatca cttccatgac gacaggatag    18900
tctgagggtt atctgtcaca gatttgaggg tggttcgtca catttgttct gacctactga    18960
gggtaatttg tcacagtttt gctgtttcct tcagcctgca tggattttct catactttt    19020 gaactgtaat ttttaaggaa gccaaatttg agggcagttt gtcacagttg atttccttct    19080
ctttcccttc gtcatgtgac ctgatatcgg gggttagttc gtcatcattg atgagggttg    19140
attatcacag tttattactc tgaattggct atccgcgtgt gtacctctac ctggagtttt    19200
tcccacggtg gatatttctt cttgcgctga gcgtaagagc tatctgacag aacagttctt    19260
ctttgcttcc tcgccagttc gctcgctatg ctcggttaca cggctgcggc gagcgctagt    19320
gataataagt gactgaggta tgtgctcttc ttatctcctt ttgtagtgtt gctcttattt    19380
taaacaactt tgcggttttt tgatgacttt gcgattttgt tgttgctttg cagtaaattg    19440
caagatttaa taaaaaacg caaagcaatg attaaaggat gttcagaatg aaactcatgg    19500
aaacacttaa ccagtgcata aacgctggtc atgaaatgac gaaggctatc gccattgcac    19560
agtttaatga tgcagcccg gaagcgagga aaataacccg cgctggaga ataggtgaag    19620 cagcggattt agttgggggtt tcttctcagg ctatcagaga tgccgagaaa gcagggcgac    19680
taccgcaccc ggatatggaa attcgaggac gggttgagca acgtgttggt tatacaattg    19740
aacaaattaa tcatatgcgt gatgtgtttg gtacgcgatt gcgacgtgct gaagacgtat    19800
ttccaccggt gatcggggtt gctgcccata aaggtggcgt ttacaaaacc tcagtttctg    19860
```

-continued

```
ttcatcttgc tcaggatctg gctctgaagg ggctacgtgt tttgctcgtg gaaggtaacg   19920
acccccaggg aacagcctca atgtatcacg gatgggtacc agatcttcat attcatgcag   19980
aagacactct cctgcctttc tatcttgggg aaaaggacga tgtcacttat gcaataaagc   20040
ccacttgctg gccggggctt gacattattc cttcctgtct ggctctgcac cgtattgaaa   20100
ctgagttaat gggcaaattt gatgaaggta aactgcccac cgatccacac ctgatgctcc   20160
gactggccat tgaaactgtt gctcatgact atgatgtcat agttattgac agcgcgccta   20220
acctgggtat cggcacgatt aatgtcgtat gtgctgctga tgtgctgatt gttcccacgc   20280
ctgctgagtt gtttgactac acctccgcac tgcagttttt cgatatgctt cgtgatctgc   20340
tcaagaacgt tgatcttaaa gggttcgagc ctgatgtacg tattttgctt accaaataca   20400
gcaatagtaa tggctctcag tccccgtgga tggaggagca aattcgggat gcctggggaa   20460
gcatggttct aaaaaatgtt gtacgtgaaa cggatgaagt tggtaaaggt cagatccgga   20520
tgagaactgt ttttgaacag gccattgatc aacgctcttc aactggtgcc tggagaaatg   20580
ctctttctat ttgggaacct gtctgcaatg aaatttttcga tcgtctgatt aaaccacgct   20640
gggagattag ataatgaagc gtgcgcctgt tattccaaaa catacgctca atactcaacc   20700
ggttgaagat acttcgttat cgacaccagc tgccccgatg gtggattcgt taattgcgcg   20760
cgtaggagta atggctcgcg gtaatgccat tactttgcct gtatgtggtc gggatgtgaa   20820
gtttactctt gaagtgctcc ggggtgatag tgttgagaag acctctcggg tatggtcagg   20880
taatgaacgt gaccaggagc tgcttactga ggacgcactg gatgatctca tcccttcttt   20940
tctactgact ggtcaacaga caccggcgtt cggtcgaaga gtatctggtg tcatagaaat   21000
tgccgatggg agtcgccgtc gtaaagctgc tgcacttacc gaaagtgatt atcgtgttct   21060
ggttggcgag ctgatgatg agcagatggc tgcattatcc agattgggta acgattatcg   21120
cccaacaagt gcttatgaac gtggtcagcg ttatgcaagc cgattgcaga atgaatttgc   21180
tggaaatatt tctgcgctgg ctgatgcgga aaatatttca cgtaagatta ttacccgctg   21240
tatcaacacc gccaaattgc ctaaatcagt tgttgctctt ttttctcacc ccggtgaact   21300
atctgcccgg tcaggtgatg cacttcaaaa agcctttaca gataaagagg aattacttaa   21360
gcagcaggca tctaaccttc atgagcagaa aaaagctggg gtgatatttg aagctgaaga   21420
agttatcact cttttaactt ctgtgcttaa acgtcatctc gcatcaagaa ctagtttaag   21480
ctcacgacat cagtttgctc ctggagcgac agtattgtat aagggcgata aatggtgct   21540
taacctggac aggtctcgtg ttccaactga gtgtatagag aaaattgagg ccattcttaa   21600
ggaacttgaa aagccagcac cctgatgcga ccacgtttta gtctacgttt atctgtcttt   21660
acttaatgtc ctttgttaca ggccagaaag cataactggc ctgaatattc tctctgggcc   21720
cactgttcca cttgtatcgt cggtctgata atcagactgg gaccacggtc ccactcgtat   21780
cgtcggtctg attattagtc tgggaccacg gtcccactcg tatcgtcggt ctgattatta   21840
gtctgggacc acggtccacc tcgtatcgtc ggtctgataa tcagactggg accacggtcc   21900
cactcgtatc gtcggtctga ttattagtct gggaccatgg tcccactcgt atcgtcggtc   21960
tgattattag tctgggacca cggtcccact cgtatcgtcg gtctgattat tagtctggaa   22020
ccacggtccc actcgtatcg tcggtctgat tattagtctg gaccacggt cccactcgta   22080
tcgtcggtct gattattagt ctgggaccac gatcccactc gtgttgtcgg tctgattatc   22140
ggtctgggac cacggtccca cttgtattgt cgatcagact atcagcgtga gactacgatt   22200
ccatcaatgc ctgtcaaggg caagtattga catgtcgtcg taacctgtag aacggagtaa   22260
```

```
cctcggtgtg cggttgtatg cctgctgtgg attgctgctg tgtcctgctt atccacaaca    22320
ttttgcgcac ggttatgtgg acaaaatacc tggttaccca ggccgtgccg gcacgttaac    22380
cgggctgcat ccgatgcaag tgtgtcgctg tcgacgagct cgcgagctcg gacatgaggt    22440
tgccccgtat tcagtgtcgc tgatttgtat tgtctgaagt tgttttttacg ttaagttgat    22500 gcagatcaat taatacgata cctgcgtcat aattgattat ttgacgtggt ttgatggcct    22560
ccacgcacgt tgtgatatgt agatgataat cattatcact ttacgggtcc tttccggtga    22620
tccgacaggt tacggggcgg cgacctcgcg ggttttcgct atttatgaaa attttccggt    22680
ttaaggcgtt tccgttcttc ttcgtcataa cttaatgttt ttatttaaaa taccctctga    22740
aaagaaagga aacgacaggt gctgaaagcg agcttttttgg cctctgtcgt ttcctttctc    22800 tgttttttgtc cgtggaatga acaatggaag tccgagctca tcgctaataa cttcgtatag    22860
catacattat acgaagttat attcgat                                        22887
```

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5

<210> SEQ ID NO 31
<211> LENGTH: 5
<212> TYPE: PRT
<213> ORGANISM: Artificial Sequence
<220> FEATURE:
<223> OTHER INFORMATION: N-glycosylation consensus sequence
<220> FEATURE:
<221> NAME/KEY: VARIANT
<222> LOCATION: (1)..(1)
<223> OTHER INFORMATION: Xaa = Asp or Glu
<220> FEATURE:
<221> NAME/KEY: VARIANT
<222> LOCATION: (2)..(2)
<223> OTHER INFORMATION: Xaa = Any natural accuring Amino acid except
      Proline
<220> FEATURE:
<221> NAME/KEY: VARIANT
<222> LOCATION: (4)..(4)
<223> OTHER INFORMATION: Xaa = Any natural accuring Amino acid except
      Proline
<220> FEATURE:
<221> NAME/KEY: VARIANT
<222> LOCATION: (5)..(5)
<223> OTHER INFORMATION: Xaa = Ser or Thr

<400> SEQUENCE: 31

Xaa Xaa Asn Xaa Xaa
1               5

The invention claimed is:

1. A composition comprising a bioconjugate, said bioconjugate comprising a carrier protein linked to an oligosaccharide or polysaccharide, wherein said oligosaccharide or polysaccharide comprises N-acetylgalactosamine at the reducing terminus, and wherein said carrier protein comprises the amino acid sequence D/E-X-N-Z-S/T (SEQ ID NO:31), wherein X and Z can be any natural amino acid except proline; and a recombinant prokaryotic host cell that comprises
(a) a heterologous nucleic acid encoding an epimerase that synthesizes N-acetylgalactosamine on undecaprenyl pyrophosphate, wherein said epimerase comprises the amino acid sequence of SEQ ID NO. 2;
(b) a heterologous nucleic acid encoding an oligosaccharyl transferase; and
(c) a heterologous nucleic acid encoding said carrier protein.

2. The composition of claim 1, wherein said carrier protein is linked to an oligosaccharide.

3. The composition of claim 1, wherein said carrier protein is linked to a polysaccharide.

4. The composition of claim 1, wherein said oligosaccharide or polysaccharide is from a Gram-negative bacterium.

5. The composition of claim 1, wherein said oligosaccharide or polysaccharide is from *E. coli*.

6. The composition of claim 5, wherein said oligosaccharide or polysaccharide is from *E. coli* O157.

7. The composition of claim 1, wherein said oligosaccharide or polysaccharide is from *Shigella flexneri*.

8. The composition of claim 7, wherein said oligosaccharide or polysaccharide is from *Shigella flexneri* 6.

9. The composition of claim 1, wherein said oligosaccharide or polysaccharide comprises a structure:

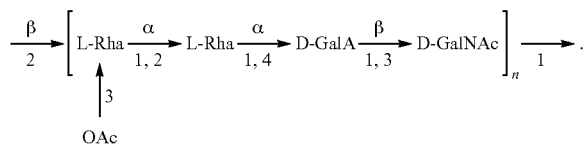

10. The composition of claim 1, wherein said oligosaccharide or polysaccharide comprises a structure, α-D-PerNAc-α-L-Fuc-β-D-Glc-α-D-GalNAc.

11. The composition of claim 1, wherein said carrier protein has been modified to comprise the amino acid sequence D/E-X-N-Z-S/T (SEQ ID NO:31), wherein X and Z can be any natural amino acid except proline.

12. The composition of claim 4, wherein said carrier protein has been modified to comprise the amino acid sequence D/E-X-N-Z-S/T (SEQ ID NO:31), wherein X and Z can be any natural amino acid except proline.

13. The composition of claim 5, wherein said carrier protein has been modified to comprise the amino acid sequence D/E-X-N-Z-S/T (SEQ ID NO:31), wherein X and Z can be any natural amino acid except proline.

14. The composition of claim 6, wherein said carrier protein has been modified to comprise the amino acid sequence D/E-X-N-Z-S/T (SEQ ID NO:31), wherein X and Z can be any natural amino acid except proline.

15. The composition of claim 7, wherein said carrier protein has been modified to comprise the amino acid sequence D/E-X-N-Z-S/T (SEQ ID NO:31), wherein X and Z can be any natural amino acid except proline.

16. The composition of claim 8, wherein said carrier protein has been modified to comprise the amino acid sequence D/E-X-N-Z-S/T (SEQ ID NO:31), wherein X and Z can be any natural amino acid except proline.

17. The composition of claim 1, wherein said carrier protein is *P. aeruginosa* exoprotein that has been modified to comprise the amino acid sequence D/E-X-N-ZSlT, wherein X and Z can be any natural amino acid except proline.

18. The composition of claim 1, wherein said carrier protein is the *Campylobacter* AcrA protein.

19. The composition of claim 1, wherein said nucleic acid encoding an oligosaccharyl transferase encodes the oligosaccharyl transferase from *Campylobacter jejuni*.

20. The composition of claim 1, wherein said nucleic acid encoding an oligosaccharyl transferase is heterologous to said host cell.

* * * * *